(12) United States Patent
Ness et al.

(10) Patent No.: US 6,613,508 B1
(45) Date of Patent: *Sep. 2, 2003

(54) METHODS AND COMPOSITIONS FOR ANALYZING NUCLEIC ACID MOLECULES UTILIZING SIZING TECHNIQUES

(75) Inventors: Jeffrey Van Ness, Seattle, WA (US); John C. Tabone, Bothell, WA (US); J. Jeffry Howbert, Bellevue, WA (US); John T. Mulligan, Seattle, WA (US)

(73) Assignee: Qiagen Genomics, Inc., Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/898,564

(22) Filed: Jul. 22, 1997

Related U.S. Application Data

(63) Continuation-in-part of application No. 08/786,834, filed on Jan. 22, 1997, now abandoned.
(60) Provisional application No. 60/014,536, filed on Jan. 23, 1996, and provisional application No. 60/020,487, filed on Jun. 4, 1996.

(51) Int. Cl.⁷ .................................................. C12Q 1/68
(52) U.S. Cl. ........................................................... 435/6
(58) Field of Search ........................... 435/6; 536/26.6; 436/501

(56) References Cited

U.S. PATENT DOCUMENTS

| | | | |
|---|---|---|---|
| 4,650,750 A | 3/1987 | Giese | 435/7 |
| 4,683,202 A | * 7/1987 | Mullis | 435/91 |
| 4,709,016 A | 11/1987 | Giese | 530/389 |
| 4,762,779 A | 8/1988 | Snitman | 435/6 |
| 4,775,619 A | 10/1988 | Urdea | 435/6 |
| 4,942,124 A | 7/1990 | Church | 435/6 |
| 4,962,020 A | 10/1990 | Tabor et al. | 435/6 |
| 4,965,349 A | 10/1990 | Woo et al. | 536/27 |
| 4,994,372 A | 2/1991 | Tabor et al. | 435/6 |
| 4,997,928 A | 3/1991 | Hobbs, Jr. | 536/27 |
| 5,118,605 A | 6/1992 | Urdea | 435/6 |
| 5,135,870 A | 8/1992 | Williams et al. | 436/173 |
| 5,149,625 A | 9/1992 | Church et al. | 435/6 |
| 5,262,536 A | 11/1993 | Hobbs, Jr. | 546/25 |
| 5,266,466 A | 11/1993 | Tabor et al. | 435/91.5 |
| 5,288,644 A | 2/1994 | Beavis et al. | 436/94 |
| 5,290,925 A | 3/1994 | Fino | 536/25.32 |
| 5,292,873 A | 3/1994 | Rokita et al. | 536/24.3 |
| 5,302,509 A | 4/1994 | Cheeseman | 435/6 |
| 5,324,631 A | 6/1994 | Helentjaris et al. | 435/6 |
| 5,346,670 A | 9/1994 | Renzoni et al. | 422/52 |
| 5,360,819 A | 11/1994 | Giese | 514/538 |

(List continued on next page.)

FOREIGN PATENT DOCUMENTS

| | | |
|---|---|---|
| CA | 2062454 A1 | 9/1992 |

(List continued on next page.)

OTHER PUBLICATIONS

Aebersold et al., "Design, synthesis, and characterization of a protein sequencing reagent yielding amino acid derivatives with enhanced detectability by mass spectrometry," *Protein Science* 1:494–503, 1992.

Amankwa and Kuhr, "Trypsin–Modified Fused–Silica Capillary Microreactor for Peptide Mapping by Capillary Zone Electrophoresis," *Anal. Chem.* 64:1610–1613, 1992.

Baldwin et al., "Synthesis of a Small Molecule Combinatorial Library Encoded with Molecular Tags," *J. Am. Chem. Soc.* 117:5588–5589, 1995. (+ Supplementary Material, 21 pages).

Borchardt and Still, "Synthetic Receptor Binding Elucidated with an Encoded Combinatorial Library," *J. Am. Chem. Soc.* 116:373–374, 1994.

Brown et al., "A single–bead decode strategy using electrospray ionization mass spectrometry and a new photolabile linker: 3–Amino–3–(2–nitrophenyl)propionic acid," *Molecular Diversity* 1:4–12, 1995.

Ching et al, "Polymers as Surface–Based Tethers with Photolytic Triggers Enabling Laser–Induced Release/Desorption of Covalently Bound Molecules," *Bioconjugate Chemistry* 7(5):525–528, 1996.

Ching et al., "Surface Chemistries Enabling Photoinduced Uncoupling/Desorption of Covalently Tethered Biomolecules," *J. Org. Chem.* 61:3582–3583, 1996.

Church et al., "New Technologies For Genome Sequencing And Analysis," in *DOE Human Genome Program Contractor–Grantee Workshop V*, Sante Fe, New Mexico, Jan. 28–Feb. 1, 1996, available NTIS, CONF–960143, 1996, p. 51.

(List continued on next page.)

Primary Examiner—Scott W. Houtteman
(74) Attorney, Agent, or Firm—SEED Intellectual Property Law Group PLLC

(57) ABSTRACT

Tags and linkers specifically designed for a wide variety of nucleic acid reactions are disclosed, which are suitable for a wide variety of nucleic acid reactions wherein separation of nucleic acid molecules based upon size is required.

40 Claims, 44 Drawing Sheets

U.S. PATENT DOCUMENTS

| | | |
|---|---|---|
| 5,403,708 A | 4/1995 | Brennan et al. ............... 435/6 |
| 5,409,811 A | 4/1995 | Tabor et al. .................... 435/6 |
| 5,451,463 A | 9/1995 | Nelson et al. .............. 428/402 |
| 5,516,931 A | 5/1996 | Giese et al. .................. 560/59 |
| 5,547,835 A | 8/1996 | Köster .......................... 435/6 |
| 5,602,273 A | 2/1997 | Giese et al. .................. 560/60 |
| 5,604,097 A | 2/1997 | Brenner ........................ 435/6 |
| 5,604,104 A | 2/1997 | Giese et al. ................ 435/7.1 |
| 5,610,020 A | 3/1997 | Giese et al. ................ 435/7.1 |
| 5,622,824 A | 4/1997 | Köster .......................... 435/6 |
| 5,635,400 A | 6/1997 | Brenner .................. 435/320.1 |
| 5,650,270 A | 7/1997 | Giese et al. .................... 435/6 |
| 5,654,413 A | 8/1997 | Brenner .................... 536/22.1 |
| 5,674,716 A | 10/1997 | Tabor et al. .............. 435/91.1 |
| 5,691,141 A | 11/1997 | Köster .......................... 435/6 |
| 5,695,934 A | 12/1997 | Brenner ........................ 435/6 |
| 5,700,921 A | 12/1997 | Westling et al. ........... 536/22.1 |
| 5,728,526 A | 3/1998 | George, Jr. et al. ............. 435/6 |
| 5,763,175 A | 6/1998 | Brenner ........................ 435/6 |
| 5,821,058 A | 10/1998 | Smith et al. ................... 435/6 |
| 5,851,765 A | 12/1998 | Köster .......................... 435/6 |
| 5,856,097 A | 1/1999 | Pinkel et al. ................... 435/6 |
| 5,863,722 A | 1/1999 | Brenner ........................ 435/6 |
| 5,872,003 A | 2/1999 | Köster .................... 435/283.1 |
| 5,908,745 A | 6/1999 | Mirzabekov et al. .......... 435/6 |
| 5,952,654 A | 9/1999 | Giese ........................ 250/288 |
| 5,962,223 A | 10/1999 | Whiteley et al. .............. 435/6 |
| 6,013,431 A | 1/2000 | Söderlund et al. ............. 435/5 |
| 6,033,909 A | 3/2000 | Uhlmann et al. ........... 435/375 |
| 6,087,095 A | 7/2000 | Rosenthal et al. ............. 435/6 |
| 6,087,186 A | 7/2000 | Cargill et al. ............... 436/518 |
| 6,312,893 B1 * | 11/2001 | Van Ness ...................... 435/6 |

FOREIGN PATENT DOCUMENTS

| | | |
|---|---|---|
| EP | 127 154 A2 | 12/1984 |
| EP | 251 786 A2 | 1/1988 |
| EP | 300 730 A1 | 1/1989 |
| EP | 0 351 138 * | 1/1990 |
| EP | 360 940 A2 | 4/1990 |
| EP | 401 821 A1 | 12/1990 |
| EP | 502 595 A2 | 9/1992 |
| EP | 514 927 A1 | 11/1992 |
| EP | 539 343 A1 | 4/1993 |
| EP | 639 647 A2 | 2/1995 |
| EP | 711 362 B1 | 5/1996 |
| JP | 6-289018 | 10/1994 |
| WO | WO 89/12694 | 12/1989 |
| WO | WO 90/13666 | 11/1990 |
| WO | WO 92/02528 | 2/1992 |
| WO | WO 92/02638 | 2/1992 |
| WO | WO 92/10587 | 6/1992 |
| WO | WO 93/20233 | 10/1993 |
| WO | WO 93/20236 | 10/1993 |
| WO | WO 93/21340 | 10/1993 |
| WO | WO 94/08051 | 4/1994 |
| WO | 94/16101 * | 7/1994 |
| WO | WO 94/16101 | 7/1994 |
| WO | WO 94/21822 | 9/1994 |
| WO | WO 94/28418 | 12/1994 |
| WO | WO 95/04160 | 2/1995 |
| WO | WO 95/06752 | 3/1995 |
| WO | WO 95/11961 | 5/1995 |
| WO | WO 95/14108 | 5/1995 |
| WO | WO 95/25737 | 9/1995 |
| WO | WO 95/28640 | 10/1995 |
| WO | WO 96/00378 | 1/1996 |
| WO | WO 96/22966 | 8/1996 |

OTHER PUBLICATIONS

Church and Kieffer–Higgins, "Multiplex DNA Sequencing," *Science* 240:185–188, 1988.

Cobb and Novotny, "High–Sensitivity Peptide Mapping by Capillary Zone Electrophoresis and Microcolumn Liquid Chromatography, Using Immobilized Trypsin for Protein Digestion," *Anal. Chem.* 61:2226–2231, 1989.

Colombo, Roberto, "Liquid–Phase Synthesis of Naturally Occurring Peptides, II. Syntheses of Three Mast Cell Degranulating Tetradecapeptide Amides from Wasp Venoms," *Hoppe–Seyler's Z. Physiol. Chem.* 362: 1393–1403, 1981.

Covey et al., "The Determination of Protein, Oligonucleotide and Peptide Molecular Weights by Ion–spray Mass Spectrometry," *Rapid Communications In Mass Spectrometry* 2(11):249–256, 1988.

Geysen et al., "Isotope or mass encoding of combinatorial libraries," *Chemistry & Biology* 3(8):679–688, 1996.

Giese et al., "Electrophore Mass Labels For TOF–MS DNA Sequencing," in *Proceedings of the 44th ASMS Conference on Mass Spectrometry and Allied Topic*, Portland, Oregon, May 12–16, 1996, p. 673.

Roger W. Giese, "Electrophoric release tags: ultrasensitive molecular labels providing multiplicity," *Trends in Analytical Chemistry* 2(7):166–168, 1983.

Greenberg and Gilmore, "Cleavage of Oligonucleotides from Solid–Phase Supports Using o–Nitrobenzyl Photochemistry," *J. Org. Chem.* 59:746–753, 1994.

Marc M. Greenberg, "Photochemical Cleavage of Oligonucleotides From Solid Phase Supports," *Tetrahedron Letters* 34(2):251–254, 1993.

Holmes and Jones, "Reagents for Combinatorial Organic Synthesis: Development of a New o–Nitrobenzyl Photolabile Linker for Solid Phase Synthesis," *J. Org. Chem.* 60:2318–2319, 1995. (+ Supplementary Material, 7 pages).

Jacobson et al., "Applications of Mass Spectrometry to DNA Sequencing," *Genetic Analysis Techniques and Applications* 8(8):223–229, 1991.

Jane et al., "High–Performance Liquid Chromatographic Analysis Of Basic Drugs on Silica Columns Using Non–Aqueous Ionic Eluents," *Journal of Chromatography* 323:191–225, 1985.

Kremsky et al., "Immobilization of DNA via oligonucleotides containing an aldehyde or carboxylic acid group at the 5'terminus," *Nucleic Acids Research* 15(7);2891–2909, 1987.

Little et al., "Rapid Sequencing of Oligonucleotides by High–Resolution Mass Spectrometry," *J. Am. Chem. Soc.* 116:4893–4897, 1994.

Lloyd–Williams et al., "Convergent Solid–Phase Peptide Synthesis," *Tetrahedron* 49(48):11065–11133, 1993.

Musch et al., "Expert System For Pharmaceutical Analysis. I. Selection Of The Detection System In High–Performance Liquid Chromatographic Analysis: UV *Versus* Amperometric Detection," *Journal of Chromatography* 348:97–110, 1985.

Nashabeh and El Rassi, "Enzymorphoresis of nucleic acids by tandem capillary enzyme reactor–capillary zone electrophoresis," *Journal of Chromatography* 596:251–264, 1992.

Nestler et al., "A General Method for Molecular Tagging of Encoded Combinatorial Chemistry Libraries," *J. Org. Chem.* 59:4723–4724, 1994.

Ordoukhanian and Taylor, "Design and Synthesis of a Versatile Photocleavable DNA Building Block. Application to Phototriggered Hybridization," *J. Am. Chem. Soc. 117*: 9570–9571, 1995.

V. N. Rajasekharan Pillai, "Photoremovable Protecting Groups in Organic Synthesis," *Synthesis 1*:1–26, 1980.

Rich and Gurwara, "Preparation of a New o–Nitrobenzyl Resin for Solid–Phase Synthesis of *tert*–Butyloxycarbonyl–Protected Peptide Acids," *J. Am. Chem. Soc. 97*:1575–1579, 1975.

Rock and Chan, "Synthesis and Photolysis Properties of a Photolabile Linker Based on 3'–Methoxybenzoin," *J. Org. Chem. 61*:1526–1529, 1996.

Sanger et al., "DNA sequencing with chain–terminating inhibitors," *Proc. Natl. Acad. Sci. USA 74*(12):5463–5467, 1977.

Senter et al., "Novel Photocleavable Protein Crosslinking Reagents And Their Use In The Preparation Of Antibody–Toxing Conjugates," *Photochemistry and Photobiology 42*(3):231–237, 1985.

Sumer et al., "Factors Determining Relative Sensitivity of Analytes in Positive Mode Atmospheric Pressure Ionization Mass Spectrometry," *Anal. Chem. 60*:1300–1307, 1988.

Simon J. Teague, "Facile Synthesis of a o–Nitrobenzyl Photolabile Linker for Combinatorial Chemistry," *Tetrahedron Letters 37*(32):5751–5754, 1996.

Thiele and Fahrenholz, "Photocleavable Biotinylated Lignads for Affinity Chromatography," *Analytical Biochemistry 218*:330–337, 1994.

Valaskovic et al., "Attomole–Sensitivity Electrospray Source for Large–Molecule Mass Spectrometry," *Anal. Chem. 67*:3802–3805, 1995.

Voivodov et al., "Surface Arrays of Energy Absorbing Polymers Enabling Covalent Attachment of Biomolecules for Subsequent Laser–Induced Uncoupling/Desorption," *Tetrahedron Letters 37*(32):5669–5672, 1996.

Charles Hignite, "Nucleic Acids And Derivatives," in *Biochemical Applications Of Mass Spectrometry, First Supplementary Volume*, Waller et al. (eds.), John Wiley & Sons, New York, 1981, pp. 527–566.

Yoo and Greenberg, "Synthesis of Oligonucleotides Containing 3'–Alkyl Carboxylic Acids Using Universal, Photolabile Solid Phase Synthesis Supports," *J. Org. Chem. 60*:3358–3364, 1995.

Zablocki et al., "Potent *in Vitro* and *in Vivo* Inhibitors of Platlet Aggregation Based Upon the Arg–Gly–Asp Sequence of Fibronogen. (Aminobenzamidino)succinyl (ABAS) Series of Orally Active Fibrinogen Receptor Antagonists," *J. Med. Chem. 38*:2378–2394, 1995.

\* cited by examiner

X<sub>1-36</sub>
FROM
EXAMPLE A

5'-Aminohexyl-tailed oligonucleotides

XI$_{1-36}$

STEP A 100 mM
Sodium Borate
pH 8.3

5'-CMST-Oligonucleotide Conjugate

XII$_{1-36}$

METHODS AND COMPOSITIONS FOR ANALYZING NUCLEIC ACID MOLECULES UTILIZING SIZING TECHNIQUES

CROSS-REFERENCE TO RELATED APPLICATIONS

This application is a continuation-in-part of U.S. patent application Ser. No. 08/786,834, filed Jan. 22, 1997, now abandoned; which application claims the benefit of provisional application No. 60/014,536, filed Jan. 23, 1996, and of provisional application No. 60/020,487, filed Jun. 4, 1996, all of which are incorporated by reference herein in their entirety.

TECHNICAL FIELD

The present invention relates generally to methods and compositions for analyzing nucleic acid molecules, and more specifically to tags which may be utilized in a wide variety of nucleic acid reactions, wherein separation of nucleic acid molecules based on size is required.

BACKGROUND OF THE INVENTION

Detection and analysis of nucleic acid molecules are among the most important techniques in biology. Such techniques are at the heart of molecular biology and play a rapidly expanding role in the rest of biology.

Generally, one type of analysis of nucleic acid reactions involves separation of nucleic acid molecules based on length. For example, one widely used technique, polymerase chain reaction (PCR) (see, U.S. Pat. Nos. 4,683,195, 4,683,202, and 4,800,159) has become a widely utilized technique to both identify sequences present in a sample and to synthesize DNA molecules for further manipulation.

Briefly, in PCR, DNA sequences are amplified by enzymatic reaction that synthesizes new DNA strands in either a geometric or linear fashion. Following amplification, the DNA sequences must be detected and identified. Because of non-specific amplifications, which would otherwise confuse analysis, or the need for purity, the PCR reaction products are generally subjected to separation prior to detection. Separation based on the size (i.e., length) of the products yields the most useful information. The method giving the highest resolution of nucleic acid molecules is electrophoretic separation. In this method, each individual PCR reaction is applied to an appropriate gel and subjected to a voltage potential. The number of samples that can be processed is limited by the number of wells in the gel. On most gel apparatus, from approximately 10 to 64 samples can be separated in a single gel. Thus, processing large numbers of samples is both labor and material intensive.

Electrophoretic separation must be coupled with some detection system in order to obtain data. Detection systems of nucleic acids commonly, and almost exclusively, utilize an intercalating dye or radioactive label, and less frequently, a nonradioactive label. Intercalating dyes, such as ethidium bromide, are simple to use. The dye is included in the gel matrix during electrophoresis or, following electrophoresis, the gel is soaked in a dye-containing solution. The dye can be directly visualized in some cases, but more often, and for ethidium bromide in particular, is excited by light (e.g., UV) to fluoresce. In spite of this apparent ease of use, such dyes have some notable disadvantages. First, the dyes are insensitive and there must be a large mass amount of nucleic acid molecules in order to visualize the products. Second, the dyes are typically mutagenic or carcinogenic.

A more sensitive detection technique than dyes uses a radioactive (or nonradioactive) label. Typically, either a radiolabeled nucleotide or a radiolabeled primer is included in the PCR reaction. Following separation, the radiolabel is "visualized" by autoradiography. Although more sensitive, the detection suffers from film limitations, such as reciprocity failure and non-linearity. These limitations can be overcome by detecting the label by phosphor image analysis. However, radiolabels have safety requirements, increasing resource utilization and necessitating specialized equipment and personnel training. For such reasons, the use of nonradioactive labels has been increasing in popularity. In such systems, nucleotides contain a label, such as a fluorophore, biotin or digoxin, which can be detected by an antibody or other molecule (e.g., other member of a ligand pair) that is labeled with an enzyme reactive with a chromogenic substrate. These systems do not have the safety concerns as described above, but use components that are often labile and may yield nonspecific reactions, resulting in high background (i.e., low signal-to-noise ratio).

The present invention provides novel compositions and methods which may be utilized in a wide variety of nucleic acid reactions, and further provides other related advantages.

SUMMARY OF THE INVENTION

Briefly stated, the present invention provides compositions and methods which may be utilized in a wide variety of ligand pair reactions wherein separation of molecules of interest, such as nucleic acid molecules, based on size is required. Representative examples of methods which may be enhanced given the disclosure provided herein include PCR, differential display, RNA fingerprinting, PCR-SSCP, oligo litations assays, nuclease digestion methods (e.g., exo- and endo-nuclease based assays), and dideoxy fingerprinting. The methods described herein may be utilized in a wide array of fields, including, for example, in the development of clinical or research-based diagnostics, the determination of polymorphisms, and the development of genetic maps.

Within one aspect of the present invention, methods are provided for determining the identity of a nucleic acid molecule, comprising the steps of (a) generating tagged nucleic acid molecules from one or more selected target nucleic acid molecules, wherein a tag is correlative with a particular nucleic acid fragment and detectable by non-fluorescent spectrometry or potentiometry, (b) separating the tagged fragments by size, (c) cleaving the tags from the tagged fragments, and (d) detecting tags by non-fluorescent spectrometry or potentiometry, and therefrom determining the identity of the nucleic acid molecules.

Within a related aspect of the invention, methods are provided for detecting a selected nucleic acid molecule, comprising the steps of (a) combining tagged nucleic acid probes with target nucleic acid molecules under conditions and for a time sufficient to permit hybridization of a tagged nucleic acid probe to a complementary selected target nucleic acid sequence, wherein a tagged nucleic acid probe is detectable by non-fluorescent spectrometry or potentiometry, (b) altering the size of hybridized tagged probes, unhybridized probes or target molecules, or the probe:target hybrids, (c) separating the tagged probes by size, (d) cleaving tags from the tagged probes, and (e) detecting the tags by non-fluorescent spectrometry or potentiometry, and therefrom detecting the selected nucleic acid molecule.

Within further aspects methods are provided for genotyping a selected organism, comprising the steps of (a) generating tagged nucleic acid molecules from a selected target molecule, wherein a tag is correlative with a particular fragment and may be detected by non-fluorescent spectrometry or potentiometry, (b) separating the tagged molecules by sequential length, (c) cleaving the tag from the tagged molecule, and (d) detecting the tag by non-fluorescent spectrometry or potentiometry, and therefrom determining the genotype of the organism.

Within another aspect, methods are provided for genotyping a selected organism, comprising the steps of (a) combining a tagged nucleic acid molecule with a selected target molecule under conditions and for a time sufficient to permit hybridization of the tagged molecule to the target molecule, wherein a tag is correlative with a particular fragment and may be detected by non-fluorescent spectrometry or potentiometry, (b) separating the tagged fragments by sequential length, (c) cleaving the tag from the tagged fragment, and (d) detecting the tag by non-fluorescent spectrometry or potentiometry, and therefrom determining the genotype of the organism.

Within the context of the present invention it should be understood that "biological samples" include not only samples obtained from living organisms (e.g., mammals, fish, bacteria, parasites, viruses, fungi and the like) or from the environment (e.g., air, water or solid samples), but biological materials which may be artificially or synthetically produced (e.g., phage libraries, organic molecule libraries, pools of genomic clones, cDNA clones, RNA clones, or the like). Representative examples of biological samples include biological fluids (e.g., blood, semen, cerebral spinal fluid, urine), biological cells (e.g., stem cells, B or T cells, liver cells, fibroblasts and the like), and biological tissues. Finally, representative examples of organisms that may be genotyped include virtually any unicellular or multicellular organism, such as warm-blooded animals, mammals or vertebrates (e.g., humans, chimps, macaques, horses, cows, pigs, sheep, dogs, cats, rats and mice, as well as cells from any of these), bacteria, parasites, viruses, fungi and plants.

Within various embodiments of the above-described methods, the nucleic acid probes and or molecules of the present invention may be generated by, for example, a ligation, cleavage or extension (e.g., PCR) reaction. Within other related aspects the nucleic acid probes or molecules may be tagged by non-3' tagged oligonucleotide primers (e.g., 5'-tagged oligonucleotide primers) or dideoxynucleotide terminators.

Within other embodiments of the invention, 4, 5, 10, 15, 20, 25, 30, 35, 40, 45, 50, 60 , 70, 80, 90, 100, 200, 250, 300, 350, 400, 450, or greater than 500 different and unique tagged molecules may be utilized within a given reaction simultaneously, wherein each tag is unique for a selected nucleic acid molecule or fragment, or probe, and may be separately identified.

Within further embodiments of the invention, the tag(s) may be detected by fluorometry, mass spectrometry, infrared spectrometry, ultraviolet spectrometry, or, potentiostatic amperometry (e.g., utilizing coulometric or amperometric detectors). Representative examples of suitable spectrometric techniques include time-of-flight mass spectrometry, quadrupole mass spectrometry, magnetic sector mass spectrometry and electric sector mass spectrometry. Specific embodiments of such techniques include ion-trap mass spectrometry, electrospray ionization mass spectrometry, ion-spray mass spectrometry, liquid ionization mass spectrometry, atmospheric pressure ionization mass spectrometry, electron ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nanospray mass spectrometry, nebulised spray ionization mass spectrometry, chemical ionization mass spectrometry, resonance ionization mass spectrometry, secondary ionization mass spectrometry and thermospray mass spectrometry.

Within yet other embodiments of the invention, the target molecules, hybridized tagged probes, unhybridized probes or target molecules, probe:target hybrids, or tagged nucleic acid probes or molecules may be separated from other molecules utilizing methods which discriminate between the size of molecules (either actual linear size, or three-dimensional size). Representative examples of such methods include gel electrophoresis, capillary electrophoresis, microchannel electrophoresis, HPLC, size exclusion chromatography, filtration, polyacrylamide gel electrophoresis, liquid chromatography, reverse size exclusion chromatography, ion-exchange chromatography, reverse phase liquid chromatography, pulsed-field electrophoresis, field-inversion electrophoresis, dialysis, and fluorescence-activated liquid droplet sorting. Alternatively, the target molecules, hybridized tagged probes, unhybridized probes or target molecules, probe:target hybrids, or tagged nucleic acid probes or molecules may be bound to a solid support (e.g., hollow fibers (Amicon Corporation, Danvers, Mass.), beads (Polysciences, Warrington, Pa.), magnetic beads (Robbin Scientific, Mountain View, Calif.), plates, dishes and flasks (Coming Glass Works, Coming, N.Y.), meshes (Becton Dickinson, Mountain View, Calif.), screens and solid fibers (see Edelman et al., U.S. Pat. No. 3,843,324; see also Kuroda etýal., U.S. Pat. No. 4,416,777), membranes (Millipore Corp., Bedford, Mass.), and dipsticks). If the first or second member, or exposed nucleic acids are bound to a solid support, within certain embodiments of the invention the methods disclosed herein may further comprise the step of washing the solid support of unbound material.

Within other embodiments, the tagged nucleic acid molecules or probes may be cleaved by a methods such as chemical, oxidation, reduction, acid-labile, base labile, enzymatic, electrochemical, heat and photolabile methods. Within further embodiments, the steps of separating, cleaving and detecting may be performed in a continuous manner, for example, on a single device which may be automated.

Within certain embodiments of the invention, the size of the hybridized tagged probes, unhybridized probes or target molecules, or probe:target hybrids are altered by a method selected from the group consisting of polymerase extension, ligation, exonuclease digestion, endonuclease digestion, restriction enzyme digestion, site-specific recombinase digestion, ligation, mismatch specific nuclease digestion, methylation-specific nuclease digestion, covalent attachment of probe to target and hybridization.

The methods an compositions described herein may be utilized in a wide variety of applications, including for example, identifying PCR amplicons, RNA fingerprinting, differential display, single-strand conformation polymorphism detection, dideoxyfingerprinting, restriction maps and restriction fragment length polymorphisms, DNA fingerprinting, genotyping, mutation detection, oligonucleotide ligation assay, sequence specific amplifications, for diagnostics, forensics, identification, developmental biology, biology, molecular medicine, toxicology, animal breeding, These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Figure 1A:
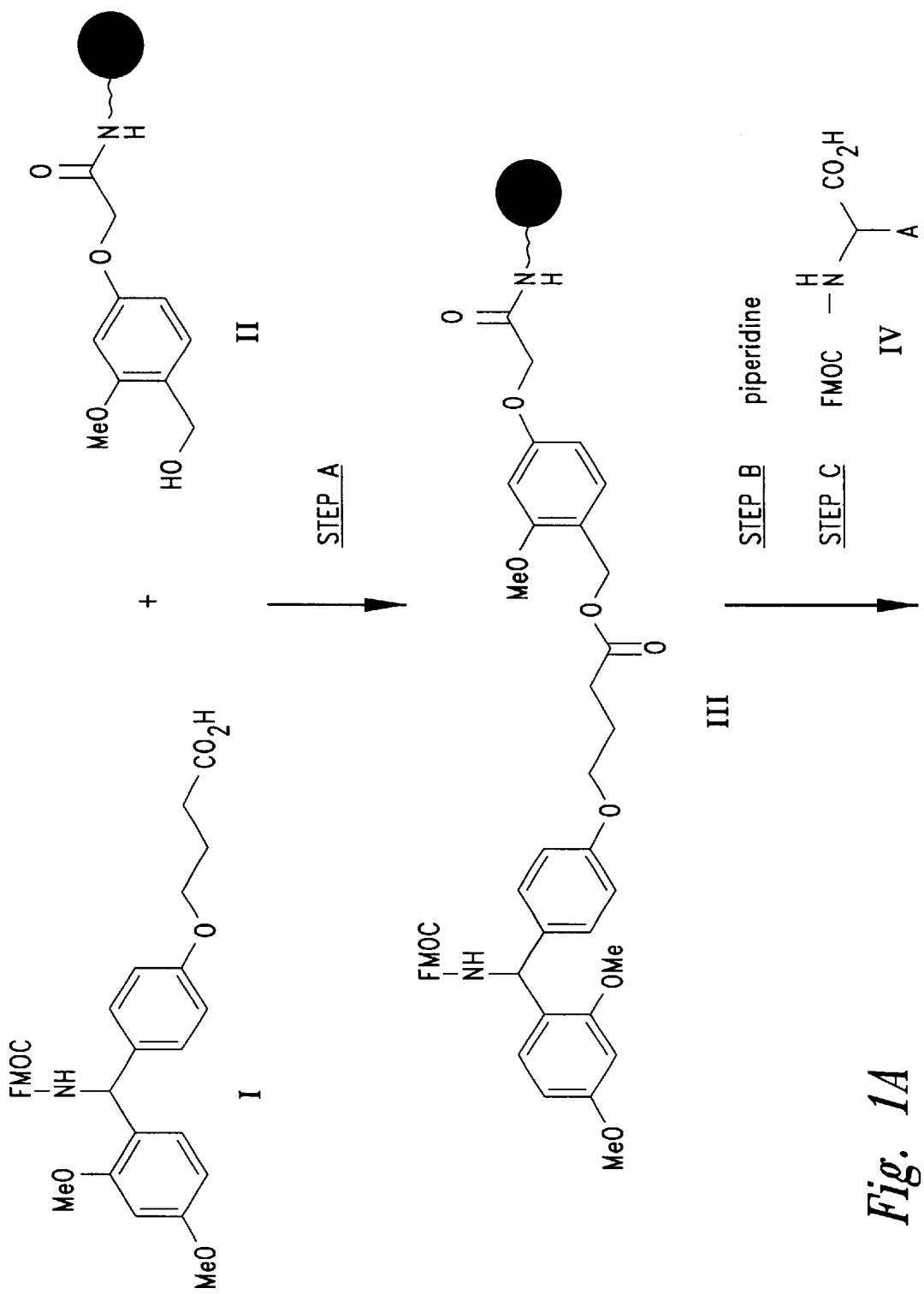
FIGS. 1A, 1B, and 1C depicts the flowchart for the synthesis of pentafluorophenyl esters of chemically cleavable mass spectroscopy tags, to liberate tags with carboxyl amide termini.

As noted above, the present invention provides compositions and methods for analyzing nucleic acid molecules, wherein separation of nucleic acid molecules based on size is required. The present methods permit the simultaneous detection of molecules of interest, which include nucleic acids and fragments, proteins, peptides, etc.

Briefly stated, in one aspect the present invention provides compounds wherein a molecule of interest, or precursor thereto, is linked via a labile bond (or labile bonds) to a tag. Thus, compounds of the invention may be viewed as having the general formula:

T—L—X wherein T is the tag component, L is the linker component that either is, or contains, a labile bond, and X is either the molecule of interest (MOI) component or a functional group component ($L_h$) through which the MOI may be joined to T—L. Compounds of the invention may therefore be represented by the more specific general formulas:

T—L—MOI and

T—L—$L_h$

For reasons described in detail below, sets of T—L—MOI compounds may be purposely subjected to conditions that cause the labile bond(s) to break, thus releasing a tag moiety from the remainder of the compound. The tag moiety is then characterized by one or more analytical techniques, to thereby provide direct information about the structure of the tag moiety, and (most importantly) indirect information about the identity of the corresponding MOI.

As a simple illustrative example of a representative compound of the invention wherein L is a direct bond, reference is made to the following structure (i):

Structure (i)

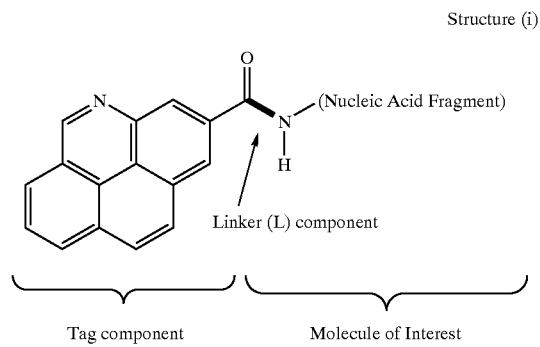

Tag component      Molecule of Interest component

In structure (i), T is a nitrogen-containing polycyclic aromatic moiety bonded to a carbonyl group, X is a MOI (and specifically a nucleic acid fragment terminating in an amine group), and L is the bond which forms an amide group. The amide bond is labile relative to the bonds in T because, as recognized in the art, an amide bond may be chemically cleaved (broken) by acid or base conditions which leave the bonds within the tag component unchanged. Thus, a tag moiety (i.e., the cleavage product that contains T) may be released as shown below:

Structure (i)

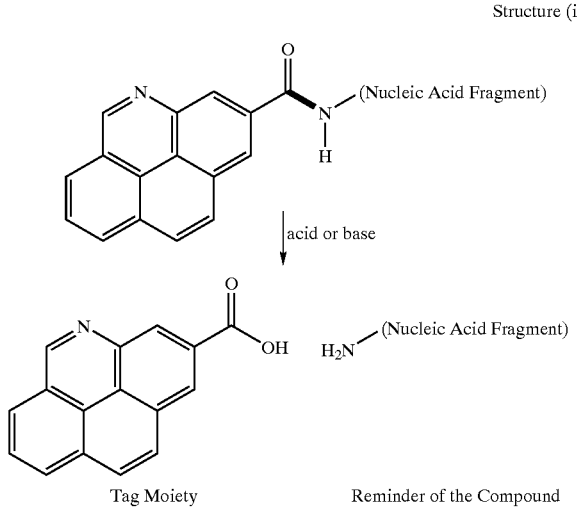

Tag Moiety        Reminder of the Compound

However, the linker L may be more than merely a direct bond, as shown in the following illustrative example, where reference is made to another representative compound of the invention having the structure (ii) shown below:

Structure (ii)

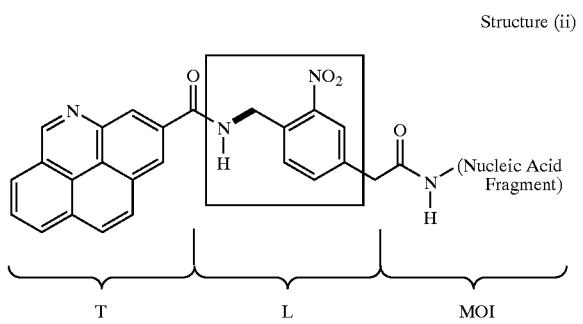

It is well-known that compounds having an ortho-nitrobenzylamine moiety (see boxed atoms within structure (ii)) are photolytically unstable, in that exposure of such compounds to actinic radiation of a specified wavelength will cause selective cleavage of the benzylamine bond (see bond denoted with heavy line in structure (ii)). Thus, structure (ii) has the same T and MOI groups as structure (i), however the linker group contains multiple atoms and bonds within which there is a particularly labile bond. Photolysis of structure (ii) thus releases a tag moiety (T-containing moiety) from the remainder of the compound, as shown below.

Structure (ii)

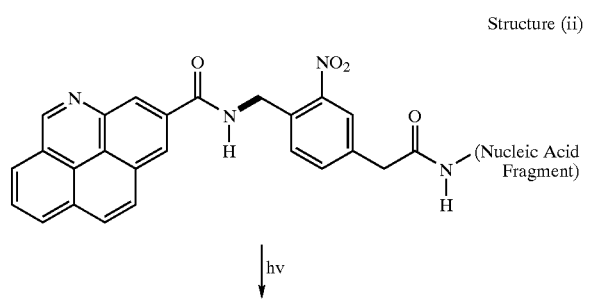

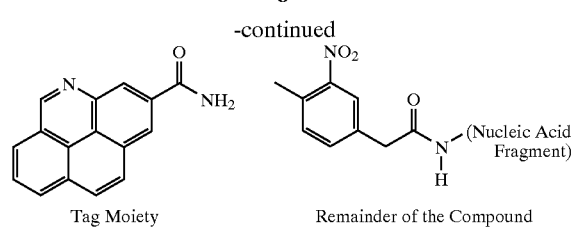

Tag Moiety        Remainder of the Compound

The invention thus provides compounds which, upon exposure to appropriate cleavage conditions, undergo a cleavage reaction so as to release a tag moiety from the remainder of the compound. Compounds of the invention may be described in terms of the tag moiety, the MOI (or precursor thereto, $L_h$), and the labile bond(s) which join the two groups together. Alternatively, the compounds of the invention may be described in terms of the components from which they are formed. Thus, the compounds may be described as the reaction product of a tag reactant, a linker reactant and a MOI reactant, as follows.

The tag reactant consists of a chemical handle ($T_h$) and a variable component ($T_{vc}$), so that the tag reactant is seen to have the general structure:

$T_{vc}$—$T_h$

To illustrate this nomenclature, reference may be made to structure (iii), which shows a tag reactant that may be used to prepare the compound of structure (ii). The tag reactant having structure (iii) contains a tag variable component and a tag handle, as shown below:

Structure (iii)

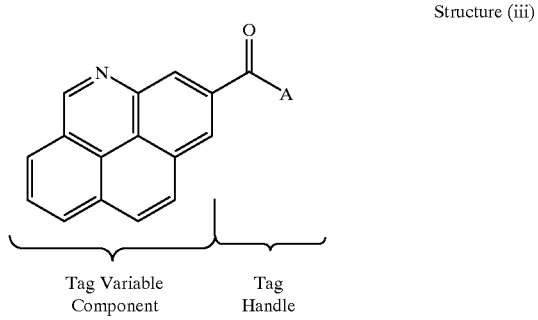

Tag Variable      Tag
Component        Handle

In structure (iii), the tag handle (—C(=O)—A) simply provides an avenue for reacting the tag reactant with the linker reactant to form a T—L moiety. The group "A" in structure (iii) indicates that the carboxyl group is in a chemically active state, so it is ready for coupling with other handles. "A" may be, for example, a hydroxyl group or pentafluorophenoxy, among many other possibilities. The invention provides for a large number of possible tag handles which may be bonded to a tag variable component, as discussed in detail below. The tag variable component is thus a part of "T" in the formula T—L—X, and will also be part of the tag moiety that forms from the reaction that cleaves L.

As also discussed in detail below, the tag variable component is so-named because, in preparing sets of compounds according to the invention, it is desired that members of a set have unique variable components, so that the individual members may be distinguished from one another by an analytical technique. As one example, the tag variable component of structure (iii) may be one member of the following set, where members of the set may be distinguished by their UV or mass spectra:

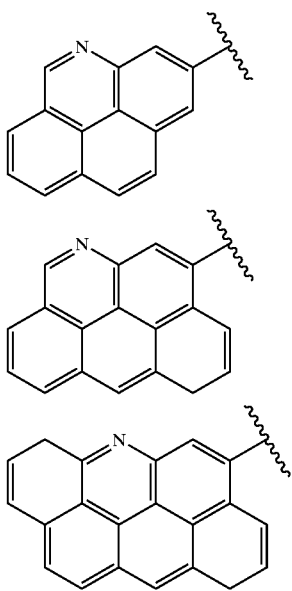

Likewise, the linker reactant may be described in terms of its chemical handles (there are necessarily at least two, each of which may be designated as $L_h$) which flank a linker labile component, where the linker labile component consists of the required labile moiety ($L^2$) and optional labile moieties ($L^1$ and $L^3$), where the optional labile moieties effectively serve to separate $L^2$ from the handles $L_h$, and the required labile moiety serves to provide a labile bond within the linker labile component. Thus, the linker reactant may be seen to have the general formula:

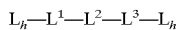

The nomenclature used to describe the linker reactant may be illustrated in view of structure (iv), which again draws from the compound of structure (ii):

Structure (iv)

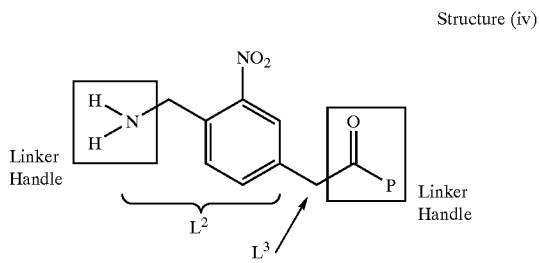

As structure (iv) illustrates, atoms may serve in more than one functional role. Thus, in structure (iv), the benzyl nitrogen functions as a chemical handle in allowing the linker reactant to join to the tag reactant via an amide-forming reaction, and subsequently also serves as a necessary part of the structure of the labile moiety $L^2$ in that the benzylic carbon-nitrogen bond is particularly susceptible to photolytic cleavage. Structure (iv) also illustrates that a linker reactant may have an $L^3$ group (in this case, a methylene group), although not have an $L^1$ group. Likewise, linker reactants may have an $L^1$ group but not an $L^3$ group, or may have $L^1$ and $L^3$ groups, or may have neither of $L^1$ nor $L^3$ groups. In structure (iv), the presence of the group "P" next to the carbonyl group indicates that the carbonyl group is protected from reaction. Given this configuration, the activated carboxyl group of the tag reactant (iii) may cleanly react with the amine group of the linker reactant (iv) to form an amide bond and give a compound of the formula T—L—$L_h$.

The MOI reactant is a suitably reactive form of a molecule of interest. Where the molecule of interest is a nucleic acid fragment, a suitable MOI reactant is a nucleic acid fragment bonded through its 5' hydroxyl group to a phosphodiester group and then to an alkylene chain that terminates in an amino group. This amino group may then react with the carbonyl group of structure (iv), (after, of course, deprotecting the carbonyl group, and preferably after subsequently activating the carbonyl group toward reaction with the amine group) to thereby join the MOI to the linker.

When viewed in a chronological order, the invention is seen to take a tag reactant (having a chemical tag handle and a tag variable component), a linker reactant (having two chemical linker handles, a required labile moiety and 0–2 optional labile moieties) and a MOI reactant (having a molecule of interest component and a chemical molecule of interest handle) to form T—L—MOI. Thus, to form T—L—MOI, either the tag reactant and the linker reactant are first reacted together to provide T—L—$L_h$, and then the MOI reactant is reacted with T—L—$L_h$ so as to provide T—L—MOI, or else (less preferably) the linker reactant and the MOI reactant are reacted together first to provide $L_h$—L—MOI, and then $L_h$—L—MOI is reacted with the tag reactant to provide T—L—MOI. For purposes of convenience, compounds having the formula T—L—MOI will be described in terms of the tag reactant, the linker reactant and the MOI reactant which may be used to form such compounds. Of course, the same compounds of formula T—L—MOI could be prepared by other (typically, more laborious) methods, and still fall within the scope of the inventive T—L—MOI compounds.

In any event, the invention provides that a T—L—MOI compound be subjected to cleavage conditions, such that a tag moiety is released from the remainder of the compound. The tag moiety will comprise at least the tag variable component, and will typically additionally comprise some or all of the atoms from the tag handle, some or all of the atoms from the linker handle that was used to join the tag reactant to the linker reactant, the optional labile moiety $L^1$ if this group was present in T—L—MOI, and will perhaps contain some part of the required labile moiety $L^2$ depending on the precise structure of $L^2$ and the nature of the cleavage chemistry. For convenience, the tag moiety may be referred to as the T-containing moiety because T will typically constitute the major portion (in terms of mass) of the tag moiety.

Given this introduction to one aspect of the present invention, the various components T, L and X will be described in detail. This description begins with the following definitions of certain terms, which will be used hereinafter in describing T, L and X.

As used herein, the term "nucleic acid fragment" means a molecule which is complementary to a selected target nucleic acid molecule (i.e., complementary to all or a portion thereof), and may be derived from nature or synthetically or recombinantly produced, including non-naturally occurring molecules, and may be in double or single stranded form where appropriate; and includes an oligonucleotide (e.g., DNA or RNA), a primer, a probe, a nucleic acid analog (e.g., PNA), an oligonucleotide which is extended in a 5' to 3' direction by a polymerase, a nucleic acid which is cleaved chemically or enzymatically, a nucleic acid that is terminated with a dideoxy terminator or capped at the 3' or 5' end with a compound that prevents polymerization at the 5' or 3' end, and combinations thereof. The complementarity of a nucleic acid fragment to a selected target nucleic acid molecule generally means the exhibition of at least about 70% specific base pairing throughout the length of the fragment. Preferably the nucleic acid fragment exhibits at least about 80% specific base pairing; and most preferably at least about 90%. Assays for determining the percent mismatch (and thus the percent specific base pairing) are well known in the art and are based upon the percent mismatch as a function of the Tm when referenced to the fully base paired control.

As used herein, the term "alkyl," alone or in combination, refers to a saturated, straight-chain or branched-chain hydrocarbon radical containing from 1 to 10, preferably from 1 to 6 and more preferably from 1 to 4, carbon atoms. Examples of such radicals include, but are not limited to, methyl, ethyl, n-propyl, iso-propyl, n-butyl, iso-butyl, sec-butyl, tert-butyl, pentyl, iso-amyl, hexyl, decyl and the like. The term "alkylene" refers to a saturated, straight-chain or branched chain hydrocarbon diradical containing from 1 to 10, preferably from 1 to 6 and more preferably from 1 to 4, carbon atoms. Examples of such diradicals include, but are not limited to, methylene, ethylene (—CH$_2$—CH$_2$—), propylene, and the like.

The term "alkenyl," alone or in combination, refers to a straight-chain or branched-chain hydrocarbon radical having at least one carbon-carbon double bond in a total of from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like. The term "alkenylene" refers to a straight-chain or branched-chain hydrocarbon diradical having at least one carbon-carbon double bond in a total of from 2 to 10, preferably from 2 to 6 and more preferably from 2 to 4, carbon atoms. Examples of such diradicals include, but are not limited to, methylidene (=CH$_2$), ethylidene (—CH=CH—), propylidene (—CH$_2$—CH=CH—) and the like.

The term "alkynyl," alone or in combination, refers to a straight-chain or branched-chain hydrocarbon radical having at least one carbon-carbon triple bond in a total of from 2 to 10, preferably from 2 to 6 and more preferably from 2 to 4, carbon atoms. Examples of such radicals include, but are not limited to, ethynyl (acetylenyl), propynyl (propargyl), butynyl, hexynyl, decynyl and the like. The term "alkynylene", alone or in combination, refers to a straight-chain or branched-chain hydrocarbon diradical having at least one carbon-carbon triple bond in a total of from 2 to 10, preferably from 2 to 6 and more preferably from 2 to 4, carbon atoms. Examples of such radicals include, but are not limited, ethynylene (—C≡C—), propynylene (—CH$_2$—C≡C—) and the like.

The term "cycloalkyl," alone or in combination, refers to a saturated, cyclic arrangement of carbon atoms which number from 3 to 8 and preferably from 3 to 6, carbon atoms. Examples of such cycloalkyl radicals include, but are not limited to, cyclopropyl, cyclobutyl, cyclopentyl, cyclohexyl and the like. The term "cycloalkylene" refers to a diradical form of a cycloalkyl.

The term "cycloalkenyl," alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like. The term "cycloalkenylene" refers to a diradical form of a cycloalkenyl.

The term "aryl" refers to a carbocyclic (consisting entirely of carbon and hydrogen) aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to four substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, 1,2-dioxyethylene, alkoxy, alkenoxy or alkynoxy, alkylamino, alkenylamino, alkynylamino, aliphatic or aromatic acyl, alkoxy-carbonylamino, alkylsulfonylamino, morpholinocarbonylamino, thiomorpholinocarbonylamino, N-alkyl guanidino, aralkylaminosulfonyl; aralkoxyalkyl; N-aralkoxyurea; N-hydroxylurea; N-alkenylurea; N,N-(alkyl, hydroxyl)urea; heterocyclyl; thioaryloxy-substituted aryl; N,N-(aryl, alkyl) hydrazino; Ar'-substituted sulfonylheterocyclyl; aralkyl-substituted heterocyclyl; cycloalkyl and cycloakenyl-substituted heterocyclyl; cycloalkyl-fused aryl; aryloxy-substituted alkyl; heterocyclylamino; aliphatic or aromatic acylaminocarbonyl; aliphatic or aromatic acyl-substituted alkenyl; Ar'-substituted aminocarbonyloxy; Ar', Ar'-disubstituted aryl; aliphatic or aromatic acyl-substituted acyl; cycloalkylcarbonylalkyl; cycloalkyl-substituted amino; aryloxycarbonylalkyl; phosphorodiamidyl acid or ester;

"Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like.

The term "alkynyloxy," alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino," alone or in combination, refers to a mono- or di-alkyl-substituted amino radical (i.e., a radical of formula alkyl-NH— or (alkyl)$_2$-N—), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino," alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino," alone or in combination, refers to a radical of formula alkynyl-NH— or (alkynyl)$_2$N—, wherein the term "alkynyl" is as defined above, provided that the radical is not an ynamine. An example of such alkynylamino radicals is the propargyl amino radical.

The term "amide" refers to either —N(R$^1$)—C(=O)— or —C(=O)—N(R$^1$)— where R$^1$ is defined herein to include hydrogen as well as other groups. The term "substituted amide" refers to the situation where R$^1$ is not hydrogen, while the term "unsubstituted amide" refers to the situation where R$^1$ is hydrogen.

The term "aryloxy," alone or in combination, refers to a radical of formula aryl-O—, wherein aryl is as defined above. Examples of aryloxy radicals include, but are not limited to, phenoxy, naphthoxy, pyridyloxy and the like.

The term "arylamino," alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "aryl-fused cycloalkyl," alone or in combination, refers to a cycloalkyl radical which shares two adjacent atoms with an aryl radical, wherein the terms "cycloalkyl" and "aryl" are as defined above. An example of an aryl-fused cycloalkyl radical is the benzofused cyclobutyl radical.

The term "alkylcarbonylamino," alone or in combination, refers to a radical of formula alkyl-CONH, wherein the term "alkyl" is as defined above.

The term "alkoxycarbonylamino," alone or in combination, refers to a radical of formula alkyl-OCONH—, wherein the term "alkyl" is as defined above.

The term "alkylsulfonylamino," alone or in combination, refers to a radical of formula alkyl-SO$_2$NH—, wherein the term "alkyl" is as defined above.

The term "arylsulfonylamino," alone or in combination, refers to a radical of formula aryl-SO$_2$NH—, wherein the term "aryl" is as defined above.

The term "N-alkylurea," alone or in combination, refers to a radical of formula alkyl-NH—CO—NH—, wherein the term "alkyl" is as defined above.

The term "N-arylurea," alone or in combination, refers to a radical of formula aryl-NH—CO—NH—, wherein the term "aryl" is as defined above.

The term "halogen" means fluorine, chlorine, bromine and iodine.

The term "hydrocarbon radical" refers to an arrangement of carbon and hydrogen atoms which need only a single hydrogen atom to be an independent stable molecule. Thus, a hydrocarbon radical has one open valence site on a carbon atom, through which the hydrocarbon radical may be bonded to other atom(s). Alkyl, alkenyl, cycloalkyl, etc. are examples of hydrocarbon radicals.

The term "hydrocarbon diradical" refers to an arrangement of carbon and hydrogen atoms which need two hydrogen atoms in order to be an independent stable molecule. Thus, a hydrocarbon radical has two open valence sites on one or two carbon atoms, through which the hydrocarbon radical may be bonded to other atom(s). Alkylene, alkenylene, alkynylene, cycloalkylene, etc. are examples of hydrocarbon diradicals.

The term "hydrocarbyl" refers to any stable arrangement consisting entirely of carbon and hydrogen having a single valence site to which it is bonded to another moiety, and thus includes radicals known as alkyl, alkenyl, alkynyl, cycloalkyl, cycloalkenyl, aryl (without heteroatom incorporation into the aryl ring), arylalkyl, alkylaryl and the like. Hydrocarbon radical is another name for hydrocarbyl.

The term "hydrocarbylene" refers to any stable arrangement consisting entirely of carbon and hydrogen having two valence sites to which it is bonded to other moieties, and thus includes alkylene, alkenylene, alkynylene, cycloalkylene, cycloalkenylene, arylene (without heteroatom incorporation into the arylene ring), arylalkylene, alkylarylene and the like. Hydrocarbon diradical is another name for hydrocarbylene.

The term "hydrocarbyl-O-hydrocarbylene" refers to a hydrocarbyl group bonded to an oxygen atom, where the oxygen atom is likewise bonded to a hydrocarbylene group at one of the two valence sites at which the hydrocarbylene group is bonded to other moieties. The terms "hydrocarbyl-S-hydrocarbylene", "hydrocarbyl-NH-hydrocarbylene" and "hydrocarbyl-amide-hydrocarbylene" have equivalent meanings, where oxygen has been replaced with sulfur, —NH— or an amide group, respectively.

The term N-(hydrocarbyl)hydrocarbylene refers to a hydrocarbylene group wherein one of the two valence sites is bonded to a nitrogen atom, and that nitrogen atom is simultaneously bonded to a hydrogen and a hydrocarbyl group. The term N,N-di(hydrocarbyl)hydrocarbylene refers to a hydrocarbylene group wherein one of the two valence sites is bonded to a nitrogen atom, and that nitrogen atom is simultaneously bonded to two hydrocarbyl groups.

The term "hydrocarbylacyl-hydrocarbylene" refers to a hydrocarbyl group bonded through an acyl (—C(=O)—) group to one of the two valence sites of a hydrocarbylene group.

The terms "heterocyclylhydrocarbyl" and "heterocylyl" refer to a stable, cyclic arrangement of atoms which include carbon atoms and up to four atoms (referred to as heteroatoms) selected from oxygen, nitrogen, phosphorus and sulfur. The cyclic arrangement may be in the form of a monocyclic ring of 3–7 atoms, or a bicyclic ring of 8–11 atoms. The rings may be saturated or unsaturated (including aromatic rings), and may optionally be benzofused. Nitrogen and sulfur atoms in the ring may be in any oxidized form, including the quaternized form of nitrogen. A heterocyclylhydrocarbyl may be attached at any endocyclic carbon or heteroatom which results in the creation of a stable structure. Preferred heterocyclylhydrocarbyls include 5–7 membered monocyclic heterocycles containing one or two nitrogen heteroatoms.

A substituted heterocyclylhydrocarbyl refers to a heterocyclylhydrocarbyl as defined above, wherein at least one ring atom thereof is bonded to an indicated substituent which extends off of the ring.

In referring to hydrocarbyl and hydrocarbylene groups, the term "derivatives of any of the foregoing wherein one or more hydrogens is replaced with an equal number of fluorides" refers to molecules that contain carbon, hydrogen and fluoride atoms, but no other atoms.

The term "activated ester" is an ester that contains a "leaving group" which is readily displaceable by a nucleophile, such as an amine, and alcohol or a thiol nucleophile. Such leaving groups are well known and include, without limitation, N-hydroxysuccinimide, N-hydroxybenzotriazole, halogen (halides), alkoxy including tetrafluorophenolates, thioalkoxy and the like. The term "protected ester" refers to an ester group that is masked or otherwise unreactive. See, e.g., Greene, "Protecting Groups In Organic Synthesis."

In view of the above definitions, other chemical terms used throughout this application can be easily understood by those of skill in the art. Terms may be used alone or in any combination thereof. The preferred and more preferred chain lengths of the radicals apply to all such combinations.

A. Generation of Tagged Nucleic Acid Fragments

As noted above, one aspect of the present invention provides a general scheme for DNA sequencing which allows the use of more than 16 tags in each lane; with continuous detection, the tags can be detected and the sequence read as the size separation is occurring, just as with conventional fluorescence-based sequencing. This scheme is applicable to any of the DNA sequencing techniques-based on size separation of tagged molecules. Suitable tags and linkers for use within the present invention, as well as methods for sequencing nucleic acids, are discussed in more detail below.

1. Tags

"Tag", as used herein, generally refers to a chemical moiety which is used to uniquely identify a "molecule of interest", and more specifically refers to the tag variable component as well as whatever may be bonded most closely to it in any of the tag reactant, tag component and tag moiety.

A tag which is useful in the present invention possesses several attributes:

1) It is capable of being distinguished from all other tags. This discrimination from other chemical moieties can be based on the chromatographic behavior of the tag (particularly after the cleavage reaction), its spectroscopic or potentiometric properties, or some combination thereof. Spectroscopic methods by which tags are usefully distinguished include mass spectroscopy (MS), infrared (IR), ultraviolet (UV), and fluorescence, where MS, IR and UV are preferred, and MS most preferred spectroscopic methods. Potentiometric amperometry is a preferred potentiometric method.

2) The tag is capable of being detected when present at $10^{-22}$ to $10^{-6}$ mole.

3) The tag possesses a chemical handle through which it can be attached to the MOI which the tag is intended to uniquely identify. The attachment may be made directly to the MOI, or indirectly through a "linker" group.

4) The tag is chemically stable toward all manipulations to which it is subjected, including attachment and cleavage from the MOI, and any manipulations of the MOI while the tag is attached to it.

5) The tag does not significantly interfere with the manipulations performed on the MOI while the tag is attached to it. For instance, if the tag is attached to an oligonucleotide, the tag must not significantly interfere with any hybridization or enzymatic reactions (e.g., PCR sequencing reactions) performed on the oligonucleotide. Similarly, if the tag is attached to an antibody, it must not significantly interfere with antigen recognition by the antibody.

A tag moiety which is intended to be detected by a certain spectroscopic or potentiometric method should possess properties which enhance the sensitivity and specificity of detection by that method. Typically, the tag moiety will have those properties because they have been designed into the tag variable component, which will typically constitute the major portion of the tag moiety. In the following discussion, the use of the word "tag" typically refers to the tag moiety (i.e., the cleavage product that contains the tag variable component), however can also be considered to refer to the tag variable component itself because that is the portion of the tag moiety which is typically responsible for providing the uniquely detectable properties. In compounds of the formula T—L—X, the "T" portion will contain the tag variable component. Where the tag variable component has been designed to be characterized by, e.g., mass spectrometry, the "T" portion of T—L—X may be referred to as $T^{ms}$. Likewise, the cleavage product from T—L—X that contains T may be referred to as the $T^{ms}$-containing moiety. The following spectroscopic and potentiometric methods may be used to characterize $T^{ms}$-containing moieties.

a. Characteristics of MS Tags

Where a tag is analyzable by mass spectrometry (i.e., is a MS-readable tag, also referred to herein as a MS tag or "$T^{ms}$-containing moiety"), the essential feature of the tag is that it is able to be ionized. It is thus a preferred element in the design of MS-readable tags to incorporate therein a chemical functionality which can carry a positive or negative charge under conditions of ionization in the MS. This feature confers improved efficiency of ion formation and greater overall sensitivity of detection, particularly in electrospray ionization. The chemical functionality that supports an ionized charge may derive from $T^{ms}$ or L or both. Factors that can increase the relative sensitivity of an analyte being detected by mass spectrometry are discussed in, e.g., Sunner, J., et al., Anal. Chem. 60:1300–1307 (1988).

A preferred functionality to facilitate the carrying of a negative charge is an organic acid, such as phenolic hydroxyl, carboxylic acid, phosphonate, phosphate, tetrazole, sulfonyl urea, perfluoro alcohol and sulfonic acid.

Preferred functionality to facilitate the carrying of a positive charge under ionization conditions are aliphatic or aromatic amines. Examples of amine functional groups which give enhanced detectability of MS tags include quaternary amines (i.e., amines that have four bonds, each to carbon atoms, see Aebersold, U.S. Pat. No. 5,240,859) and tertiary amines (i.e., amines that have three bonds, each to carbon atoms, which includes C=N—C groups such as are present in pyridine, see Hess et al., Anal. Biochem. 224:373, 1995; Bures et al., Anal. Biochem. 224:364, 1995). Hindered tertiary amines are particularly preferred. Tertiary and quaternary amines may be alkyl or aryl. A $T^{ms}$-containing moiety must bear at least one ionizable species, but may possess more than one ionizable species. The preferred charge state is a single ionized species per tag. Accordingly, it is preferred that each $T^{ms}$-containing moiety (and each tag variable component) contain only a single hindered amine or organic acid group.

Suitable amine-containing radicals that may form part of the $T^{ms}$-containing moiety include the following:

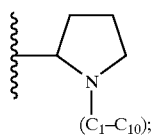

-continued

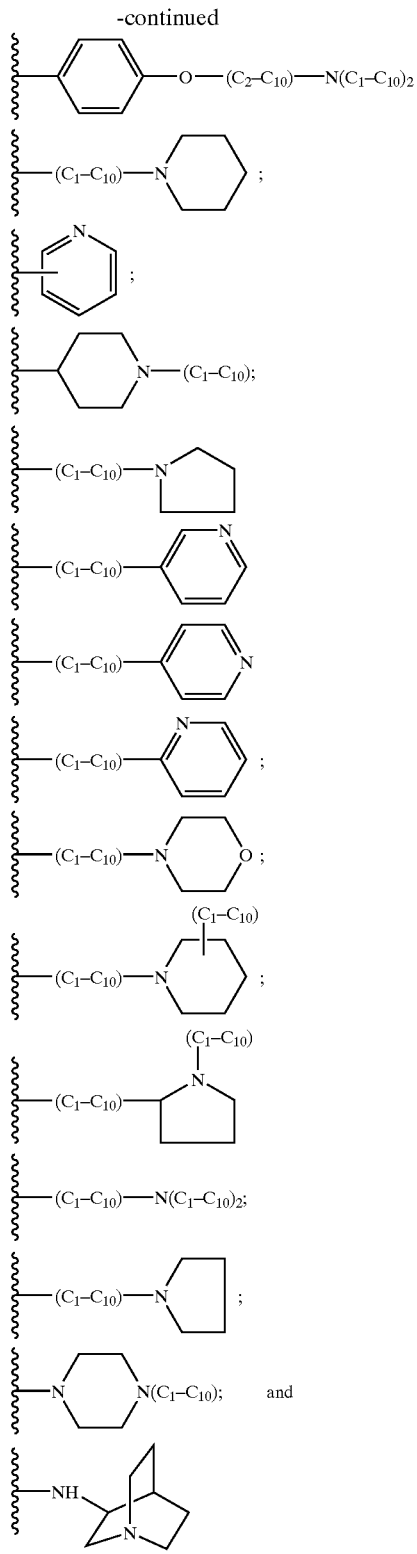

The identification of a tag by mass spectrometry is preferably based upon its molecular mass to charge ratio (m/z). The preferred molecular mass range of MS tags is from about 100 to 2,000 daltons, and preferably the $T^{ms}$-containing moiety has a mass of at least about 250 daltons, more preferably at least about 300 daltons, and still more preferably at least about 350 daltons. It is generally difficult for mass spectrometers to distinguish among moieties having parent ions below about 200–250 daltons (depending on the precise instrument), and thus preferred $T^{ms}$-containing moieties of the invention have masses above that range.

As explained above, the $T^{ms}$-containing moiety may contain atoms other than those present in the tag variable component, and indeed other than present in $T^{ms}$ itself. Accordingly, the mass of $T^{ms}$ itself may be less than about 250 daltons, so long as the $T^{ms}$-containing moiety has a mass of at least about 250 daltons. Thus, the mass of $T^{ms}$ may range from 15 (i.e., a methyl radical) to about 10,000 daltons, and preferably ranges from 100 to about 5,000 daltons, and more preferably ranges from about 200 to about 1,000 daltons.

It is relatively difficult to distinguish tags by mass spectrometry when those tags incorporate atoms that have more than one isotope in significant abundance. Accordingly, preferred T groups which are intended for mass spectroscopic identification ($T^{ms}$ groups), contain carbon, at least one of hydrogen and fluoride, and optional atoms selected from oxygen, nitrogen, sulfur, phosphorus and iodine. While other atoms may be present in the $T^{ms}$, their presence can render analysis of the mass spectral data somewhat more difficult. Preferably, the $T^{ms}$ groups have only carbon, nitrogen and oxygen atoms, in addition to hydrogen and/or fluoride.

Fluoride is an optional yet preferred atom to have in a $T^{ms}$ group. In comparison to hydrogen, fluoride is, of course, much heavier. Thus, the presence of fluoride atoms rather than hydrogen atoms leads to $T^{ms}$ groups of higher mass, thereby allowing the $T^{ms}$ group to reach and exceed a mass of greater than 250 daltons, which is desirable as explained above. In addition, the replacement of hydrogen with fluoride confers greater volatility on the $T^{ms}$-containing moiety, and greater volatility of the analyte enhances sensitivity when mass spectrometry is being used as the detection method.

The molecular formula of $T^{ms}$ falls within the scope of $C_{1-500}N_{0-100}O_{0-100}S_{0-10}P_{0-10}H_\alpha F_\beta I_\delta$ wherein the sum of $\alpha$, $\beta$ and $\delta$ is sufficient to satisfy the otherwise unsatisfied valencies of the C, N, O, S and P atoms. The designation $C_{1-500}N_{0-100}O_{0-100}S_{0-10}P_{0-10}H_\alpha F_\beta I_\delta$ means that $T^{ms}$ contains at least one, and may contain any number from 1 to 500 carbon atoms, in addition to optionally containing as many as 100 nitrogen atoms ("$N_0$" means that $T^{ms}$ need not contain any nitrogen atoms), and as many as 100 oxygen atoms, and as many as 10 sulfur atoms and as many as 10 phosphorus atoms. The symbols $\alpha$, $\beta$ and $\delta$ represent the number of hydrogen, fluoride and iodide atoms in $T^{ms}$, where any two of these numbers may be zero, and where the sum of these numbers equals the total of the otherwise unsatisfied valencies of the C, N, O, S and P atoms. Preferably, $T^{ms}$ has a molecular formula that falls within the scope of $C_{1-50}N_{0-10}O_{0-10}H_\alpha F_\beta$ where the sum of $\alpha$ and $\beta$ equals the number of hydrogen and fluoride atoms, respectively, present in the moiety.

b. Characteristics of IR Tags

There are two primary forms of IR detection of organic chemical groups: Raman scattering IR and absorption IR. Raman scattering IR spectra and absorption IR spectra are complementary spectroscopic methods. In general, Raman excitation depends on bond polarizability changes whereas IR absorption depends on bond dipole moment changes. Weak IR absorption lines become strong Raman lines and vice versa. Wavenumber is the characteristic unit for IR spectra. There are 3 spectral regions for IR tags which have separate applications: near IR at 12500 to 4000 cm$^{-1}$, mid IR at 4000 to 600 cm$^{-1}$, far IR at 600 to 30 cm$^{-1}$. For the uses described herein where a compound is to serve as a tag to identify an MOI, probe or primer, the mid spectral regions would be preferred. For example, the carbonyl stretch (1850 to 1750 cm$^{-1}$) would be measured for carboxylic acids, carboxylic esters and amides, and alkyl and aryl carbonates, carbamates and ketones. N—H bending (1750 to 160 cm$^{-1}$) would be used to identify amines, ammonium ions, and amides. At 1400 to 1250 cm$^{-1}$, R—OH bending is detected as well as the C—N stretch in amides. Aromatic substitution patterns are detected at 900 to 690 cm$^{-1}$ (C—H bending, N—H bending for ArNH$_2$). Saturated C—H, olefins, aromatic rings, double and triple bonds, esters, acetals, ketals, ammonium salts, N—O compounds such as oximes, nitro, N-oxides, and nitrates, azo, hydrazones, quinones, carboxylic acids, amides, and lactams all possess vibrational infrared correlation data (see Pretsch et al., *Spectral Data for Structure Determination of Organic Compounds,* Springer-Verlag, New York, 1989). Preferred compounds would include an aromatic nitrile which exhibits a very strong nitrile stretching vibration at 2230 to 2210 cm$^{-1}$. Other useful types of compounds are aromatic alkynes which have a strong stretching vibration that gives rise to a sharp absorption band between 2140 and 2100 cm$^{-1}$. A third compound type is the aromatic azides which exhibit an intense absorption band in the 2160 to 2120 cm$^{-1}$ region. Thiocyanates are representative of compounds that have a strong absorption at 2275 to 2263 cm$^{-1}$.

c. Characteristics of UV Tags

A compilation of organic chromophore types and their respective UV-visible properties is given in Scott (*Interpretation of the UV Spectra of Natural Products,* Permagon Press, New York, 1962). A chromophore is an atom or group of atoms or electrons that are responsible for the particular light absorption. Empirical rules exist for the $\pi$ to $\pi^*$ maxima in conjugated systems (see Pretsch et al., *Spectral Data for Structure Determination of Organic Compounds,* p. B65 and B70, Springer-Verlag, New York, 1989). Preferred compounds (with conjugated systems) would possess n to $\pi^*$ and $\pi$ to $\pi^*$ transitions. Such compounds are exemplified by Acid Violet 7, Acridine Orange, Acridine Yellow G, Brilliant Blue G, Congo Red, Crystal Violet, Malachite Green oxalate, Metanil Yellow, Methylene Blue, Methyl Orange, Methyl Violet B, Naphtol Green B, Oil Blue N, Oil Red O, 4-phenylazophenol, Safranie O, Solvent Green 3, and Sudan Orange G, all of which are commercially available (Aldrich, Milwaukee, Wis.). Other suitable compounds are listed in, e.g., Jane, I., et al., *J. Chrom.* 323:191–225 (1985).

d. Characteristic of a Fluorescent Tag

Fluorescent probes are identified and quantitated most directly by their absorption and fluorescence emission wavelengths and intensities. Emission spectra (fluorescence and phosphorescence) are much more sensitive and permit more specific measurements than absorption spectra. Other photophysical characteristics such as excited-state lifetime and fluorescence anisotropy are less widely used. The most generally useful intensity parameters are the molar extinction coefficient ($\epsilon$) for absorption and the quantum yield (QY) for fluorescence. The value of $\epsilon$ is specified at a single wavelength (usually the absorption maximum of the probe), whereas QY is a measure of the total photon emission over the entire fluorescence spectral profile. A narrow optical bandwidth (<20 nm) is usually used for fluorescence excitation (via absorption), whereas the fluorescence detection bandwidth is much more variable, ranging from full spectrum for maximal sensitivity to narrow band (~20 nm) for maximal resolution. Fluorescence intensity per probe molecule is proportional to the product of $\epsilon$ and QY. The range of these parameters among fluorophores of current practical importance is approximately 10,000 to 100,000 cm$^{-1}$M$^{-1}$ for $\epsilon$ and 0.1 to 1.0 for QY. Compounds that can serve as fluorescent tags are as follows: fluorescein, rhodamine, lambda blue 470, lambda green, lambda red 664, lambda red 665, acridine orange, and propidium iodide, which are commercially available from Lambda Fluorescence Co. (Pleasant Gap, Pa.). Fluorescent compounds such as nile red, Texas Red, lissamine™, BODIPY™s are available from Molecular Probes (Eugene, Oreg.).

e. Characteristics of Potentiometric Tags

The principle of electrochemical detection (ECD) is based on oxidation or reduction of compounds which at certain applied voltages, electrons are either donated or accepted thus producing a current which can be measured. When certain compounds are subjected to a potential difference, the molecules undergo a molecular rearrangement at the working electrodes' surface with the loss (oxidation) or gain (reduction) of electrons, such compounds are said to be electronic and undergo electrochemical reactions. EC detectors apply a voltage at an electrode surface over which the HPLC eluent flows. Electroactive compounds eluting from the column either donate electrons (oxidize) or acquire electrons (reduce) generating a current peak in real time. Importantly the amount of current generated depends on both the concentration of the analyte and the voltage applied, with each compound having a specific voltage at which it begins to oxidize or reduce. The currently most popular electrochemical detector is the amperometric detector in which the potential is kept constant and the current produced from the electrochemical reaction is then measured. This type of spectrometry is currently called "potentiostatic amperometry". Commercial amperometers are available from ESA, Inc., Chelmford, Mass.

When the efficiency of detection is 100%, the specialized detectors are termed "coulometric". Coulometric detectors are sensitive which have a number of practical advantages with regard to selectivity and sensitivity which make these types of detectors useful in an array. In coulometric detectors, for a given concentration of analyte, the signal current is plotted as a function of the applied potential (voltage) to the working electrode. The resultant sigmoidal graph is called the current-voltage curve or hydrodynamic voltammagram (HDV). The HDV allows the best choice of applied potential to the working electrode that permits one to maximize the observed signal. A major advantage of ECD is its inherent sensitivity with current levels of detection in the subfemtomole range.

Numerous chemicals and compounds are electrochemically active including many biochemicals, pharmaceuticals and pesticides. Chromatographically coeluting compounds can be effectively resolved even if their half-wave potentials (the potential at half signal maximum) differ by only 30–60 mV.

Recently developed coulometric sensors provide selectivity, identification and resolution of co-eluting compounds when used as detectors in liquid chromatography based separations. Therefore, these arrayed detectors add another set of separations accomplished in the detector itself. Current instruments possess 16 channels which are in principle limited only by the rate at which data can be acquired. The number of compounds which can be resolved on the EC array is chromatographically limited (i.e., plate count limited). However, if two or more compounds that chromatographically co-elute have a difference in half wave potentials of 30–60 mV, the array is able to distinguish the compounds. The ability of a compound to be electrochemically active relies on the possession of an EC active group (i.e., —OH, —O, —N, —S).

Compounds which have been successfully detected using coulometric detectors include 5-hydroxytryptamine, 3-methoxy-4-hydroxyphenyl-glycol, homogentisic acid, dopamine, metanephrine, 3-hydroxykyneninr, acetominophen, 3-hydroxytryptophol, 5-hydroxyindoleacetic acid, octanesulfonic acid, phenol, o-cresol, pyrogallol, 2-nitrophenol, 4-nitrophenol, 2,4-dinitrophenol, 4,6-dinitrocresol, 3-methyl-2-nitrophenol, 2,4-dichlorophenol, 2,6-dichlorophenol, 2,4,5-trichlorophenol, 4-chloro-3-methylphenol, 5-methylphenol, 4-methyl-2-nitrophenol, 2-hydroxyaniline, 4-hydroxyaniline, 1,2-phenylenediamine, benzocatechin, buturon, chlortholuron, diuron, isoproturon, linuron, methobromuron, metoxuron, monolinuron, monuron, methionine, tryptophan, tyrosine, 4-aminobenzoic acid, 4-hydroxybenzoic acid, 4-hydroxycoumaric acid, 7-methoxycoumarin, apigenin baicalein, caffeic acid, catechin, centaurein, chlorogenic acid, daidzein, datiscetin, diosmetin, epicatechin gallate, epigallo catechin, epigallo catechin gallate, eugenol, eupatorin, ferulic acid, fisetin, galangin, gallic acid, gardenin, genistein, gentisic acid, hesperidin, irigenin, kaemferol, leucoyanidin, luteolin, mangostin, morin, myricetin, naringin, narirutin, pelargondin, peonidin, phloretin, pratensein, protocatechuic acid, rhamnetin, quercetin, sakuranetin, scutellarein, scopoletin, syringaldehyde, syringic acid, tangeritin, troxerutin, umbelliferone, vanillic acid, 1,3-dimethyl tetrahydroisoquinoline, 6-hydroxydopamine, r-salsolinol, N-methyl-r-salsolinol, tetrahydroisoquinoline, amitriptyline, apomorphine, capsaicin, chlordiazepoxide, chlorpromazine, daunorubicin, desipramine, doxepin, fluoxetine, flurazepam, imipramine, isoproterenol, methoxamine, morphine, morphine-3-glucuronide, nortriptyline, oxazepam, phenylephrine, trimipramine, ascorbic acid, N-acetyl serotonin, 3,4-dihydroxybenzylamine, 3,4-dihydroxymandelic acid (DOMA), 3,4-dihydroxyphenylacetic acid (DOPAC), 3,4-dihydroxyphenylalanine (L-DOPA), 3,4-dihydroxyphenylglycol (DHPG), 3-hydroxyanthranilic acid, 2-hydroxyphenylacetic acid (2HPAC), 4-hydroxybenzoic acid (4HBAC), 5-hydroxyindole-3-acetic acid (5HIAA), 3-hydroxykynurenine, 3-hydroxymandelic acid, 3-hydroxy-4-methoxyphenylethylamine, 4-hydroxyphenylacetic acid (4HPAC), 4-hydroxyphenyllactic acid (4HPLA), 5-hydroxytryptophan (5HTP), 5-hydroxytryptophol (5HTOL), 5-hydroxytryptamine (5HT), 5-hydroxytryptamine sulfate, 3-methoxy-4-hydroxyphenylglycol (MHPG), 5-methoxytryptamine, 5-methoxytryptophan, 5-methoxytryptophol, 3-methoxytyramine (3MT), 3-methoxytyrosine (3-OM-DOPA), 5-methylcysteine, 3-methylguanine, bufotenin, dopamine dopamine-3-glucuronide, dopamine-3-sulfate, dopamine-4-sulfate, epinephrine, epinine, folic acid, glutathione (reduced), guanine, guanosine, homogentisic acid (HGA), homovanillic acid (HVA), homovanillyl alcohol (HVOL), homoveratic acid, hva sulfate, hypoxanthine, indole, indole-3-acetic acid, indole-3-lactic acid, kynurenine, melatonin, metanephrine, N-methyltryptamine, N-methyltyramine, N,N-dimethyltryptamine, N,N-dimethyltyramine, norepinephrine, normetanephrine, octopamine, pyridoxal, pyridoxal phosphate, pyridoxamine, synephrine, tryptophol, tryptamine, tyramine, uric acid, vanillylmandelic acid (vma), xanthine and xanthosine. Other suitable compounds are set forth in, e.g., Jane, I., et al. *J. Chrom.* 323:191–225 (1985) and Musch, G., et al.,*J. Chrom.* 348:97–110 (1985). These compounds can be incorporated into compounds of formula T—L—X by methods known in the art. For example, compounds having a carboxylic acid group may be reacted with amine, hydroxyl, etc. to form amide, ester and other linkages between T and L.

In addition to the above properties, and regardless of the intended detection method, it is preferred that the tag have a modular chemical structure. This aids in the construction of large numbers of structurally related tags using the techniques of combinatorial chemistry. For example, the $T^{ms}$ group desirably has several properties. It desirably contains a functional group which supports a single ionized charge state when the $T^{ms}$-containing moiety is subjected to mass spectrometry (more simply referred to as a "mass spec sensitivity enhancer" group, or MSSE). Also, it desirably can serve as one member in a family of $T^{ms}$-containing moieties, where members of the family each have a different mass/charge ratio, however have approximately the same sensitivity in the mass spectrometer. Thus, the members of the family desirably have the same MSSE. In order to allow the creation of families of compounds, it has been found convenient to generate tag reactants via a modular synthesis scheme, so that the tag components themselves may be viewed as comprising modules.

In a preferred modular approach to the structure of the $T^{ms}$ group, $T^{ms}$ has the formula

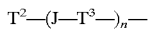

$$T^2-(J-T^3-)_n-$$

wherein $T^2$ is an organic moiety formed from carbon and one or more of hydrogen, fluoride, iodide, oxygen, nitrogen, sulfur and phosphorus, having a mass range of 15 to 500 daltons; $T^3$ is an organic moiety formed from carbon and one or more of hydrogen, fluoride, iodide, oxygen, nitrogen, sulfur and phosphorus, having a mass range of 50 to 1000 daltons; J is a direct bond or a functional group such as amide, ester, amine, sulfide, ether, thioester, disulfide, thioether, urea, thiourea, carbamate, thiocarbamate, Schiff base, reduced Schiff base, imine, oxime, hydrazone, phosphate, phosphonate, phosphoramide, phosphonamide, sulfonate, sulfonamide or carbon-carbon bond; and n is an integer ranging from 1 to 50, such that when n is greater than 1, each $T^3$ and J is independently selected.

The modular structure $T^2-(J-T^3)_n-$ provides a convenient entry to families of T—L—X compounds, where each member of the family has a different T group. For instance, when T is $T^{ms}$, and each family member desirably has the same MSSE, one of the $T^3$ groups can provide that MSSE structure. In order to provide variability between members of a family in terms of the mass of $T^{ms}$, the $T^2$ group may be varied among family members. For instance, one family member may have $T^2$=methyl, while another has $T^2$=ethyl, and another has $T^2$=propyl, etc.

Figure 12:
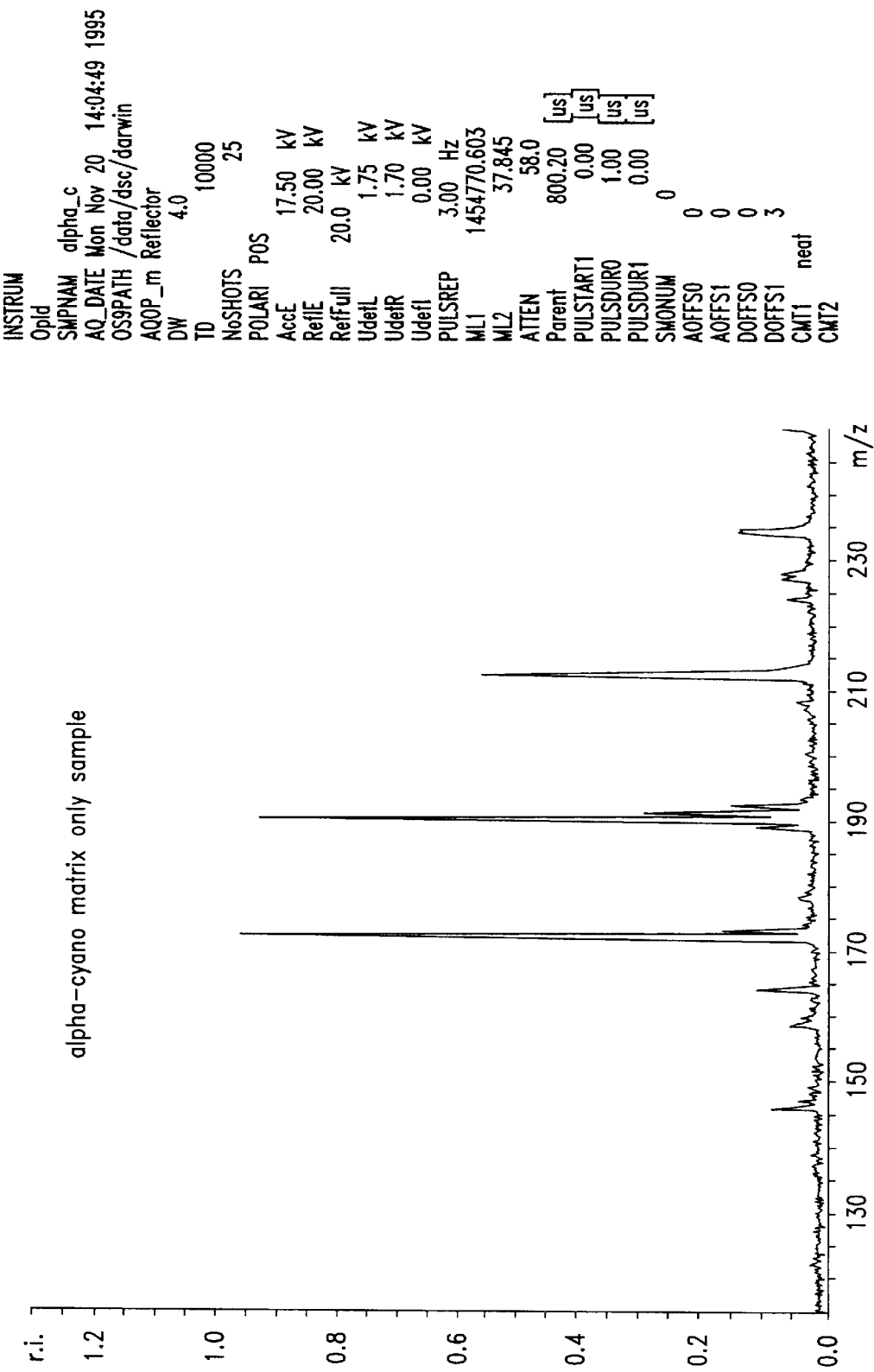
FIG. 12 shows the mass spectrogram of the alpha-cyano matrix alone.
Figure 13:
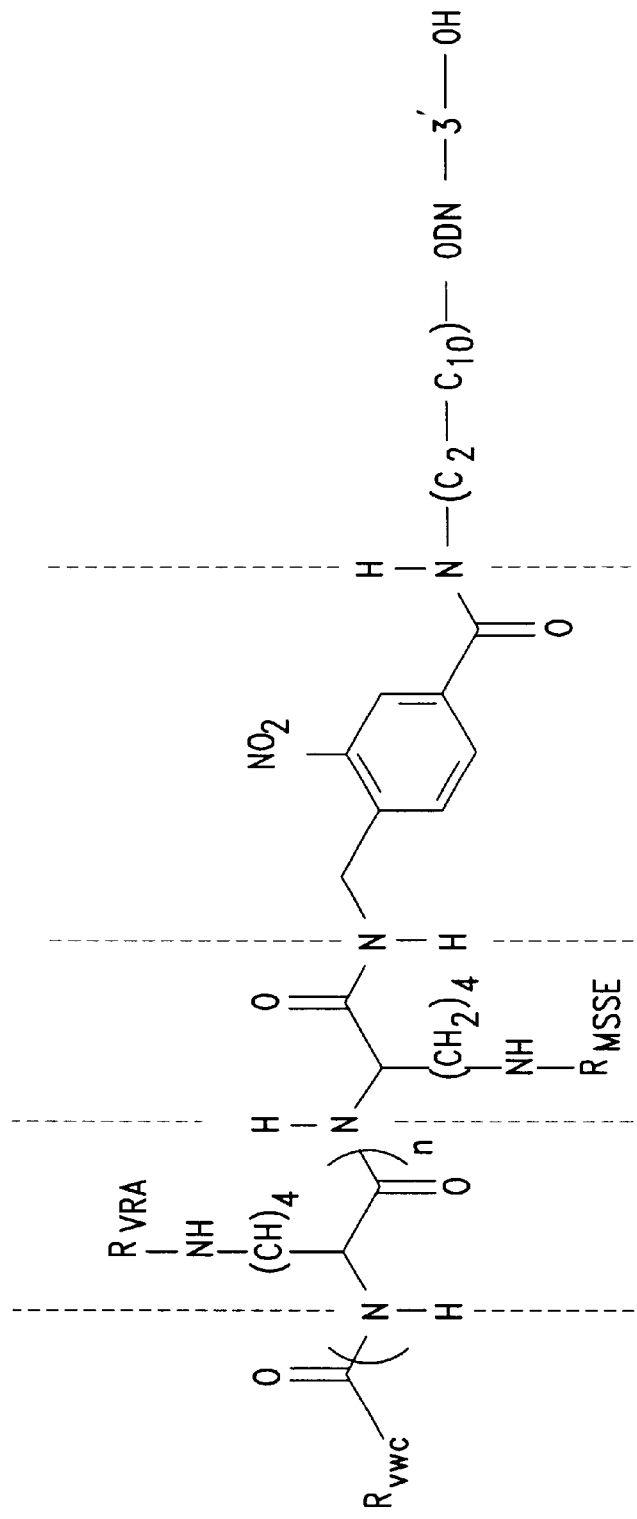
FIG. 13 depicts a modularly-constructed tagged nucleic acid fragment.
Figure 14A:
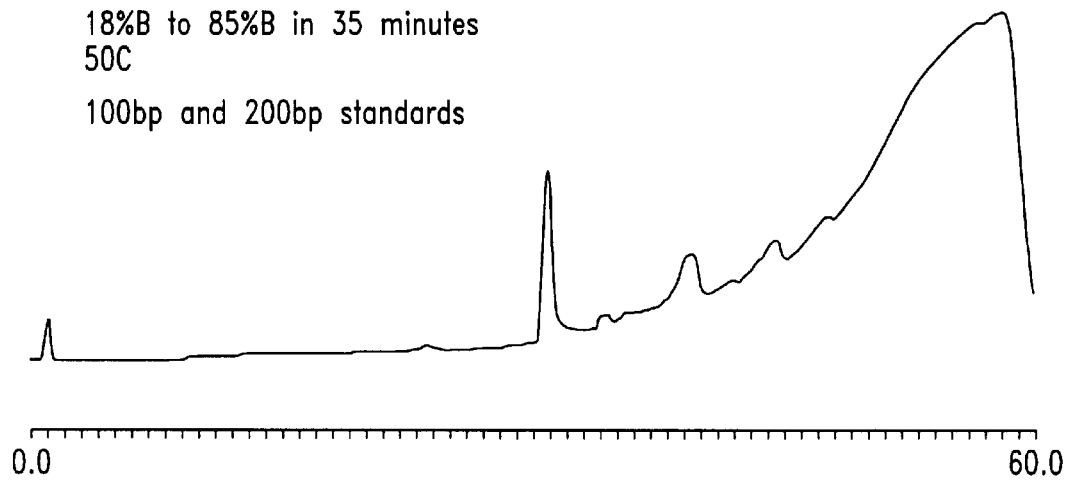
FIGS. 14A–14I show the separation of DNA fragments by HPLC using a variety of different buffer solutions.
Figure 14B:
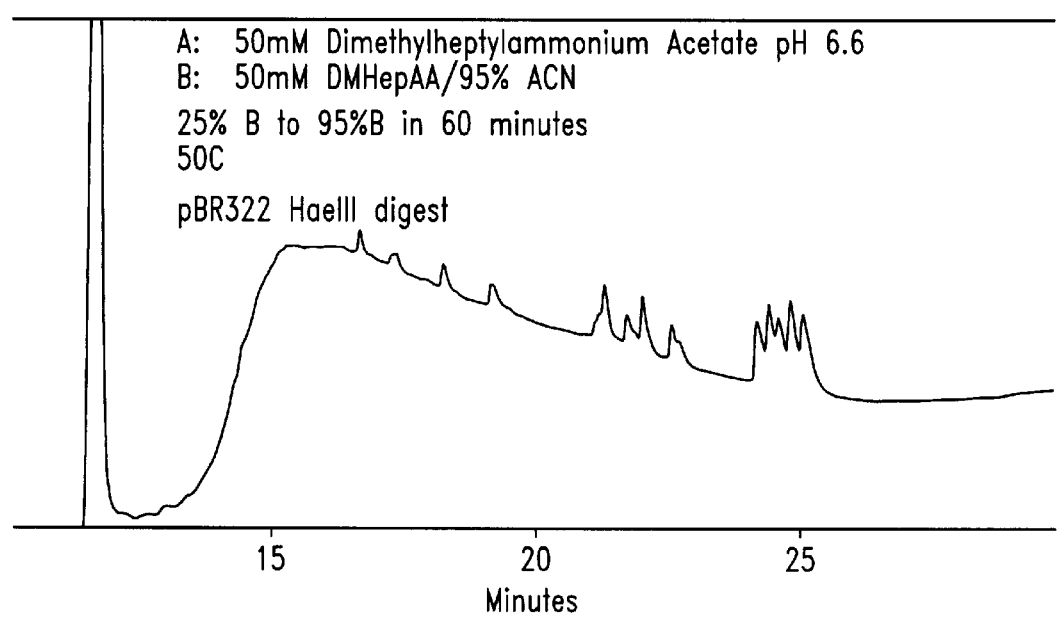
Figure 14C:
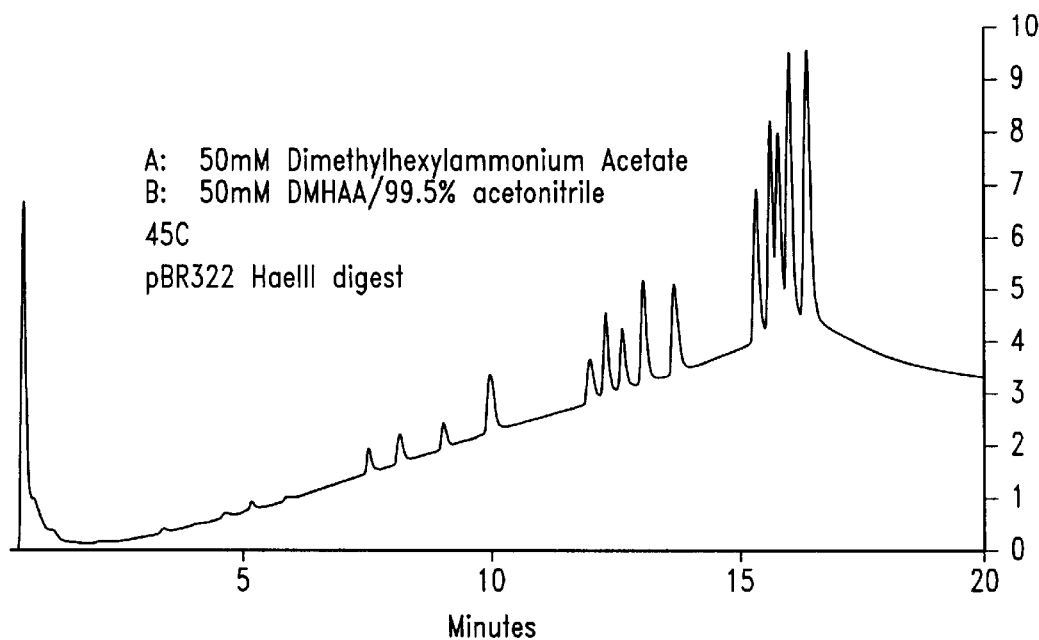
Figure 14D:
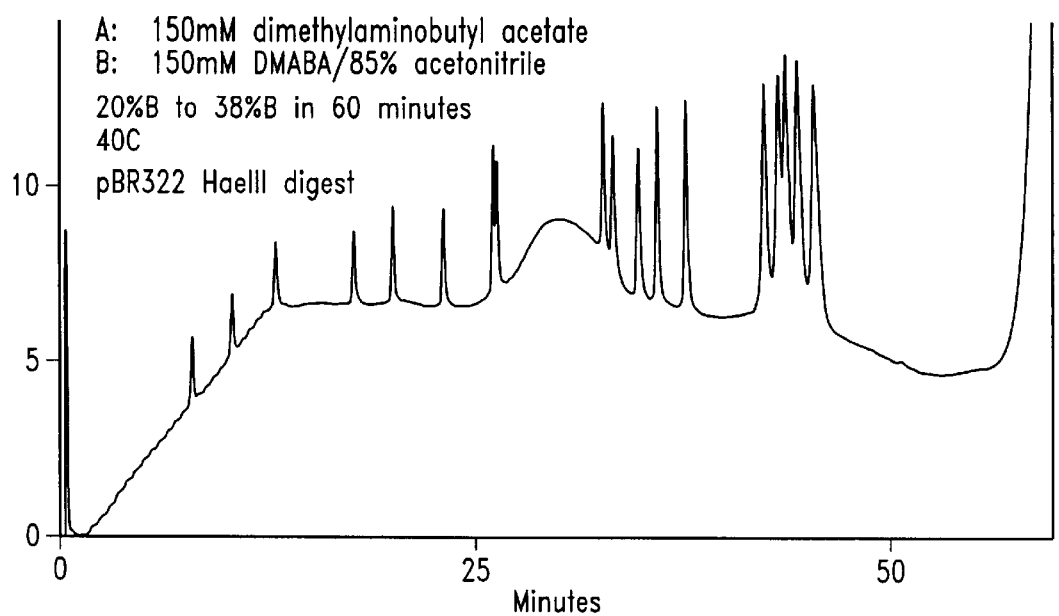
Figure 14E:
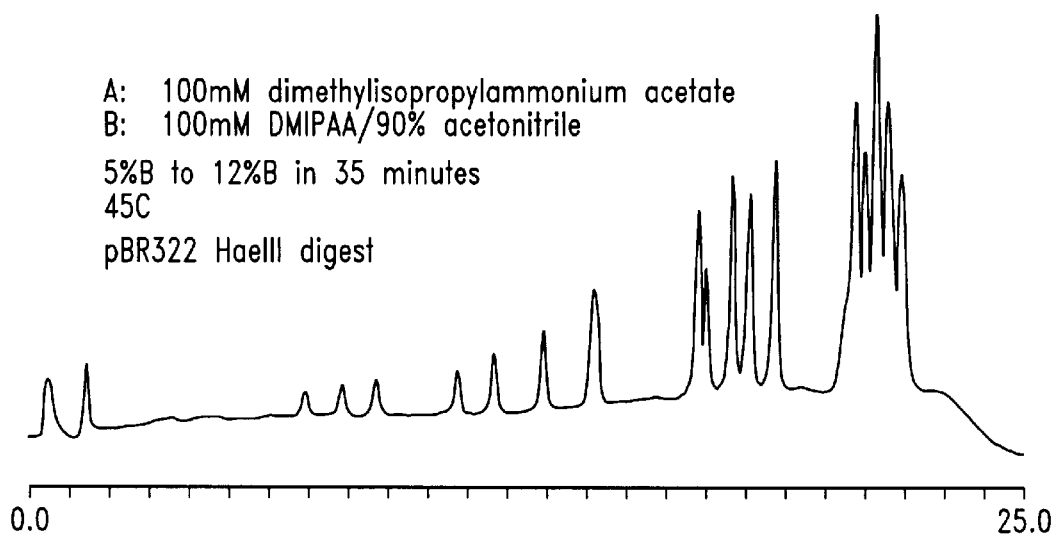
Figure 14F:
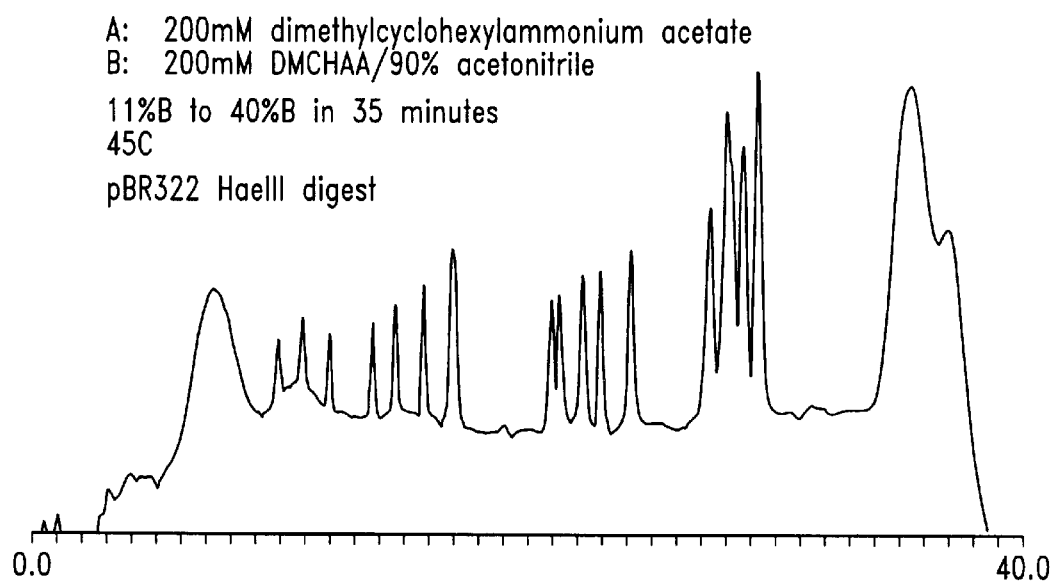
Figure 14G:
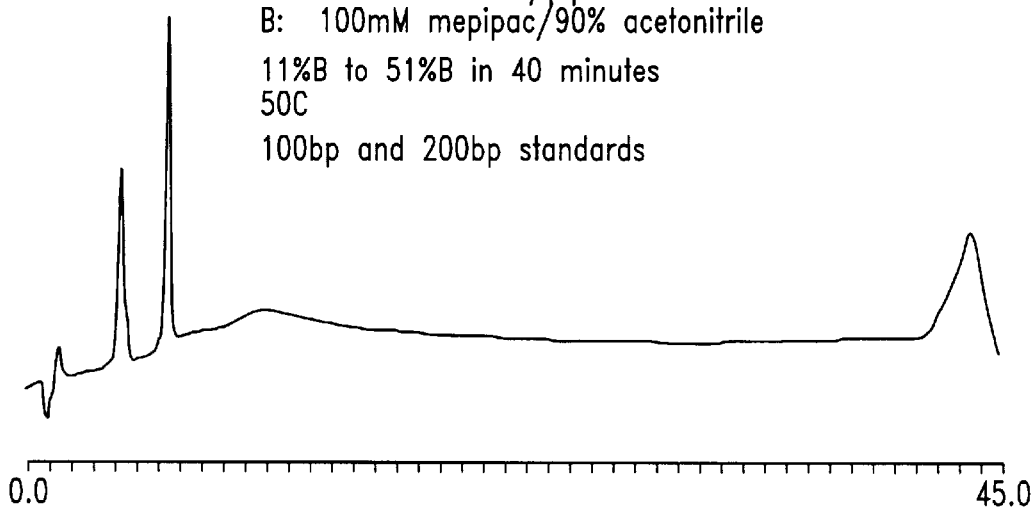
Figure 14H:
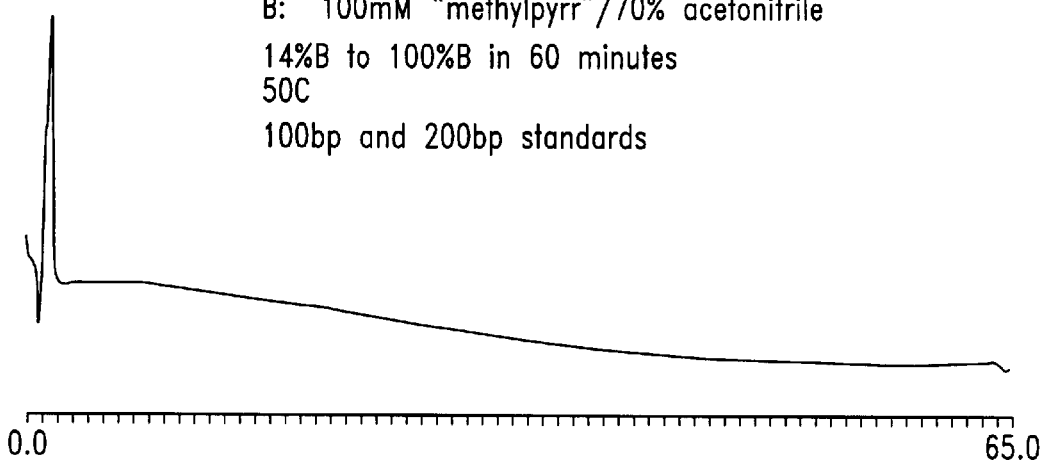
Figure 14I:
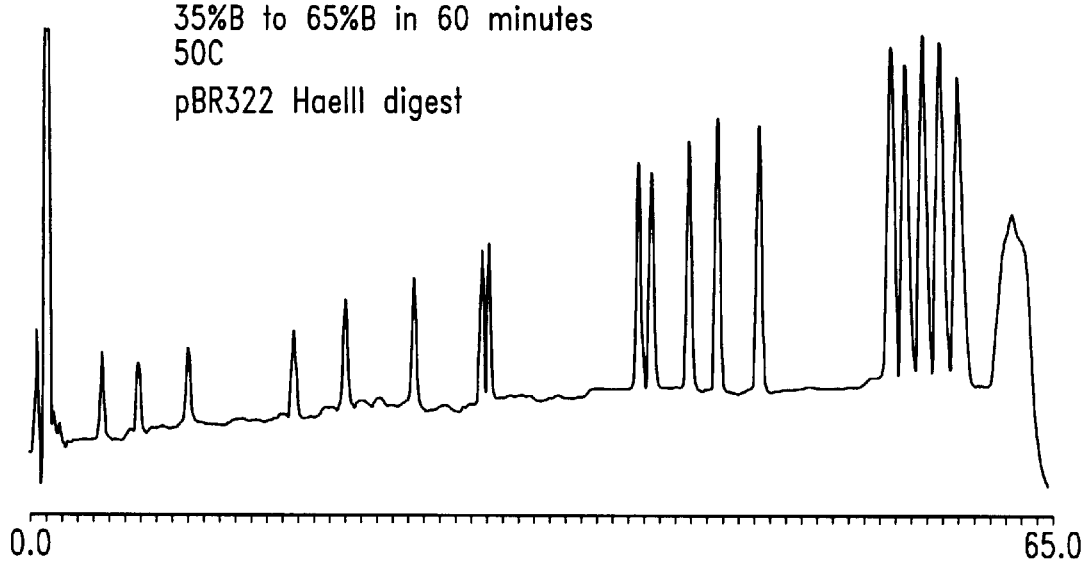

In order to provide "gross" or large jumps in mass, a $T^3$ group may be designed which adds significant (e.g., one or several hundreds) of mass units to T—L—X. Such a $T^3$ group may be referred to as a molecular weight range adjuster group("WRA"). A WRA is quite useful if one is working with a single set of $T^2$ groups, which will have masses extending over a limited range. A single set of $T^2$ groups may be used to create $T^{ms}$ groups having a wide range of mass simply by incorporating one or more WRA $T^3$ groups into the $T^{ms}$. Thus, using a simple example, if a set of $T^2$ groups affords a mass range of 250–340 daltons for the $T^{ms}$, the addition of a single WRA, having, as an exemplary number 100 dalton, as a $T^3$ group provides access to the mass range of 350–440 daltons while using the same set of $T^2$ groups. Similarly, the addition of two 100 dalton MWA groups (each as a $T^3$ group) provides access to the mass range of 450–540 daltons, where this incremental addition of WRA groups can be continued to provide access to a very large mass range for the $T^{ms}$ group. Preferred compounds of the formula $T^2-(J-T^3-)_n-L-X$ have the formula $R_{VWC}-(R_{WRA})_w-R_{MSSE}-L-X$ where VWC is a "$T^2$" group, and each of the WRA and MSSE groups are "$T^3$" groups. This structure is illustrated in FIG. 12, and represents one modular approach to the preparation of $T^{ms}$.

In the formula $T^2-(J-T^3-)_n-$, $T^2$ and $T^3$ are preferably selected from hydrocarbyl, hydrocarbyl-O-hydrocarbylene, hydrocarbyl-S-hydrocarbylene, hydrocarbyl-NH-hydrocarbylene, hydrocarbyl-amide-hydrocarbylene, N-(hydrocarbyl)hydrocarbylene, N,N-di(hydrocarbyl)hydrocarbylene, hydrocarbylacylhydrocarbylene, heterocyclylhydrocarbyl wherein the heteroatom(s) are selected from oxygen, nitrogen, sulfur and phosphorus, substituted heterocyclyl-hydrocarbyl wherein the heteroatom(s) are selected from oxygen, nitrogen, sulfur and phosphorus and the substituents are selected from hydrocarbyl, hydrocarbyl-O-hydrocarbylene, hydrocarbyl-NH-hydrocarbylene, hydrocarbyl-S-hydrocarbylene, N-(hydrocarbyl)hydrocarbylene, N,N-di(hydrocarbyl)hydrocarbylene and hydrocarbylacyl-hydrocarbylene. In addition, $T^2$ and/or $T^3$ may be a derivative of any of the previously listed potential $T^2/T^3$ groups, such that one or more hydrogens are replaced fluorides.

Also regarding the formula $T^2-(J-T^3-)_n-$, a preferred $T^3$ has the formula $-G(R^2)-$, wherein G is $C_{1-6}$ alkylene chain having a single $R^2$ substituent. Thus, if G is ethylene ($-CH_2-CH_2-$) either one of the two ethylene carbons may have a $R^2$ substituent, and $R^2$ is selected from alkyl, alkenyl, alkynyl, cycloalkyl, aryl-fused cycloalkyl, cycloalkenyl, aryl, aralkyl, aryl-substituted alkenyl or alkynyl, cycloalkyl-substituted alkyl, cycloalkenyl-substituted cycloalkyl, biaryl, alkoxy, alkenoxy, alkynoxy, aralkoxy, aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl; cycloalkenyl, aryl-substituted alkyl and, aralkyl, hydroxy-substituted alkyl, alkoxy-substituted alkyl, aralkoxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, hydrocarbylacylamino-substituted alkyl, heterocyclylacylamino-substituted alkyl, hydrocarbyl-substituted-heterocyclylacylamino-substituted alkyl, alkylsulfonylamino-substituted alkyl, arylsulfonylamino-substituted alkyl, morpholino-alkyl, thiomorpholino-alkyl, morpholino carbonyl-substituted alkyl, thiomorpholinocarbonyl-substituted alkyl, [N-(alkyl, alkenyl or alkynyl)- or N,N-[dialkyl, dialkenyl, dialkynyl or (alkyl, alkenyl)-amino]carbonyl-substituted alkyl, heterocyclylaminocarbonyl, heterocylylalkyleneaminocarbonyl, heterocyclylaminocarbonyl-substituted alkyl, heterocylylalkyleneaminocarbonyl-substituted alkyl, N,N-[dialkyl]alkyleneaminocarbonyl, N,N-[dialkyl]alkyleneaminocarbonyl-substituted alkyl, alkyl-substituted heterocyclylcarbonyl, alkyl-substituted heterocyclylcarbonyl-alkyl, carboxyl-substituted alkyl, dialkylamino-substituted acylaminoalkyl and amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine; alynyl and heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, alkyl optionally substituted by substituents selected from amino, carboxy, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy and heterocyclyl.

A preferred compound of the formula $T^2-(J-T^3-)_n-L-X$ has the structure:

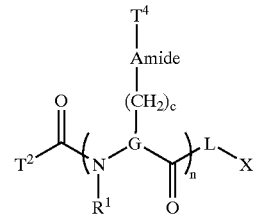

wherein G is $(CH_2)_{1-6}$ such that a hydrogen on one and only one of the $CH_2$ groups represented by a single "G" is replaced with $-(CH_2)_c$-Amide-$T^4$; $T^2$ and $T^4$ are organic moieties of the formula $C_{1-25}N_{0-9}O_{0-9}H_\alpha F_\beta$ such that the sum of $\alpha$ and $\beta$ is sufficient to satisfy the otherwise unsatisfied valencies of the C, N, and O atoms; amide is

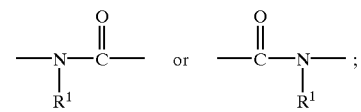

$R^1$ is hydrogen or $C_{1-10}$ alkyl; c is an integer ranging from 0 to 4; and n is an integer ranging from 1 to 50 such that when n is greater than 1, G, c, Amide, $R^1$ and $T^4$ are independently selected.

In a further preferred embodiment, a compound of the formula $T^2-(J-T^3-)_n-L-X$ has the structure:

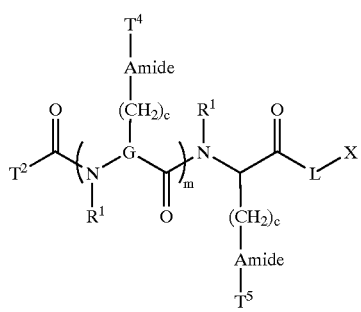

wherein $T^5$ is an organic moiety of the formula $C_{1-25}N_{0-9}O_{0-9}H_\alpha F_\beta$ such that the sum of α and β is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, $R^1$, L and X have been previously defined.

Another preferred compound having the formula $T^2$—$(J$—$T^3$—$)_n$—L—X has the particular structure:

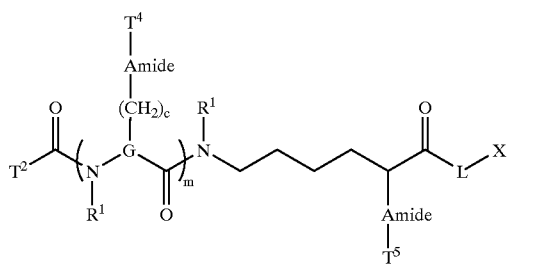

wherein $T^5$ is an organic moiety of the formula $C_{1-25}N_{0-9}O_{0-9}H_\alpha F_\beta$ such that the sum of α and β is sufficient to satisfy the otherwise unsatisfied valencies of the C, N, and O atoms; and $T^5$ includes a tertiary or quaternary amine or an organic acid; m is an integer ranging from 0–49, and $T^2$, $T^4$, c, $R^1$, "Amide", L and X have been previously defined.

In the above structures that have a $T^5$ group, -Amide-$T^5$ is preferably one of the following, which are conveniently made by reacting organic acids with free amino groups extending from "G":

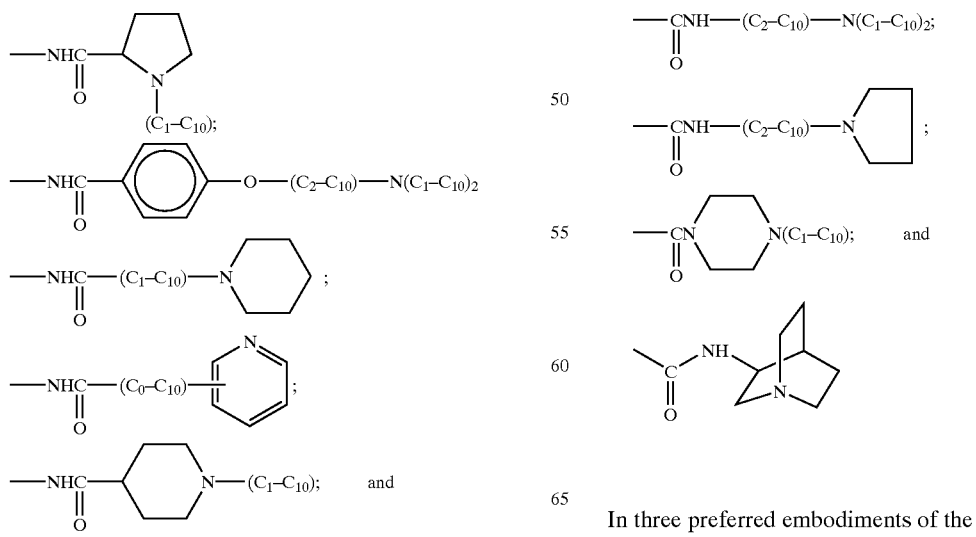

Where the above compounds have a $T^5$ group, and the "G" group has a free carboxyl group (or reactive equivalent thereof), then the following are preferred -Amide-$T^5$ group, which may conveniently be prepared by reacting the appropriate organic amine with a free carboxyl group extending from a "G" group:

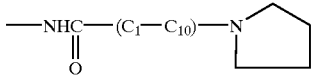

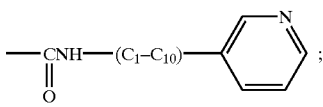

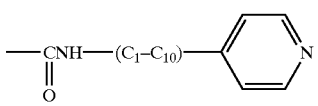

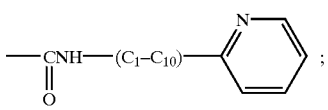

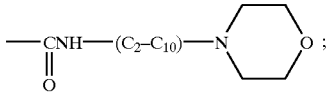

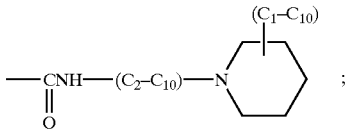

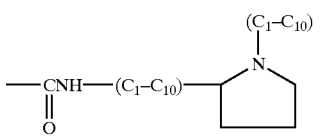

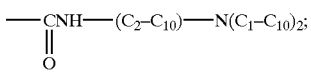

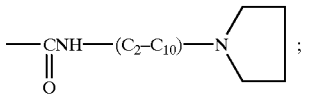

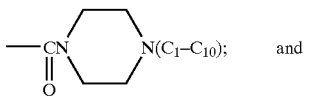 and

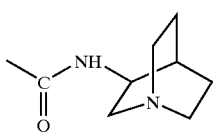

In three preferred embodiments of the invention, T—L—MOI has the structure:

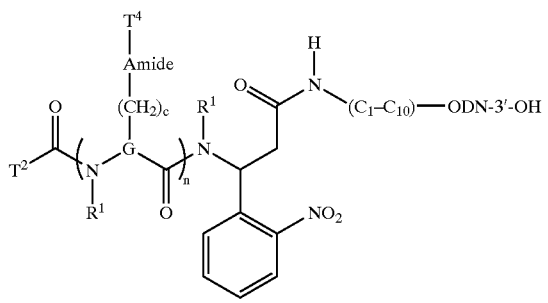

or the structure:

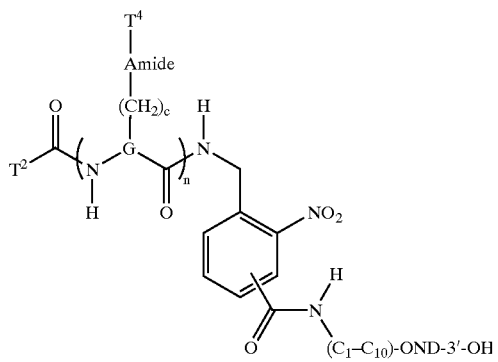

or the structure:

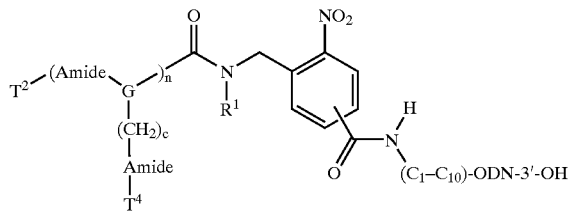

wherein $T^2$ and $T^4$ are organic moieties of the formula $C_{1-25}N_{0-9}O_{0-9}S_{0-3}P_{0-3}H_\alpha F_\beta I_\delta$ such that the sum of $\alpha$, $\beta$ and $\delta$ is sufficient to satisfy the otherwise unsatisfied valencies of the C, N, O, S and P atoms; G is $(CH_2)_{1-6}$ wherein one and only one hydrogen on the $CH_2$ groups represented by each G is replaced with $—(CH_2)_c$-Amide-$T^4$; Amide is

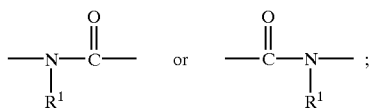

$R^1$ is hydrogen or $C_{1-10}$ alkyl; c is an integer ranging from 0 to 4; "$C_2–C_{10}$" represents a hydrocarbylene group having from 2 to 10 carbon atoms, "ODN-3'—OH" represents a nucleic acid fragment having a terminal 3' hydroxyl group (i.e., a nucleic acid fragment joined to $(C_1–C_{10})$ at other than the 3' end of the nucleic acid fragment); and n is an integer ranging from 1 to 50 such that when n is greater than 1, then G, c, Amide, $R^1$ and $T^4$ are independently selected. Preferably there are not three heteroatoms bonded to a single carbon atom.

In structures as set forth above that contain a $T^2—C(=O)—N(R^1)—$ group, this group may be formed by reacting an amine of the formula $HN(R^1)—$ with an organic acid selected from the following, which are exemplary only and do not constitute an exhaustive list of potential organic acids: Formic acid, Acetic acid, Propiolic acid, Propionic acid, Fluoroacetic acid, 2-Butynoic acid, Cyclopropanecarboxylic acid, Butyric acid, Methoxyacetic acid, Difluoroacetic acid, 4-Pentynoic acid, Cyclobutanecarboxylic acid, 3,3-Dimethylacrylic acid, Valeric acid, N,N-Dimethylglycine, N-Formyl-Gly-OH, Ethoxyacetic acid, (Methylthio)acetic acid, Pyrrole-2-carboxylic acid, 3-Furoic acid, Isoxazole-5-carboxylic acid, trans-3-Hexenoic acid, Trifluoroacetic acid, Hexanoic acid, Ac-Gly-OH, 2-Hydroxy-2-methylbutyric acid, Benzoic acid, Nicotinic acid, 2-Pyrazinecarboxylic acid, 1-Methyl-2-pyrrolecarboxylic acid, 2-Cyclopentene-1-acetic acid, Cyclopentylacetic acid, (S)-(−)-2-Pyrrolidone-5-carboxylic acid, N-Methyl-L-proline, Heptanoic acid, Ac-b-Ala-OH, 2-Ethyl-2-hydroxybutyric acid, 2-(2-Methoxyethoxy)acetic acid, p-Toluic acid, 6-Methylnicotinic acid, 5-Methyl-2-pyrazinecarboxylic acid, 2,5-Dimethylpyrrole-3-carboxylic acid, 4-Fluorobenzoic acid, 3,5-Dimethylisoxazole-4-carboxylic acid, 3-Cyclopentylpropionic acid, Octanoic acid, N,N-Dimethylsuccinamic acid, Phenylpropiolic acid, Cinnamic acid, 4-Ethylbenzoic acid, p-Anisic acid, 1,2,5-Trimethylpyrrole-3-carboxylic acid, 3-Fluoro-4-methylbenzoic acid, Ac-DL-Propargylglycine, 3-(Trifluoromethyl)butyric acid, 1-Piperidinepropionic acid, N-Acetylproline, 3,5-Difluorobenzoic acid, Ac-L-Val-OH, Indole-2-carboxylic acid, 2-Benzofurancarboxylic acid, Benzotriazole-5-carboxylic acid, 4-n-Propylbenzoic acid, 3-Dimethylaminobenzoic acid, 4-Ethoxybenzoic acid, 4-(Methylthio)benzoic acid, N-(2-Furoyl)glycine, 2-(Methylthio)nicotinic acid, 3-Fluoro-4-methoxybenzoic acid, Tfa-Gly-OH, 2-Napthoic acid, Quinaldic acid, Ac-L-Ile-OH, 3-Methylindene-2-carboxylic acid, 2-Quinoxalinecarboxylic acid, 1-Methylindole-2-carboxylic acid, 2,3,6-Trifluorobenzoic acid, N-Formyl-L-Met-OH, 2-[2-(2-Methoxyethoxy)ethoxy]acetic acid, 4-n-Butylbenzoic acid, N-Benzoylglycine, 5-Fluoroindole-2-carboxylic acid, 4-n-Propoxybenzoic acid, 4-Acetyl-3,5-dimethyl-2-pyrrolecarboxylic acid, 3,5-Dimethoxybenzoic acid, 2,6-Dimethoxynicotinic acid, Cyclohexanepentanoic acid, 2-Naphthylacetic acid, 4-(1H-Pyrrol-1-yl)benzoic acid, Indole-3-propionic acid, m-Trifluoromethylbenzoic acid, 5-Methoxyindole-2-carboxylic acid, 4-Pentylbenzoic acid, Bz-b-Ala-OH, 4-Diethylaminobenzoic acid, 4-n-Butoxybenzoic acid, 3-Methyl-5-CF3-isoxazole-4-carboxylic acid, (3,4-Dimethoxyphenyl)acetic acid, 4-Biphenylcarboxylic acid, Pivaloyl-Pro-OH, Octanoyl-Gly-OH, (2-Naphthoxy)acetic acid, Indole-3-butyric acid, 4-(Trifluoromethyl)phenylacetic acid, 5-Methoxyindole-3-acetic acid, 4-(Trifluoromethoxy)benzoic acid, Ac-L-Phe-OH, 4-Pentyloxybenzoic acid, Z-Gly-OH, 4-Carboxy-N-(fur-2-ylmethyl)pyrrolidin-2-one, 3,4-Diethoxybenzoic acid, 2,4-Dimethyl-5-CO$_2$Et-pyrrole-3-carboxylic acid, N-(2-Fluorophenyl)succinamic acid, 3,4,5-Trimethoxybenzoic acid, N-Phenylanthranilic acid, 3-Phenoxybenzoic acid, Nonanoyl-Gly-OH, 2-Phenoxypyridine-3-carboxylic acid, 2,5-Dimethyl-1-phenylpyrrole-3-carboxylic acid, trans-4-(Trifluoromethyl) cinnamic acid, (5-Methyl-2-phenyloxazol-4-yl)acetic acid, 4-(2-Cyclohexenyloxy)benzoic acid, 5-Methoxy-2-methylindole-3-acetic acid, trans-4-Cotininecarboxylic acid, Bz-5-Aminovaleric acid, 4-Hexyloxybenzoic acid, N-(3-Methoxyphenyl)succinamic acid, Z-Sar-OH, 4-(3,4-Dimethoxyphenyl)butyric acid, Ac-o-Fluoro-DL-Phe-OH, N-(4-Fluorophenyl)glutaramic acid, 4'-Ethyl-4-biphenylcarboxylic acid, 1,2,3,4-

Tetrahydroacridinecarboxylic acid, 3-Phenoxyphenylacetic acid, N-(2,4-Difluorophenyl)succinamic acid, N-Decanoyl-Gly-OH, (+)-6-Methoxy-a-methyl-2-naphthaleneacetic acid, 3-(Trifluoromethoxy)cinnamic acid, N-Formyl-DL-Trp-OH, (R)-(+)-a-Methoxy-a-(trifluoromethyl) phenylacetic acid, Bz-DL-Leu-OH, 4-(Trifluoromethoxy) phenoxyacetic acid, 4-Heptyloxybenzoic acid, 2,3,4-Trimethoxycinnamic acid, 2,6-Dimethoxybenzoyl-Gly-OH, 3-(3,4,5-Trimethoxyphenyl)propionic acid, 2,3,4,5,6-Pentafluorophenoxyacetic acid, N-(2,4-Difluorophenyl) glutaramic acid, N-Undecanoyl-Gly-OH, 2-(4-Fluorobenzoyl)benzoic acid, 5-Trifluoromethoxyindole-2-carboxylic acid, N-(2,4-Difluorophenyl)diglycolamic acid, Ac-L-Trp-OH, Tfa-L-Phenylglycine-OH, 3-Iodobenzoic acid, 3-(4-n-Pentylbenzoyl)propionic acid, 2-Phenyl-4-quinolinecarboxylic acid, 4-Octyloxybenzoic acid, Bz-L-Met-OH, 3,4,5-Triethoxybenzoic acid, N-Lauroyl-Gly-OH, 3,5-Bis(trifluoromethyl)benzoic acid, Ac-5-Methyl-DL-Trp-OH, 2-Iodophenylacetic acid, 3-Iodo-4-methylbenzoic acid, 3-(4-n-Hexylbenzoyl)propionic acid, N-Hexanoyl-L-Phe-OH, 4-Nonyloxybenzoic acid, 4'-(Trifluoromethyl)-2-biphenylcarboxylic acid, Bz-L-Phe-OH, N-Tridecanoyl-Gly-OH, 3,5-Bis(trifluoromethyl)phenylacetic acid, 3-(4-n-Heptylbenzoyl)propionic acid, N-Hepytanoyl-L-Phe-OH, 4-Decyloxybenzoic acid, N-($\alpha,\alpha,\alpha$-trifluoro-m-tolyl) anthranilic acid, Niflumic acid, 4-(2-Hydroxyhexafluoroisopropyl)benzoic acid, N-Myristoyl-Gly-OH, 3-(4-n-Octylbenzoyl)propionic acid, N-Octanoyl-L-Phe-OH, 4-Undecyloxybenzoic acid, 3-(3,4,5-Trimethoxyphenyl)propionyl-Gly-OH, 8-Iodonaphthoic acid, N-Pentadecanoyl-Gly-OH, 4-Dodecyloxybenzoic acid, N-Palmitoyl-Gly-OH, and N-Stearoyl-Gly-OH. These organic acids are available from one or more of Advanced ChemTech, Louisville, Ky.; Bachem Bioscience Inc., Torrance, Calif.; Calbiochem-Novabiochem Corp., San Diego, Calif.; Farchan Laboratories Inc., Gainesville Fla.; Lancaster Synthesis, Windham N.H.; and MayBridge Chemical Company (c/o Ryan Scientific), Columbia, S.C. The catalogs from these companies use the abreviations which are used above to identify the acids.

f. Combinatorial Chemistry as a Means for Preparing Tags

Combinatorial chemistry is a type of synthetic strategy which leads to the production of large chemical libraries (see, for example, PCT Application Publication No. WO 94/08051). These combinatorial libraries can be used as tags for the identification of molecules of interest (MOIs). Combinatorial chemistry may be defined as the systematic and repetitive, covalent connection of a set of different "building blocks" of varying structures to each other to yield a large array of diverse molecular entities. Building blocks can take many forms, both naturally occurring and synthetic, such as nucleophiles, electrophiles, dienes, alkylating or acylating agents, diamines, nucleotides, amino acids, sugars, lipids, organic monomers, synthons, and combinations of the above. Chemical reactions used to connect the building blocks may involve alkylation, acylation, oxidation, reduction, hydrolysis, substitution, elimination, addition, cyclization, condensation, and the like. This process can produce libraries of compounds which are oligomeric, non-oligomeric, or combinations thereof. If oligomeric, the compounds can be branched, unbranched, or cyclic. Examples of oligomeric structures which can be prepared by combinatorial methods include oligopeptides, oligonucleotides, oligosaccharides, polylipids, polyesters, polyamides, polyurethanes, polyureas, polyethers, poly(phosphorus derivatives), e.g., phosphates, phosphonates, phosphoramides, phosphonamides, phosphites, phosphinamides, etc., and poly(sulfur derivatives), e.g., sulfones, sulfonates, sulfites, sulfonamides, sulfenamides, etc.

One common type of oligomeric combinatorial library is the peptide combinatorial library. Recent innovations in peptide chemistry and molecular biology have enabled libraries consisting of tens to hundreds of millions of different peptide sequences to be prepared and used. Such libraries can be divided into three broad categories. One category of libraries involves the chemical synthesis of soluble non-support-bound peptide libraries (e.g., Houghten et al., *Nature* 354:84, 1991). A second category involves the chemical synthesis of support-bound peptide libraries, presented on solid supports such as plastic pins, resin beads, or cotton (Geysen et al., *Mol. Immunol.* 23:709, 1986; Lam et al., *Nature* 354:82, 1991; Eichler and Houghten, *Biochemistry* 32:11035, 1993). In these first two categories, the building blocks are typically L-amino acids, D-amino acids, unnatural amino acids, or some mixture or combination thereof. A third category uses molecular biology approaches to prepare peptides or proteins on the surface of filamentous phage particles or plasmids (Scott and Craig, *Curr. Opinion Biotech.* 5:40, 1994). Soluble, nonsupport-bound peptide libraries appear to be suitable for a number of applications, including use as tags. The available repertoire of chemical diversities in peptide libraries can be expanded by steps such as permethylation (Ostresh et al., *Proc. Natl. Acad. Sci., USA* 91:11138, 1994).

Numerous variants of peptide combinatorial libraries are possible in which the peptide backbone is modified, and/or the amide bonds have been replaced by mimetic groups. Amide mimetic groups which may be used include ureas, urethanes, and carbonylmethylene groups. Restructuring the backbone such that sidechains emanate from the amide nitrogens of each amino acid, rather than the alpha-carbons, gives libraries of compounds known as peptoids (Simon et al., *Proc. Natl. Acad Sci., USA* 89:9367, 1992).

Another common type of oligomeric combinatorial library is the oligonucleotide combinatorial library, where the building blocks are some form of naturally occurring or unnatural nucleotide or polysaccharide derivatives, including where various organic and inorganic groups may substitute for the phosphate linkage, and nitrogen or sulfur may substitute for oxygen in an ether linkage (Schneider et al., *Biochem.* 34:9599, 1995; Freier et al., *J. Med. Chem.* 38:344, 1995; Frank, *J. Biotechnology* 41:259, 1995; Schneider et al., Published PCT WO 942052; Ecker et al., *Nucleic Acids Res.* 21:1853, 1993).

More recently, the combinatorial production of collections of non-oligomeric, small molecule compounds has been described (DeWitt et al., *Proc. Natl. Acad. Sci., USA* 90:690, 1993; Bunin et al., *Proc. Natl. Acad. Sci., USA* 91:4708, 1994). Structures suitable for elaboration into small-molecule libraries encompass a wide variety of organic molecules, for example heterocyclics, aromatics, alicyclics, aliphatics, steroids, antibiotics, enzyme inhibitors, ligands, hormones, drugs, alkaloids, opioids, terpenes, porphyrins, toxins, catalysts, as well as combinations thereof.

g. Specific Methods for Combinatorial Synthesis of Tags

Two methods for the preparation and use of a diverse set of amine-containing MS tags are outlined below. In both methods, solid phase synthesis is employed to enable simultaneous parallel synthesis of a large number of tagged linkers, using the techniques of combinatorial chemistry. In the first method, the eventual cleavage of the tag from the oligonucleotide results in liberation of a carboxyl amide. In the second method, cleavage of the tag produces a carboxylic acid. The chemical components and linking elements used in these methods are abbreviated as follows:

R=resin
FMOC=fluorenylmethoxycarbonyl protecting group
All=allyl protecting group
$CO_2H$=carboxylic acid group
$CONH_2$=carboxylic amide group
$NH_2$=amino group
OH=hydroxyl group
CONH=amide linkage
COO=ester linkage
$NH_2$-Rink-$CO_2H$=4-[(α-amino)-2,4-dimethoxybenzyl]-phenoxybutyric acid (Rink linker)
OH-1MeO—$CO_2H$=(4-hydroxymethyl)phenoxybutyric acid
OH-2MeO—$CO_2H$=(4-hydroxymethyl-3-methoxy)phenoxyacetic acid
$NH_2$—A—COOH=amino acid with aliphatic or aromatic amine functionality in side chain
X1 . . . Xn-COOH=set of n diverse carboxylic acids with unique molecular weights
oligo1 . . . oligo(n)=set of n oligonucleotides
HBTU=O-benzotriazol-1-yl-N,N,N',N'-tetramethyluronium hexafluorophosphate The sequence of steps in Method 1 is as follows:

---

OH—2MeO—CONH—R
    ↓ FMOC—NH—Rink—$CO_2H$; couple (e.g., HBTU)
FMOC—NH—Rink—COO—2MeO—CONH—R
    ↓ piperidine (remove FMOC)
$NH_2$—Rink—COO—2MeO—CONH—R
    ↓ FMOC—NH—A—COOH; couple (e.g., HBTU)
FMOC—NH—A—CONH—Rink—COO—2MeO—CONH—R
    ↓ piperidine (remove FMOC)
$NH_2$—A—CONH—Rink—COO—2MeO—CONH—R
    ↓ divide into n aliquots
    ↓↓↓↓ couple to n different acids X1 . . . Xn—COOH
X1 . . . Xn—CONH—A—CONH—Rink—COO—2MeO—CONH—R
    ↓↓↓↓ Cleave tagged linkers from resin with 1% TFA
X1 . . . Xn—CONH—A—CONH—Rink—$CO_2H$
    ↓↓↓↓ couple to n oligos (oligo1 . . . oligo(n))
    (e.g., via Pfp esters)
X1 . . . Xn—CONH—A—CONH—Rink—CONH-oligo1 . . . oligo(n)
    ↓ pool tagged oligos
    ↓ perform sequencing reaction
    ↓ separate different length fragments from sequencing reaction (e.g, via HPLC or CE)
    ↓ cleave tags from linkers with 25%–100% TFA
X1 . . . Xn—CONH—A—CONH
    ↓
analyze by mass spectrometry

---

The sequence of steps in Method 2 is as follows:

---

OH—1MeO—$CO_2$-All
    ↓ FMOC—NH—A—$CO_2H$; couple (e.g., HBTU)
FMOC—NH—A—COO—1MeO—$CO_2$-All
    ↓ Palladium (remove Allyl)
FMOC—NH—A—COO—1MeO—$CO_2H$
    ↓ OH—2MeO—CONH—R; couple (e.g, HBTU)
FMOC—NH—A—COO—1MeO—COO—2MeO—CONH—R
    ↓ piperidine (remove FMOC)
$NH_2$—A—COO—1MeO—COO—2MeO—CONH—R
    ↓ divide into n aliquots
    ↓↓↓↓ couple to n different acids X1 . . . Xn—$CO_2H$
X1 . . . Xn—CONH—A—COO—1MeO—COO—2MeO—CONH—R
    ↓↓↓↓ cleave tagged linkers from resin with 1% TFA
X1 . . . Xn—CONH—A—COO—1MeO—$CO_2H$
    ↓↓↓↓ couple to n oligos (oligo1 . . . oligo(n))
    (e.g., via Pfp esters)
X1 . . . Xn—CONH—A—COO—1MeO—CONH-oligo1 . . . oligo(n)
    ↓ pool tagged oligos
    ↓ perform sequencing reaction
    ↓ separate different length fragments from sequencing reaction (e.g, via HPLC orCE)
    ↓ cleave tags from linkers with 25–100% TFA
X1 . . . Xn—CONH—A—$CO_2H$
    ↓
analyze by mass spectrometry

---

2. Linkers

A "linker" component (or L), as used herein, means either a direct covalent bond or an organic chemical group which is used to connect a "tag" (or T) to a "molecule of interest" (or MOI) through covalent chemical bonds. In addition, the direct bond itself, or one or more bonds within the linker component is cleavable under conditions which allows T to be released (in other words, cleaved) from the remainder of the T—L—X compound (including the MOI component). The tag variable component which is present within T should be stable to the cleavage conditions. Preferably, the cleavage can be accomplished rapidly; within a few minutes and preferably within about 15 seconds or less.

In general, a linker is used to connect each of a large set of tags to each of a similarly large set of MOIs. Typically, a single tag-linker combination is attached to each MOI (to give various T—L—MOI), but in some cases, more than one tag-linker combination may be attached to each individual MOI (to give various (T—L)n-MOI). In another embodiment of the present invention, two or more tags are bonded to a single linker through multiple, independent sites on the linker, and this multiple tag-linker combination is then bonded to an individual MOI (to give various (T)n-L—MOI).

After various manipulations of the set of tagged MOIs, special chemical and/or physical conditions are used to cleave one or more covalent bonds in the linker, resulting in the liberation of the tags from the MOIs. The cleavable bond(s) may or may not be some of the same bonds that were formed when the tag, linker, and MOI were connected together. The design of the linker will, in large part, determine the conditions under which cleavage may be accomplished. Accordingly, linkers may be identified by the cleavage conditions they are particularly susceptible too. When a linker is photolabile (i.e., prone to cleavage by exposure to actinic radiation), the linker may be given the designation $L^{hv}$. Likewise, the designations $L^{acid}$, $L^{base}$, $L^{[O]}$, $L^{[R]}$, $L^{enz}$, $L^{elc}$, $L^A$ and $L^{ss}$ may be used to refer to linkers that are particularly susceptible to cleavage by acid, base, chemical oxidation, chemical reduction, the catalytic activity of an enzyme (more simply "enzyme"), electrochemical oxidation or reduction, elevated temperature ("thermal") and thiol exchange, respectively.

Certain types of linker are labile to a single type of cleavage condition, whereas others are labile to several types of cleavage conditions. In addition, in linkers which are capable of bonding multiple tags (to give (T)n-L—MOI type structures), each of the tag-bonding sites may be labile to different cleavage conditions. For example, in a linker having two tags bonded to it, one of the tags may be labile only to base, and the other labile only to photolysis.

A linker which is useful in the present invention possesses several attributes:

1) The linker possesses a chemical handle ($L_h$) through which it can be attached to an MOI.

2) The linker possesses a second, separate chemical handle ($L_h$) through which the tag is attached to the linker. If multiple tags are attached to a single linker ((T)n-L—MOI type structures), then a separate handle exists for each tag.

3) The linker is stable toward all manipulations to which it is subjected, with the exception of the conditions which allow cleavage such that a T-containing moiety is released from the remainder of the compound, including the MOI. Thus, the linker is stable during attachment of the tag to the linker, attachment of the linker to the MOI, and any manipulations of the MOI while the tag and linker (T—L) are attached to it.

4) The linker does not significantly interfere with the manipulations performed on the MOI while the T—L is attached to it. For instance, if the T—L is attached to an oligonucleotide, the T—L must not significantly interfere with any hybridization or enzymatic reactions (e.g., PCR) performed on the oligonucleotide. Similarly, if the T—L is attached to an antibody, it must not significantly interfere with antigen recognition by the antibody.

5) Cleavage of the tag from the remainder of the compound occurs in a highly controlled manner, using physical or chemical processes that do not adversely affect the detectability of the tag.

For any given linker, it is preferred that the linker be attachable to a wide variety of MOIs, and that a wide variety of tags be attachable to the linker. Such flexibility is advantageous because it allows a library of T—L conjugates, once prepared, to be used with several different sets of MOIs.

As explained above, a preferred linker has the formula

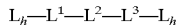

wherein each $L_h$ is a reactive handle that can be used to link the linker to a tag reactant and a molecule of interest reactant. $L^2$ is an essential part of the linker, because $L^2$ imparts lability to the linker. $L^1$ and $L^3$ are optional groups which effectively serve to separate $L^2$ from the handles $L_h$.

$L^1$ (which, by definition, is nearer to T than is $L^3$), serves to separate T from the required labile moiety $L^2$. This separation may be useful when the cleavage reaction generates particularly reactive species (e.g., free radicals) which may cause random changes in the structure of the T-containing moiety. As the cleavage site is further separated from the T-containing moiety, there is a reduced likelihood that reactive species formed at the cleavage site will disrupt the structure of the T-containing moiety. Also, as the atoms in L1 will typically be present in the T-containing moiety, these $L^1$ atoms may impart a desirable quality to the T-containing moiety. For example, where the T-containing moiety is a $T^{ms}$-containing moiety, and a hindered amine is desirably present as part of the structure of the $T^{ms}$-containing moiety (to serve, e.g., as a MSSE), the hindered amine may be present in $L^1$ labile moiety.

In other instances, $L^1$ and/or $L^3$ may be present in a linker component merely because the commercial supplier of a linker chooses to sell the linker in a form having such a $L^1$ and/or $L^3$ group. In such an instance, there is no harm in using linkers having $L^1$ and/or $L^3$ groups, (so long as these group do not inhibit the cleavage reaction) even though they may not contribute any particular performance advantage to the compounds that incorporate them. Thus, the present invention allows for $L^1$ and/or $L^3$ groups to be present in the linker component.

$L^1$ and/or $L^3$ groups may be a direct bond (in which case the group is effectively not present), a hydrocarbylene group (e.g., alkylene, arylene, cycloalkylene, etc.), —O-hydrocarbylene (e.g., —O—CH$_2$—, O—CH$_2$CH ($CH_3$)—, etc.) or hydrocarbylene-(O-hydrocarbylene)$_w$- wherein w is an integer ranging from 1 to about 10 (e.g., —CH$_2$—O—Ar—, —CH$_2$—(O—CH$_2$CH$_2$)$_4$—, etc.).

With the advent of solid phase synthesis, a great body of literature has developed regarding linkers that are labile to specific reaction conditions. In typical solid phase synthesis, a solid support is bonded through a labile linker to a reactive site, and a molecule to be synthesized is generated at the reactive site. When the molecule has been completely synthesized, the solid support-linker-molecule construct is subjected to cleavage conditions which releases the molecule from the solid support. The labile linkers which have been developed for use in this context (or which may be used in this context) may also be readily used as the linker reactant in the present invention.

Lloyd-Williams, P., et al., "Convergent Solid-Phase Peptide Synthesis", Tetrahedron Report No. 347, 49(48):11065–11133 (1993) provides an extensive discussion of linkers which are labile to actinic radiation (i.e., photolysis), as well as acid, base and other cleavage conditions. Additional sources of information about labile linkers may be readily obtained.

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill). Examples include:

ethylene glycobis(succinimidylsuccinate) (EGS), an amine reactive cross-linking reagent which is cleavable by hydroxylamine (1 M at 37° C. for 3–6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSOCOES) and sulfo-BSOCOES, which are amine reactive cross-linking reagents, cleavable by base (pH 11.6);

1,4-di-[3'-(2'-pyridyldithio(propionamido))butane (DPDPB), a pyridyldithiol crosslinker which is cleavable by thiol exchange or reduction;

N-[4-(p-azidosalicylamido)-butyl]-3'-(2'-pyridydithio) propionamide (APDP), a pyridyldithiol crosslinker which is cleavable by thiol exchange or reduction;

bis-[beta-4-(azidosalicylamido)ethyl]-disulfide, a photo-reactive crosslinker which is cleavable by thiol exchange or reduction;

N-succinimidyl-(4-azidophenyl)-1,3'dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithiopropionate (SAED), a photoreactive crosslinker which is cleavable by thiol exchange or reduction;

sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $O_sO_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substitued-2-alkyl-1,3-dioxlane-2-yl linking groups can be cleaved by $H_3O^+$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to MOIs. Some of these linkers are described in a recent review by Lloyd-Williams et al. (Tetrahedron 49:11065–11133, 1993). One useful type of linker is based upon p-alkoxybenzyl alcohols, of which two, 4-hydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review). These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Cleavage of the linkers results in liberation of a primary amide on the tag. Examples of photocleavable linkers include nitrophenyl glycine esters, exo- and endo-2-benzonorborneyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

A preferred linker component has an ortho-nitrobenzyl structure as shown below:

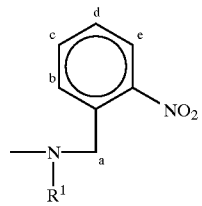

wherein one carbon atom at positions a, b, c, d or e is substituted with —$L^3$—X, and $L^1$ (which is preferably a direct bond) is present to the left of $N(R^1)$ in the above structure. Such a linker component is susceptible to selective photo-induced cleavage of the bond between the carbon labeled "a" and $N(R^1)$. The identity of $R^1$ is not typically critical to the cleavage reaction, however $R^1$ is preferably selected from hydrogen and hydrocarbyl. The present invention provides that in the above structure, —$N(R^1)$— could be replaced with —O—. Also in the above structure, one or more of positions b, c, d or e may optionally be substituted with alkyl, alkoxy, fluoride, chloride, hydroxyl, carboxylate or amide, where these substituents are independently selected at each occurrence.

A further preferred linker component with a chemical handle $L_h$ has the following structure:

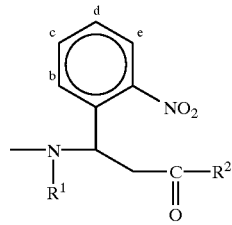

wherein one or more of positions b, c, d or e is substituted with hydrogen, alkyl, alkoxy, fluoride, chloride, hydroxyl, carboxylate or amide, $R^1$ is hydrogen or hydrocarbyl, and $R^2$ is —OH or a group that either protects or activates a carboxylic acid for coupling with another moiety. Fluorocarbon and hydrofluorocarbon groups are preferred groups that activate a carboxylic acid toward coupling with another moiety.

3. Molecule of Interest (MOI)

Examples of MOIs include nucleic acids or nucleic acid analogues (e.g., PNA), fragments of nucleic acids (i.e., nucleic acid fragments), synthetic nucleic acids or fragments, oligonucleotides (e.g., DNA or RNA), proteins, peptides, antibodies or antibody fragments, receptors, receptor ligands, members of a ligand pair, cytokines, hormones, oligosaccharides, synthetic organic molecules, drugs, and combinations thereof.

Preferred MOIs include nucleic acid fragments. Preferred nucleic acid fragments are primer sequences that are complementary to sequences present in vectors, where the vectors are used for base sequencing. Preferably a nucleic acid fragment is attached directly or indirectly to a tag at other than the 3' end of the fragment; and most preferably at the 5' end of the fragment. Nucleic acid fragments may be purchased or prepared based upon genetic databases (e.g., Dib et al., Nature 380:152–154, 1996 and CEPH Genotype Database, http://www.cephb.fr) and commercial vendors (e.g., Promega, Madison, Wis.).

As used herein, MOI includes derivatives of an MOI that contain functionality useful in joining the MOI to a T—L—$L_h$ compound. For example, a nucleic acid fragment that has a phosphodiester at the 5' end, where the phosphodiester is also bonded to an alkyleneamine, is an MOI. Such an MOI is described in, e.g., U.S. Pat. No. 4,762,779 which is incorporated herein by reference. A nucleic acid fragment with an internal modification is also an MOI. An exemplary internal modification of a nucleic acid fragment is where the base (e.g., adenine, guanine, cytosine, thymidine, uracil) has been modified to add a reactive functional group. Such internally modified nucleic acid fragments are commercially available from, e.g., Glen Research, Herndon, Va. Another exemplary internal modification of a nucleic acid fragment is where an abasic phosphoramidate is used to synthesize a modified phosphodiester which is interposed between a sugar and phosphate group of a nucleic acid fragment. The abasic phosphoramidate contains a reactive group which allows a nucleic acid fragment that contains this phosphoramidate-derived moiety to be joined to another moiety, e.g., a T—L—$L_h$ compound. Such abasic phosphoramidates are commercially available from, e.g., Clonetech Laboratories, Inc., Palo Alto, Calif.

4. Chemical Handles ($L_h$)

A chemical handle is a stable yet reactive atomic arrangement present as part of a first molecule, where the handle can undergo chemical reaction with a complementary chemical handle present as part of a second molecule, so as to form a covalent bond between the two molecules. For example, the chemical handle may be a hydroxyl group, and the complementary chemical handle may be a carboxylic acid group (or an activated derivative thereof, e.g., a hydrofluroaryl ester), whereupon reaction between these two handles forms a covalent bond (specifically, an ester group) that joins the two molecules together.

Chemical handles may be used in a large number of covalent bond-forming reactions that are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e.g., dithiothreitol.

Of particular interest for linking tags (or tags with linkers) to oligonucleotides is the formation of amide bonds. Primary aliphatic amine handles can be readily introduced onto synthetic oligonucleotides with phosphoramidites such as 6-monomethoxytritylhexylcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

5. Linker Attachment

Typically, a single type of linker is used to connect a particular set or family of tags to a particular set or family of MOIs. In a preferred embodiment of the invention, a single, uniform procedure may be followed to create all the various T—L—MOI structures. This is especially advantageous when the set of T—L—MOI structures is large, because it allows the set to be prepared using the methods of combinatorial chemistry or other parallel processing technology. In a similar manner, the use of a single type of linker allows a single, uniform procedure to be employed for cleaving all the various T—L—MOI structures. Again, this is advantageous for a large set of T—L—MOI structures, because the set may be processed in a parallel, repetitive, and/or automated manner.

There are, however, other embodiment of the present invention, wherein two or more types of linker are used to connect different subsets of tags to corresponding subsets of MOIs. In this case, selective cleavage conditions may be used to cleave each of the linkers independently, without cleaving the linkers present on other subsets of MOIs.

A large number of covalent bond-forming reactions are suitable for attaching tags to linkers, and linkers to MOIs. Such reactions include alkylation (e.g., to form ethers, thioethers), acylation (e.g., to form esters, amides, carbamates, ureas, thioureas), phosphorylation (e.g., to form phosphates, phosphonates, phosphoramides, phosphonamides), sulfonylation (e.g., to form sulfonates, sulfonamides), condensation (e.g., to form imines, oximes, hydrazones), silylation, disulfide formation, and generation of reactive intermediates, such as nitrenes or carbenes, by photolysis. In general, handles and bond-forming reactions which are suitable for attaching tags to linkers are also suitable for attaching linkers to MOIs, and vice-versa. In some cases, the MOI may undergo prior modification or derivitization to provide the handle needed for attaching the linker.

One type of bond especially useful for attaching linkers to MOIs is the disulfide bond. Its formation requires the presence of a thiol group ("handle") on the linker, and another thiol group on the MOI. Mild oxidizing conditions then suffice to bond the two thiols together as a disulfide. Disulfide formation can also be induced by using an excess of an appropriate disulfide exchange reagent, e.g., pyridyl disulfides. Because disulfide formation is readily reversible, the disulfide may also be used as the cleavable bond for liberating the tag, if desired. This is typically accomplished under similarly mild conditions, using an excess of an appropriate thiol exchange reagent, e g., dithiothreitol.

Of particular interest for linking tags to oligonucleotides is the formation of amide bonds. Primary aliphatic amine handles can be readily introduced onto synthetic oligonucleotides with phosphoramidites such as 6-monomethoxytritylhexyclcyanoethyl-N,N-diisopropyl phosphoramidite (available from Glenn Research, Sterling, Va.). The amines found on natural nucleotides such as adenosine and guanosine are virtually unreactive when compared to the introduced primary amine. This difference in reactivity forms the basis of the ability to selectively form amides and related bonding groups (e.g., ureas, thioureas, sulfonamides) with the introduced primary amine, and not the nucleotide amines.

As listed in the Molecular Probes catalog (Eugene, Oreg.), a partial enumeration of amine-reactive functional groups includes activated carboxylic esters, isocyanates, isothiocyanates, sulfonyl halides, and dichlorotriazenes. Active esters are excellent reagents for amine modification since the amide products formed are very stable. Also, these reagents have good reactivity with aliphatic amines and low reactivity with the nucleotide amines of oligonucleotides. Examples of active esters include N-hydroxysuccinimide esters, pentafluorophenyl esters, tetrafluorophenyl esters, and p-nitrophenyl esters. Active esters are useful because they can be made from virtually any molecule that contains a carboxylic acid. Methods to make active esters are listed in Bodansky (*Principles of Peptide Chemistry* (2d ed.), Springer Verlag, London, 1993).

Numerous commercial cross-linking reagents exist which can serve as linkers (e.g., see Pierce Cross-linkers, Pierce Chemical Co., Rockford, Ill.). Among these are homobifunctional amine-reactive cross-linking reagents which are exemplified by homobifunctional imidoesters and N-hydroxysuccinimidyl (NHS) esters. There also exist heterobifunctional cross-linking reagents possess two or more different reactive groups that allows for sequential reactions. Imidoesters react rapidly with amines at alkaline pH. NHS-esters give stable products when reacted with primary or secondary amines. Maleimides, alkyl and aryl halides, alpha-haloacyls and pyridyl disulfides are thiol reactive. Maleimides are specific for thiol (sulfhydryl) groups in the pH range of 6.5 to 7.5, and at alkaline pH can become amine reactive. The thioether linkage is stable under physiological conditions. Alpha-haloacetyl cross-linking reagents contain the iodoacetyl group and are reactive towards sulfhydryls. Imidazoles can react with the iodoacetyl moiety, but the reaction is very slow. Pyridyl disulfides react with thiol groups to form a disulfide bond. Carbodiimides couple carboxyls to primary amines of hydrazides which give rises to the formation of an acyl-hydrazine bond. The arylazides are photoaffinity reagents which are chemically inert until exposed to UV or visible light. When such compounds are photolyzed at 250–460 nm, a reactive aryl nitrene is formed. The reactive aryl nitrene is relatively non-specific. Glyoxals are reactive towards guanidinyl portion of arginine.

In one typical embodiment of the present invention, a tag is first bonded to a linker, then the combination of tag and linker is bonded to a MOI, to create the structure T—L—MOI. Alternatively, the same structure is formed by first bonding a linker to a MOI, and then bonding the combination of linker and MOI to a tag. An example is where the MOI is a DNA primer or oligonucleotide. In that case, the tag is typically first bonded to a linker, then the T—L is bonded to a DNA primer or oligonucleotide, which is then used, for example, in a sequencing reaction.

One useful form in which a tag could be reversibly attached to an MOI (e.g., an oligonucleotide or DNA sequencing primer) is through a chemically labile linker. One preferred design for the linker allows the linker to be cleaved when exposed to a volatile organic acid, for example, trifluoroacetic acid (TFA). TFA in particular is compatible with most methods of MS ionization, including electrospray.

As described in detail below, the invention provides methodology for genotyping. A composition which is useful in the genotyping method comprises a a plurality of compounds of the formula:

$$T^{ms}—L—MOI$$

wherein, $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to the MOI at a location other than the 3' end of the MOI. In the composition, at least two compounds have the same $T^{ms}$ but the MOI groups of those molecules have non-identical nucleotide lengths.

Another composition that is useful in the genotyping method comprises a plurality of compounds of the formula:

$$T^{ms}—L—MOI$$

wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to the MOI at a location other than the 3' end of the MOI. In the composition, at least two compounds have the same $T^{ms}$ but those compounds have non-identical elution times by column chromatography.

Another composition that may be used in the genotyping method comprises a plurality of compounds of the formula:

$$T^{ms}—L—MOI$$

wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to the MOI at a location other than the 3' end of the MOI. In the composition, no two compounds which have the same MOI nucleotide length also have the same $T^{ms}$.

In the above composition, the plurality is preferably greater than 2, and preferably greater than 4. Also, the nucleic acid fragment in the MOI have a sequence complementary to a portion of a vector, wherein the fragment is capable of priming polynucleotide synthesis. Preferably, the $T^{ms}$ groups of members of the plurality differ by at least 2 amu, and may differ by at least 4 amu.

The invention also provides for a composition comprising a plurality of sets of compounds, each set of compounds having the formula:

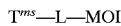
$T^{ms}$—L—MOI wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. Also, in the formula, MOI is a nucleic acid fragment wherein L is conjugated to the MOI at a location other than the 3' end of the MOI. In the composition, members within a first set of compounds have identical Tms groups, however have non-identical MOI groups with differing numbers of nucleotides in the MOI and there are at least ten members within the first set, wherein between sets, the $T^{ms}$ groups differ by at least 2 amu. The plurality is preferably at least 3, and more preferably at least 5.

The invention also provides for a composition comprising a plurality of sets of compounds, each set of compounds having the formula

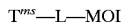
$T^{ms}$—L—MOI wherein, $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to the MOI at a location other than the 3' end of the MOI. In the composition, the compounds within a set have the same elution time but non-identical $T^{ms}$ groups.

In addition, the invention provides a kit for genotyping. The kit comprises a plurality of amplification primer pairs, wherein at least one of the primers has the formula:

$T^{ms}$—L—MOI wherein $T^{ms}$ is an organic group detectable by mass spectrometry, comprising carbon, at least one of hydrogen and fluoride, and optional atoms selected from oxygen, nitrogen, sulfur, phosphorus and iodine. In the formula, L is an organic group which allows a $T^{ms}$-containing moiety to be cleaved from the remainder of the compound, wherein the $T^{ms}$-containing moiety comprises a functional group which supports a single ionized charge state when the compound is subjected to mass spectrometry and is selected from tertiary amine, quaternary amine and organic acid. In the formula, MOI is a nucleic acid fragment wherein L is conjugated to the MOI at a location other than the 3' end of the MOI; and each primer pair associates with a different loci. In the kit, the plurality is preferably at least 3, and more preferably at least 5.

As noted above, the present invention provides compositions and methods for determining the sequence of nucleic acid molecules. Briefly, such methods generally comprise the steps of (a) generating tagged nucleic acid fragments which are complementary to a selected nucleic acid molecule (e.g., tagged fragments) from a first terminus to a second terminus of a nucleic acid molecule), wherein a tag is correlative with a particular or selected nucleotide, and may be detected by any of a variety of methods, (b) separating the tagged fragments by sequential length, (c) cleaving a tag from a tagged fragment, and (d) detecting the tags, and thereby determining the sequence of the nucleic acid molecule. Each of the aspects will be discussed in more detail below.

B. Diagnostic Methods

1. Introduction

As noted above, the present invention also provides a wide variety of methods wherein the above-described tags and/or linkers may be utilized in place of traditional labels (e.g., radioactive or enzymatic), in order to enhance the specificity, sensitivity, or number of samples that may be simultaneously analyzed, within a given method. Representative examples of such methods which may be enhanced include, for example, RNA amplification (see Lizardi et al., *Bio/Technology* 6:1197–1202, 1988; Kramer et al., *Nature* 339:401–402, 1989; Lomeli et al., *Clinical Chem.* 35(9) :1826–1831, 1989; U.S. Pat. No. 4,786,600), and DNA amplification utilizing LCR or polymerase chain reaction ("PCR") (see, U.S. Pat. Nos. 4,683,195, 4,683,202, and 4,800,159).

Within one aspect of the present invention, methods are provided for determining the identity of a nucleic acid molecule or fragment (or for detecting the presence of a selected nucleic acid molecule or fragment), comprising the steps of (a) generating tagged nucleic acid molecules from one or more selected target nucleic acid molecules, wherein a tag is correlative with a particular nucleic acid molecule and detectable by non-fluorescent spectrometry or potentiometry, (b) separating the tagged molecules by size, (c) cleaving the tags from the tagged molecules, and (d) detecting the tags by non-fluorescent spectrometry or potentiometry, and therefrom determining the identity of the nucleic acid molecules.

Within a related aspect of the invention, methods are provided for detecting a selected nucleic acid molecule, comprising the steps of (a) combining tagged nucleic acid probes with target nucleic acid molecules under conditions and for a time sufficient to permit hybridization of a tagged nucleic acid probe to a complementary selected target nucleic acid sequence, wherein a tagged nucleic acid probe is detectable by non-fluoescent spectrometry or potentiometry, (b) altering the size of hybridized tagged probes, unhybridized probes or target molecules, or the probe:target hybrids, (c) separating the tagged probes by size, (d) cleaving tags from the tagged probes, and (e) detecting tags by non-fluorescent spectrometry or potentiometry, and therefrom detecting the selected nucleic acid molecule. These, other related techniques are discussed in more detail below.

2. PCR

PCR can amplify a desired DNA sequence of any origin (virus, bacteria, plant, or human) hundreds of millions of times in a matter of hours. PCR is especially valuable because the reaction is highly specific, easily automated, and capable of amplifying minute amounts of sample. For these reasons, PCR has had a major impact on clinical medicine, genetic disease diagnostics, forensic science and evolutionary biology.

Briefly, PCR is a process based on a specialized polymerase, which can synthesize a complementary strand to a given DNA strand in a mixture containing the 4 DNA bases and 2 DNA fragments (primers, each about 20 bases long) flanking the target sequence. The mixture is heated to separate the strands of double-stranded DNA containing the target sequence and then cooled to allow (1) the primers to find and bind to their complementary sequences on the separated strands and (2) the polymerase to extend the primers into new complementary strands. Repeated heating and cooling cycles multiply the target DNA exponentially, since each new double strand separates to become two templates for further synthesis. In about 1 hour, 20 PCR cycles can amplify the target by a millionfold.

Within one embodiment of the invention, methods are provided for determining the identity of a nucleic acid molecule, or for detecting the selected nucleic acid molecule in, for example, a biological sample, utilizing the technique of PCR. Briefly, such methods comprise the steps of generating a series of tagged nucleic acid fragments or molecules during the PCR and separating the resulting fragments are by size. The size separation step can be accomplished utilizing any of the techniques described herein, including for example gel electrophoresis (e.g., polyacrylamide gel electrophoresis) or preferably HPLC The tags are then cleaved from the separated fragments and detected by the respective detection technology. Examples of such technologies have been described herein, and include for example mass spectrometry, infra-red spectrometry, potentiostatic amperometry or UV spectrometry.

3. RNA Fingerprinting and Differential Display

When the template is RNA, the first step in fingerprinting is reverse transcription. Liang and Pardee (*Science* 257:967, 1992) were the first to describe an RNA fingerprinting protocol, using a primer for reverse transcription based on oligo (dT) but with an 'anchor' of two bases at the 5' end (e.g., oligo 5'-(dT$_{11}$)CA-3'. Priming occurs mainly at the 5' end of the poly(rA) tail and mainly in sequences that end 5'-UpG-poly(rA)-3', with a selectivity approaching one out of 12 polyadenylated RNAs. After reverse transcription and denaturation, arbitrary priming is performed on the resulting first strand of cDNA. PCR can now be used to generate a fingerprint of products that best matches the primers and that are derived from the 3' end of the mRNAs and polyadenylated heterogeneous RNAs. This protocol has been named 'differential display'.

Alternatively, an arbitrary primer can be used in the first step of reverse transcription, selecting those regions internal to the RNA that have 6–8 base matches with the 3' end of the primer. This is followed by arbitrary priming of the resulting first strand of cDNA with the same or a different arbitrary primer and then PCR. This particular protocol samples anywhere in the RNA, including open reading frames (Welsh et al., *Nuc. Acids. Res.* 20:4965, 1992). In addition, it can be used on RNAs that are not polyadenylated, such as many bacterial RNAs. This variant of RNA fingerprinting by arbitrarily primed PCR has been called RAP-PCR.

If arbitrarily primed PCR fingerprinting of RNA is performed on samples derived from cells, tissues or other biological material that have been subjected to different experimental treatments or have different developmental histories, differences in gene expression between the samples can be detected. For each reaction, it is assumed that the same number of effective PCR doubling events occur and any differences in the initial concentrations of cDNA products are preserved as a ratio of intensities in the final fingerprint. There are no meaningful relationships between the intensities of bands within a single lane on a gel, which are a function of match and abundance. However, the ratio between lanes is preserved for each sampled RNA, allowing differentially expressed RNAs to be detected. The ratio of starting materials between samples is maintained even when the number of cycles is sufficient to allow the PCR reaction to saturate. This is because the number of doublings needed to reach saturation are almost completely controlled by the invariant products that make up the majority of the fingerprint. In this regard, PCR fingerprinting is different from conventional PCR of a single product in which the ratio of starting materials between samples is not preserved unless products are sampled in the exponential phase of amplification.

Within one embodiment of the invention methods are provided for determining the identity of a nucleic acid molecule, or for detecting a selecting nucleic acid molecule, in, for example a biological sample, utilizing the technique of RNA fingerprinting. Briefly, such methods generally comprise the steps of generating a series of tagged nucleic acid fragments. The fragments generated by PCR or similar amplification schemes and are then subsequently separated by size. The size separation step can be, for example, any of the techniques described herein, including for example gel electrophoresis (e.g., polyacrylamide gel electrophoresis) or preferably HPLC. The tags are then cleaved from the separated fragments, and then the tags are detected by the respective detection technology. Representative examples of suitable technologies include mass spectrometry, infra-red spectrometry, potentiostatic amperometry or UV spectrometry. The relative quantities of any given nucleic acid fragments are not important, but the size of the band is informative when referenced to a control sample.

4. Fluorescence-Based PCR Single-Strand Conformation Polymorphism (PCR-SSCP)

A number of methods in addition to the RFLP approach are available for analyzing base substitution polymorphisms. Orita, et al. have devised a way of analyzing these polymorphisms on the basis of conformational differences in denatured DNA. Briefly, restriction enzyme digestion or PCR is used to produce relatively small DNA fragments which are then denatured and resolved by electrophoresis on non-denaturing polyacrylamide gels. Conformational differences in the single-stranded DNA fragments resulting from base substitutions are detected by electrophoretic mobility shifts. Intra-strand base pairing creates single strand conformations that are highly sequence-specific and distinctive in electrophoretic mobility. However, detection rates in different studies using conventional SSCP range from 35% to nearly 100% with the highest detection rates most often requiring several different conditions. In principle, the method could also be used to analyze polymorphisms based on short insertions or deletions. This method is one of the most powerful tools for identifying point mutations and deletions in DNA (SSCP-PCR, Dean et al., *Cell* 61:863, 1990).

Within one embodiment of the invention methods are provided for determining the identity of a nucleic acid molecule, or for detecting a selecting nucleic acid molecule, in, for example a biological sample, utilizing the technique of PCR-SSP. Briefly, such methods generally comprise the steps of generating a series of tagged nucleic acid fragments. The fragments generated by PCR are then separated by size. Preferably, the size separation step is non-denaturing and the nucleic acid fragments are denatured prior to the separation methodology. The size separation step can be accomplished, for example gel electrophoresis (e.g., polyacrylamide gel electrophoresis) or preferably HPLC. The tags are then cleaved from the separated fragments, and then the tags are detected by the respective detection technology (e.g., mass spectrometry, infra-red spectrometry, potentiostatic amperometry or UV spectrometry).

5. Dideoxy Fingerprinting (ddF)

Another method has been described (ddF, Sarkar et al., *Genomics* 13:441, 1992) that detected 100% of single-base changes in the human factor IX gene when tested in a retrospective and prospective manner. In total, 84 of 84 different sequence changes were detected when genomic DNA was analyzed from patients with hemophilia B.

Briefly, in the applications of tags for genotyping or other purposes, one method that can be used is dideoxy-fingerprinting. This method utilizes a dideoxy terminator in a Sanger sequencing reation. The principle of the method is as follows: a target nucleic acid that is to be sequenced is placed in a reaction which possesses a dideoxy-terminator complementary to the base known to be mutated in the target nucleic acid. For example, if the mutation results in a A→G change, the reaction would be carried out in a C dideoxy-terminator reaction. PCR primers are used to locate and amplify the target sequence of interest. If the hypothetical target sequence contains the A→G change, the size of a population of sequences is changed due to the incorporation of a dideoxy-terminator in the amplified sequences. In this particular application of tags, a fragment would be generated which would possess a predictable size in the case of a mutation. The tags would be attached to the 5'-end of the PCR primers and provide a "map" to sample type and dideoxy-terminator type. A PCR amplification reaction would take place, the resulting fragments would be separated by size by for example HPLC or PAGE. At the end of the separation procedure, the DNA fragments are collected in a temporal reference frame, the tags are cleaved and the presence or absence of mutation is determined by the chain length due to premature chain terminator by the incorporation of a given dideoxy-terminator.

It is important to note that ddf results in the gain or loss of a dideoxy-termination segment and or a shift in the mobility of at least one of the termination segments or products. Therefore, in this method, a search is made of the shift of one fragment mobility in a high background of other molecular weight fragments. One advantage is the foreknowledge of the length of fragment associated with a given mutation.

Within one embodiment of the invention methods are provided for determining the identity of a nucleic acid molecule, or for detecting a selecting nucleic acid molecule, in, for example a biological sample, utilizing the technique of ddF. Briefly, such methods generally comprise the steps of generating a series of tagged nucleic acid fragments, followed by separation based upon size. Preferably, the size separation step is non-denaturing and the nucleic acid fragments are denatured prior to the separation methodology. The size separation step can be accomplished, for example gel electrophoresis (e.g., polyacrylamide gel electrophoresis) or preferably HPLC. The tags are then cleaved from the separated fragments, and then the tags are detected by the respective detection technology (e.g., mass spectrometry, infra-red spectrometry, potentiostatic amperometry or UV spectrometry).

6. Restriction Maps and RFLPs

Restriction endonucleases recognize short DNA sequences and cut DNA molecules at those specific sites. Some restriction enzymes (rare-cutters) cut DNA very infrequently, generating a small number of very large fragments (several thousand to a million bp). Most enzymes cut DNA more frequently, thus generating a large number of small fragments (less than a hundred to more than a thousand bp). On average, restriction enzymes with 4-base recognition sites will yield pieces 256 bases long, 6-base recognition sites will yield pieces 4000 bases long, and 8-base recognition sites will yield pieces 64,000 bases long. Since hundreds of different restriction enzymes have been characterized, DNA can be cut into many different small fragments.

A wide variety of techniques have been developed for the analysis of DNA polymorphisms. The most widely used method, the restriction fragment length polymorphism (RFPL) approach, combines restriction enzyme digestion, gel electrophoresis, blotting to a membrane and hybridization to a cloned DNA probe. Polymorphisms are detected as variations in the lengths of the labeled fragments on the blots. The RFLP approach can be used to analyze base substitutions when the sequence change falls within a restriction enzyme site or to analyze minisatellites/VNTRs by choosing restriction enzymes that cut outside the repeat units. The agarose gels do not usually afford the resolution necessary to distinguish minisatellite/VNTR alleles differing by a single repeat unit, but many of the minisatellite/VNTRs are so variable that highly informative markers can still be obtained.

Within one embodiment of the invention methods are provided for determining the identity of a nucleic acid molecule, or for detecting a selecting nucleic acid molecule, in, for example a biological sample, utilizing the technique of restriction mapping or RFLPs. Briefly, such methods generally comprise the steps of generating a series of tagged nucleic acid fragments in which the fragments generated are digested with restriction enzymes. The tagged fragments are generated by conducting a hybridization step of the tagged probes with the digested target nucleic acid. The hybridization step can take place prior to or after the restriction nuclease digestion. The resulting digested nucleic acid fragments are then separated by size. The size separation step can be accomplished, for example gel electrophoresis (e.g., polyacrylamide gel electrophoresis) or preferably HPLC. The tags are then cleaved from the separated fragments, and then the tags are detected by the respective detection technology (e.g., mass spectrometry, infra-red spectrometry, potentiostatic amperometry or UV spectrometry).

7. DNA Fingerprinting

DNA fingerprinting involves the display of a set of DNA fragments from a specific DNA sample. A variety of DNA fingerprinting techniques are presently available (Jeffreys et al., *Nature* 314:67–73, 1985; Zabeau and Vos, 1992); "Selective Restriction Fragment Amplification: A General Method for DNA Fingerprinting," European Patent Application 92402629.7.; Vos et al., "DNA FINGERPRINTING. A New Technique for DNA Fingerprinting." *Nucl. Acids Res.* 23: 4407–4414, 1996; Bates, S. R. E., Knorr, D. A., Weller, J. W., and Ziegle, J. S., "Instrumentation for Automated Molecular Marker Acquisition and Analysis." Chapter 14, pp. 239–255, in The Impact of Plant Molecular Genetics, edited by B. W. S. Sobral, published by Birkhauser, 1996.

Thus, one embodiment of the invention methods are provided for determining the identity of a nucleic acid molecule, or for detecting a selecting nucleic acid molecule, in, for example a biological sample, utilizing the technique of DNA fingerprinting. Briefly, such methods generally comprise the steps of generating a series of tagged nucleic acid fragments, followed by separation of the fragments by size. The size separation step can be accomplished, for example gel electrophoresis (e.g., polyacrylamide gel electrophoresis) or preferably HPLC. The tags are then cleaved from the separated fragments, and then the tags are detected by the respective detection technology (e.g., mass spectrometry, infra-red spectrometry, potentiostatic amperometry or UV spectrometry).

Briefly, DNA fingerprinting is based on the selective PCR amplification of restriction fragments from a total digest of genomic DNA. The technique involves three steps: 1) restriction of the DNA fragments and subsequent ligation of oligonucleotide adaptors, 2) selective amplification of sets of restriction fragments, 3) gel analysis of the amplified fragments. PCR amplification of the restriction fragments is achieved by using the adaptor and restriction site sequence as target sites for primer annealing. The selective amplification is achieved by the use of primers that extend into the restriction fragments, amplifying only those fragments in which the primer extensions match the nucleotides flanking the restriction sites.

This method therefore yields sets of restriction fragments which may be visualized by a variety of methods (i.e., PAGE, HPLC, or other types of spectrometry) without prior knowledge of the nucleotide sequence. The method also allows the co-amplification of large numbers of restriction fragments. The number of fragments however is dependent on the resolution of the detection system. Typically, 50–100 restriction fragments are amplified and detected on denaturing polyacrylamide gels. In the application described herein, the separation will be performed by HPLC.

The DNA fingerprinting technique is based on the amplification of subsets of genomic restriction fragments using PCR. DNA is cut with restriction enzymes and double strand adapters and the are ligated to the ends of the DNA fragments to generate template DNA for the amplification reactions. The sequence of the ligated adapters and the adjacent restriction enzymes (sites) serve as binding sites for the DNA fingerprinting of primers for PCR-based amplification. Selective nucleotides are included at the 3' end of the of the PCR primers which therefore can only prime DNA synthesis from a subset of the restriction sites. Only restriction fragments in which the nucleotides flanking the restriction site can match the selective nucleotide will be amplified.

The DNA fingerprinting process produces "fingerprint" patterns of different fragment lengths that are characteristic and reproducible for an individual organism. These fingerprints can be use to distinguish even very closely related organisms, including near-isogenic lines. The differences in fragment lengths can be traced to base changes in the restriction site or the primer extension site, or to insertions or deletions in the body of the DNA fragment.

Dependence on sequence knowledge of the target genome is eliminated by the use of adaptors of known sequence that are ligated to the restriction fragments. The PCR primers are specific for the known sequences of the adaptors and restriction sites. The steps of the genetic fingerprinting process are described below.

1) Restriction and Ligation. Restriction fragments of genomic DNA are generated by using two different restriction enzymes: a rare cutter (the six-base recognition enzyme EcoRI) and a frequent cutter (the four-base recognition enzyme MseI). Three different types of fragments are produced: ones with EcoRI cuts at both ends, ones with MseI cuts at both ends, and ones with an EcoRI cut at one end and an MseI cut at the other end. Double-stranded adaptors are then ligated to the sticky ends of the DNA fragments, generating template DNA for amplification. The adaptors are specific for either the EcoRI site or the MseI site. Restriction and ligation take place in a single reaction. Ligation of the adaptor to the restricted DNA alters the restriction site so as to prevent a second restriction from taking place after ligation has occurred.

2) Preselective Amplification. The sequences of the adaptors and restriction sites serve as primer binding sites for the "preselective PCR amplification." The preselective primers each have a "selective" nucleotide that will recognize the subset of restriction fragments having the matching nucleotide downstream from the restriction site. The primary products of the preselective PCR are those fragments having one MseI cut and one EcoRI cut, and also having the matching internal nucleotide. The preselective amplification achieves a 16-fold reduction of the complexity of the fragment mixture.

3) Selective Amplification with CMST-Labeled Primers. The complexity of the PCR product mixture is further reduced (256-fold) and fragments are labeled with a set of CMSTs by carrying out a second PCR using selective primers labeled with CMSTs. It is possible to choose from among 64 different primer pairs (resulting from all possible combinations of eight MseI and eight EcoRI primers) for this amplification. Each of these primers possesses three selective nucleotides. The first is the same as that used in the pre-selective amplification; the others can be any of the 16 possible combinations of the four nucleotides. Only that subset of fragments having matching nucleotides at all three positions will be amplified at this stage in the amplification.

8. Application of Cleavable Tags to Genotyping and Polymorphism Detection a. Introduction Although a few known human DNA polymorphisms are based upon insertions, deletions or other rearrangements of non-repeated sequences, the vast majority are based either upon single base substitutions or upon variations in the number of tandem repeats. Base substitutions are very abundant in the human genome, occurring on average once every 200–500 bp. Length variations in blocks of tandem repeats are also common in the genome, with at least tens of thousands of interspersed polymorphic sites (termed loci). Repeat lengths for tandem repeat polymorphisms range from 1 bp in $(dA)_n(dT)_n$ sequences to at least 170 bp in $\alpha$-satellite DNA. Tandem repeat polymorphisms can be divided into two major groups which consist of minisatellites/variable number of tandem repeats (VNTRs), with typical repeat lengths of tens of base pairs and with tens to thousands of total repeat units, and microsatellites, with repeat lengths of up to 6 bp and with maximum total lengths of about 70 bp. Most of the microsatellite polymorphisms identified to date have been based on $(dC-dA)_n$ or $(dG-dT)_n$ dinucleotide repeat sequences. Analysis of microsatellite polymorphisms involves amplification by the polymerase chain reaction (PCR) of a small fragment of DNA containing a block of repeats followed by electrophoresis of the amplified DNA on denaturing polyacrylamide gel. The PCR primers are complementary to unique sequences that flank the blocks of repeats. Polyacrylamide gels, rather than agarose gels, are traditionally used for microsatellites because the alleles often only differ in size by a single repeat.

Thus, within one aspect of the present invention methods are provided for genotyping a selected organism, comprising the steps of (a) generating tagged nucleic acid molecules from a selected target molecule, wherein a tag is correlative with a particular fragment and may be detected by non-fluorescent spectrometry or potentiometry, (b) separating the tagged molecules by sequential length, (c) cleaving the tag from the tagged molecule, and (d) detecting the tag by non fluorescent spectrometry or potentiometry, and therefrom determining the genotype of the organism.

Within another aspect, methods are provided for genotyping a selected organism, comprising the steps of (a) combining a tagged nucleic acid molecule with a selected target molecule under conditions and for a time sufficient to permit hybridization of the tagged molecule to the target molecule, wherein a tag is correlative with a particular fragment and may be detected by non-fluorescent spectrometry or potentiometry, (b) separating the tagged fragments by sequential length, (c) cleaving the tag from the tagged fragment, and (d) detecting the tag by non-fluorescent spectrometry or potentiometry, and therefrom determining the genotype of the organism.

b. Application of Cleavable Tags to Genotyping

A PCR approach to identify restriction fragment length polymorphism (RFPL) combines gel electrophoresis and detection of tags assoicated with specific PCR primers. In general, one PCR primer will possess one specific tag. The tag will therefore represent one set of PCR primers and therefore a pre-determined DNA fragment length. Polymorphisms are detected as variations in the lengths of the labeled fragments in a gel or eluting from a gel. Polyacrylamide gel electrophoresis will usually afford the resolution necessary to distinguish minisatellite/VNTR alleles differing by a single repeat unit. Analysis of microsatellite polymorphisms involves amplification by the polymerase chain reaction (PCR) of a small fragment of DNA containing a block of repeats followed by electrophoresis of the amplified DNA on denaturing polyacrylamide gel or followed by separation of DNA fragments by HPLC. The amplified DNA will be labeled using primers that have cleavable tags at the 5' end of the primer. The primers are incorporated into the newly synthesized strands by chain extension. The PCR primers are complementary to unique sequences that flank the blocks of repeats. Minisatellite/VNTR polymorphisms can also be amplified, much as with the microsatellites described above.

Descriptions of many types of DNA sequence polymorphisms have provided the fundamental basis for the understanding of the structure of the human genome (Botstein et al., *Am. J. Human Genetics* 32:p314, 1980; Donis-Keller, *Cell* 51:319, 1981; Weissenbach et al., *Nature* 359:794). The construction of extensive framework linkage maps has been facilitated by the use of these DNA polymorphisms and has provided a practical means for localization of disease genes by linkage. Microsatellite dinucleotide markers are proving to be very powerful tools in the identification of human genes which have been shown to contain mutations and in some instances cause disease. Genomic dinucleotide repeats are highly polymorphic (Weber, 1990, Genomic Analysis, Vol 1, pp 159–181, Cold Spring Laboratory Press, Cold Spring Harbor, N.Y.; Weber and Wong, 1993, Hum. Mol. Genetics, 2, p1123) and may possess up to 24 alleles. Microsatellite dinucleotide repeats can be amplified using primers complementary to the unique regions surrounding the dinucleotide repeat by PCR. Following amplification, several amplified loci and be combined (multiplexed) prior to a size separation step. The process of applying the amplified microsatellite fragments to a size separation step and then identifying the size and therefore the allele is known as genotyping. Chromosome specific markers which permit a high level of multiplexing have been reported for performing whole genome scans for linkage analysis (Davies et al., 1994, Nature, 371, p130).

Tags can be used to great effect in genotyping with microsatellites. Briefly, the PCR primers are constructed to carry tags and used in a carefully chosen PC reaction to amplify di-, tri-, or tetra-nucleotide repeats. The amplification products are then separated according to size by methods such as HPLC or PAGE. The DNA fragments are then collected in a temporal fashion, the tags cleaved from their respective DNA fragments and length deduced from comparison to internal standards in the size separation step. Allele identification is made from reference to size of the amplified products.

With cleavable tags approach to genotyping, it is possible to combine multiple samples on a single separation step. There are two general ways in which this can performed. The first general method for high through-put screening is the detection of a single polymorphism in a large group of individuals. In this senario a single or nested set of PCR primers is used and each amplification is done with one DNA sample type per reaction. The number of samples that can be combined in the separation step is proportional to the number of cleavable tags that can be generated per detection technology (i.e., 400–600 for mass spectrometer tags). It is therefore possible to identify 1 to several polymorphisms in a large group of individuals simultaneously. The second approach is to use multiple sets of PCR primers which can identify numerous polymorphisms on a single DNA sample (genotyping an individual for example). In this approach PCR primers are combined in a single amplification reaction which generate PCR products of different length. Each primer pair or nested set is encoded by a specific cleavable Tag which implies each PCR fragment will be encoded with a specific tag. The reaction is run on a single separation step (see below). The number of samples that can be combined in the separation step is proportional to the number of cleavable tags that can be generated per detection technology (i.e., 400–600 for mass spectrometer tags).

c. Enzymatic Detection of Mutation and the Applications of Tags

In this particular application or method, mismatches in heteroduplexes are detected by enzymatic cleavage of mismatched base pairs in a given nucleic acid duplex. DNA sequences to be tested for the presence of a mutation are amplified by PCR using a specific set of primers, the amplified products are denatured and mixed with denatured reference fragments and hybridized which result in the formation of heteroduplexes. The heteroduplexes are then treated with enzymes which recognize and cleave the duplex if a mismatch is present. Such enzymes are nuclease S1, Mung bean nuclease, "resolvases", T4 endonuclease IV, etc. Essentially any enzyme can be used which recognizes mismatches in vitro and cleave the resulting mismatch. The treatment with the appropriate enzyme, the DNA duplexes are separated by size, by, for example HPLC or PAGE. The DNA fragments are collected temporally. Tags are cleaved and detected. The presence of a mutation is detected by the shift in mobility of a fragments relative to a wild-type reference fragment.

d. Applications of Tags to the Oligonucleotide Ligation Assay (OLA)

The oligonucleotide ligation assay as originally described by Landegren et al. (Landegen et al., *Science* 241:487, 1988) is a useful technique for the identification of sequences (known) in very large and complex genomes. The principle of the OLA reaction is based on the ability of ligase to covalently join two diagnostic oligonucleotides as they hybridize adjacent to one another on a given DNA target. If the sequences at the probe junctions are not perfectly based-paired, the probes will not be joined by the ligase. The ability of a thermostable ligase to discriminate potential single base-pair differences when positioned at the 3' end of the "upstream" probe provides the opportunity for single base-pair resolution (Barony, *PNAS USA* 88:189, 1991). In the application of tags, the tags can be attached to a probe which is ligated to the amplified product. After completion of the OLR, the fragments are separated on the basis of size, the tags cleaved and detected by mass spectrometry.

e. Sequence Specific Amplification

PCR primers with a 3' end complementary either to a mutant or normal oligonucleotide sequence can be used to selectively amplify one or the other allele (Newton et al., Nuc. Acids Res., 17, p2503; et al., 1989, Genomics, 5, p535; Okayama et al., 1989, J. Lab. Clin. Med., 114, p105; Sommer et al., 1989, Mayo Clin.Proc., 64, 1361; Wu et al., PNAS USA, 86, p2757). Usually the PCR products are visualized after amplification by PAGE, but the principle of sequence specific amplification can be applied to solid phase formats.

f. Application of Tags to Some Amplification Based Assays

Genotyping of viruses: One application of tags is the genotyping or identification of viruses by hybridization with tagged probes. For example, F+ RNA coliphages may be useful candidates as indicators for enteric virus contamination. Genotyping by nucleic acid hybridization methods is a reliable, rapid, simple, and inexpensive alternative to serotyping (Kafatos et. al., *Nucleic Acids Res.* 7:1541, 1979). Amplification techniques and nucleic aid hybridization techniques have been successfully used to classify a variety of microorganisms including *E. coli* (Feng, *Mol. Cell Probes* 7:151, 1993). Representative examples of viruses that may be detected utilizing the present invention include rotavirus (Sethabutr et. al., *J. Med Virol.* 37:192, 1992), hepatitis viruses such as hepatitis C virus (Stuyver et. al., *J. Gen Virol.* 74:1093, 1993), herpes simplex virus (Matsumoto et. al., *J. Virol Methods* 40:119, 1992).

Prognostic applications of mutational analysis in cancers: Genetic alterations have been described in a variety of experimental mammalian and human neoplasms and represent the morphological basis for the sequence of morphological alterations observed in carcinogenesis (Vogelstein et al., *NEJM* 319:525, 1988). In recent years with the advent of molecular biology techniques, allelic losses on certain chromosomes or mutation of tumor suppressor genes as well as mutations in several oncogenes (e.g., c-myc, c-jun, and the ras family) have been the most studied entities. Previous work (Finkelstein et al., *Arch Surg.* 128:526, 1993) has identified a correlation between specific types of point mutations in the K-ras oncogene and the stage at diagnosis in colorectal carcinoma. The results suggested that mutational analysis could provide important information of tumor aggressiveness, including the pattern and spread of metastasis. The prognostic value of TP53 and K-ras-2 mutational analysis in stage III carcinoma of the colon has more recently been demonstrated (Pricolo et al., *Am. J. Surg.* 171:41, 1996). It is therefore apparent that genotyping of tumors and pre-cancerous cells, and specific mutation detection will become increasingly important in the treatment of cancers in humans.

9. Single Nucleotide Extension Assay

The primer extension technique for the detection of single nucleotide in genomic DNA was first described by Sokolov in 1989 (*Nucleic Acids Res.* 18(12): 3671, 1989). In this paper, Sokolov described the single nucleotide extension of 30-mers and 20-mers complementary to the known sequence of the cystic fibrosis gene. It was shown that the method had the ability to correctly identify a single nucleotide change within t the gene. The method was based on the use of radiolabelled deoxynucleotides for a labeling method in the single nucleotide extension assay. Later publications described the use of single nucleotide extension assays for genetic diseases such as hemophilia B (factor IX) and the cyctic fibrosis gene (Kuppuswamy et al., *PNAS USA* 88:p1143–1147, 1991). Recently, the parameters of the single nucleotide extension assay in terms of the quantitative range, variability, and multiplex analysis has been described in detail (Greenwood, A. D. and Burke, D. T., *Genome Research* 6:336–348, 1996).

The strategy is based on the fidelity of the DNA polymerase to add only the correctly paired nucleotide onto the 3' end of the template hybridized primer. Since only one dideoxy-terminator nucleotide is added per reaction, it is a simple matter to sort out which primer has been extended in all four types of dNTPs.

Hence, within one aspect of the invention methods are provided for the detection of a single selected nucleic acid within a nucleic acid molecule, comprising the steps of (a) hybridizing in at least two separate reactions a tagged primer and a target nucleic acid molecule under conditions and for a time sufficient to permit hybridization of the primer to the target nucleic acid molecule, wherein each reaction contains an enzyme which will add a nucleotide chain terminator, and, a nucleotide chain terminator complementary to adenosine, cytosine, guanosine, thymidine or uracil, and wherein each reaction contains a different nucleotide chain terminator, (b) separating tagged primers by size, (c) cleaving the tag from the tagged primer, and (d) detecting the tag by non-fluorescent spectrometry or potentiometry, and therefrom determining the presence of the selected nucleotide within the nucleic acid molecule.

As noted herein a wide variety of separation methods may be utilized, including for example liquid chromatographic means such as HPLC. In addition, a wide variety of detection methodologies may be utilized, including for example, mass spectrometry, infrared spectrometry, ultraviolet spectrometry, or, potentiostatic amperometry. Also, several different enzymes may be utilized (e.g., a polymerase), as well as any of the tags provided herein. Within certain preferred embodiments, each primer which is utilized within a reaction has a different unique tag. In this manner, multiple samples (or multiple sites) may be simulataneously probed for the presence of selected nucleotides.

Single nucleotide assays such as those described herein may be utilized to detect polymorphic variants, or to interrogate a biological sample for the presence a specific nucleotide within or near a known sequence. Target nucleic acid molecules include not only DNA (e.g., genomic DNA), but RNA as well.

In general, this method involves hybridizing a primer to the target DNA sequence such that the 3' end of the primer is immediately adjacent to the mutation to be detected and identified. The procedure is similar to the Sanger sequencing reaction except that only the dideoxynucleotide of a given nucleotide is added to the reaction mixture. Each dideoxynucleotide is labeled with a unique tag. Of the four reaction mixtures, solely one will add a dideoxyterminator on to the primer sequence. If the mutation is present, it will be detected through the unique tag on the dideoxynucleotide and its identity established. Multiple mutations can be ascertained simultaneously by tagging the DNA primer with a unique tag as well. Within one aspect of the invention methods are provided for analyzing single nucleotide mutations from a selected biological sample, comprising the steps of exposing nucleic acids from a biological sample and combining the exposed nucleic acids with one or more selected nucleic acid probes, which may or may not be tagged, under conditions and for a time sufficient for said probes to hybridize to said nucleic acids, wherein the tag, if used, is correlative with a particular nucleic acid probe and detectable by non-fluorescent spectrometry, or potentiometry. The DNA fragments are reacted in four separate reactions each including a different tagged dideoxyterminator, wherein the tag is correlative with a particular dideoxynucleotide and detectable by non-fluorescent spectrometry, or potentiometry. The DNA fragments are separated according to size by, for example, gel electrophoresis (e.g., polyacrylamide gel electrophoresis) or preferably HPLC. The tags are cleaved from the separated fragments and detected by the respective detection technology (e.g., mass spectrometry, infrared spectrometry, potentiostatic amperometry or UV/visible spectrophotometry). The tags detected can be correlated to the particular DNA fragment under investigation as well as the identity of the mutant nucleotide.

10. Amplified Fragment Length Polymorphism (AFLP)

AFLP was designed as a highly sensitive method for DNA fingerprinting to be used in a variety of fields, including plant and animal breeding, medical diagnostics, forensic analysis and microbial typing, to name a few. (Vos et al., *Nucleic Acids Res.* 23:4407–4414, 1995.) The power of AFLP is based upon the molecular genetic variations that exist between closely related species, varieties or cultivars. These variations in DNA sequence are exploited by the genetic fingerprinting technology such that "fingerprints" of particular genotypes can be routinely generated. These "fingerprints" are simply RFLPs visualized by selective PCR amplification of DNA restriction fragments. Briefly genetic fingerprinting technology consists of the following steps: genomic DNA is digested to completion by two different restriction enzymes. Specific double strand oligonucleotide adapters (~25–30 bp) are ligated to the restricted DNA fragments. Oligonucleotide primers homologous to the adapters, but having extensions at the 3'-end are used to amplify a subset of the DNA fragments. (A pre-amplification step can also be performed where the extension is only 1 bp in length. Amplification with the primer having a 3 base-pair extension would follow.) These extensions can vary in length from 1 to 3 base-pair, but are of defined length for a given primer. The sequence of the extension can also vary from one primer to another but is of a single, defined sequence within a given primer. The selective nature of AFLP-PCR is based on the 3' extensions on the oligonucleotide primers. Since these extensions are not homologous to adapter sequence, only DNA fragments complementary to the extensions will be amplified due to the inability of Taq DNA polymerase, unlike some other DNA polymerases, to extend DNAs if mismatches occur at the 3'-end of a molecule that is being synthesized. Therefore only a subset of the entire genome is amplified in any reaction. For example, if 2 base-pair (bp) extensions are used, only one in 256 molecules is amplified. To further limit the number of fragments that are actually visualized (so that a manageable number is observed), only one of the primers is labeled. Finally, the amplified DNAs are separated on a polyacrylamide gel (sequencing type) and an autoradiograph or phosphor image is generated.

Within one embodiment of the invention methods are provided for determining the identity of a nucleic acid molecule, or for detecting a selecting nucleic acid molecule, in, for example a biological sample, utilizing the technique of genetic fingerprinting. Briefly, such methods generally comprise the steps of digesting (e.g., genomic DNA) to completion by two different restriction enzymes. Specific double-strand oligonucleotide adapters (~25–30 bp) are ligated to the restricted DNA fragments. Optional pre-amplification utilizing primers with a 1 bp extension may be performed. The PCR product is then diluted, and tagged primers homologous to the adapters, but having extensions at the 3'-end are used to amplify by PCR a subset of the DNA fragments. The resulting PCR products are then separated by size. The size separation step can be accomplished by a variety of methods, including for example, HPLC. The tags are then cleaved from the separated fragments, and detected by the respective detection technology (e.g., mass spectrometry, infrared spectrometry, potentiostatic amperometry or UV/visible spectrophotometry).

11. Gene Expression Analysis

One of the inventions disclosed herein is a high throughput method for measuring the expression of numerous genes (1–2000) in a single measurement. The method also has the ability to be done in parallel with greater than one hundred samples per process. The method is applicable to drug screening, developmental biology, molecular medicine studies and the like. Within one aspect of the invention methods are provided for analyzing the pattern of gene expression from a selected biological sample, comprising the steps of (a) exposing nucleic acids from a biological sample, (b) combining the exposed nucleic acids with one or more selected tagged nucleic acid probes, under conditions and for a time sufficient for the probes to hybridize to the nucleic acids, wherein the tag is correlative with a particular nucleic acid probe and detectable by non-fluorescent spectrometry, or potentiometry, (c) separating hybridized probes from unhybridized probes, (d) cleaving the tag from the tagged fragment, and (e) detecting the tag by non-fluorescent spectrometry, or potentiometry, and therefrom determining the pattern of gene expression of the biological sample.

Within a particularly preferred embodiment of the invention, assays or methods are provided which are described as follows: RNA from a target source is bound to a solid support through a specific hybridization step (i.e., capture of poly(A) mRNA by a tethered oligo(dT) capture probe). The solid support is then washed and cDNA is synthesized on the solid support using standard methods (i.e., reverse transcriptase). The RNA strand is then removed via hydrolysis. The result is the generation of a DNA population which is covalently immobilized to the solid support which reflects the diversity, abundance, and complexity of the RNA from which the cDNA was synthesized. The solid support then interrogated (hybridized) with 1 to several thousand probes that are complementary to a gene sequence of interest. Each probe type is labeled with a cleavable mass spectrometry tag or other type of cleavable tag. After the interrogation step, excess or unhybridized probe is washed away, the solid support is placed, for example, in the well of a microtiter plate and the mass spectrometry tag is cleaved from the solid support. The solid support is removed from the well of sample container, and the contents of the well are measured with a mass spectrometer. The appearance of specific mass spectrometer tags indicates the presence of RNA in the sample and evidence that a specific gene is expressed in a given biological sample. The method can also be quantifiable.

The compositions and methods for the rapid measurement of gene expression using cleavable tags can be described in detail as follows. Briefly, tissue (liver, muscle, etc.), primary or transformed cell lines, isolated or purified cell types or any other source of biological material in which determining genetic expression is useful can be used as a source of RNA. In the preferred method, the biological source material is lysed in the presence of a chaotrope in order to suppress nucleases and proteases and support stringent hybridization of target nucleic acid to the solid support. Tissues, cells and biological sources can be effectively lysed in 1 to 6 molar chaotropic salts (guanidine hydrochloride, guanidine thiocyanate, sodium perchlorate, etc.). After the source biological sample is lysed, the solution is mixed with a solid support to effect capture of target nucleic acid present in the lysate. In one permutation of the method, RNA is captured using a tethered oligo(dT) capture probe. Solid supports can include nylon beads, polystyrene microbeads, glass beads and glass surfaces or any other type of solid support to which oligonucleotides can be covalently attached. The solid supports are preferentially coated with an amine-polymer such as polyethylene(imine), acrylamide, amine-dendrimers,. etc. The amines on the polymers are used to covalently immobilize oligonucleotides. Oligonucleotides are preferentially synthesized with a 5'-amine (generally a hexylamine that includes a six carbon spacer-arm and a distal amine). Oligonucleotides can be 15 to 50 nucleotides in length. Oligonucleotides are activated with homo-bifunctional or heterobifunctional cross-linking reagents such as cyanuric chloride. The activated oligonucleotides are purified from excess cross-linking reagent (i.e., cyanuric chloride) by exclusion chromatography. The activated oligonucleotide are then mixed with the solid supports to effect covalent attachment. After covalent attachment of the oligonucleotides, the unreacted amines of the solid support are capped (i.e., with succinic anhydride) to eliminate the positive charge of the solid support. The solid supports can be used in parallel and are preferentially configured in a 96-well or 384-well format. The solid supports can be attached to pegs, stems, or rods in a 96-well or, 384-well configuration, the solid supports either being detachable or alternatively integral to the particular configuration. The particular configuration of the solid supports is not of critical importance to the functioning of the assay, but rather, affects the ability of the assay to be adapted to automation. The solid supports are mixed with the lysate for 15 minutes to several hours to effect capture of the target nucleic acid onto the solid support. In general, the "capture" of the target nucleic acid is through complementary base pairing of target RNA and the capture probe immobilized on the solid support. One permutation utilizes the 3' poly(A) stretch found on most eucaryotic messengers RNAs to hybridize to a tethered oligo(dT) on the solid support. Another permutation is to utilize a specific oligonucleotide or long probes (greater than 50 bases) to capture an RNA containing a defined sequence. Another possibility is to employ degenerate primers (oligonucleotides) that would effect the capture of numerous related sequences in the target RNA population. The sequence complexity of the RNA population and the type of capture probe employed guide hybridization times. Hybridization temperatures are dictated by the type of chaotrope employed and the final concentration of chaotrope (see Van Ness and Chen, Nuc. Acids Res. 1991, for general guidelines). The lysate is preferentially agitated continually with the solid support to effect diffusion of the target RNA. Once the step of capturing the target nucleic acid is accomplished, the lysate is washed from the solid support and all chaotrope or hybridization solution is removed. The solid support is preferentially washed with solutions containing ionic or non-ionic detergents, buffers and salts. The next step is the synthesis of DNA complementary to the captured RNA. In this step, the tethered capture oligonucleotide serves as the extension primer for reverse transcriptase. The reaction is generally performed at 25 to 37° C. and preferably agitated during the polymerization reaction. After the cDNA is synthesized, it becomes covalently attached to the solid support since the capture oligonucleotide serves as the extension primer. The RNA is then hydrolyzed from the cDNA/RNA duplex. The step can be effected by the use of heat that denatures the duplex or the use of base (i.e., 0.1 N NaOH) to chemically hydrolyze the RNA. The key result at this step is to make the cDNA available for subsequent hybridization with defined probes. The solid support or set of solid supports is then further washed to remove RNA or RNA fragments. At this point, the solid support contains a approximate representative population of cDNA molecules that represents the RNA population in terms of sequence abundance, complexity, and diversity. The next step is to hybridize selected probes to the solid support to identify the presence or absence and the relative abundance of specific cDNA sequences. Probes are preferentially oligonucleotides in length of 15 to 50 nucleotides. The sequence of the probes is dictated by the end-user of the assay. For example, if the end-user intended to study gene expression in an inflammatory response in a tissue, probes would be selected to be complementary to numerous cytokine mRNAs, RNAs that encode enzymes that modulate lipids, RNAs that encode factors that regulate cells involved in an inflammatory response, etc. Once a set of defined sequences are defined for study, each sequence is made into an oligonucleotide probe and each probe is assigned a specific cleavable tag. The tag(s) is then attached to the respective oligonucleotide(s). The oligonucleotide(s) are hybridized to the cDNA on the solid support under appropriate hybridization conditions. After completion of the hybridization step; the solid support is washed to remove any unhybridized probe. The solid support or array of supports is then heated to cleave the covalent bond between the cDNA and the solid support. The tagged cDNA fragments are then separated according to size by gel electrophoresis (e.g., polyacrylamide gel electrophoresis) or preferably HPLC. The tags are then cleaved from the DNA probe molecules, and detected by the respective detection technology (e.g., mass spectrometry, infrared spectrometry, potentiostatic amperometry or UV/visible spectrophotometry). Each tag present is identified, and the presence (and abundance) or absence of an expressed mRNA is determined.

An alternative procedure would hybridize the tagged DNA probes directly to the tethered mRNA target molecules under the appropriate hybridization conditions. After completion of the hybridization step, the solid support is washed to remove any unhybridized probe. The RNA is then hydrolyzed from the DNA probe/RNA duplex. The step can be effected by the use of heat which denatures the duplex or the use of base (i.e., 0.1 N NaOH) to chemically hydrolyze the RNA. This step will leave free mRNA and their corresponding DNA probes that can then be isolated through a size separation step generally consisting of gel electrophoresis (e.g., polyacrylamide gel electrophoresis) or preferably HPLC. The tags are then cleaved from the DNA probe molecules, and detected by the respective detection technology (e.g., mass spectrometry, infrared spectrometry, potentiostatic amperometry or UV/visible spectrophotometry). Each tag present is identified, and the presence (and abundance) or absence of an expressed mRNA is determined.

12. Hybridization Techniques

The successful cloning and sequencing of a gene leads to the investigation of its structure and expression by making it possible to detect the gene or its mRNA in a large pool of unrelated DNA or RNA molecules. The amount of mRNA encoding a specific protein in a tissue is an important parameter for the activity of a gene and may be significantly related to the activity of function systems. Its regulation is dependent upon the interaction between sequences within the gene (cis-acting elements) and sequence-specific DNA binding proteins (trans-acting factors), which are activated tissue-specifically or by hormones and second messenger systems.

Several techniques are available for analysis of a particular gene, its regulatory sequences, its specific mRNA and the regulation of its expression; these include Southern or Northern blot analysis and ribonuclease (RNase) protection assay.

Variations in the nucleotide composition of a certain gene may be of great pathophysiological relevance. When localized in the non-coding regions (5', 3'-flanking regions and intron), they can affect the regulation of gene expression, causing abnormal activation or inhibition. When localized in the coding regions of the gene (exons), they may result in alteration of the protein function or dysfunctional proteins. Thus, a certain sequence within a gene can correlate to a specific disease and can be useful as a marker of the disease. One primary goal of research in the medical field is, therefore, to detect those genetic variations as diagnostic tools, and to gain important information for the understanding of pathophysiological phenomena. The basic method for the analysis of a population regarding the variations within a certain gene is DNA analysis using the Southern blot technique. Briefly, prepared genomic DNA is digested with a restriction enzyme (RE), resulting in a large number of DNA fragments of different lengths, determined by the presence of the specific recognition site of the RE on the genome. Alleles of a certain gene with mutations inside this restriction site will be cleaved into fragments of different number and length. This is called restriction fragment length polymorphism (RFLP) and can be an important diagnostic marker with many applications. The fragment to be analyzed has to be separated from the pool of DNA fragments and distinguished from other DNA species using a specific probe. Thus, DNA is subjected to electrophoretic fractionation using an agarose gel, followed by transfer and fixation to a nylon or nitrocellulose membrane. The fixed, single-stranded DNA is hybridized to a tagged DNA that is complementary to the DNA to be detected, After removing non-specific hybridizations, the DNA fragment of interest can be visualized according to the probes characteristics (autoradiography or phosphor image analysis).

Within one embodiment of the invention methods are provided for determining the identity of a nucleic acid molecule, or for detecting a selecting nucleic acid molecule, in, for example a biological sample, utilizing the techniques similar to Southern blotting. Briefly, such methods generally comprise the steps of generating a series of tagged nucleic acid fragments in which the fragments generated are digested with restriction enzymes. The tagged fragments are generated by conducting a hybridization step of the tagged probes with the digested target nucleic acid. The hybridization step can take place prior to or after the restriction nuclease digestion. The resulting digested nucleic acid fragments are then separated by size. The size separation step can be accomplished, for example, by gel electrophoresis (e.g. polyacrylamide gel electrophoresis) or preferably HPLC. The tags are then cleaved from the separated fragments, and then the tags are detected by the respective detection technology (e.g., mass spectrometry, infrared spectrometry, potentiostatic amperometry or UV/visible spectrophotometry).

The presence and quantification of a specific gene transcript and its regulation by physiological parameters can be analyzed by means of Northern blot analysis and RNase protection assay. The principle basis of these methods is hybridization of a pool of total cellular RNA to a specific probe. In the Northern blot technique, total RNA of a tissue is fractionated using an HPLC or LC method, hybridized to a labeled antisense RNA (cRNA), complementary to the RNA to be detected. By applying stringent washing conditions, non-specifically bound molecules are eliminated. Specifically bound molecules, would subsequently be detected according to the type of probe utilized (mass spectrometry, or with a electrochemical detector). In addition, specificity can be controlled by comparing the size of the detected mRNA with the predicted length of the mRNA of interest.

Within one embodiment of the invention methods are provided for determining the identity of a ribonucleic acid molecule, or for detecting a selecting ribonucleic acid molecule, in, for example a biological sample, utilizing the techniques similar to Northern blotting. Briefly, such methods generally comprise the steps of generating a series of tagged RNA molecules by conducting a hybridization step of the tagged probes with the target RNA. The tagged RNA molecules are then separated by size. The size separation step can be accomplished, for example by preferably HPLC. The tags are cleaved from the separated RNA molecules, and then the tags are detected by the respective detection technology (e.g., mass spectrometry, infrared spectrometry, potentiostatic amperometry or UV/visible spectrophotometry).

The most specific method for detection of a mRNA species is the RNase protection assay. Briefly, total RNA from a tissue or cell culture is hybridized to a tagged specific cRNA of complete homology. Specificity is accomplished by subsequent RNase digestion. Non-hybridized, single-stranded RNA and non-specifically hybridized fragments with even small mismatches will be recognized and cleaved, while double-stranded RNA of complete homology is not accessible to the enzyme and will be protected. After removing RNase by proteinase K digestion and phenol extraction, the specific protected fragment can be separated from degradation products, usually by HPLC.

Within one embodiment of the invention methods are provided for determining the identity of a ribonucleic acid molecule, or for detecting a selecting ribonucleic acid molecule, in, for example a biological sample, utilizing the technique of RNase protection assay. Briefly, such methods generally comprise the steps of total RNA from a tissue or cell culture being hybridized to a tagged specific cRNA of complete homology, a RNase digestion, treatment with proteinase K and a phenol extraction. The tagged, protected RNA fragment is isolated from the degradation products. The size separation step can be accomplished, for example by LC or HPLC. The tag is cleaved from the separated RNA molecules, and then is detected by the respective detection technology (e.g., mass spectrometry, infrared spectrometry, potentiostatic amperometry or UV/visible spectrophotometry).

13. Mutation Detection Techniques

The detection of diseases is increasingly important in prevention and treatments. While multifactorial diseases are difficult to devise genetic tests for, more than 200 known human disorders are caused by a defect in a single gene, often a change of a single amino acid residue (Olsen, Biotechnology: An industry comes of age, National Academic Press, 1986). Many of these mutations result in an altered amino acid that causes a disease state.

Sensitive mutation detection techniques offer extraordinary possibilities for mutation screening. For example, analyses may be performed even before the implantation of a fertilized egg (Holding and Monk, Lancet 3:532, 1989). Increasingly efficient genetic tests may also enable screening for oncogenic mutations in cells exfoliated from the respiratory tract or the bladder in connection with health checkups (Sidransky et al., Science 252:706, 1991). Also, when an unknown gene causes a genetic disease, methods to monitor DNA sequence variants are useful to study the inheritance of disease through genetic linkage analysis. However, detecting and diagnosing mutations in individual genes poses technological and economic challenges. Several different approaches have been pursued, but none are both efficient and inexpensive enough for truly wide-scale application.

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants. Several scanning techniques for mutation detection have been developed in heteroduplexes of mismatched complementary DNA strands, derived from wild type and mutant sequences, exhibit an abnormal behavior especially when denatured. This phenomenon is exploited in denaturing and temperature gradient gel electrophoresis (DGGE and TGGE, respectively) methods. Duplexes mismatched in even a single nucleotide position can partially denature, resulting in retarded migration, when electrophoresed in an increasingly denaturing gradient gel (Myers et al., Nature 313:495, 1985; Abrades et al., Genomics 7:463, 1990; Henco et al., Nucl. Acids Res. 18:6733, 1990). Although mutations may be detected, no information is obtained regarding the precise location of a mutation. Mutant forms must be further isolated and subjected to DNA sequence analysis. Alternatively, RNase A may cleave a heteroduplex of an RNA probe and a target strand at a position where the two strands are not properly paired. The site of cleavage can then be determined by electrophoresis of the denatured probe. However, some mutations may escape detection because not all mismatches are efficiently cleaved by RNase A. Mismatched bases in a duplex are also susceptible to chemical modification. Such modifications can render the strands susceptible to cleavage at the site of the mismatch or cause a polymerase to stop in a subsequent extension reaction. The chemical cleavage technique allows identification of a mutation in target sequences of up to 2 kb and it provides information on the approximate location of mismatched nucleotide(s) (Cotton et al., PNAS USA 85:4397, 1988; Ganguly et al., Nucl. Acids Res. 18:3933, 1991). However, this technique is labor intensive and may not identify the precise location of the mutation.

An alternative strategy for detecting a mutation in a DNA strand is by substituting (during synthesis) one of the normal nucleotides with a modified nucleotide, altering the molecular weight or other physical parameter of the product. A strand with an increased or decreased number of this modified nucleotide relative to the wild-type sequence exhibits altered electrophoretic mobility (Naylor et al., Lancet 337:635, 1991). This technique detects the presence of a mutation, but does not provide the location.

Two other strategies visualize mutations in a DNA segment by altered gel migration. In the single-strand conformation polymorphism technique (SSCP), mutations cause denatured strands to adopt different secondary structures, thereby influencing mobility during native gel electrophoresis. Heteroduplex DNA molecules, containing internal mismatches, can also be separated from correctly matched molecules by electrophoresis (Orita, Genomics 5:874, 1989; Keen, Trends Genet. 7:5, 1991). As with the techniques discussed above, the presence of a mutation may be determined but not the location. As well, many of these techniques do not distinguish between a single and multiple mutations. All of the above-mentioned techniques indicate the presence of a mutation in a limited segment of DNA and some of them allow approximate localization within the segment. However, sequence analysis is still required to unravel the effect of the mutation on the coding potential of the segment. Sequence analysis is very powerful, allowing, for example, screening for the same mutation in other individuals of an affected family, monitoring disease progression in the case of malignant disease or for detecting residual malignant cells in the bone marrow before autologous transplantation. Despite these advantages, the procedure is unlikely to be adopted as a routine diagnostic method because of the high expense involved.

A large number of other techniques have been developed to analyze known sequence variants. Automation and economy are very important considerations for these types of analyses that may be applied, for screening individuals and the general population. None of the techniques discussed below combine economy and automation with the required specificity.

Mutations may be identified via their destabilizing effects on the hybridization of short oligonucleotide probes to a target sequence (see Wetmur, Crit. Rev. Biochem. Mol. Biol. 26:227, 1991). Generally, this technique, allele-specific oligonucleotide hybridization, involves amplification of target sequences and subsequent hybridization with short oligonucleotide probes. An amplified product can thus be scanned for many possible sequence variants by determining its hybridization pattern to an array of immobilized oligonucleotide probes. However, establishing conditions that distinguish a number of other strategies for nucleotide sequence distinction all depend on enzymes to identify sequence differences (Saiki, PNAS USA 86:6230, 1989; Zhang, Nucl. Acids Res. 19:3929, 1991).

For example, restriction enzymes recognize sequences of about 4–8 nucleotides. Based on an average G+C content, approximately half of the nucleotide positions in a DNA segment can be monitored with a panel of 100 restriction enzymes. As an alternative, artificial restriction enzyme recognition sequences may be created around a variable position by using partially mismatched PCR primers. With this technique, either the mutant or the wild-type sequence alone may be recognized and cleaved by a restriction enzyme after amplification (Chen et al., Anal. Biochem. 195:51, 1991; Levi et al., Cancer Res. 51:3497, 1991). Another method exploits the property that an oligonucleotide primer that is mismatched to a target sequence at the 3' penultimate position exhibits a reduced capacity to serve as a primer in PCR. However, some 3' mismatches, notably G–T, are less inhibitory than others limiting its usefulness are. In attempts to improve this technique, additional mismatches are incorporated into the primer at the third position from the 3' end. This results in two mismatched positions in the three 3' nucleotides of the primer hybridizing with one allelic variant, and one mismatch in the third position in from the 3' end when the primer hybridizes to the other allelic variant (Newton et al., *Nucl. Acids Res.* 17:2503, 1989). It is necessary to define amplification conditions that significantly favor amplification of a 1 bp mismatch.

DNA polymerases have also been used to distinguish allelic sequence variants by determining which nucleotide is added to an oligonucleotide primer immediately upstream of a variable position in the target strand.

A ligation assay has been developed. In this method, two oligonucleotide probes hybridizing in immediate juxtaposition on a target strand are joined by a DNA ligase. Ligation is inhibited if there is a mismatch where the two oligonucleotide probes abut.

14. Assays for Mutation Detection

Mutations are a single-base pair change in genomic DNA. Within the context of this invention, most such changes are readily detected by hybridization with oligonucleotides that are complementary to the sequence in question. In the system described here, two oligonucleotides are employed to detect a mutation. One oligonucleotide possesses the wild-type sequence and the other oligonucleotide possesses the mutant sequence. When the two oligonucleotides are used as probes on a wild-type target genomic sequence, the wild-type oligonucleotide will form a perfectly based paired structure and the mutant oligonucleotide sequence will form a duplex with a single base pair mismatch. As discussed above, a 6 to 7° C. difference in the Tm of a wild type versus mismatched duplex permits the ready identification or discrimination of the two types of duplexes. To effect this discrimination, hybridization is performed at the Tm of the mismatched duplex in the respective hybotropic solution. The extent of hybridization is then measured for the set of oligonucleotide probes. When the ratio of the extent of hybridization of the wild-type probe to the mismatched probe is measured, a value to 10/1 to greater than 20/1 is obtained. These types of results permit the development of robust assays for mutation detection.

For exemplary purposes, one assay format for mutation detection utilizes target nucleic acid (e.g., genomic DNA) and oligonucleotide probes that span the area of interest. The oligonucleotide probes are greater or equal to 24 nt in length (with a maximum of about 36 nt) and labeled with a fluorochrome at the 3' or 5' end of the oligonucleotide probe. The target nucleic acid is obtained via the lysis of tissue culture cells, tissues, organisms, etc., in the respective hybridization solution. The lysed solution is then heated to a temperature that denatures the target nucleic acid (15–25° C. above the Tm of the target nucleic acid duplex). The oligonucleotide probes are added at the denaturation temperature, and hybridization is conducted at the Tm of the mismatched duplex for 0.5 to 24 hours. The genomic DNA is then collected and by passage through a GF/C (GF/B, and the like) glass fiber filter. The filter is then washed with the respective hybridization solution to remove any non-hybridized oligonucleotide probes (RNA, short oligos and nucleic acid does not bind to glass fiber filters under these conditions). The hybridization oligo probe can then be thermally eluted from the target DNA and measured (by fluorescence for example). For assays requiring very high levels of sensitivity, the probes are concentrated and measured.

Other highly sensitive hybridization protocols may be used. The methods of the present invention enable one to readily assay for a nucleic acid containing a mutation suspected of being present in cells, samples, etc., i.e., a target nucleic acid. The target nucleic acid contains the nucleotide sequence of deoxyribonucleic acid (DNA) or ribonucleic acid (RNA) whose presence is of interest, and whose presence or absence is to be detected for in the hybridization assay. The hybridization methods of the present invention may also be applied to a complex biological mixture of nucleic acid (RNA and/or DNA). Such a complex biological mixture includes a wide range of eucaryotic and procaryotic cells, including protoplasts; and/or other biological materials which harbor polynucleotide nucleic acid. The method is thus applicable to tissue culture cells, animal cells, animal tissue, blood cells (e.g., reticulocytes, lymphocytes), plant cells, bacteria, yeasts, viruses, mycoplasmas, protozoa, fungi and the like. By detecting a specific hybridization between nucleic acid probes of a known source, the specific presence of a target nucleic acid can be established. A typical hybridization assay protocol for detecting a target nucleic acid in a complex population of nucleic acids is described as follows: Target nucleic acids are separated by size on an LC or HPLC, cloned and isolated, sub-divided into pools, or left as a complex population. Within one embodiment of the invention methods are provided for determining the identity of a nucleic acid molecule, or for detecting a selecting nucleic acid molecule, in, for example a biological sample, utilizing the general techniques of hybridization assays. Briefly, such methods generally comprise the steps of target nucleic acids being cloned and isolated, sub-divided into pools, or left as a complex population. The target nucleic acids are hybridized with tagged oligonucleotide probes under conditions described above. The target nucleic acids are separated according to size by LC or HPLC. The tags are cleaved from the separated fragments, and then the tags are detected by the respective detection technology (e.g., mass spectrometry, infrared spectrometry, potentiostatic amperometry or UV/visible spectrophotometry).

15. Sequencing by Hybridization

DNA sequence analysis is conventionally performed by hybridizing a primer to target DNA and performing chain extensions using a polymerase. Specific stops are controlled by the inclusion of a dideoxynucleotide. The specificity of priming in this type of analysis can be increased by including a hybotrope in the annealing buffer and/or incorporating an abasic residue in the primer and annealing at a discriminating temperature.

Within one embodiment of the invention methods are provided for determining the identity of a nucleic acid molecule, or for detecting a selecting nucleic acid molecule, in, for example a biological sample, utilizing the general techniques of sequencing by hybridization using the Sanger method. Briefly, such methods generally comprise the steps of hybridizing a tagged primer to target DNA and performing chain extensions using a polymerase. Specific stops are controlled by the inclusion of a dideoxynucleotide that may also be tagged. The target nucleic acids are separated according to size by HPLC. The tags are cleaved from the separated fragments, and are detected by the respective detection technology (e.g., mass spectrometry, infrared spectrometry, potentiostatic amperometry or UV/visible spectrophotometry). Other sequence analysis methods involve hybridization of the target with an assortment of random, short oligonucleotides. The sequence is constructed by overlap hybridization analysis. In this technique, precise hybridization is essential. Use of hybotropes or abasic residues and annealing at a discriminating temperature is beneficial for this technique to reduce or eliminate mismatched hybridization. The goal is to develop automated hybridization methods in order to probe large arrays of oligonucleotide probes or large arrays of nucleic acid samples. Applications of such technologies include gene mapping, clone characterization, medical genetics and gene discovery, DNA sequence analysis by hybridization, and finally, sequencing verification. Many parameters must be controlled in order to automate or multiplex oligonucleotide probes. The stability of the respective probes must be similar, the degree of mismatch with the target nucleic acid, the temperature, ionic strength, the A+T content of the probe (or target), as well as other parameters when the probe is short (i.e., 6 to 50 nucleotides) should be similar. Usually, the conditions of the experiment and the sequence of the probe are adjusted until the formation of the perfectly based-paired probe is thermodynamically favored over the any duplex that contains a mismatch. Very large-scale applications of probes such as sequencing by hybridization (SBH), or testing highly polymorphic loci such as the cystic fibrosis trans-membrane protein locus require a more stringent level of control of multiplexed probes. Within one embodiment of the invention methods are provided for determining the identity of a nucleic acid molecule, or for detecting a selecting nucleic acid molecule, in, for example a biological sample, utilizing the general techniques of sequencing by hybridization. Briefly, such methods generally comprise of hybridizing a series of tagged primers to a DNA target or a series of target DNA fragments under carefully controlled conditions. The target nucleic acids are separated according to size by HPLC. The tags are then cleaved from the separated fragments, and detected by the respective detection technology (e.g., mass spectrometry, infrared spectrometry, potentiostatic amperometry or UV/visible spectrophotometry).

16. Oligonucleotide-ligation Assay

Oligonucleotide-ligation assay is an extension of PCR-based screening that uses an ELISA-based assay (OLA, Nickerson et al., *Proc. Natl. Acad. Sci. USA* 15 87:8923, 1990) to detect the PCR products that contain the target sequence. Thus, both gel electrophoresis and colony hybridization are eliminated. Briefly, the OLA employs two adjacent oligonucleotides: a "reporter" probe (tagged at the 5' end) and a 5'-phosphorylated/3'-biotinylated "anchor" probe. The two oligonucleotides, which are complementary to sequences internal to the PCR primers, are annealed to target DNA and, if there is perfect complementarity, the two probes are ligated by T4 DNA ligase. Capture of the biotinylated anchor probe on immobilized streptavidin and analysis for the covalently linked reporter probe test for the presence or absence of the target sequences among the PCR products. Within one embodiment of the invention methods are provided for determining the identity of a nucleic acid molecule, or for detecting a selecting nucleic acid molecule, in, for example a biological sample, utilizing the technique of oligonucleotide ligation assay. Briefly, such methods generally comprise the steps of performing PCR on the target DNA followed by hybridization with the 5' tagged ireporteri DNA probe and a 5' phosphorylated/non-biotinylated probe. The sample is incubated with T4 DNA ligase. The DNA strands with ligated probes can be separated from the DNA with non-ligated probes by, for example, preferably by LC or HPLC. The tags are cleaved from the separated fragments, and then the tags are detected by the respective detection technology (e.g., mass spectrometry, infrared spectrophotometry, potentiostatic amperometry or UV/visible spectrophotometry. Recent advances in the OLA assay have allowed for the analysis multiple samples and multiple mutations concurrently. (Baron et al., *Nature Biotechnology* 87:1279, 1996.) Briefly, the method consists of amplifying the gene fragment containing the mutation of interest with PCR. The PCR product is then hybridized with a common and two allele-specific oligonucleotide probes (one containing the mutation while the other does not) such that the 3' ends of the allele-specific probes are immediately adjacent to the 5' end of the common probe. This sets up a competitive hybridization-ligation process between the two allelic probes and the common probe at each locus. The thermostable DNA ligase then discriminates between single-base mismatches at the junction site, thereby producing allele-specific ligation products. The common probe is labeled with one of four fluorophores and the allele-specific probes are each labeled with one or more pentaethyleneoxide mobility modifying tails which provide a sizing difference between the different allele-specific probes. The samples are then separated by gel electrophoresis based upon the length of the modifying tails and detected by the fluorescent tag on the common probe. Through the use in sizing differences on the allele-specific probes and four fluorophores available for the common probe, many samples can be analyzed on one lane of the electrophoretic gel. Within one embodiment of the invention methods are provided for determining the identity of a nucleic acid molecule, or for detecting a selecting nucleic acid molecule, in, for example a biological sample, utilizing the technique of oligonucleotide ligation assay for concurrent multiple sample detection. Briefly, such methods generally comprise the steps of performing PCR on the target DNA followed by hybridization with the common probe (untagged) and two allele-specific probes tagged according to the specifications of the invention. The sample is incubated with DNA ligase and fragments separated by, for example, preferably by LC or HPLC. The tags are cleaved from the separated fragments, and then the tags are detected by the respective detection technology (e.g., mass spectrometry, infrared spectrophotometry, potentiostatic amperometry or UV/visible spectrophotometry.

17. Differential Display a. Overview

Mammals, such as human beings, have about 100,000 different genes in their genome, of which only a small fraction, perhaps 15%, are expressed in any individual cell. The choice of genes expressed determine the biochemical character of any given cell or tissue. The process of normal cellular growth and differentiation, as well as the pathological changes that arise in diseases like cancer, are all driven by changes in gene expression. Differential display methods permits the identification of genes specifically expressed in individual cell types.

The differential display technique amplifies the 3' terminal portions of corresponding cDNAs by using a primer designed to bind to the 5' boundary of a poly(A) tail and primers of, arbitrary sequence that bind upstream. Amplified populations with each primer pair are visualized by a size separation method (PAGE, HPLC, etc.), allowing direct comparison of the mRNAs between two biological samples of interest. The differential display method has the potential to visualize all the expressed genes (about 10,000 to 15,000 mRNA species) in a mammalian cell and enables sequence analysis. It is possible to compare: (1) the total number of peaks amplified in the parents, (2) the number of polymorphic peaks between parents, and (3) the segregation ratios of polymorphic peaks in the progeny of crosses in animals or plants. Differential display is also used for the identification of up- and down-regulated genes, known or unknown, after a variety of stimuli. Differential display PCR fragments can be used as probes for cDNA cloning (discovering an unknown gene from a cDNA or genomic library).

Briefly, the steps in differential display are as follows: 1) RNA is isolated from biological sample of interest. Total RNA, cytoplasmic RNA or mRNA can be used. 2) first strand cDNAs are generated using an anchored oligodT (oligodTdN, where N is A, C, or G). 3) Amplification of cDNA using oligodTdN and short primers with arbitrary sequence. For a complete differential display analysis of two cell populations or two samples of interest, 9 different primers are required. The detection limit of differential display for a specific mRNA is less than 0.001% of the total mRNA population.

Because of the simplicity, sensitivity, and reproducibility of the method disclosed here, the CMST differential display method is a significant advance over traditional gel based systems. With the CMST-based differential display analysis of two cell types, including 64×24 PCR runs can be completed rapidly as opposed to a labor intensive, lengthy time by the traditional method. Moreover, sequence heterogeneity of bands isolated from differential display gels has been found to be a contributing factor to the high failure rate of this technique. This is completely avoided with the CMST-based differential display methology described here.

b. CMST-based Differential Display Example.

The starting material for differential display is RNA isolated from two different populations of cells. Generally, the cells are of similar origin, and differ with respect to their treatment with drugs, their being "normal" versus "transformed", or their expression of various introduced genes.

Plant tissue or animal material (2–3 g) is harvested and minced or chopped in sterile petri dishes. The material is then ground to a fine powder in a precooled pestle and mortar under liquid $N_2$. 1 g of frozen powder is transferred to a 12 ml poly-propelene tubes (1 g ca. 5 ml powder) containing 8 ml of a hot (80° C.) 1:1 mixture of RNA extraction buffer (100 mM Tris-HCl (pH 8.0), 100 mM LiCl, 10 mM EDTA, 1.0% LiDS) and phenol (base vol.: 4 ml). The sample is mixed (vortexed) at high speed for at least 30 seconds. A volume of chloroform is added (4 ml) and again mixed and spun for 20 mins in a centrifuge at 5000 to 10,000×g. The aqueous phase is transferred to a new 12 ml tube and 1/3 volume of cold 8M LiCl is added to precipitate the RNA (3 h at 0° C.). The RNA is centrifuged at 0° C. for 20 mins and resuspended in 1 ml $H_2O$. Residual genomic DNA is removed by treating the RNA sample with DNase I. Reverse transcription is performed on each RNA sample using 500 ng of DNA free RNA in 1× reverse transcription buffer, 10 mM DTT, 20 $\mu$M dNTPs, 0.2 $\mu$M 5'RS H-T11C (one base anchored primer with 5' restriction site), 200 U MoMuLV reverse transcriptase and 1.5U RNA Guard per 20 $\mu$l reaction volume.

Although using a downstream primer reduces the number of cDNA subfractions to three, it does not reduce the number of PCR reactions required to display most of the cDNA species present in the pool. On the contrary, it decreases the theoretical chance of identifying those cDNA species which are present. The best results are obtained using a combination of nine different primers of the type DMO-VV, where V can be A,G,C but not T. With a T in the terminal 3' position, incomplete hybridization of the primer leads to smearing of bands on the gels. The optimal concentration of RNA is 200–300 ng per cDNA synthesis.

CMST-based differential display is performed essentially as previously described (Liang and Pardee, *Science* 257:967–971, 1992) except for the design of primers used for reverse transcription and amplification steps, and the choice of radiolabeled nucleotide. A complete differential display analysis of the cDNAs from two biological samples of interest using nine downstream primers and 24 upstream primers would generate 9×24×2 CMST-based differential display reactions Amplification products can be separated by HPLC and reamplified if desired.

Following incubation of the RNA at 65° C. for 5 minutes, samples are chilled on ice, added to the reverse transcription mix and incubated for 60 minutes at 37° C. followed by 95° C. for 5 minutes. Duplicate cDNA samples are then amplified using the same 5'-primer in combination with a series of 13 mers of arbitrary but defined sequence: H-AP: AAGCTTCGACTGT (Seq. ID No. 2), H-AP: AAGCTTTGGTCAG (Seq. ID No. 3), H-AP4: AAGCTTCTCAACG (Seq. ID No. 4), H-AP5: AAGCTTAGTAGGC (Seq. ID No. 5).

Amplification is performed in reaction mixes containing 0.1× volume of reverse transcription reaction, 1×PCR buffer (10×PCR buffer=100 mM TRIS-HCl, 15 mM MgCl2, 10 mM KCl pH 8.3) 2 $\mu$M dNTPs, 0.2 $\mu$M RS H-T11C anchored primer, 0.2 $\mu$M appropriate arbitrary primer, 1.5 U Expand™ high fidelity DNA polymerase, and water to a final volume of 20 $\mu$l. Amplification of the cDNA is performed under the following conditions: 94° C. (1 minute) followed by 40 cycles of 94° C. (30 seconds), 40° C. (2 minutes), 72° C. (30 seconds) and finished with 72° C. (5 minutes).

Amplification for each gene is performed with gene specific primers spanning a known intron/exon boundry (see tables below). All amplifications are done in 20 $\mu$l volumes containing 10 mM Tris HCl pH 8.3, 1 mM NH4Cl, 1.5 M MgCl2, 100 mM KCl, 0.125 mM NTPs, 10 ng/ml of the respective oligonucleotide primers and 0.75 units of Taq DNA polymerase (Gibco-BRL). Cycling parameters were 94° C. preheating step for 5 minutes followed by 94° C. denaturing step for 1 minute, 55° C. annealing step for 2 minutes, and a 72° C. extension step for 30 seconds to 1 minute and a final extension at 72° C. for 10 minutes. Amplification cycles are generally 30–45 in number.

Amplification products are gel purified (Zhen and Swank, *BioTechniques* 14::894–898, 1993) on 1% agarose gels run in 0.04 M Tris-acetate, 0.001 M EDTA (1×TEA) buffer and stained with ethidium bromide. A trough is cut just in front of the band of interest and filled with 50–200 $\mu$l of 10% PEG in 1×TAE buffer. Electrophoresis is continued until the band has completely entered the trough. The contents are then removed and extracted with phenol, cholorform extracted, and precipitated in 0.1 volume of 7.5 M ammonium acetate and 2.5 volumes of 100% EtOH. Samples are washed with 75% EtOH and briefly dried at ambient temperature. Quantitation of yield is done by electrophoresis of a small aliquot on 1% agarose gel in 1×TBE buffer with ethidium bromide staining and comparison to a known standard.

The products from the amplification reactions are analyzed by HPLC. HPLC ias carried out using automated HPLC instrumentation (Rainin, Emeryville, Calif., or Hewlett Packard, Palo Alto, Calif.). Unpurified DNA fingerprinting products which are denatured for 3 minutes at 95 prior into injection into an HPLC are eluted with linear acetonitrile (ACN, J. T. Baker, N.J.) gradient of 1.8%/minute at a flow rate of 0.9 ml/minute. The start and end points are adjusted according to the size of the amplified products. The temperature required for the successful resolution of the molecules generated during the DNA fingerprinting technique is 50° C. The effluent from the HPLC is then directed into a mass spectrometer (Hewlett Packard, Palo Alto, Calif.) for the detection of tags.

Comparison of the chromatograms (mass spectrometry-based) indicates that bands at 220 bp and 468 bp are observed in the stimulated Jurkat cells and not observed in the unstimulated Jurkat cells.

C. Separation of Nucleic Acid Fragments

A sample that requires analysis is often a mixture of many components in a complex matrix. For samples containing unknown compounds, the components must be separated from each other so that each individual component can be identified by other analytical methods. The separation properties of the components in a mixture are constant under constant conditions, and therefore once determined they can be used to identify and quantify each of the components. Such procedures are typical in chromatographic and electrophoretic analytical separations.

1. High-Performance Liquid Chromatography (HPLC)

High-Performance liquid chromatography (HPLC) is a chromatographic separations technique to separate compounds that are dissolved in solution. HPLC instruments consist of a reservoir of mobile phase, a pump, an injector, a separation column, and a detector. Compounds are separated by injecting an aliquot of the sample mixture onto the column. The different components in the mixture pass through the column at different rates due to differences in their partitioning behavior between the mobile liquid phase and the stationary phase.

Recently, IP-RO-HPLC on non-porous PS/DVB particles with chemically bonded alkyl chains have been shown to be rapid alternatives to capillary electrophoresis in the analysis of both single and double-strand nucleic acids providing similair degrees of resolution (Huber et al, *Anal.Biochem.* 212:351, 1993; Huber et al., 1993, *Nuc. Acids Res.* 21:1061; Huber et al., *Biotechniques* 16:898, 1993). In contrast to ion-excahnge chromoatrography, which does not always retain double-strand DNA as a function of strand length (Since AT base pairs intereact with the positively charged stationary phase, more strongly than GC base-pairs), IP-RP-HPLC enables a strictly size-dependent separation.

A method has been developed using 100 mM triethylammonium acetate as ion-pairing reagent, phosphodiester oligonucleotides could be successfully separated on alkylated non-porous 2.3 μM poly(styrene-divinylbenzene) particles by means of high performance liquid chromatography (Oefner et al., *Anal. Biochem.* 223:39, 1994). The technique described allowed the separation of PCR products differing only 4 to 8 base pairs in length within a size range of 50 to 200 nucleotides.

2. Electrophoresis

Electrophoresis is a separations technique that is based on the mobility of ions (or DNA as is the case described herein) in an electric field. Negatively charged DNA charged migrate towards a positive electrode and positively-charged ions migrate toward a negative electrode. For safety reasons one electrode is usually at ground and the other is biased positively or negatively. Charged species have different migration rates depending on their total charge, size, and shape, and can therefore be separated. An electrode apparatus consists of a high-voltage power supply, electrodes, buffer, and a support for the buffer such as a polyacrylamide gel, or a capillary tube. Open capillary tubes are used for many types of samples and the other gel supports are usually used for biological samples such as protein mixtures or DNA fragments.

3. Capillary Electrophoresis (CE)

Capillary electrophoresis (CE) in its various manifestations (free solution, isotachophoresis, isoelectric focusing, polyacrylamide gel, micellar electrokinetic "chromatography") is developing as a method for rapid high resolution separations of very small sample volumes of complex mixtures. In combination with the inherent sensitivity and selectivity of MS, CE-MS is a potential powerful technique for bioanalysis. In the novel application disclosed herein, the interfacing of these two methods will lead to superior DNA sequencing methods that eclipse the current rate methods of sequencing by several orders of magnitude.

The correspondence between CE and electrospray ionization (ESI) flow rates and the fact that both are facilitated by (and primarily used for) ionic species in solution provide the basis for an extremely attractive combination. The combination of both capillary zone electrophoresis (CZE) and capillary isotachophoresis with quadrapole mass spectrometers based upon ESI have been described (Olivares et al., *Anal. Chem.* 59:1230, 1987; Smith et al., *Anal. Chem.* 60:436, 1988; Loo et al., *Anal. Chem.* 179:404, 1989; Edmonds et al., *J. Chroma.* 474:21, 1989; Loo et al., *J. Microcolumn Sep.* 1:223, 1989; Lee et al., *J. Chromatog.* 458:313, 1988; Smith et al., *J. Chromatog.* 480:211, 1989; Grese et al., *J. Am. Chem. Soc.* 111:2835, 1989). Small peptides are easily amenable to CZE analysis with good (femtomole) sensitivity.

The most powerful separation method for DNA fragments is polyacrylamide gel electrophoresis (PAGE), generally in a slab gel format. However, the major limitation of the current technology is the relatively long time required to perform the gel electrophoresis of DNA fragments produced in the sequencing reactions. An increase magnitude (10-fold) can be achieved with the use of capillary electrophoresis which utilize ultrathin gels. In free solution to a first approximation all DNA migrate with the same mobility as the addition of a base results in the compensation of mass and charge. In polyacrylamide gels, DNA fragments sieve and migrate as a function of length and this approach has now been applied to CE. Remarkable plate number per meter has now been achieved with cross-linked polyacrylamide ($10^{-7}$ plates per meter, Cohen et al., *Proc. Natl. Acad. Sci., USA* 85:9660, 1988). Such CE columns as described can be employed for DNA sequencing. The method of CE is in principle 25 times faster than slab gel electrophoresis in a standard sequencer. For example, about 300 bases can be read per hour. The separation speed is limited in slab gel electrophoresis by the magnitude of the electric field which can be applied to the gel without excessive heat production. Therefore, the greater speed of CE is achieved through the use of higher field strengths (300 V/cm in CE versus 10 V/cm in slab gel electrophoresis). The capillary format reduces the amperage and thus power and the resultant heat generation.

Smith and others (Smith et al., *Nuc. Acids. Res.* 18:4417, 1990) have suggested employing multiple capillaries in parallel to increase throughput. Likewise, Mathies and Huang (Mathies and Huang, *Nature* 359:167, 1992) have introduced capillary electrophoresis in which separations are performed on a parallel array of capillaries and demonstrated high through-put sequencing (Huang et al., *Anal. Chem.* 64:967, 1992, Huang et al., *Anal. Chem.* 64:2149, 1992). The major disadvantage of capillary electrophoresis is the limited amount of sample that can be loaded onto the capillary. By concentrating a large amount of sample at the beginning of the capillary, prior to separation, loadability is increased, and detection levels can be lowered several orders of magnitude. The most popular method of preconcentration in CE is sample stacking. Sample stacking has recently been reviewed (Chien and Burgi, *Anal. Chem.* 64:489A, 1992). Sample stacking depends of the matrix difference, (pH, ionic strength) between the sample buffer and the capillary buffer, so that the electric field across the sample zone is more than in the capillary region. In sample stacking, a large volume of sample in a low concentration buffer is introduced for preconcentration at the head of the capillary column. The capillary is filled with a buffer of the same composition, but at higher concentration. When the sample ions reach the capillary buffer and the lower electric field, they stack into a concentrated zone. Sample stacking has increased detectabilities 1–3 orders of magnitude.

Another method of preconcentration is to apply isotachophoresis (ITP) prior to the free zone CE separation of analytes. ITP is an electrophoretic technique which allows microliter volumes of sample to be loaded on to the capillary. in contrast to the low nL injection volumes typically associated with CE. The technique relies on inserting the sample between two buffers (leading and trailing electrolytes) of higher and lower mobility respectively, than the analyte. The technique is inherently a concentration technique, where the analytes concentrate into pure zones migrating with the same speed. The technique is currently less popular than the stacking methods described above because of the need for several choices of leading and trailing electrolytes, and the ability to separate only cationic or anionic species during a separation process.

The heart of the DNA sequencing process is the remarkably selective electrophoretic separation of DNA or oligonucleotide fragments. It is remarkable because each fragment is resolved and differs by only nucleotide. Separations of up to 1000 fragments (1000 bp) have been obtained. A further advantage of sequencing with cleavable tags is as follows. There is no requirement to use a slab gel format when DNA fragments are separated by polyacrylamide gel electrophoresis when cleavable tags are employed. Since numerous samples are combined (4 to 2000) there is no need to run samples in parallel as is the case with current dye-primer or dye-terminator methods (i.e., ABI373 sequencer). Since there is no reason to run parallel lanes, there is no reason to use a slab gel. Therefore, one can employ a tube gel format for the electrophoretic separation method. Grossman (Grossman et al., *Genet. Anal. Tech. Appl.* 9:9, 1992) have shown that considerable advantage is gained when a tube gel format is used in place of a slab gel format. This is due to the greater ability to dissipate Joule heat in a tube format compared to a slab gel which results in faster run times (by 50%), and much higher resolution of high molecular weight DNA fragments (greater than 1000 nt). Long reads are critical in genomic sequencing. Therefore, the use of cleavable tags in sequencing has the additional advantage of allowing the user to employ the most efficient and sensitive DNA separation method which also possesses the highest resolution.

4. Microfabricated Devices

Capillary electrophoresis (CE) is a powerful method for DNA sequencing, forensic analysis, PCR product analysis and restriction fragment sizing. CE is far faster than traditional slab PAGE since with capillary gels a far higher potential field can be applied. However, CE has the drawback of allowing only one sample to be processed per gel. The method combines the faster separations times of CE with the ability to analyze multiple samples in parallel. The underlying concept behind the use of microfabricated devices is the ability to increase the information density in electrophoresis by miniaturizing the lane dimension to about 100 micrometers. The electronics industry routinely uses microfabrication to make circuits with features of less than one micron in size. The current density of capillary arrays is limited the outside diameter of the capillary tube. Microfabrication of channels produces a higher density of arrays. Microfabrication also permits physical assemblies not possible with glass fibers and links the channels directly to other devices on a chip. Few devices have been constructed on microchips for separation technologies. A gas chromatograph (Terry et al., *IEEE Trans. Electron Device*, ED-26:1880, 1979) and a liquid chromatograph (Manz et al., *Sens. Actuators* B1:249, 1990) have been fabricated on silicon chips, but these devices have not been widely used. Several groups have reported separating fluorescent dyes and amino acids on microfabricated devices (Manz et al., *J. Chromatography* 593:253, 1992, Effenhauser et al., *Anal. Chem.* 65:2637, 1993). Recently Woolley and Mathies (Woolley and Mathies, *Proc. Natl. Acad. Sci.* 91:11348, 1994) have shown that photolithography and chemical etching can be used to make large numbers of separation channels on glass substrates. The channels are filled with hydroxyethyl cellulose (HEC) separation matrices. It was shown that DNA restriction fragments could be separated in as little as two minutes.

D. Cleavage of Tags

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

- ethylene glycobis(succinimidylsuccinate) (EGS), an amine reactive cross-linking reagent which is cleavable by hydroxylamine (1 M at 37° C. for 3–6 hours);
- disuccinimidyl tartarate (DST) and sulfo-DST, which are amine reactive cross-linking reagents, cleavable by 0.015 M sodium periodate;
- bis[2-(succinimidyloxycarbonyloxy)ethyl]sulfone (BSOCOES) and sulfo-BSOCOES, which are amine reactive cross-linking reagents, cleavable by base (pH 11.6);
- 1,4-di-[3'-(2'-pyridyldithio(propionamido))butane (DPDPB), a pyridyldithiol crosslinker which is cleavable by thiol exchange or reduction;
- N-[4-(p-azidosalicylamido)-butyl]-3'-(2'-pyridydithio) propionamide (APDP), a pyridyldithiol crosslinker which is cleavable by thiol exchange or reduction;
- bis-[beta-4-(azidosalicylamido)ethyl]-disulfide, a photoreactive crosslinker which is cleavable by thiol exchange or reduction;
- N-succinimidyl-(4-azidophenyl)-1,3'dithiopropionate (SADP), a photoreactive crosslinker which is cleavable by thiol exchange or reduction;
- sulfosuccinimidyl-2-(7-azido-4-methylcoumarin-3-acetamide)ethyl-1,3'-dithiopropionate: (SAED), a photoreactive crosslinker which is cleavable by thiol exchange or reduction;
- sulfosuccinimidyl-2-(m-azido-o-nitrobenzamido)-ethyl-1,3'dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $O_sO_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O^+$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-, 4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to MOIs. Some of these linkers are described in a recent review by Lloyd-Williams et al. (*Tetrahedron* 49:11065–11133, 1993). One useful type of linker is based upon p-alkoxybenzyl alcohols, of which two, 4-hydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing MOI via an amide linkage to the carboxylic acid. Tags linked by these molecules are released from the MOI with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review). These linkers are usually based on 2-nitrobenzylesters or 2-nitrobenzylamides. Two examples of photolabile linkers that have recently been reported in the literature are 4-(4-(1-Fmoc-amino)ethyl)-2-methoxy-5-nitrophenoxy)butanoic acid (Holmes and Jones, *J. Org. Chem.* 60:2318–2319, 1995) and 3-(Fmoc-amino)-3-(2-nitrophenyl)propionic acid (Brown et al., *Molecular Diversity* 1:4–12, 1995). Both linkers can be attached via the carboxylic acid to an amine on the MOI. The attachment of the tag to the linker is made by forming an amide between a carboxylic acid on the tag and the amine on the linker. Cleavage of photolabile linkers is usually performed with UV light of 350 nm wavelength at intensities and times known to those in the art. Examples of commercial sources of instruments for photochemical cleavage are Aura Industries Inc. (Staten Island, N.Y.) and Agrenetics (Wilmington, Mass.). Cleavage of the linkers results in liberation of a primary amide on the tag. Examples of photocleavable linkers include nitrophenyl glycine esters, exo- and endo-2-benzonorborneyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

E. Detection of Tags

Detection methods typically rely on the absorption and emission in some type of spectral field. When atoms or molecules absorb light, the incoming energy excites a quantized structure to a higher energy level. The type of excitation depends on the wavelength of the light. Electrons are promoted to higher orbitals by ultraviolet or visible light, molecular vibrations are excited by infrared light, and rotations are excited by microwaves. An absorption spectrum is the absorption of light as a function of wavelength. The spectrum of an atom or molecule depends on its energy level structure. Absorption spectra are useful for identification of compounds. Specific absorption spectroscopic methods include atomic absorption spectroscopy (AA), infrared spectroscopy (IR), and UV-vis spectroscopy (uv-vis).

Atoms or molecules that are excited to high energy levels can decay to lower levels by emitting radiation. This light emission is called fluorescence if the transition is between states of; the same spin, and phosphorescence if the transition occurs between states of different spin. The emission intensity of an analyte is linearly proportional to concentration (at low concentrations), and is useful for quantifying the emitting species. Specific emission spectroscopic methods include atomic emission spectroscopy (AES), atomic fluorescence spectroscopy (AFS), molecular laser-induced fluorescence (LIF), and X-ray fluorescence (XRF).

When electromagnetic radiation passes through matter, most of the radiation continues in its original direction but a small fraction is scattered in other directions. Light that is scattered at the same wavelength as the incoming light is called Rayleigh scattering. Light that is scattered in transparent solids due to vibrations (phonons) is called Brillouin scattering. Brillouin scattering is typically shifted by 0.1 to 1 wave number from the incident light. Light that is scattered due to vibrations in molecules or optical phonons in opaque solids is called Raman scattering. Raman scattered light is shifted by as much as 4000 wavenumbers from the incident light. Specific scattering spectroscopic methods include Raman spectroscopy.

IR spectroscopy is the measurement of the wavelength and intensity of the absorption of mid-infrared light by a sample. Mid-infrared light (2.5–50 $\mu$m, 4000–200 $cm^{-1}$) is energetic enough to excite molecular vibrations to higher energy levels. The wavelength of IR absorption bands are characteristic of specific types of chemical bonds and IR spectroscopy is generally most useful for identification of organic and organometallic molecules.

Near-infrared absorption spectroscopy (NIR) is the measurement of the wavelength and intensity of the absorption of near-infrared light by a sample. Near-infrared light spans the 800 nm–2.5 $\mu$m (12,500–4000 $cm^{-1}$) range and is energetic enough to excite overtones and combinations of molecular vibrations to higher energy levels. NIR spectroscopy is typically used for quantitative measurement of organic functional groups, especially O—H, N—H, and C=O. The components and design of NIR instrumentation are similar to uv-vis absorption spectrometers. The light source is usually a tungsten lamp and the detector is usually a PbS solid-state detector. Sample holders can be glass or quartz and typical solvents are $CCl_4$ and $CS_2$. The convenient instrumentation of NIR spectroscopy makes it suitable for on-line monitoring and process control.

Ultraviolet and Visible Absorption Spectroscopy (uv-vis) spectroscopy is the measurement of the wavelength and intensity of absorption of near-ultraviolet and visible light by a sample. Absorption in the vacuum UV occurs at 100–200 nm; ($10^5$–50,000 $cm^{-1}$) quartz UV at 200–350 nm; (50,000–28,570 $cm^{-1}$) and visible at 350–800 nm; (28,570–12,500 $cm^{-1}$) and is described by the Beer-Lambert-Bouguet law. Ultraviolet and visible light are energetic enough to promote outer electrons to higher energy levels. UV-vis spectroscopy can be usually applied to molecules and inorganic ions or complexes in solution. The uv-vis spectra are limited by the broad features of the spectra. The light source is usually a hydrogen or deuterium lamp for uv measurements and a tungsten lamp for visible measurements. The wavelengths of these continuous light sources are selected with a wavelength separator such as a prism or grating monochromator. Spectra are obtained by scanning the wavelength separator and quantitative measurements can be made from a spectrum or at a single wavelength.

Mass spectrometers use the difference in the mass-to-charge ratio (m/z) of ionized atoms or molecules to separate them from each other. Mass spectrometry is therefore useful for quantitation of atoms or molecules and also for determining chemical and structural information about molecules. Molecules have distinctive fragmentation patterns that provide structural information to identify compounds. The general operations of a mass spectrometer are as follows. Gas-phase ions are created, the ions are separated in space or time based on their mass-to-charge ratio, and the quantity of ions of each mass-to-charge ratio is measured. The ion separation power of a mass spectrometer is described by the resolution, which is defined as R=m/delta m, where m is the ion mass and delta m is the difference in mass between two resolvable peaks in a mass spectrum. For example, a mass spectrometer with a resolution of 1000 can resolve an ion with a m/z of 100.0 from an ion with a m/z of 100.1.

In general, a mass spectrometer (MS) consists of an ion source, a mass-selective analyzer, and an ion detector. The magnetic-sector, quadrupole, and time-of-flight designs also require extraction and acceleration ion optics to transfer ions from the source region into the mass analyzer. The details of several mass analyzer designs (for magnetic-sector MS, quadrupole MS or time-of-flight MS) are discussed below. Single Focusing analyzers for magnetic-sector MS utilize a particle beam path of 180, 90, or 60 degrees. The various forces influencing the particle separate ions with different mass-to-charge ratios: With double-focusing analyzers, an electrostatic analyzer is added in this type of instrument to separate particles with difference in kinetic energies.

A quadrupole mass filter for quadrupole MS consists of four metal rods arranged in parallel. The applied voltages affect the trajectory of ions traveling down the flight path centered between the four rods. For given DC and AC voltages, only ions of a certain mass-to-charge ratio pass through the quadrupole filter and all other ions are thrown out of their original path. A mass spectrum is obtained by monitoring the ions passing through the quadrupole filter as the voltages on the rods are varied.

A time-of-flight mass spectrometer uses the differences in transit time through a "drift region" to separate ions of different masses. It operates in a pulsed mode so ions must be produced in pulses and/or extracted in pulses. A pulsed electric field accelerates all ions into a field-free drift region with a kinetic energy of qV, where q is the ion charge and V is the applied voltage. Since the ion kinetic energy is 0.5 $mV^2$, lighter ions have a higher velocity than heavier ions and reach the detector at the end of the drift region sooner. The output of an ion detector is displayed on an oscilloscope as a function of time to produce the mass spectrum.

The ion formation process is the starting point for mass spectrometric analyses. Chemical ionization is a method that employs a reagent ion to react with the analyte molecules (tags) to form ions by either a proton or hydride transfer. The reagent ions are produced by introducing a large excess of methane (relative to the tag) into an electron impact (EI) ion source. Electron collisions produce $CH_4^+$ and $CH_3^+$ which further react with methane to form $CH_5^-$ and $C_2H_5^+$. Another method to ionize tags is by plasma and glow discharge. Plasma is a hot, partially-ionized gas that effectively excites and ionizes atoms. A glow discharge is a low-pressure plasma maintained between two electrodes. Electron impact ionization employs an electron beam, usually generated from a tungsten filament, to ionize gas-phase atoms or molecules. An electron from the beam knocks an electron off analyte atoms or molecules to create ions. Electrospray ionization utilizes a very fine needle and a series of skimmers. A sample solution is sprayed into the source chamber to form droplets. The droplets carry charge when the exit the capillary and as the solvent vaporizes the droplets disappear leaving highly charged analyte molecules. ESI is particularly useful for large biological molecules that are difficult to vaporize or ionize. Fast-atom bombardment (FAB) utilizes a high-energy beam of neutral atoms, typically Xe or Ar, that strikes a solid sample causing desorption and ionization. It is used for large biological molecules that are difficult to get into the gas phase. FAB causes little fragmentation and usually gives a large molecular ion peak, making it useful for molecular weight determination. The atomic beam is produced by accelerating ions from an ion source though a charge-exchange cell. The ions pick up an electron in collisions with neutral atoms to form a beam of high energy atoms. Laser ionization (LIMS) is a method in which a laser pulse ablates material from the surface of a sample and creates a microplasma that ionizes some of the sample constituents. Matrix-assisted laser desorption ionization (MALDI) is a LIMS method of vaporizing and ionizing large biological molecules such as proteins or DNA fragments. The biological molecules are dispersed in a solid matrix such as nicotinic acid. A UV laser pulse ablates the matrix which carries some of the large molecules into the gas phase in an ionized form so they can be extracted into a mass spectrometer. Plasma-desorption ionization (PD) utilizes the decay of $^{252}Cf$ which produces two fission fragments that travel in opposite directions. One fragment strikes the sample knocking out 1–10 analyte ions. The other fragment strikes a detector and triggers the start of data acquisition. This ionization method is especially useful for large biological molecules. Resonance ionization (RIMS) is a method in which one or more laser beams are tuned in resonance to transitions of a gas-phase atom or molecule to promote it in a stepwise fashion above its ionization potential to create an ion. Secondary ionization (SIMS) utilizes an ion beam; such as $^3He^+$, $^{16}O^+$, or $^{40}Ar^+$; is focused onto the surface of a sample and sputters material into the gas phase. Spark source is a method which ionizes analytes in solid samples by pulsing an electric current across two electrodes.

A tag may become charged prior to, during or after cleavage from the molecule to which it is attached. Ionization methods based on ion "desorption", the direct formation or emission of ions from solid or liquid surfaces have allowed increasing application to nonvolatile and thermally labile compounds. These methods eliminate the need for neutral molecule volatilization prior to ionization and generally minimize thermal degradation of the molecular species. These methods include field desorption (Becky, *Principles of Field Ionization and Field Desorption Mass Spectrometry*, Pergamon, Oxford, 1977), plasma desorption (Sundqvist and Macfarlane, *Mass Spectrom. Rev.* 4:421, 1985), laser desorption (Karas and Hillenkamp, *Anal. Chem.* 60:2299, 1988; Karas et al., *Angew. Chem.* 101:805, 1989), fast particle bombardment (e.g., fast atom bombardment, FAB, and secondary ion mass spectrometry, SIMS, Barber et al., *Anal. Chem.* 54:645A, 1982), and thermospray (TS) ionization (Vestal, *Mass Spectrom. Rev.* 2:447, 1983). Thermospray is broadly applied for the on-line combination with liquid chromatography. The continuous flow FAB methods (Caprioli et al., *Anal. Chem.* 58:2949, 1986) have also shown significant potential. A more complete listing of ionization/mass spectrometry combinations is ion-trap mass spectrometry, electrospray ionization mass spectrometry, ion-spray mass spectrometry, liquid ionization mass spectrometry, atmospheric pressure ionization mass spectrometry, electron ionization mass spectrometry, metastable atom bombardment ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nano-spray mass spectrometry, nebulised spray ionization mass spectrometry, chemical ionization mass spectrometry, resonance ionization mass spectrometry, secondary ionization mass spectrometry, thermospray mass spectrometry.

The ionization methods amenable to nonvolatile biological compounds have overlapping ranges of applicability. Ionization efficiencies are highly dependent on matrix composition and compound type. Currently available results indicate that the upper molecular mass for TS is about 8000 daltons (Jones and Krolik, *Rapid Comm. Mass Spectrom.* 1:67, 1987). Since TS is practiced mainly with quadrapole mass spectrometers, sensitivity typically suffers disporportionately at higher mass-to-charge ratios (m/z). Time-of-flight (TOF) mass spectrometers are commercially available and possess the advantage that the m/z range is limited only by detector efficiency. Recently, two additional ionization methods have been introduced. These two methods are now referred to as matrix-assisted laser desorption (MALDI, Karas and Hillenkamp, *Anal. Chem.* 60:2299, 1988; Karas et al., *Angew. Chem.* 101:805, 1989) and electrospray ionization (ESI). Both methodologies have very high ionization efficiency (i.e., very high [molecular ions produced]/[molecules consumed]). Sensitivity, which defines the ultimate potential of the technique, is dependent on sample-size, quantity of ions, flow rate, detection efficiency and actual ionization efficiency.

Electrospray-MS is based on an idea first proposed in the 1960s (Dole et al., *J. Chem. Phys.* 49:2240, 1968). Electrospray ionization (ESI) is one means to produce charged molecules for analysis by mass spectroscopy. Briefly, electrospray ionization produces highly charged droplets by nebulizing liquids in a strong electrostatic field. The highly charged droplets, generally formed in a dry bath gas at atmospheric pressure, shrink by evaporation of neutral solvent until the charge repulsion overcomes the cohesive forces, leading to a "Coulombic explosion". The exact mechanism of ionization is controversial and several groups have put forth hypotheses (Blades et al., *Anal. Chem.* 63:2109–14, 1991; Kebarle et al., *Anal. Chem.* 65:A972–86, 1993; Fenn, *J. Am. Soc. Mass. Spectrom.* 4:524–35, 1993). Regardless of the ultimate process of ion formation, ESI produces charged molecules from solution under mild conditions.

The ability to obtain useful mass spectral data on small amounts of an organic molecule relies on the efficient production of ions. The efficiency of ionization for ESI is related to the extent of positive charge associated with the molecule. Improving ionization experimentally has usually involved using acidic conditions. Another method to improve ionization has been to use quaternary amines when possible (see Aebersold et al., *Protein Science* 1:494–503, 1992; Smith et al., *Anal. Chem.* 60:436–41, 1988).

Electrospray ionization is described in more detail as follows. Electrospray ion production requires two steps: dispersal of highly charged droplets at near atmospheric pressure, followed by conditions to induce evaporation. A solution of analyte molecules is passed through a needle that is kept at high electric potential. At the end of the needle, the solution disperses into a mist of small highly charged droplets containing the analyte molecules. The small droplets evaporate quickly and by a process of field desorption or residual evaporation, protonated protein molecules are released into the gas phase. An electrospray is generally produced by application of a high electric field to a small flow of liquid (generally 1–10 uL/min) from a capillary tube. A potential difference of 3–6 kV is typically applied between the capillary and counter electrode located 0.2–2 cm away (where ions, charged clusters, and even charged droplets, depending on the extent of desolvation, may be sampled by the MS through a small orifice). The electric field results in charge accumulation on the liquid surface at the capillary terminus; thus the liquid flow rate, resistivity, and surface tension are important factors in droplet production. The high electric field results in disruption of the liquid surface and formation of highly charged liquid droplets. Positively or negatively charged droplets can be produced depending upon the capillary bias. The negative ion mode requires the presence of an electron scavenger such as oxygen to inhibit electrical discharge.

A wide range of liquids can be sprayed electrostatically into a vacuum, or with the aid of a nebulizing agent. The use of only electric fields for nebulization leads to some practical restrictions on the range of liquid conductivity and dielectric constant. Solution conductivity of less than $10^{-5}$ ohms is required at room temperature for a stable electrospray at useful liquid flow rates corresponding to an aqueous electrolyte solution of $<10^{-4}$ M. In the mode found most useful for ESI-MS, an appropriate liquid flow rate results in dispersion of the liquid as a fine mist. A short distance from the capillary the droplet diameter is often quite uniform and on the order of 1 $\mu$m. Of particular importance is that the total electrospray ion current increases only slightly for higher liquid flow rates. There is evidence that heating is useful for manipulating the electrospray. For example, slight heating allows aqueous solutions to be readily electrosprayed, presumably due to the decreased viscosity and surface tension. Both thermally-assisted and gas-nebulization-assisted electrosprays allow higher liquid flow rates to be used, but decrease the extent of droplet charging. The formation of molecular ions requires conditions effecting evaporation of the initial droplet population. This can be accomplished at higher pressures by a flow of dry gas at moderate temperatures (<60° C.), by heating during transport through the interface, and (particularly in the case of ion trapping methods) by energetic collisions at relatively low pressure.

Although the detailed processes underlying ESI remain uncertain, the very small droplets produced by ESI appear to allow almost any species carrying a net charge in solution to be transferred to the gas phase after evaporation of residual solvent. Mass spectrometric detection then requires that ions have a tractable m/z range (<4000 daltons for quadrupole instruments) after desolvation, as well as to be produced and transmitted with sufficient efficiency. The wide range of solutes already found to be amenable to ESI-MS, and the lack of substantial dependence of ionization efficiency upon molecular weight, suggest a highly non-discriminating and broadly applicable ionization process.

The electrospray ion "source" functions at near atmospheric pressure. The electrospray "source" is typically a metal or glass capillary incorporating a method for electrically biasing the liquid solution relative to a counter electrode. Solutions, typically water-methanol mixtures containing the analyte and often other additives such as acetic acid, flow to the capillary terminus. An ESI source has been described (Smith et al., *Anal. Chem.* 62:885, 1990) which can accommodate essentially any solvent system. Typical flow rates for ESI are 1–10 uL/min. The principal requirement of an ESI-MS interface is to sample and transport ions from the high pressure region into the MS as efficiently as possible.

The efficiency of ESI can be very high, providing the basis for extremely sensitive measurements, which is useful for the invention described herein. Current instrumental performance can provide a total ion current at the detector of about $2 \times 10^{-12}$ A or about $10^7$ counts/s for singly charged species. On the basis of the instrumental performance, concentrations of as low as $10^{-10}$ M or about $10^{-18}$ mol/s of a singly charged species will give detectable ion current (about 10 counts/s) if the analyte is completely ionized. For example, low attomole detection limits have been obtained for quaternary ammonium ions using an ESI interface with capillary zone electrophoresis (Smith et al., *Anal. Chem.* 59:1230, 1988). For a compound of molecular weight of 1000, the average number of charges is 1, the approximate number of charge states is 1, peak width (m/z) is 1 and the maximum intensity (ion/s) is $1 \times 10^{12}$.

Remarkably little sample is actually consumed in obtaining an ESI mass spectrum (Smith et al., *Anal. Chem.* 60:1948, 1988). Substantial gains might be also obtained by the use of array detectors with sector instruments, allowing simultaneous detection of portions of the spectrum. Since currently only about $10^{-5}$ of all ions formed by ESI are detected, attention to the factors limiting instrument performance may provide a basis for improved sensitivity. It will be evident to those in the art that the present invention contemplates and accommodates for improvements in ionization and detection methodologies.

An interface is preferably placed between the separation instrumentation (e.g., gel) and the detector (e.g., mass spectrometer). The interface preferably has the following properties: (1) the ability to collect the DNA fragments at discreet time intervals, (2) concentrate the DNA fragments, (3) remove the DNA fragments from the electrophoresis buffers and milieu, (4) cleave the tag from the DNA fragment, (5) separate the tag from the DNA fragment, (6) dispose of the DNA fragment, (7) place the tag in a volatile solution, (8) volatilize and ionize the tag, and (9) place or transport the tag to an electrospray device that introduces the tag into mass spectrometer.

The interface also has the capability of "collecting" DNA fragments as they elute from the bottom of a gel. The gel may be composed of a slab gel, a tubular gel, a capillary, etc.

The DNA fragments can be collected by several methods. The first method is that of use of an electric field wherein DNA fragments are collected onto or near an electrode. A second method is that wherein the DNA fragments are collected by flowing a stream of liquid past the bottom of a gel. Aspects of both methods can be combined wherein DNA collected into a flowing stream which can be later concentrated by use of an electric field. The end result is that DNA fragments are removed from the milieu under which the separation method was performed. That is, DNA fragments can be "dragged" from one solution type to another by use of an electric field.

Once the DNA fragments are in the appropriate solution (compatible with electrospray and mass spectrometry) the tag can be cleaved from the DNA fragment. The DNA fragment (or remnants thereof) can then be separated from the tag by the application of an electric field (preferably, the tag is of opposite charge of that of the DNA tag). The tag is then introduced into the electrospray device by the use of an electric field or a flowing liquid.

Fluorescent tags can be identified and quantitated most directly by their absorption and fluorescence emission wavelengths and intensities.

While a conventional spectrofluorometer is extremely flexible, providing continuous ranges of excitation and emission wavelengths ($l_{EX}$, $l_{S1}$, $l_{S2}$), more specialized instruments such as flow cytometers and laser-scanning microscopes require probes that are excitable at a single fixed wavelength. In contemporary instruments, this is usually the 488-nm line of the argon laser.

Fluorescence intensity per probe molecule is proportional to the product of e and QY. The range of these parameters among fluorophores of current practical importance is approximately 10,000 to 100,000 $cm^{-1}M^{-1}$ for $\epsilon$ and 0.1 to 1.0 for QY. When absorption is driven toward saturation by high-intensity illumination, the irreversible destruction of the excited fluorophore (photobleaching) becomes the factor limiting fluorescence detectability. The practical impact of photobleaching depends on the fluorescent detection technique in question.

It will be evident to one in the art that a device (an interface) may be interposed between the separation and detection steps to permit the continuous operation of size separation and tag detection (in real time). This unites the separation methodology and instrumentation with the detection methodology and instrumentation forming a single device. For example, an interface is interposed between a separation technique and detection by mass spectrometry or potentiostatic amperometry.

The function of the interface is primarily the release of the (e.g., mass spectrometry) tag from analyte. There are several representative implementations of the interface. The design of the interface is dependent on the choice of cleavable linkers. In the case of light or photo-cleavable linkers, an energy or photon source is required. In the case of an acid-labile linker, a base-labile linker, or a disulfide linker, reagent addition is required within the interface. In the case of heat-labile linkers, an energy heat source is required. Enzyme addition is required for an enzyme-sensitive linker such as a specific protease and a peptide linker, a nuclease and a DNA or RNA linker, a glycosylase, HRP or phosphatase and a linker which is unstable after cleavage (e.g., similar to chemiluminescent substrates). Other characteristics of the interface include minimal band broadening, separation of DNA from tags before injection into a mass spectrometer. Separation techniques include those based on electrophoretic methods and techniques, affinity techniques, size retention (dialysis), filtration and the like.

It is also possible to concentrate the tags (or nucleic acid-linker-tag construct), capture electrophoretically, and then release into alternate reagent stream which is compatible with the particular type of ionization method selected. The interface may also be capable of capturing the tags (or nucleic acid-linker-tag construct) on microbeads, shooting the bead(s) into chamber and then preforming laser desorption/vaporization. Also it is possible to extract in flow into alternate buffer (e.g., from capillary electrophoresis buffer into hydrophobic buffer across a permeable membrane). It may also be desirable in some uses to deliver tags into the mass spectrometer intermittently which would comprise a further function of the interface. Another function of the interface is to deliver tags from multiple columns into a mass spectrometer, with a rotating time slot for each column. Also, it is possible to deliver tags from a single column into multiple MS detectors, separated by time, collect each set of tags for a few milliseconds, and then deliver to a mass spectrometer.

The following is a list of representative vendors for separation and detection technologies which may be used in the present invention. Hoefer Scientific Instruments (San Francisco, Calif.) manufactures electrophoresis equipment (Two Step™, Poker Face™ II) for sequencing applications. Pharmacia Biotech (Piscataway, N.J.) manufactures electrophoresis equipment for DNA separations and sequencing (PhastSystem for PCR-SSCP analysis, MacroPhor System for DNA sequencing). Perkin Elmer/Applied Biosystems Division (ABI, Foster City, Calif.) manufactures semi-automated sequencers based on fluorescent-dyes (ABI373 and ABI377). Analytical Spectral Devices (Boulder, Colo.) manufactures UV spectrometers. Hitachi Instruments (Tokyo, Japan) manufactures Atomic Absorption spectrometers. Fluorescence spectrometers, LC and GC Mass Spectrometers, NMR spectrometers, and UV-VIS Spectrometers. PerSeptive Biosystems (Framingham, Mass.) produces Mass Spectrometers (Voyager™ Elite). Bruker Instruments Inc. (Manning Park, Mass.) manufactures FTIR Spectrometers (Vector 22), FT-Raman Spectrometers, Time of Flight Mass Spectrometers (Reflex II™), Ion Trap Mass Spectrometer (Esquire™) and a Maldi Mass Spectrometer. Analytical Technology Inc. (ATI, Boston, Mass.) makes Capillary Gel Electrophoresis units, UV detectors, and Diode Array Detectors. Teledyne Electronic Technologies (Mountain View, Calif.) manufactures an Ion Trap Mass Spectrometer (3DQ Discovery™ and the 3DQ Apogee™). Perkin Elmer/Applied Biosystems Division (Foster City, Calif.) manufactures a Sciex Mass Spectrometer (triple quadrupole LC/MS/MS, the API 100/300) which is compatible with electrospray. Hewlett-Packard (Santa Clara, Calif.) produces Mass Selective Detectors (HP 5972A), MALDI-TOF Mass Spectrometers (HP G2025A), Diode Array Detectors, CE units, HPLC units (HP1090) as well as UV Spectrometers. Finnigan Corporation (San Jose, Calif.) manufactures mass spectrometers (magnetic sector (MAT 95 S™), quadrupole spectrometers (MAT 95 SQ™) and four other related mass spectrometers). Rainin (Emeryville, Calif.) manufactures HPLC instruments.

The methods and compositions described herein permit the use of cleaved tags to serve as maps to particular sample type and nucleotide identity. At the beginning of each sequencing method, a particular (selected) primer is assigned a particular unique tag. The tags map to either a sample type, a dideoxy terminator type (in the case of a Sanger sequencing reaction) or preferably both. Specifically, the tag maps to a primer type which in turn maps to a vector type which in turn maps to a sample identity. The tag may also may map to a dideoxy terminator type (ddTTP, ddCTP, ddGTP, ddATP) by reference into which dideoxynucleotide reaction the tagged primer is placed. The sequencing reaction is then performed and the resulting fragments are sequentially separated by size in time.

The tags are cleaved from the fragments in a temporal frame and measured and recorded in a temporal frame. The sequence is constructed by comparing the tag map to the temporal frame. That is, all tag identities are recorded in time after the sizing step and related become related to one another in a temporal frame. The sizing step separates the nucleic acid fragments by a one nucleotide increment and hence the related tag identities are separated by a one nucleotide increment. By foreknowledge of the dideoxy-terminator or nucleotide map and sample type, the sequence is readily deduced in a linear fashion.

Figure 15:
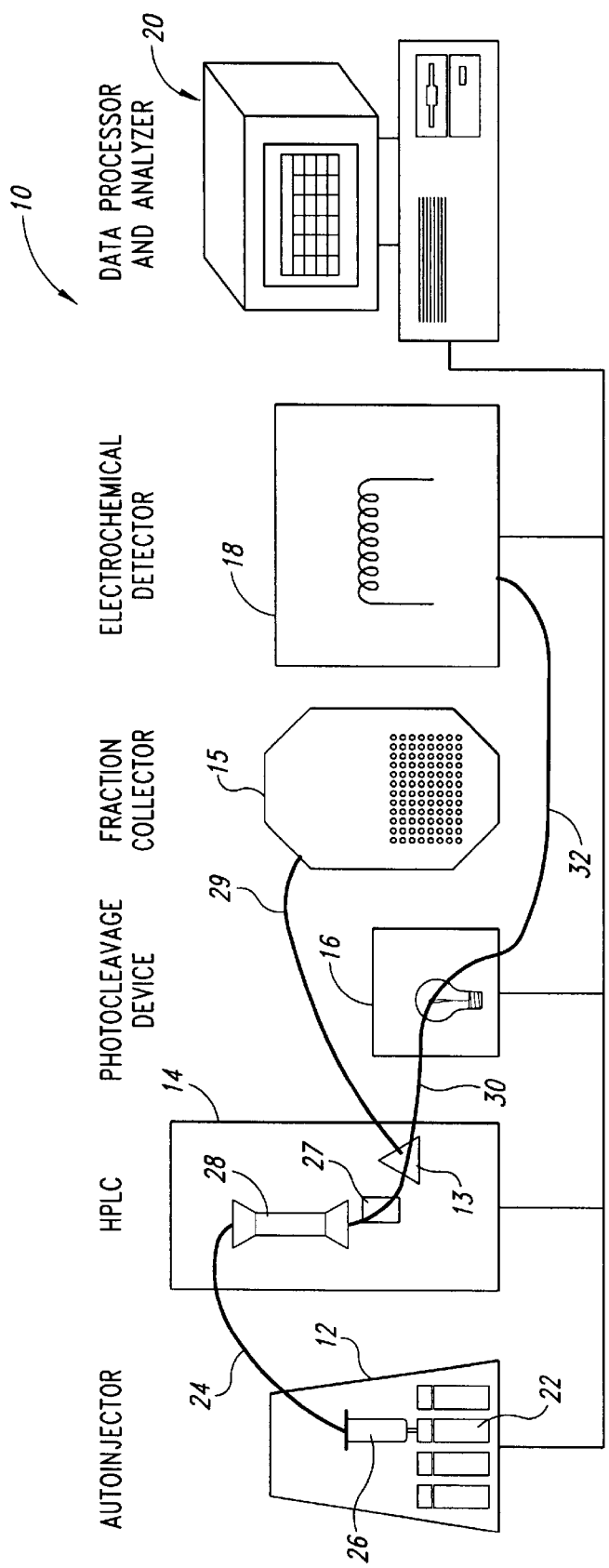
FIG. 15 is a schematic representation of genetic fingerprinting and differential display systems in accordance with an exemplary embodiment of the present invention.

A genetic fingerprinting system of the present invention consists of, in general, a sample introduction device, a device to separate the tagged samples of interest, a splitting device to deviate a variable amount of the sample to a fraction collector, a device to cleave the tags from the samples of interest, a device for detecting the tag, and a software program to analyze the data collected and display it in a differential display mode. It will be evident to one of ordinary skill in the art when in possession of the present disclosure that this general description may have many variances for each of the components listed. As best seen in FIG. 15, an exemplary genetic fingerprinting system 10 of the present invention consists of a sample introduction device 12, a separation device 14 that separates the samples by high-performance liquid chromatography (HPLC), a splitting device 13, a fraction collector 15, a photocleavage device 16 to cleave the tags from the samples of interest, a detection device 18 that detects the tags by means of an electrochemical detector, and a data processing device 20 with a data analysis software program that analyzes the results from the detection device. Each component is discussed in more detail below.

The sample introduction device 12 automatically takes a measured aliquot 22 of the PCR products generated in the genetic fingerprinting procedure and delivers it through a conventional tube 24 to the separation device 14 (generally an HPLC). The sample introduction device 12 of the exemplary embodiment consists of a temperature-controlled autosampler 26 that can accommodate micro-titer plates. The autosampler 26 is temperature controlled to maintain the integrity of the nucleic acid samples generated and is able to inject 25 μl or less of sample. Manufacturers of this type of sample introduction device 12 are, for example, Gilson (Middleton, Wis.).

The sample introduction device is operatively connected in series to the separation device 14 by the conventional tube 24. The PCR products in the measured aliquot 22 received in the separation device 14 are separated temporally by high performance liquid chromatography to provide separated DNA fragments. The high-performance liquid chromatograph may have an isocratic, binary, or quaternary pump(s) 27 and can be purchased from multiple manufacturers (e.g., Hewlett Packard (Palo Alto, Calif.) HP 1100 or 1090 series, Beckman Instruments Inc. (800-742-2345), Bioanalytical Systems, Inc. (800845-4246), ESA, Inc. (508) 250-700), Perkin-Elmer Corp. (800-762-4000), Varian Instruments (800-926-3000), Waters Corp. (800-254-4752)).

The separation device 14 includes an analytical HPLC column 28 suitable for use to separate the oligonucleotides. The column 28 is an analytical HPLC, for example, non-porous polystyrene divinylbenzene (2.2 μm particle size)

solid support modified which can operate within a pH range of 2 to 12, pressures of up to 3000 psi and a temperature range of 10 to 70° C. A temperature-control device (e.g. a column oven) (not shown) may be used to control the temperature of the column. Such temperature-control devices are known in the art, and may be obtained from, for example, Rainin Instruments (subsidiary of Varian Instrument, Palo Alto, Calif.). A suitable column 28 is available under the commercial name of DNAsep® and is available from Serasep (San Jose, Calif.). Other suitable analytical HPLC columns are available from other manufacturers (e.g., Hewlett Packard (Palo Alto, Calif.), Beckman Industries (Brea, Calif.), Waters Corp. (Milford, Mass.), and Supelco (Bellefonte, Pa.).

The separation device 14 in the illustrated embodiment incorporates the sample splitter 13, and the sample splitter is connected to the flowing stream of the sample. The sample splitter 13 is adapted to divert in a conventional manner variable amounts of sample to the fraction collector 15 either for further analysis or storage. The fraction collector 15 must be able to accommodate small volumes, have temperature control to low temperatures, and have adjustable sampling times. Manufacturers of in-line splitters include Upchurch (Oak Harbor, Wash.).

The fraction collector 15 is attached to the HPLC/LC device via a stream-splitter line 29. Fraction collectors 15 permit the collection of specific peaks, DNAs, RNAs, and nucleic acid fragments or molecules of interest into tubes, wells of microtiter plates, or containers. Additionally, fraction collectors 15 can collect all or part of a set of nucleic acid fragments separated by HPLC or LC. Manufacturers of fraction collectors include Gilson (Middleton, Wis.), and Isco (Lincoln, Nebr.). The use of a fraction collector 15 in this technology provides considerable substantial advantages over gel based systems. For example, it is possible to directly clone nucleic acids fragments recovered by HPLC or LC methods. In addition, it is possible to amplify nucleic acids fragments recovered by HPLC or LC methods by PCR. These two methods permit the rapid identification of nucleic acid fragments of interest on a sequence level. Both methods are tedious and ineffective when used in conjunction with gel-based systems.

In the illustrated embodiment, the fraction collector 15 is an individual component of the genetic fingerprinting system 10. In an alternate embodiment (not shown), the fraction collector 15 is incorporated in the sample introduction device 12. Accordingly, the stream-splitter line 32 directs the diverted sample from the sample splitter 13 back to the sample introduction device 12.

A stream of the separated DNA fragments (e.g., sequencing reaction products) flows through a conventional tube 30 from the separation device 14 downstream of the sample splitter 13 to the cleavage device 16. Each of the DNA fragments is labeled with a unique cleavable (e.g., photocleavable) tag. The flowing stream of separated DNA fragments pass through or past the cleaving device 16, where the tag is removed for detection (e.g., by mass spectrometry or with an electrochemical detector). In the exemplary embodiment, the cleaving device 16 is a photocleaving unit such that flowing stream of sample is exposed to selected light energy and wave length. In one embodiment, the sample enters the photocleaving unit 16 and is exposed to the selected light source for a selected duration of time. In an alternate embodiment, the flowing stream of sample is carried adjacent to the light source along a path that provides a sufficient exposure to the light energy to cleave the tags from the separated DNA fragments.

A photocleaving unit is available from Supelco (Bellefonte, Pa.). Photocleaving can be performed at multiple wavelengths with a mercury/xenon arc lamp. The wavelength accuracy is about 2 nm with a bandwidth of 10 nm. The area irradiated is circular and typically of an area of 10–100 square centimeters. In alternate embodiments, other cleaving devices, which cleave by acid, base, oxidation, reduction, fluoride, thiol exchange, photolysis, or enzymatic conditions, can be used to remove the tags from the separated DNA fragments.

After the cleaving device 16 cleaves the tags from the separated DNA fragments, the tags flow through a conventional tube 32 to the detection device 18 for detection of each tag. Detection of the tags can be based upon the difference in electrochemical potential between each of the tags used to label each kind of DNA generated in the PCR step. The electrochemical detector 18 can operate on either coulometric or amperometric principles. The preferred electromechanical detector 18 is the coulometric detector, which consists of a flow-through or porous-carbon graphite amperometric detector where the column eland passes through the electrode resulting in 100% detection efficiency. To fully detect each component, an array of 16 coulometric detectors each held at a different potential (generally at 60 mV increments) is utilized. Examples of manufacturers of this type of detector are ESA (Bedford, Mass.) and Bioanalytical Systems Inc. (800-845-4246).

Figure 16:
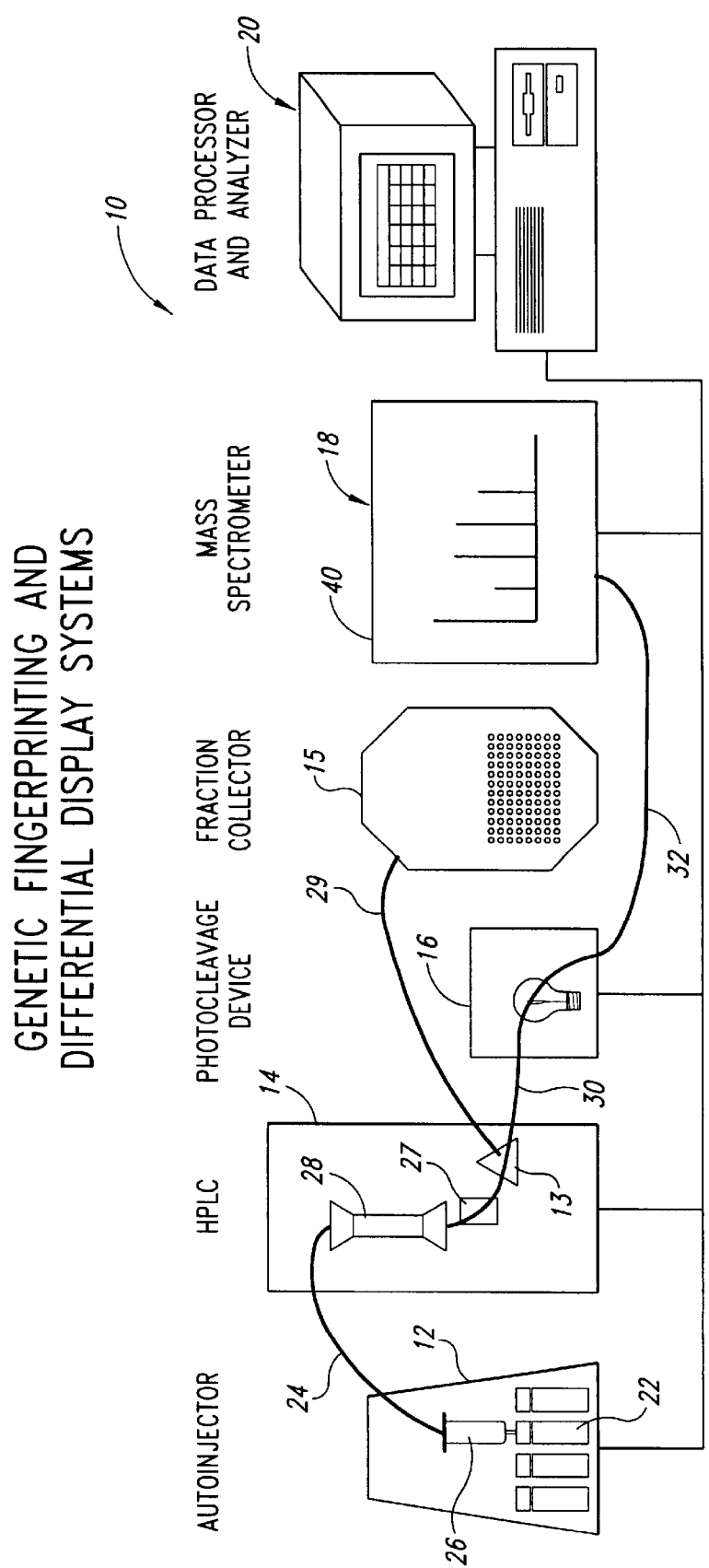
FIG. 16 is a schematic representation of genetic fingerprinting and differential display systems in accordance with an exemplary embodiment of the present invention.

In an alternate embodiment illustrated schematically in FIG. 16, the sample introduction device 12, the separating device 14, and the cleavage device 16 are serially connected as discussed above for maintaining the flow of sample. The cleavage device 16 is connected to a detection device 18 which is a mass spectrometer 40 or the like that detects the tags based upon the difference in molecular weight between each of the tags used to label each kind of DNA generated in the PCR step. The best detector based upon differences in mass is the mass spectrometer. For this use, the mass spectrometer 40 will typically have an atmospheric pressure ionization (API) interface with either electrospray or chemical ionization, a quadrupole mass analyzer, and a mass range of at least 50 to 2600 m/z. Examples of manufacturers of a suitable mass spectrometer are: Hewlett Packard (Palo Alto, Calif.) HP 1100 LC/MSD, Hitachi Instruments (San Jose, Calif.), M-1200H LC/MS, Perkin Elmer Corporation, Applied Biosystems Division (Foster City, Calif.) API 100 LC/MS or API 300 LC/MS/MS, Finnigan Corporation (San Jose, Calif.) LCQ, MAT 95 S, Bruker Analytical Systems, Inc. (Billerica, Mass.) APEX, BioAPEX, and ESQUIRE and Micromass (U.K.).

The detection device 18 is electrically connected to a data processor and analyzer 20 that receives data from the detection device. The data processor and analyzer 20 includes a software program that identifies the detected tag. The data processor and analyzer 230 in alternate embodiments is operatively connected to the injection device 12, the separation device 14, the fraction collector 15, and/or the cleaving device 16 to control the different components of the genetic fingerprinting system 10.

The software package maps the electrochemical signature of a given tag to a specific primer, and a retention time. Software generated nucleic acid profiles are then compared (length to length, fragment to fragment) and the results are reported to the user. The software will highlight both similarities and differences in the nucleic acid fragment profiles. The software will also be able to direct the collection of specific nucleic acid fragments by the fraction collector 15.

The software package maps the m/z signature of a given tag to a specific primer, and a retention time. Software generated nucleic acid profiles are then compared (length to length, fragment to fragment) and the results are reported to the user. The software will highlight both similarities and differences in the nucleic acid fragment profiles. The software will also be able to direct the collection of specific nucleic acid fragments by the fraction collector.

The system 18 in accordance with the present invention is provided by operatively interconnecting the system's multiple components. Accordingly, one or more system components, such as the sample introducing device 12 and the detecting device 18 that, are in operation in a lab can be combined with the system's other components, (e.g., the separating device 14, cleaving device 16, and the data processor and analyzer 20 in order to equip the lab with the DNA sequencing system 10 of the present invention.

Another embodiment of the present invention provides a differential display system which consists of, in general, a sample introduction device, a device to separate the tagged samples of interest, a splitting device to deviate a variable amount of the sample to a fraction collector, a unit to cleave the tags from the samples of interest, a device for detecting the tag, and a software program to analyze the data collected and display it in a differential display mode. It will be evident to one of ordinary skill in possession of the present disclosure that the general description may have many variances for each of the components listed. The differential display system of an exemplary embodiments of the present invention consists of similar components illustrated in FIG. 15, including the sample introduction device 12, the separation device 14 for separating the samples by high-performance liquid chromatography (HPLC), the splitting device 13, the fraction collector 15, the photocleavage device 16 to cleave the tags from the samples of interest, the detection device 18 for detection of the tags by electrochemistry, and the data processor and analyzer 20 with a software program. Each component is discussed in more detail below.

In the differential display system, the sample introduction device 12 automatically takes a measured aliquot 22 of the PCR product generated in the differential display procedure and delivers it through a conventional tube 24 to the separation device 14 (generally an HPLC). The sample introduction device 12 of the exemplary embodiment consists of a temperature-controlled autosampler 26 that can accommodate micro-titer plates. The autosampler 26 must be temperature controlled to maintain the integrity of the nucleic acid samples generated and be able to inject 25 $\mu$l or less of sample. Manufacturers of this type of product are represented, for example, by Gilson (Middleton, Wis.).

The sample introduction device is operatively connected in series to the separation device by the conventional tube 24. The PCR products in the measured aliquot 22 received in the separation device 14 are separated temporally by high performance liquid chromatography to provide separated DNA fragments. The high-performance liquid chromatograph may have an isocratic, binary, or quaternary pump(s) 27 and can be purchased from multiple manufacturers (e.g., Hewlett Packard (Palo Alto, Calif.) HP 1100 or 1090 series, Analytical Technology Inc. (Madison, Wis.), Perkin Elmer, Waters, etc.). The separation device 14 includes an analytical HPLC column 28 suitable for use to separate the oligonucleotides. The column 28 is an analytical HPLC, for example, non-porous polystyrene divinylbenzene (2.2 $\mu$m particle size) solid support modified which can operate within a pH range of 2 to 12, pressures of up to 3000 psi and a temperature range of 10 to 70° C. A temperature-control device (e.g., a column oven) (not shown) may be used to control the temperature of the column. Such temperature-control devices are known in the art, and may be obtained from, for example, Rainin Instruments (subsidiary of Varian Instrument, Palo Alto, Calif.). A suitable column 28 is available under the commercial name of DNAsep® and is available from Serasep (San Jose, Calif.). Other suitable analytical HPLC columns are available from other manufacturers (e.g., Hewlett Packard (Palo Alto, Calif.) (Beckman Industries (Brea, Calif.), Waters Corp. (Milford, Mass.), and Supelco (Bellefonte, Pa.).

In the illustrated embodiment, the fraction collector 15 is an individual component of the differential display system 10 that is coupled to the system's other components. In an alternate embodiment, the fraction collector 15 is incorporated in the sample introduction device 12. Accordingly, the stream-splitter line 32 directs the diverted sample from the sample splitter 13 back to the sample introduction device 12.

The separation device 14 in the illustrated embodiment incorporates the sample splitter 13 that is connected to the flowing stream of the sample. The sample splitter 13 is adapted to divert in a conventional manner variable amounts of sample to the fraction collector 15 either for further analysis or storage. The fraction collector 15 must be able to accommodate small volumes, have temperature control to low temperatures, and have adjustable sampling times. Manufacturers of in-line splitters include Upchurch (Oak Harbor, Wash.).

A stream of the separated DNA fragments flow through a conventional tube 30 from the separation device 14 downstream of the sample splitter 113 to the cleavage device 16. Each of the PCR products is labeled with a unique cleavable (e.g., photocleavable) tag. The flowing stream of separated DNA fragments pass through or past the cleaving device 16 where the tag is removed for detection by electrochemical detection. In the exemplary embodiment, the cleaving device 16 is a photocleaving unit such that flowing stream of sample is exposed to selected light energy. In one embodiment, the sample enters the photocleaving unit 16 and is exposed to the selected light source for a selected duration of time. In an alternate embodiment, the flowing stream of sample is carried in a suitable tube portion or the like adjacent to the light source along a path that provides a sufficient exposure to the light source to cleave the tags from the separated DNA fragments.

A photocleaving unit is available from Supelco (Bellefonte, Pa.). Photocleaving can be performed at multiple wavelengths with a mercury/xenon arc lamp. The wavelength accuracy is about 2 nm with a bandwidth of 10 nm. The area irradiated is circular and typically of an area of 10–100 square centimeters. In alternate embodiments, other cleaving devices, which cleave by acid, base, oxidation, reduction, fluoride, thil exchange, photolysis, or enzymatic conditions, can be used to remove the tags from the separated DNA fragments.

After the cleaving device 16 cleaves the tags from the separated DNA fragments, the tags flow through a conventional tube 32 to the detection device 18 for detection of each tag. Detection of the tags is based upon the difference in electrochemical potential between each of the tags used to label each kind of DNA generated in the PCR step. The electrochemical detector 18 can operate on either coulometric or amperometric principles. The preferred electromechanical detector 18 is the coulometric detector, which consists of a flow-through or porous-carbon graphite amperometric detector where the column eluent passes through the electrode resulting in 100% detection efficiency. To fully detect each component, an array of 16 coulometric detectors each held at a different potential (generally at 60 mV increments) is utilized. The manufacturers of this type of detector include ESA (Bedford, Mass.) and Bioanalytical Systems Inc. (800-845-4246).

In an alternate embodiment of the differential display system illustrated schematically in FIG. 16, the sample introduction device 12, the separating device 14, and the cleavage device 16 are serially connected as discussed above for maintaining the flow of sample. The cleavage device 16 is connected to a detection device 18 that detects the tags based upon the difference in molecular weight between each of the tags used to label each kind of DNA generated in the PCR step. The best detector based upon differences in mass is the mass spectrometer 40. For this use, the mass spectrometer will typically have an atmospheric pressure ionization (API) interface with either electrospray or chemical ionization, a quadrupole mass analyzer, and a mass range of at least 50 to 2600 m/z. Examples of manufacturers of a suitable mass spectrometer are: Hewlett Packard (Palo Alto, Calif.) HP 1100 LC/MSD, Hitachi Instruments (San Jose, Calif.), M-1200H LC/MS, JEOL. USA, Inc. (Peabody, Mass.), Perkin Elmer Corporation, Applied Biosystems Division (Foster City, Calif.) API 100 LC/MS or API 300 LC/MS/MS, Finnigan Corporation (San Jose, Calif.) LCQ, MAT 95 S, MAT 95 S Q, MAT 900 S, MAT 900 S Q, and SSQ 7000, Bruker Analytical Systems, Inc. (Billerica, Mass.) APEX, BioAPEX, and ESQUIRE.

The detection device 18 is electrically connected to a data processor and analyzer 20 that receives data from the detection device. The data processor and analyzer 20 includes a software program that identifies the detected tag and its position in the DNA sequence. The data processor and analyzer 20 in alternate embodiments is operatively connected to the injection device 12, the separation device 14, the fraction collector 15, and/or the cleaving device 16 to control the different components of the differential display system.

The software package maps the signature of a given tag to a specific primer, and a retention time. Software generated nucleic acid profiles are then compared (length to length, fragment to fragment) and the results are reported to the user. The software will highlight both similarities and differences in the nucleic acid fragment profiles. The software will also be able to direct the collection of specific nucleic acid fragments by the fraction collector 15.

The software package maps the m/z signature of a given tag to a specific primer, and a retention time. Software generated nucleic acid profiles are then compared (length to length, fragment to fragment) and the results are reported to the user. The software highlights both similarities and differences in the nucleic acid fragment profiles. The software is also able to direct the collection of specific nucleic acid fragments by the fraction collector.

The differential display system is provided by operatively interconnecting the system's multiple components. Accordingly, one or more system components, such as the sample introducing device 12 and the detecting device 18 that are in operation in a lab can be combined with the system's other components, e.g., the separating device 14, cleaving device 16, and the data processor and analyzer 20, in order to equip the lab with a system in accordance with the present invention.

Figure 17:
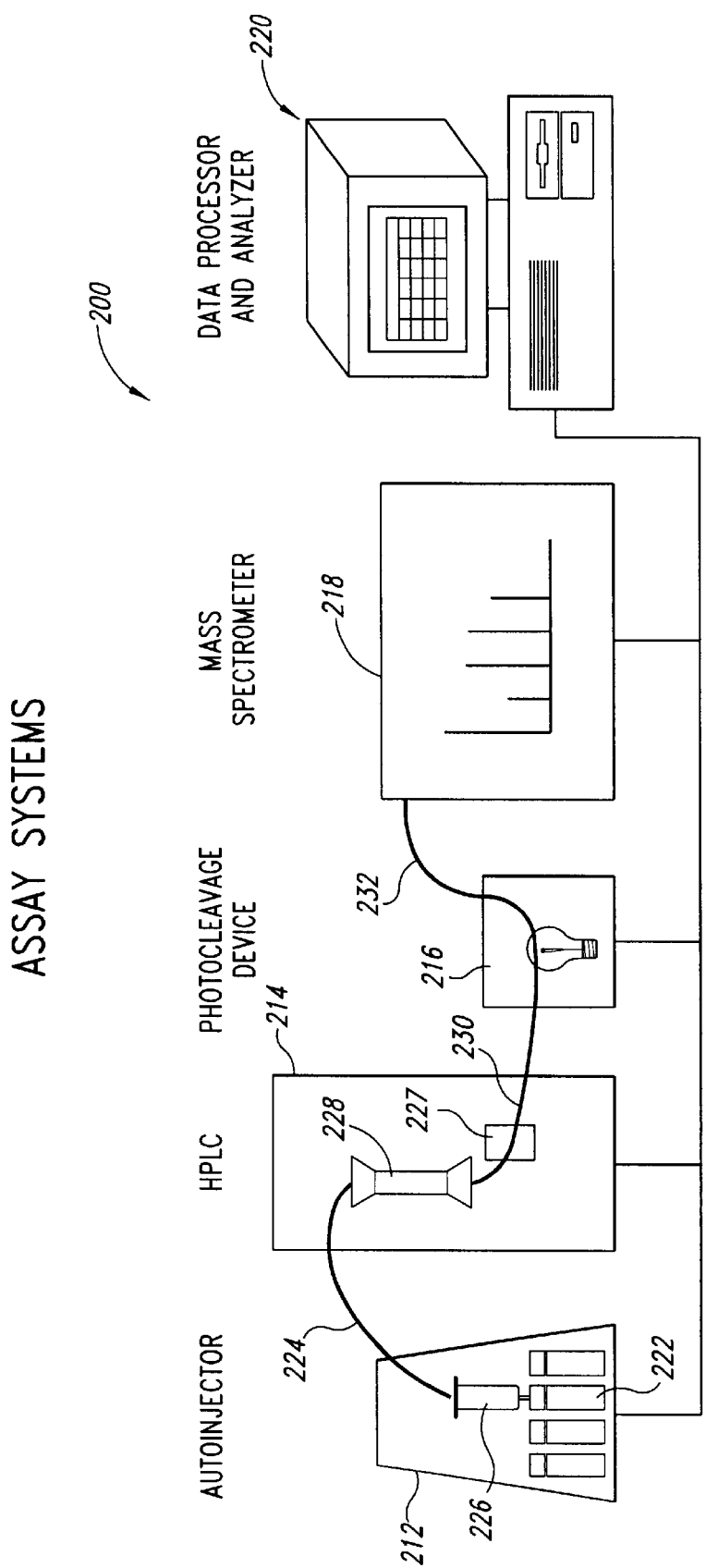
FIG. 17 is a schematic representation of assay systems in accordance with an exemplary embodiment of the present invention.

Single nucleotide extension assay, oligo-ligation assay or oligonucleotide probe based assay systems of the present invention consist of, in general, a sample introduction device, a device to separate the tagged samples of interest, a device to cleave the tags from the samples of interest, a device for detecting the tag, and a software program to analyze the data collected. It will be evident to one of ordinary skill in the art when in possession of the present disclosure that the general description may have many variances for each of the components listed. As best seen in FIG. 17, (need Figure #) a preferred single-nucleotide extension assay, oligo-ligation assay or oligonucleotide-probe based assay system 200 consists of a sample introduction device 212, a separation device 214 that separates the samples by high-performance liquid chromatography, a cleaving device 216 to cleave the tags from the samples of interest, a detection device 218 of the tags by mass spectrometry, and a data processor and analyzer 220 which includes a software program. Each component is discussed in more detail below.

The sample introduction device 212 automatically takes a measured aliquot 222 of the nucleic acid fragment generated by a variety of methods (PCR, ligations, digestion, nucleases, etc.) and delivers it through a conventional tube 224 to the separation device 214 (generally an HPLC). The sample introduction device 212 of the exemplary embodiment consists of a temperature-controlled autosampler 226 that can accommodate micro-titer plates. The autosampler 226 must be temperature controlled to maintain the integrity of the nucleic acid samples generated and be able to inject 25 µl or less of sample. Manufacturers of this product are represented, for example, by Gilson (Middleton Wis.).

The sample introduction device is operatively connected in series to the separation device by the conventional tube 224. The nucleic acid products (which may be produced by PCR, ligation reactions, digestion, nucleases, etc.) in the measured aliquot 222 receive in the separation device 214 are separated temporally by high performance liquid chromatography. The high-performance liquid chromatograph may have an isocratic, binary, or quaternary pump(s) 227 and can be purchased from multiple manufacturers (e.g., Hewlett Packard (Palo Alto, Calif.) HP 1100 or 1090 series, Beckman Instruments Inc. (800-742-2345), Bioanalytical Systems, Inc. (800-845-4246), ESA, Inc. (508) 250-700), Perkin-Elmer Corp. (800-762-4000), Varian Instruments (800-926-3000), Waters Corp. (800-254-4752)).

The separations device 214 includes an analytical HPLC column 228 suitable for use to separate the nucleic acid fragments. The column 228 is an analytical HPLC, for example, non-porous polystyrene divinylbenzene (2.2 µm particle size) solid support which can operate within a pH range of 2 to 12, pressures of up to 3000 psi and a temperature range of 10 to 70° C. A temperature-control device (e.g., a column oven) (not shown) may be used to control the temperature of the column. Such temperature-control devices are known in the art, and may be obtained from, for example, Rainin Instruments (subsidiary of Varian Instrument, Palo Alto, Calif.). A suitable column 228 is available under the commercial name of DNAsep® and is available from Serasep (San Jose, Calif.). A wide variety of HPLC columns 228 can be used for this particular technological unit since single-base pair resolution is not necessarily required. Other suitable analytical HPLC columns are available from other manufacturers (e.g., Hewlett Packard (Palo Alto, Calif.), Beckman Instruments, Inc. (Brea, Calif.), and Waters Corp. (Milford, Mass.)).

A stream of the separated DNA fragments (e.g., sequencing reaction product) flows through a conventional tube 230 from the separation device 214 to the cleavage device 216. Each of the DNA fragments is labeled with a unique cleavable (e.g., photocleavable) tag. The flowing stream of separated DNA fragments pass through or past the cleaving device 216 where the tag is removed for detection by mass spectrometry or with a electrochemical detector. The photocleaving unit is available from Supelco (Bellefonte, Pa.). Photocleaving can be performed at multiple wavelengths with a mercury/xenon arc lamp. The wavelength accuracy is about 2 nm with a bandwidth of 10 nm. The area irradiated is circular and typically of an area of 10–100 square centimeters. In alternate embodiments, other cleaving devices, which cleave by acid, base, oxidation, reduction, fluoride, thiol exchange, photolysis, or enzymatic conditions, can be used to remove the tags from the separated DNA fragments.

After the cleaving device 216 cleaves the tags from the separated DNA fragments, the tags flow through a conventional tube 232 to the detection device 218 for detection of each tag. Detection of the tags can be based upon the difference in molecular weight between each of the tags used to label each kind of DNA generated in the various assay steps. The best detector based upon differences in mass is the mass spectrometer. For this use, the mass spectrometer will typically have an atmospheric pressure ionization (API) interface with either electrospray or chemical ionization, a quadrupole mass analyzer, and a mass range of at least 50 to 2600 m/z. Examples of manufacturers of a suitable mass spectrometer are: Hewlett Packard (Palo Alto, Calif.) HP 1100 LC/MSD, Hitachi Instruments (San Jose, Calif.) M-1200H LC/MS, Perkin Elmer Corporation, Applied Biosystems Division (Foster City, Calif.) API 100 LC/MS or API 300 LC/MS/MS, Finnigan Corporation (San Jose, Calif.) LCQ, Bruker Analytical Systems, Inc. (Billerica, Mass.), ESQUIRE, and Micromers (U.K).

Figure 18:
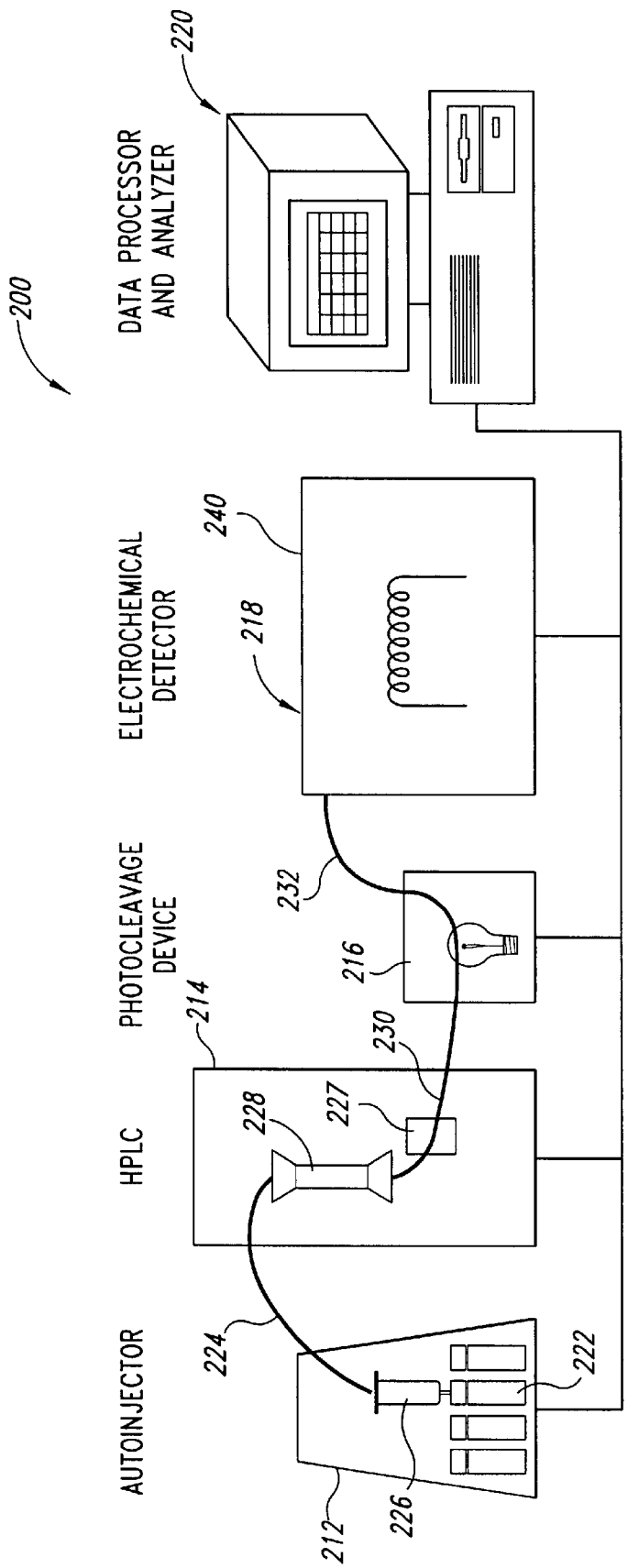
FIG. 18 is a schematic representation of assay systems in accordance with an exemplary embodiment of the present invention.

In an alternate embodiment illustrated schematically in FIG. 18, the sample introduction device 212, the separating device 214, and the cleavage device 216 are serially connected as discussed above for maintaining the flow of sample. The cleavage device 216 is connected to a detection device 218, which is an electrochemical detector 240 that detects the tags based upon the difference in electrochemical potential between each of the tags used to label each kind of DNA generated in the sequencing reaction step. The electrochemical detector 240 of the exemplary embodiment can operate on either coulometric or amperometric principles. The preferred electrochemical detector 240 is the coulometric detector, which consists of a flow-through or porous-carbon graphite amperometric detector where the column eluent passes through the electrode resulting in 100% detection efficiency. To fully detect each component, an array of 16 coulometric detectors each held at a different potential (generally at 60 mV increments) is utilized. Examples of manufacturers of this type of detector are ESA (Bedford, Mass.) and Bioanalytical Systems Inc. (800-845-4246). Additional manufacturers of electrochemical detectors can be found in the list of other manufacturers found below.

The electrochemical detector 240 is electrically connected to the data processor and analyzer 220 with the software package discussed above. The software package maps the detected property (e.g., the mass or electrochemical signature) of a given tag to a specific sample ID. The software will be able to identify the nucleic acid fragment of interest and load the ID information into respective databases.

The DNA analysis systems described herein have numerous advantages over the traditional gel based systems. One of the principal advantages is that these systems may be fully automated. By utilizing an HPLC based separation system, samples can be automatically injected into the HPLC whereas gel based systems require manual loading. There is also a significant time savings found in the set-up time (no gel forms to clean, no gel to pour), and the analysis time (greater than 4 hours for a large gel versus much shorter times (5 minutes to an hour) for an HPLC analysis Additionally, there is a sample throughput advantage. By utilizing the tags described in this invention, many samples can be analyzed in one batch (potentially 384 samples/lane) whereas the gel-based analyses are limited to the 4 fluorophores available or one sample/lane. The gels used are inherently delicate and can easily break or contain an air bubble or other flaw rendering the whole gel or several lanes useless. HPLC columns are rugged and, when purchased pre-packed, are free of packing defects creating a consistent, generally uniform separation path. The HPLC systems also lend towards better quality assurance in that internal standards can be utilized due to the reproducibility of the HPLC columns. Gel quality is inconsistent both between gels as well as within a gel making use of standards nearly impossible. Finally, both the mass spectrometry and electrochemical detectors are more sensitive than the detectors utilized in the gel based systems allowing for lower limits of detection and analysis of less sample which would be useful for non-PCR based analyses.

Tagged Probes in Array-Based Assays

Arrays with covalently attached oligonucleotides have been made used to perform DNA sequence analysis by hybridization (Southern et al., *Genomics* 13: 1008, 1992; Drmanac et al., *Science* 260: 1649, 1993), determine expression profiles, screen for mutations and the like. In general, detection for these assays uses fluorescent or radioactive labels. Fluorescent labels can be identified and quantitated most directly by their absorption and fluorescence emission wavelengths and intensity. A microscope/camera setup using a fluorescent light source is a convenient means for detecting fluorescent label. Radioactive labels may be visualized by standard autoradiography, phosphor image analysis or CCD detector. For such labels the number of different reactions that can be detected at a single time is limited. For example, the use of four fluorescent molecules, such as commonly employed in DNA sequence analysis, limits anaylsis to four samples at a time. Essentially, because of this limitation, each reaction must be individually assessed when using these detector methods.

A more advantageous method of detection allows pooling of the sample reactions on at least one array and simultaneous detection of the products. By using a tag, such as the ones described herein, having a different molecular weight or other physical attribute in each reaction, the entire set of reaction products can be harvested together and analyzed.

As noted above, the methods described herein are applicable for a variety of purposes. For example, the arrays of oligonucleotides may be used to control for quality of making arrays, for quantitation or qualitative analysis of nucleic acid molecules, for detecting mutations, for determining expression profiles, for toxicology testing, and the like.

1. Probe Quantitation or Typing

In this embodiment, oligonucleotides are immobilized per element in an array where each oligonucleotide in the element is a different or related sequence. Preferably, each element possesses a known or related set of sequences. The hybridization of a labeled probe to such an array permits the characterization of a probe and the identification and quantification of the sequences contained in a probe population.

A generalized assay format that may be used in the particular applications discussed below is a sandwich assay format. In this format, a plurality of oligonucleotides of known sequence are immobilized on a solid substrate. The immobilized oligonucleotide is used to capture a nucleic acid (e.g., RNA, rRNA, a PCR product, fragmented DNA) and then a signal probe is hybridized to a different portion of the captured target nucleic acid.

Another generalized assay format is a secondary detection system. In this format, the arrays are used to identify and quantify labeled nucleic acids that have been used in a primary binding assay. For example, if an assay results in a labeled nucleic acid, the identity of that nucleic acid can be determined by hybridization to an array. These assay formats are particularly useful when combined with cleavable mass spectometry tags.

2. Mutation Detection

Mutations involving a single nucleotide can be identified in a sample by scanning techniques, which are suitable to identify previously unknown mutations, or by techniques designed to detect, distinguish, or quantitate known sequence variants. Several scanning techniques for mutation detection have been developed based on the observation that heteroduplexes of mismatched complementary DNA strands, derived from wild type and mutant sequences, exhibit an abnormal migratory behavior.

The methods described herein may be used for mutation screening. One strategy for detecting a mutation in a DNA strand is by hybridization of the test sequence to target sequences that are wild-type or mutant sequences. A mismatched sequence has a destabilizing effect on the hybridization of short oligonucleotide probes to a target sequence (see Wetmur, *Crit. Rev. Biochem. Mol. Biol.,* 26:227, 1991). The test nucleic acid source can be genomic DNA, RNA, cDNA, or amplification of any of these nucleic acids. Preferably, amplification of test sequences is first performed, followed by hybridization with short oligonucleotide probes immobilized on an array. An amplified product can be scanned for many possible sequence variants by determining its hybridization pattern to an array of immobilized oligonucleotide probes.

A label, such as described herein, is generally incorporated into the final amplification product by using a labeled nucleotide or by using a labeled primer. The amplification product is denatured and hybridized to the array. Unbound product is washed off and label bound to the array is detected by one of the methods herein. For example, when cleavable mass spectrometry tags are used, multiple products can be simultaneously detected.

3. Expression Profiles/differential Display

Mammals, such as human beings, have about, 100,000 different genes in their genome, of which only a small fraction, perhaps 15%, are expressed in any individual cell. Differential display techniques permit the identification of genes specific for individual cell types. Briefly, in differential display, the 3' terminal portions of mRNAs are amplified and identified on the basis of size. Using a primer designed to bind to the 5' boundary of a poly(A) tail for reverse transcription, followed by amplification of the cDNA using upstream arbitrary sequence primers, mRNA subpopulations are obtained.

As disclosed herein, a high throughput method for measuring the expression of numerous genes (e.g., 1–2000) is provided. Within one embodiment of the invention, methods are provided for analyzing the pattern of gene expression from a selected biological sample, comprising the steps of (a) amplifying cDNA from a biological sample using one or more tagged primers, wherein the tag is correlative with a particular nucleic acid probe and detectable by non-fluorescent spectrometry or potentiometry, (b) hybridizing amplified fragments to an array of oligonucleotides as described herein, (c) washing away non-hybridized material, and (d) detecting the tag by non-fluorescent spectrometry or potentiometry, and therefrom determining the pattern of gene expression of the biological sample. Tag-based differential display, especially using cleavable mass spectometry tags, on solid substrates allows characterization of differentially expressed genes.

4. Single Nucleotide Extension Assay

The primer extension technique may be used for the detection of single nucleotide changes in a nucleic acid template (Sokolov, *Nucleic Acids Res.,* 18:3671, 1989). The technique is generally applicable to detection of any single base mutation (Kuppuswamy et al., *Proc. Natl, Acad. Sci. USA,* 88:1143–1147, 1991). Briefly, this method first hybridizes a primer to a sequence adjacent to a known single nucleotide polymorphism. The primed DNA is then subjected to conditions in which a DNA polymerase adds a labeled dNTP, typically a ddNTP, if the next base in the template is complementary to the labeled nucleotide in the reaction mixture. In a modification, cDNA is first amplified for a sequence of interest containing a single-base difference between two alleles. Each amplified product is then analyzed for the presence, absence, or relative amounts of each allele by annealing a primer that is 1 base 5' to the polymorphism and extending by one labeled base (generally a dideoxynucleotide). Only when the correct base is available in the reaction will a base to incorporated at the 3'-end of the primer. Extension products are then analyzed by hybridization to an array of oligonucleotides such that a non-extended product will not hybridize.

Briefly, in the present invention, each dideoxynucleotide is labeled with a unique tag. Of the four reaction mixtures, only one will add a dideoxy-terminator on to the primer sequence. If the mutation is present, it will be detected through the unique tag on the dideoxynucleotide after hybridization to the array. Multiple mutations can be simultaneously determined by tagging the DNA primer with a unique tag as well. Thus, the DNA fragments are reacted in four separate reactions each including a different tagged dideoxyterminator, wherein the tag is correlative with a particular dideoxynucleotide and detectable by non-fluorescent spectrometry, or potentiometry. The DNA fragments are hybridized to an array and non-hybridized material is washed away. The tags are cleaved from the hybridized fragments and detected by the respective detection technology (e.g., mass spectrometry, infrared spectrometry, potentiostatic amperometry or UV/visible spectrophotometry). The tags detected can be correlated to the particular DNA fragment under investigation as well as the identity of the mutant nucleotide.

5. Oligonucleotide Ligation Assay

The oligonucleotide ligation assay (OLA). (Landegen et al., *Science* 241:487, 1988) is used for the identification of known sequences in very large and complex genomes. The principle of OLA is based on the ability of ligase to covalently join two diagnostic oligonucleotides as they hybridize adjacent to one another on a given DNA target. If the sequences at the probe junctions are not perfectly based-paired, the probes will not be joined by the ligase. When tags are used, they are attached to the probe, which is ligated to the amplified product. After completion of OLA, fragments are hybridized to an array of complementary sequences, the tags cleaved and detected by mass spectrometry.

Within one embodiment of the invention methods are provided for determining the identity of a nucleic acid molecule, or for detecting a selecting nucleic acid molecule, in, for example a biological sample, utilizing the technique of oligonucleotide ligation assay. Briefly, such methods generally comprise the steps of performing amplification on the target DNA followed by hybridization with the 5' tagged reporter DNA probe and a 5' phosphorylated probe. The sample is incubated with T4 DNA ligase. The DNA strands with ligated probes are captured on the array by hybridization to an array, wherein non-ligated products do not hybridize. The tags are cleaved from the separated fragments, and then the tags are detected by the respective detection technology (e.g., mass spectrometry, infrared spectrophotometry, potentiostatic amperometry or UV/visible spectrophotometry.

6. Other Assays

The methods described herein may also be used to genotype or identification of viruses or microbes. For example, F+ RNA coliphages may be useful candidates as indicators for enteric virus contamination. Genotyping by nucleic acid amplification and hybridization methods are reliable, rapid, simple, and inexpensive alternatives to serotyping (Kafatos et. al., *Nucleic Acids Res.* 7:1541, 1979). Amplification techniques and nucleic aid hybridization techniques have been successfully used to classify a variety of microorganisms including *E. coli* (Feng, *Mol. Cell Probes* 7:151, 1993), rotavirus (Sethabutr et. al., *J. Med Virol.* 37:192, 1992), hepatitis C virus (Stuyver et. al., *J. Gen Virol.* 74:1093, 1993), and herpes simplex virus (Matsumoto et. al., *J. Virol. Methods* 40:119, 1992).

Genetic alterations have been described in a variety of experimental mammalian and human neoplasms and represent the morphological basis for the sequence of morphological alterations observed in carcinogenesis (Vogelstein et al., *NEJM* 319:525, 1988). In recent years with the advent of molecular biology techniques, allelic losses on certain chromosomes or mutation of tumor suppressor genes as well as mutations in several oncogenes (e.g., c-myc, c-jun, and the ras family) have been the most studied entities. Previous work (Finkelstein et al., *Arch Surg.* 128:526, 1993) has identified a correlation between specific types of point mutations in the K-ras oncogene and the stage at diagnosis in colorectal carcinoma. The results suggested that mutational analysis could provide important information of tumor aggressiveness, including the pattern and spread of metastasis. The prognostic value of TP53 and K-ras-2 mutational analysis in stage III carconoma of the colon has more recently been demonstrated (Pricolo et al., *Am. J. Surg.* 171:41, 1996). It is therefore apparent that genotyping of tumors and pre-cancerous cells, and specific mutation detection will become increasingly important in the treatment of cancers in humans.

Tagged Probes in Array-Based Assays

The tagged biomolecules as disclosed herein may be used to interrogate (untagged) arrays of biomolecules. Preferred arrays of biomolcules contain a solid substrate comprising a surface, where the surface is at least partially covered with a layer of poly(ethylenimine) (PEI). The PEI layer comprises a plurality of discrete first regions abutted and surrounded by a contiguous second region. The first regions are defined by the presence of a biomolecule and PEI, while the second region is defined by the presence of PEI and the substantial absence of the biomolecule. Preferably, the substrate is a glass plate or a silicon wafer. However, the substrate may be, for example, quartz, gold, nylon-6,6, nylon or polystyrene, as well as composites thereof, as described above.

The PEI coating preferably contains PEI having a molecular weight ranging from 100 to 100,000. The PEI coating may be directly bonded to the substrate using, for example, silylated PEI. Alternatively, a reaction product of a bifunctional coupling agent may be disposed between the substrate surface and the PEI coating, where the reaction product is covalently bonded to both the surface and the PEI coating, and secures the PEI coating to the surface. The bifunctional coupling agent contains a first and a second reactive functional group, where the first reactive functional group is, for example, a tri(O—$C_1$–$C_5$alkyl)silane, and the second reactive functional group is, for example, an epoxide, isocyanate, isothiocyanate and anhydride group. Preferred bifunctional coupling agents include 2-(3,4-epoxycyclohexyl)ethyltrimethoxysilane; 3,4-epoxybutyltrimethoxysilane; 3-isocyanatopropyltriethoxysilane, 3-(triethoxysilyl)-2-methylpropylsuccinic anhydride and 3-(2,3-epoxypropoxy) propyltrimethoxysilane.

The array of the invention contains first, biomolecule-containing regions, where each region has an area within the range of about 1,000 square microns to about 100,000 square microns. In a preferred embodiment, the first regions have areas that range from about 5,000 square microns to about 25,000 square microns.

The first regions are preferably substantially circular, where the circles have an average diameter of about 10 microns to 200 microns. Whether circular or not, the boundaries of the first regions are preferably separated from one another (by the second region) by an average distance of at least about 25 microns, however by not more than about 1 cm (and preferably by no more than about 1,000 microns). In a preferred array, the boundaries of neighboring first regions are separated by an average distance of about 25 microns to 100 microns, where that distance is preferably constant throughout the array, and the first regions are preferably positioned in a repeating geometric pattern as shown in the FIGures attached hereto. In a preferred repeating geometric pattern, all neighboring first regions are separated by approximately the same distance (about 25 microns to about 100 microns).

In preferred arrays, there are from 10 to 50 first regions on the substrate. In another embodiment, there are 50 to 400 first regions on a substrate. In yet another preferred embodiment, there are 400 to 800 first regions on the substrate.

The biomolecule located in the first regions is preferably a nucleic acid polymer. A preferred nucleic acid polymer is an oligonucleotide having from about 15 to about 50 nucleotides. The biomolecule may be amplification reaction products having from about 50 to about 1,000 nucleotides.

In each first region, the biomolecule is preferably present at an average concentration ranging from $10^5$ to $10^9$ biomolecules per 2,000 square microns of a first region. More preferably, the average concentration of biomolecule ranges from $10^7$ to $10^9$ biomolecules per 2,000 square microns. In the second region, the biomolecule is preferably present at an average concentration of less than $10^3$ biomolecules per 2,000 square microns of said second region, and more preferably at an average concentration of less than $10^2$ biomolecules per 2,000 square microns. Most preferably, the second regions does not contain any biomolecule.

The chemistry used to adhere the layer of PEI to the substrate depends, in substantial part, upon the chemical identity of the substrate. The prior art provides numerous examples of suitable chemistries that may adhere PEI to a solid support. For example, when the substrate is nylon-6,6, the PEI coating may be applied by the methods disclosed in Van Ness, J. et al. *Nucleic Acids Res.* 19:3345–3350, 1991 and PCT International Publication WO 94/00600, both of which are incorporated herein by reference. When the solid support is glass or silicon, suitable methods of applying a layer of PEI are found in, e.g., Wasserman, B. P. *Biotechnology and Bioengineering* XXII:271–287, 1980; and D'Souza, S. F. *Biotechnology Letters* 8:643–648, 1986.

Preferably, the PEI coating is covalently attached to the solid substrate. When the solid substrate is glass or silicon, the PEI coating may be covalently bound to the substrate using silylating chemistry. For example, PEI having reactive siloxy endgroups is commercially available from Gelest, Inc. (Tullytown, Pa.). Such reactive PEI may be contacted with a glass slide or silicon wafer, and after gentle agitation, the PEI will adhere to the substrate. Alternatively, a bifunctional silylating reagent may be employed. According to this process, the glass or silicon substrate is treated with the bifunctional silylating reagent to provide the substrate with a reactive surface. PEI is then contacted with the reactive surface, and covalently binds to the surface through the bifunctional reagent.

The biomolecules being placed into the array format are originally present in a so-called "arraying solution". In order to place biomolecule in discrete regions on the PEI-coated substrate, the arraying solution preferably contains a thickening agent at a concentration of about 35 vol % to about 80 vol % based on the total volume of the composition, a biomolecule which is preferably an oligonucleotide at a concentration ranging from 0.001 $\mu$g/mL to 10 $\mu$g/mL, and water.

The concentration of the thickening agent is 35% V/V to 80% V/V for liquid thickening agents such as glycerol. The preferred concentration of thickening agent in the composition depends, to some extent, on the temperature at which the arraying is performed. The lower the arraying temperature, the lower the concentration of thickening agent that needs to be used. The combination of temperature and liquid thickening agent concentration control permits arrays to be made on most types of solid supports (e.g., glass, wafers, nylon 6/6, nylon membranes, etc.).

The presence of a thickening agent has the additional benefit of allowing the concurrent presence of low concentrations of various other materials to be present in combination with the biomolecule. For. example 0.001% V/V to 1% V/V of detergents may be present in the arraying solution. This is useful because PCR buffer contains a small amount of Tween-20 or NP-40, and it is frequently desirable to array sample nucleic acids directly from a PCR vial without prior purification of the amplicons. The use of a thickening agent permits the presence of salts (for example NaCl, KCl, or $MgCl_2$), buffers (for example Tris), and/or chelating reagents (for example EDTA) to also be present in the arraying solution. The use of a thickening agent also has the additional benefit of permitting the use of cross-linking reagents and/or organic solvents to be present in the arraying solution. As commercially obtained, cross-linking reagents are commonly dissolved in organic solvent such as DMSO, DMF, NMP, methanol, ethanol and the like. Commonly used organic solvents can be used in arraying solutions of the invention at levels of 0.05% to 20% (V/V) when thickening agents are used.

In general, the thickening agents impart increased viscosity to the arraying solution. When a proper viscosity is achieved in the arraying solution, the first drop is the substantially the same size as, for example, the 100th drop deposited. When an improper viscosity is used in the arraying solution, the first drops deposited are significantly larger than latter drops which are deposited. The desired viscosity is between those of pure water and pure glycerin.

The biomolecule in the array may be a nucleic acid polymer or analog thereof, such as PNA, phosphorothioates and methylphosphonates. Nucleic acid refers to both ribonucleic acid and deoxyribonucleic acid. The biomolecule may comprise unnatural and/or synthetic bases. The biomolecule may be single or double stranded nucleic acid polymer.

A preferred biomolecule is an nucleic acid polymer, which includes oligonucleotides (up to about 100 nucleotide bases) and polynucleotides (over about 100 bases). A preferred nucleic acid polymer is formed from 15 to 50 nucleotide bases. Another preferred nucleic acid polymer has 50 to 1,000 nucleotide bases. The nucleic acid polymer may be a PCR product, PCR primer, or nucleic acid duplex, to list a few examples. However, essentially any nucleic acid type can be covalently attached to a PEI-coated surface when the nucleic acid contains a primary amine, as disclosed below. The typical concentration of nucleic acid polymer in the arraying solution is 0.001–10 $\mu$g/mL, preferably 0.01–1 $\mu$g/mL, and more preferably 0.05–0.5 $\mu$g/mL.

Preferred nucleic acid polymers are "amine-modified" in that they have been modified to contain a primary amine at the 5'-end of the nucleic acid polymer, preferably with one or more methylene ($—CH_2—$) groups disposed between the primary amine and the nucleic acid portion of the nucleic acid polymer. Six is a preferred number of methylene groups. Amine-modified nucleic acid polymers are preferred because they can be covalently coupled to a solid support through the 5'-amine group. PCR products can be arrayed using 5'-hexylamine modified PCR primers. Nucleic acid duplexes can be arrayed after the introduction of amines by nick translation using aminoallyl-dUTP (Sigma, St. Louis, Mo.). Amines can be introduced into nucleic acids by polymerases such as terminal transferase with amino allyl-dUTP or by ligation of short amine-containing nucleic acid polymers onto nucleic acids by ligases.

Preferably, the nucleic acid polymer is activated prior to be contacted with the PEI coating. This can be conveniently accomplished by combining amine-functionalized nucleic acid polymer with a multi-functional amine-reactive chemical such as trichlorotriazine. When the nucleic acid polymer contains a 5'-amine group, that 5'-amine can be reacted with trichlorotriazine, also known as cyanuric chloride (Van Ness et al., *Nucleic Acids Res.* 19(2):3345–3350, 1991) Preferably, an excess of cyanuric chloride is added to the nucleic acid polymer solution, where a 10- to 1000-fold molar excess of cyanuric chloride over the number of amines in the nucleic acid polymer in the arraying solution is preferred. In this way, the majority of amine-terminated nucleic acid polymers have reacted with one molecule of trichlorotriazine, so that the nucleic acid polymer becomes terminated with dichlorotriazine.

Preferably, the arraying solution is buffered using a common buffer such as sodium phosphate, sodium borate, sodium carbonate, or Tris HCl. A preferred pH range for the arraying solution is 7 to 9, with a preferred buffer being freshly prepared sodium borate at pH 8.3 to pH 8.5. To prepare a typical arraying solution, hexylamine-modified nucleic acid polymer is placed in 0.2 M sodium borate, pH 8.3, at 0.1 $\mu$g/mL, to a total volume of 50 $\mu$l. Ten $\mu$l of a 15 mg/mL solution of cyanuric chloride is then added, and the reaction is allowed to proceed for 1 hour at 25 C. with constant agitation. Glycerol (Gibco Brl®, Grand Island, N.Y.) is added to a final concentration of 56%.

The biomolecular arraying solutions may be applied to the PEI coating by any of the number of techniques currently used in microfabrication. For example, the solutions may be placed into an ink jet print head, and ejected from such a head onto the coating.

A preferred approach to delivering biomolecular solution onto the PEI coating employs a modified spring probe. Spring probes are available from several vendors including Everett Charles (Pomona, Calif.), Interconnect Devices Inc. (Kansas City, Kans.) and Test Connections Inc., (Upland, Calif.). In order for the commercially available spring probes as described above to satisfactorily function as liquid deposition devices according to the present invention, approximately 1/1000th to 5/1000th of an inch of metal material must be removed from the tip of the probe. The process must result in a flat surface which is perpendicular to the longitudinal axis of the spring probe. The removal of approximately 1/1000th to 5/1000th of an inch of material from the bottom of the tip is preferred and can be accomplished easily with a very fine grained wet stone. Specific spring probes which are commercially available and may be modified to provide a planar tip as described above include the XP54 probe manufactured by Ostby Barton (a division of Everett Charles (Pomona, Calif.)); the SPA 25P probe manufactured by Everett Charles (Pomona, Calif.) and 43-P fluted spring probe from Test Connections Inc., (Upland, Calif.).

The arraying solutions as described above may be used directly in an arraying process. That is, the activated nucleic acid polymers need not be purified away from unreacted cyanuric chloride prior to the printing step. Typically the reaction which attaches the activated nucleic acid to the solid support is allowed to proceed for 1 to 20 hours at 20 to 50 C. Preferably, the reaction time is 1 hour at 25 C.

The arrays as described herein are particularly useful in conducting hybridization assays, for example, using CMST labeled probes. However, in order to perform such assays, the amines on the solid support must be capped prior to conducting the hybridization step. This may be accomplished by reacting the solid support with 0.1–2.0 M succinic anhydride. The preferred reaction conditions are 1.0 M succinic anhydride in 70% m-pyrol and 0.1 M sodium borate. The reaction typically is allowed to occur for 15 minutes to 4 hours with a preferred reaction time of 30 minutes at 25 C. Residual succinic anhydride is removed with a 3× water wash.

The solid support is then incubated with a solution containing 0.1–5 M glycine in 0.1–10.0 M sodium borate at pH 7–9. This step "caps" any dichloro-triazine which may be covalently bound to the PEI surface by conversion into monochlorotriazine. The preferred conditions are 0.2 M glycine in 0.1 M sodium borate at pH 8.3. The solid support may then be washed with detergent-containing solutions to remove unbound materials, for example, trace NMP. Preferably, the solid support is heated to 95 C. in 0.01 M NaCl, 0.05 M EDTA and 01 M Tris pH 8.0 for 5 minutes. This heating step removes non-covalently attached nucleic acid polymers, such as PCR products. In the case where double strand nucleic acid are arrayed, this step also has the effect of converting the double strand to single strand form (denaturation).

The arrays are may be interrogated by probes (e.g., oligonucleotides, nucleic acid fragments, PCR products, etc.) which may be tagged with, for example CMST tags as described herein, radioisotopes, fluorophores or biotin. The methods for biotinylating nucleic acids are well known in the art and are adequately described by Pierce (Avidin-Biotin Chemistry: A Handbook, Pierce Chemical Company, 1992. Rockford Ill.). Probes are generally used at 0.1 ng/ml, to 10/µg/mL in standard hybridization solutions that include GuSCN, GuHCl, formamide, etc. (see Van Ness and Chen, *Nucleic Acids Res.*, 19:5143–5151, 1991).

To detect the hybridization event (i.e., the presence of the biotin), the solid support is incubated with streptavidin/horseradish peroxidase conjugate. Such enzyme conjugates are commercially available from, for example, Vector Laboratories (Burlingham, Calif.). The streptavidin binds with high affinity to the biotin molecule bringing the horseradish peroxidase into proximity to the hybridized probe. Unbound streptavidin/horseradish peroxidase conjugate is washed away in a simple washing step. The presence of horseradish peroxidase enzyme is then detected using a precipitating substrate in the presence of peroxide and the appropriate buffers.

A blue enzyme product deposited on a reflective surface such as a wafer has a many-fold lower level of detection (LLD) compared to that expected for a calorimetric substrate. Furthermore, the LLD is vastly different for different colored enzyme products. For example, the LLD for 4-methoxynapthol (which produces a precipitated blue product) per 50 µM diameter spot is approximately 1000 molecules, whereas a red precipitated substrate gives an LLD about 1000-fold higher at 1,000,000 molecules per 50 µM diameter spot. The LLD is determined by interrogating the surface with a microscope (such as the Axiotech microscope commercially available from Zeiss) equipped with a visible light source and a CCD camera (Princeton Instruments, Princeton, N.J.). An image of approximately 10,000 µM×10,000 µM can be scanned at one time.

In order to use the blue colorimetric detection scheme, the surface must be very clean after the enzymatic reaction and the wafer or slide must be scanned in a dry state. In addition, the enzymatic reaction must be stopped prior to saturation of the reference spots. For horseradish peroxidase this is approximately 2–5 minutes.

It is also possible to use chemiluminescent substrates for alkaline phosphatase or horesradish peroxidase (HRP), or fluoroescence substrates for HRP or alkaline phosphatase. Examples include the dioxetane substrates for alkaline phosphatase available from Perkin Elmer or Attophos HRP substrate from JBL Scientific (San Luis Obispo, Calif.).

The following examples are offered by way of illustration, and not by way of limitation.

Unless otherwise stated, chemicals as used in the examples may be obtained from Aldrich Chemical Company, Milwaukee, Wis. The following abbreviations, with the indicated meanings, are used herein:

ANP-=3-(Fmoc-amino)-3-(2-nitrophenyl)propionic acid
NBA=4-(Fmoc-aminomethyl)-3-nitrobenzoic acid
HATU=O-7-azabenzotriazol-1-yl-N,N,N',N'-tetramethyluronium hexafluorophosphate
DIEA=diisopropylethylamine
MCT=monochlorotriazine
NMM=4-methylmorpholine
NMP=N-methylpyrrolidone
ACT357=ACT357 peptide synthesizer from Advanced ChemTech, Inc., Louisville, Ky.
ACT=Advanced ChemTech, Inc., Louisville, Ky.
NovaBiochem=CalBiochem-NovaBiochem International, San Diego, Calif.
TFA=Trifluoroacetic acid
Tfa=Trifluoroacetyl
iNIP=N-Methylisonipecotic acid
Tfp=Tetrafluorophenyl
DIAEA=2-(Diisopropylamino)ethylamine
MCT=monochlorotriazene
5'-AH-ODN=5'-aminohexyl-tailed oligodeoxynucleotide

EXAMPLES

Example 1

Figure 1B:
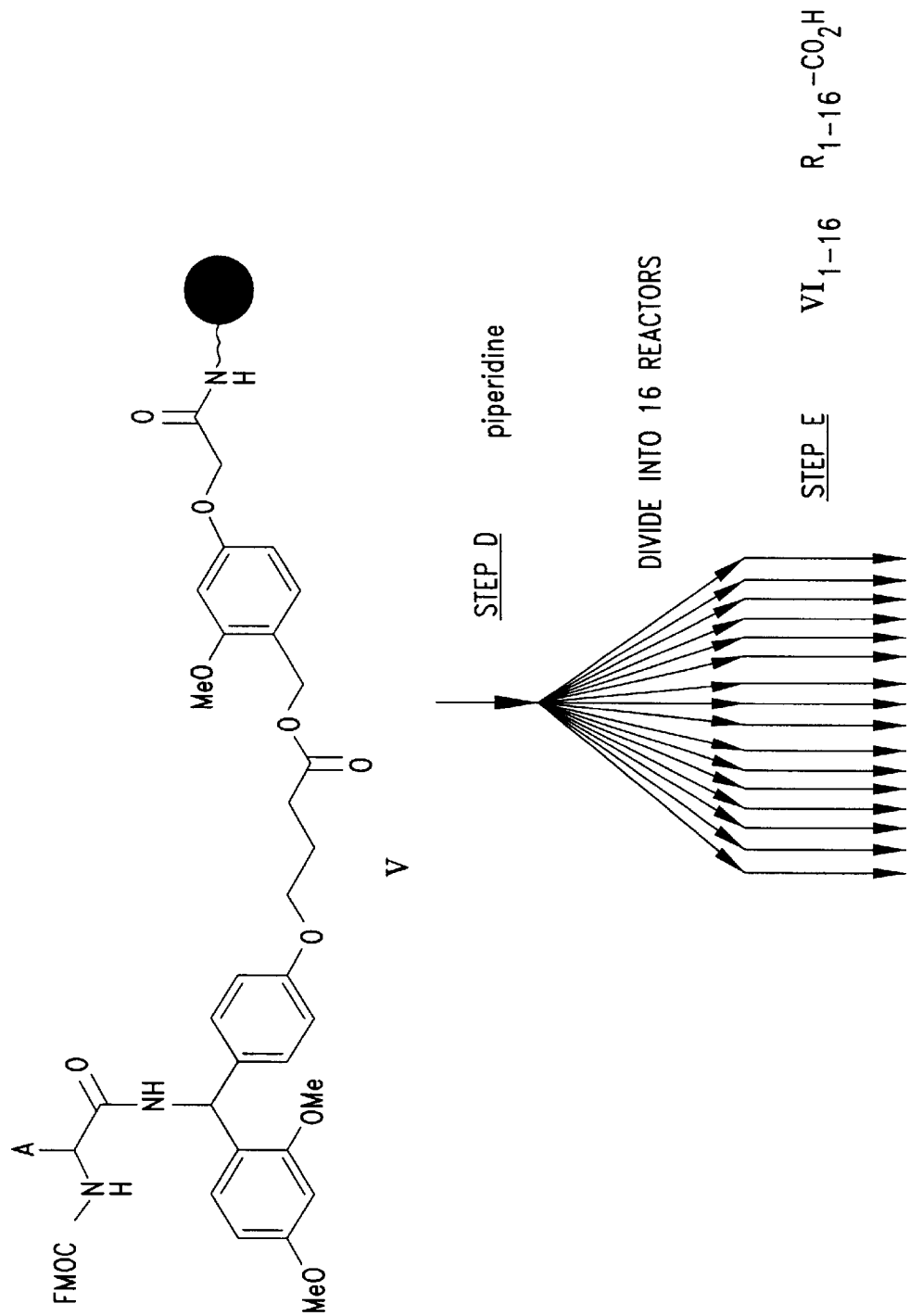
Figure 1C:
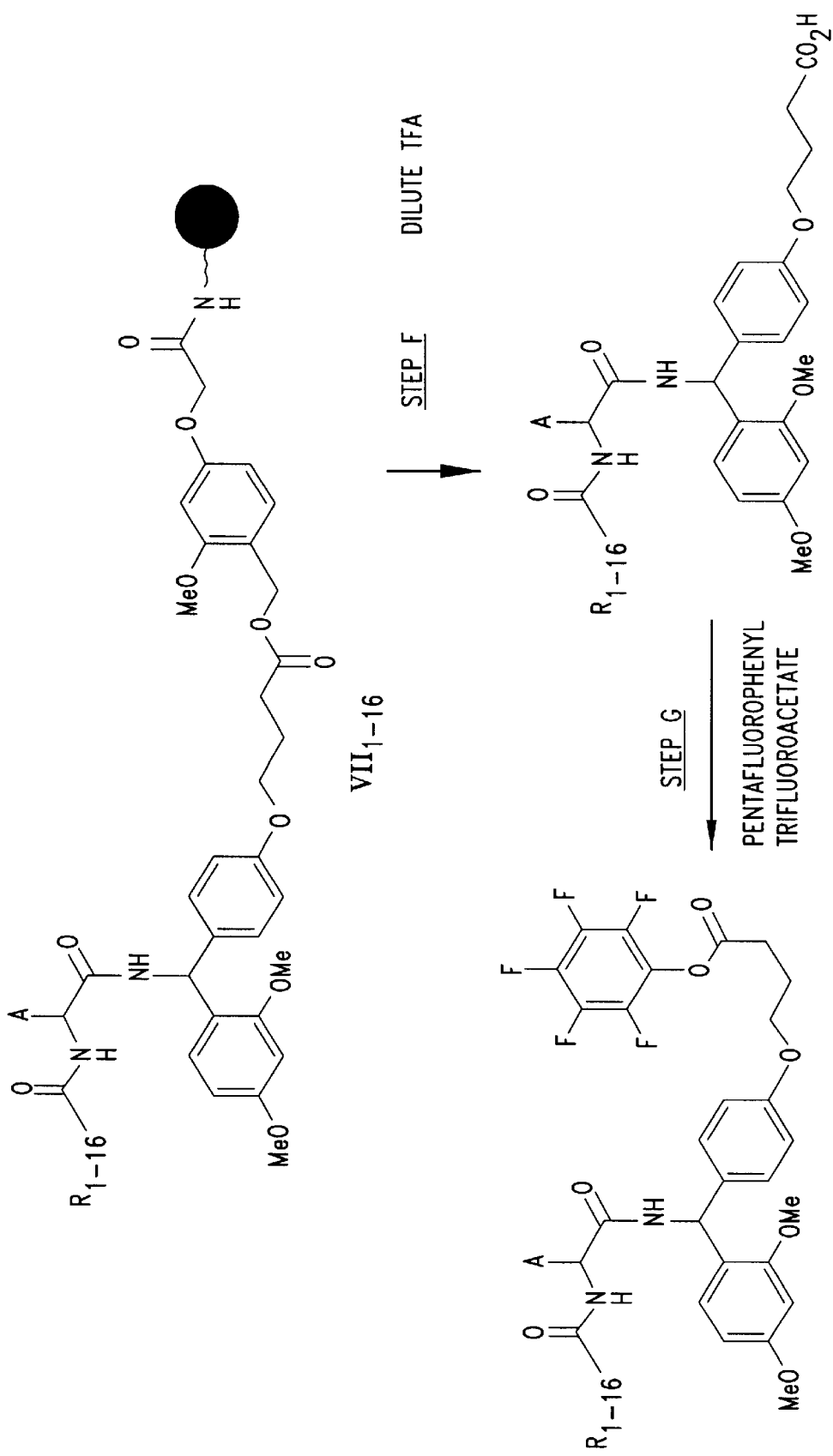

Preparation of Avid Labile Linkers for Use in Cleavable-MW-Identifier Sequencing A. Synthesis of Pentafluorophenyl Esters of Chemically Cleavable Mass Spectroscopy Tags, to Liberate Tags with Carboxyl Amide Termini FIG. 1 shows the reaction scheme.

Step A. TentaGel S AC resin (compound II; available from ACT; 1 eq.) is suspended with DMF in the collection vessel of the ACT357 peptide synthesizer (ACT). Compound 1 (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound III.

Step B. The resin (compound III) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step C.

Step C. The deprotected resin from step B is suspended in DMF and to it is added an FMOC-protected amino acid, containing amine functionality in its side chain (compound IV, e.g., alpha-N-FMOC-3-(3-pyridyl)-alanine, available from Synthetech, Albany, Oreg.; 3 eq.), HATU (3 eq.), and DIEA (7.5 eq.) in DMF. The vessel is shaken for 1 hr. The solvent is removed and the resin washed with NMP (2×), MeOH (2×), and DMF (2×). The coupling of IV to the resin and the wash steps are repeated, to give compound V.

Step D. The resin (compound V) is treated with piperidine as described in step B to remove the FMOC group. The deprotected resin is then divided equally by the ACT357 from the collection vessel into 16 reaction vessels.

Step E. The 16 aliquots of deprotected resin from step D are suspended in DMF. To each reaction vessel is added the appropriate carboxylic acid $VI_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VI_{1-16}$ to the aliquots of resin and the wash steps are repeated, to give compounds $VII_{1-16}$.

Step F. The aliquots of resin (compounds $VII_{1-16}$) are washed with $CH_2Cl_2$ (3×). To each of the reaction vessels is added 1% TFA in $CH_2Cl_2$ and the vessels shaken for 30 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $VIII_{1-16}$.

Step G. Each of the free carboxylic acids $VIII_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. $NaHCO_3$ (3×), dried over $Na_2SO_4$, filtered, and evaporated in vacuo, providing compounds $IX_{1-16}$.

Figure 2A:
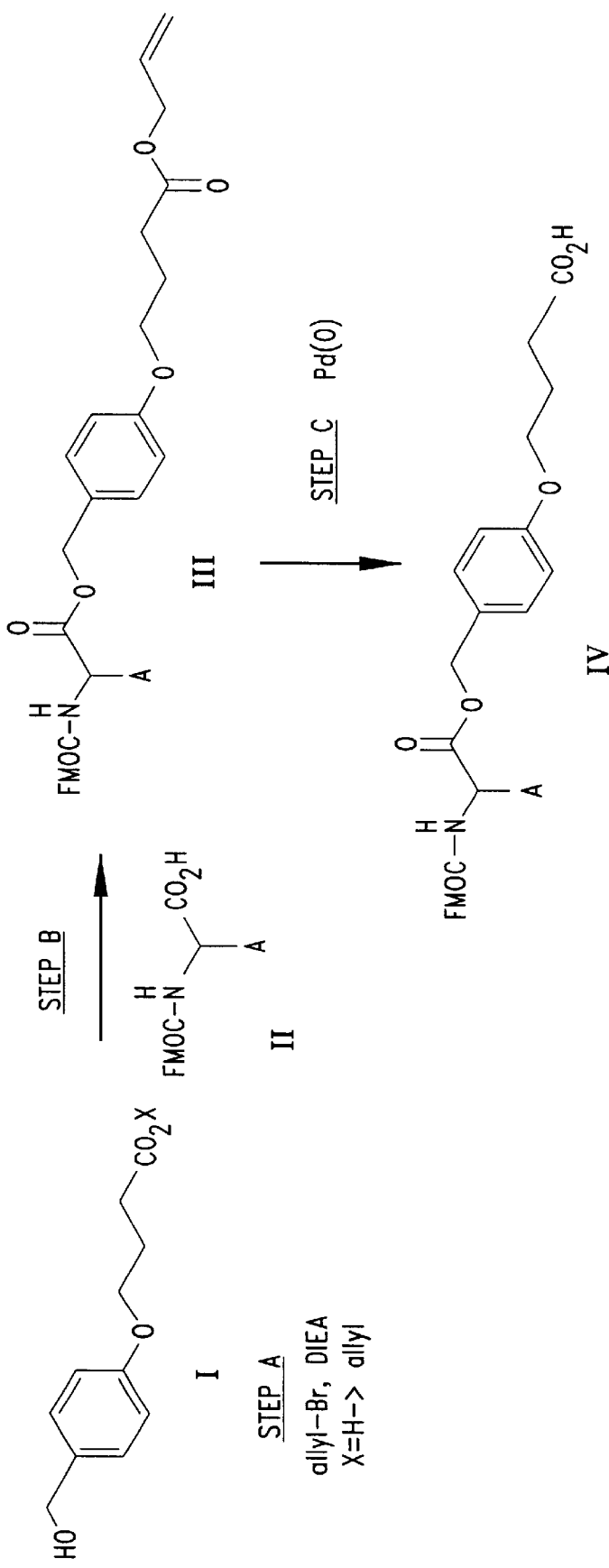
FIGS. 2A, 2B, and 2C depicts the flowchart for the synthesis of pentafluorophenyl esters of chemically cleavable mass spectroscopy tags, to liberate tags with carboxyl acid termini.
Figure 2B:
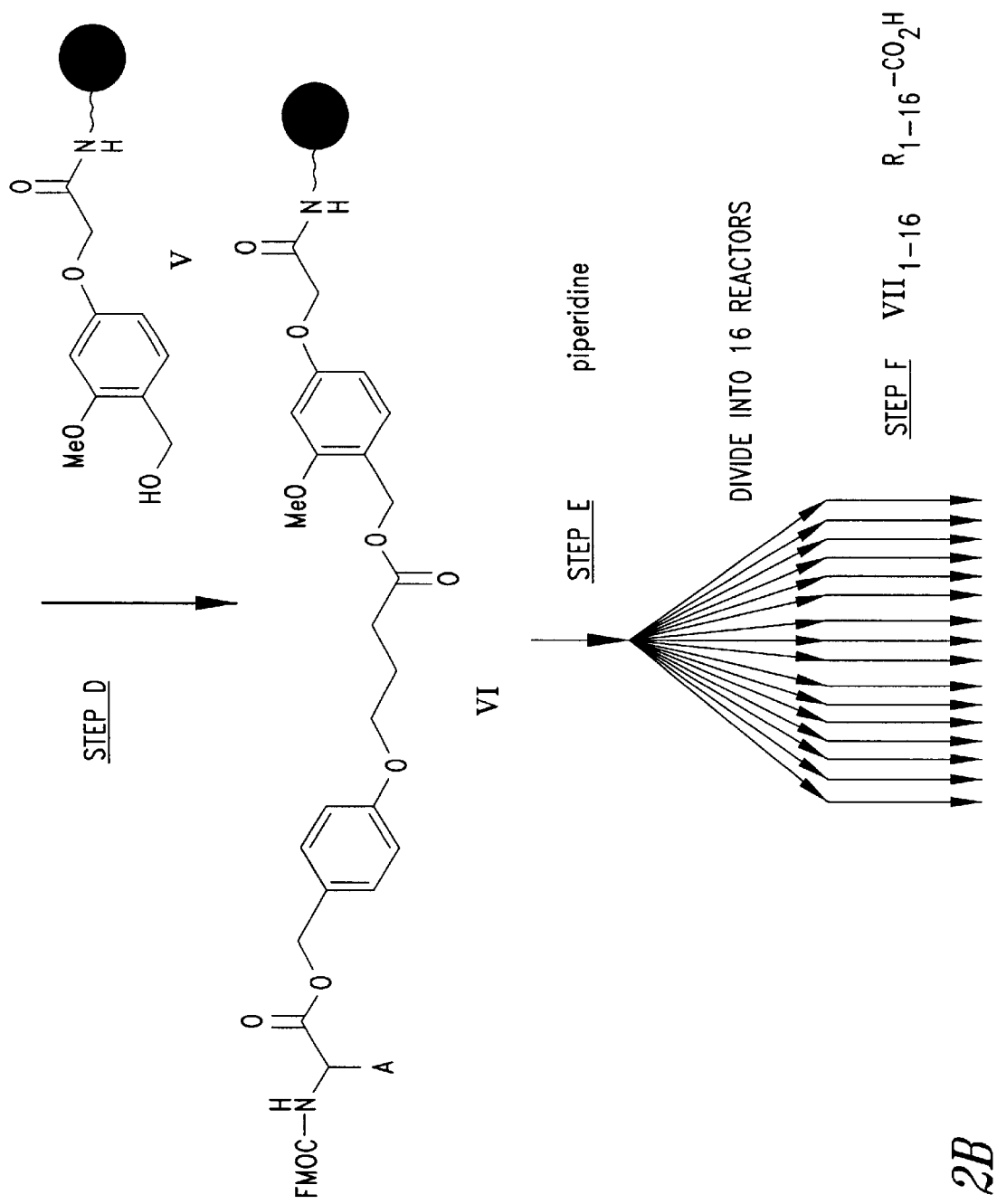
Figure 2C:
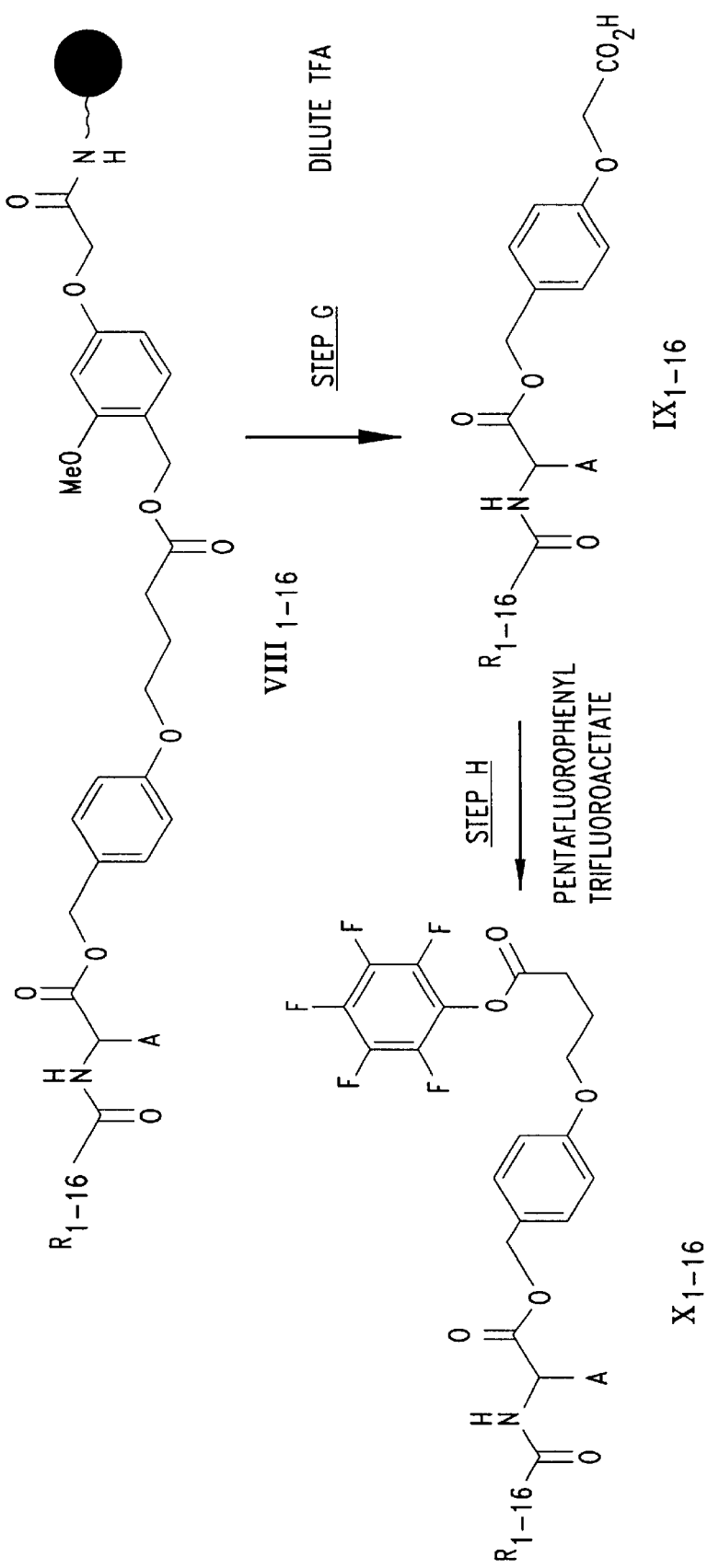

A. Synthesis of Pentafluorophenyl Esters of Chemically Cleavable Mass Spectroscopy Tags, to Liberate Tars with Carboxyl Acid Termini FIG. 2 shows the reaction scheme.

Step A. 4-(Hydroxymethyl)phenoxybutyric acid (compound I; 1 eq.) is combined with DIEA (2.1 eq.) and allyl bromide (2.1 eq.) in $CHCl_3$ and heated to reflux for 2 hr. The mixture is diluted with EtOAc, washed with 1 N HCl (2×), pH 9.5 carbonate buffer (2×), and brine (1×), dried over $Na_2SO_4$, and evaporated in vacuo to give the allyl ester of compound I.

Step B. The allyl ester of compound I from step A (1.75 eq.) is combined in $CH_2Cl_2$ with an FMOC-protected amino acid containing amine functionality in its side chain (compound II, e.g., alpha-N-FMOC-3-(3-pyridyl)-alanine, available from Synthetech, Albany, Oreg.; 1 eq.), N-methylmorpholine (2.5 eq.), and HATU (1.1 eq.), and stirred at room temperature for 4 hr. The mixture is diluted with $CH_2Cl_2$, washed with 1 M aq. citric acid (2×), water (1×), and 5% aq. $NaHCO_3$ (2×), dried over $Na_2SO_4$, and evaporated in vacuo. Compound III is isolated by flash chromatography ($CH_2Cl_2 \rightarrow EtOAc$).

Step C. Compound III is dissolved in $CH_2Cl_2$, $Pd(PPh_3)_4$ (0.07 eq.) and N-methylaniline (2 eq.) are added, and the mixture stirred at room temperature for 4 hr. The mixture is diluted with $CH_2Cl_2$, washed with 1 M aq. citric acid (2×) and water (1×), dried over $Na_2SO_4$, and evaporated in vacuo. Compound IV is isolated by flash chromatography ($CH_2Cl_2 \rightarrow EtOAc+HOAc$).

Step D. TentaGel S AC resin (compound V; 1 eq.) is suspended with DMF in the collection vessel of the ACT357 peptide synthesizer (Advanced ChemTech Inc. (ACT), Louisville, Ky.). Compound IV (3 eq.), HATU (3 eq.) and DIEA (7.5 eq.) in DMF are added and the collection vessel shaken for 1 hr. The solvent is removed and the resin washed with NMP (2×), MeOH (2×), and DMF (2×). The coupling of IV to the resin and the wash steps are repeated, to give compound VI.

Step E. The resin (compound VI) is mixed with 25% piperidine in DMF and shaken for 5 min. The resin is filtered, then mixed with 25% piperidine in DMF and shaken for 10 min. The solvent is removed and the resin washed with NMP (2×), MeOH (2×), and DMF (2×). The deprotected resin is then divided equally by the ACT357 from the collection vessel into 16 reaction vessels.

Step F. The 16 aliquots of deprotected resin from step E are suspended in DMF. To each reaction vessel is added the appropriate carboxylic acid $VII_{1-16}$ ($R_{1-16}CO_2H$; 3 eq.), HATU (3 eq.), and DIEA (7.5 eq.) in DMF. The vessels are shaken for 1 hr. The solvent is removed and the aliquots of resin washed with NMP (2×), MeOH (2×), and DMF (2×). The coupling of $VII_{1-16}$ to the aliquots of resin and the wash steps are repeated, to give compounds $VII_{1-16}$.

Step G. The aliquots of resin (compounds $VIII_{1-16}$) are washed with $CH_2Cl_2$ (3×). To each of the reaction vessels is added 1% TFA in $CH_2Cl_2$ and the vessels shaken for 30 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $IX_{1-16}$.

Step H. Each of the free carboxylic acids $IX_{1-16}$ is dissolved in DMF. To each solution is added pyridine (1.05 eq.), followed by pentafluorophenyl trifluoroacetate (1.1 eq.). The mixtures are stirred for 45 min. at room temperature. The solutions are diluted with EtOAc, washed with 1 M aq. citric acid (3×) and 5% aq. $NaHCO_3$ (3×), dried over $Na_2SO_4$, filtered, and evaporated in vacuo, providing compounds $X_{1-16}$.

Example 2

Demonstration of Photolytic Cleavage of T—L—X

A T—L—X compound as prepared in Example 11 was irradiated with near-UV light for 7 min at room temperature. A Rayonett fluorescence UV lamp (Southern New England Ultraviolet Co., Middletown, Conn.) with an emission peak at 350 nm is used as a source of UV light. The lamp is placed at a 15-cm distance from the Petri dishes with samples. SDS gel electrophoresis shows that >85% of the conjugate is cleaved under these conditions.

Example 3

Preparation of Fluorescent Labeled Primers and Demonstration of Cleavage of Fluorophore Synthesis and Purification of Oligonucleotides The oligonucleotides (ODNs) are prepared on automated DNA synthesizers using the standard phosphoramidite chemistry supplied by the vendor, or the H-phosphonate chemistry (Glenn Research Sterling, Va.). Appropriately blocked dA, dG, dC, and T phosphoramidites are commercially available in these forms, and synthetic nucleosides may readily be converted to the appropriate form. The oligonucleotides are prepared using the standard phosphoramidite supplied by the vendor, or the H-phosphonate chemistry. Oligonucleotides are purified by adaptations of standard methods. Oligonucleotides with 5'-trityl groups are chromatographed on HPLC using a 12 micrometer, 300 # Rainin (Emeryville, Calif.) Dynamax C-8 4.2×250 mm reverse phase column using a gradient of 15% to 55% MeCN in 0.1 N $Et_3NH^+OAc^-$, pH 7.0, over 20 min. When detritylation is performed, the oligonucleotides are further purified by gel exclusion chromatography. Analytical checks for the quality of the oligonucleotides are conducted with a PRP-column (Alitech, Deerfield, Ill.) at alkaline pH and by PAGE.

Preparation of 2,4,6-trichlorotriazine derived oligonucleotides: 10 to 1000 µg of 5'-terminal amine linked oligonucleotide are reacted with an excess recrystallized cyanuric chloride in 10% n-methyl-pyrrolidone in alkaline (pH 8.3 to 8.5 preferably) buffer at 19° C. to 25° C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex (Pharmacia, Piscataway, N.J.) column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with amine-reactive fluorochromes. The derived ODN preparation is divided into 3 portions and each portion is reacted with either (a) 20-fold molar excess of Texas Red sulfonyl chloride (Molecular Probes, Eugene, Oreg.), with (b) 20-fold molar excess of Lissamine sulfonyl chloride (Molecular Probes, Eugene, Oreg.), (c) 20-fold molar excess of fluorescein isothiocyanate. The final reaction conditions consist of 0.15 M sodium borate at pH 8.3 for 1 hour at room temperature. The unreacted fluorochromes are removed by size exclusion chromatography on a G-50 Sephadex column.

To cleave the fluorochrome from the oligonucleotide, the ODNs are adjusted to $1\times10^{-5}$ molar and then dilutions are made (12, 3-fold dilutions) in TE (TE is 0.01 M Tris, pH 7.0, 5 mM EDTA). To 100 µl volumes of ODNs 25 µl of 0.01 M dithiothreitol (DTT) is added. To an identical set of controls no DDT is added. The mixture is incubated for 15 minutes at room temperature. Fluorescence is measured in a black microtiter plate. The solution is removed from the incubation tubes (150 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine.

| Moles of Fluorochrome | RFU non-cleaved | RFU cleaved | RFU free |
|---|---|---|---|
| $1.0 \times 10^5$ M | 6.4 | 1200 | 1345 |
| $3.3 \times 10^6$ M | 2.4 | 451 | 456 |
| $1.1 \times 10^6$ M | 0.9 | 135 | 130 |
| $3.7 \times 10^7$ M | 0.3 | 44 | 48 |
| $1.2 \times 10^7$ M | 0.12 | 15.3 | 16.0 |
| $4.1 \times 10^7$ M | 0.14 | 4.9 | 5.1 |
| $1.4 \times 10^8$ M | 0.13 | 2.5 | 2.8 |
| $4.5 \times 10^9$ M | 0.12 | 0.8 | 0.9 |

The data indicate that there is about a 200-fold increase in relative fluorescence when the fluorochrome is cleaved from the ODN.

Example 4

Preparation of Tagged M13 Sequence Primers and Demonstration of Cleavage of Tags Preparation of 2,4,6-trichlorotriazine derived oligonucleotides: 1000 µg of 5'-terminal amine linked oligonucleotide (5'-hexylamine-TGTAAAACGACGGCCAGT-3") (Seq. ID No. 1) are reacted with an excess recrystallized cyanuric chloride in 10% n-methyl-pyrrolidone alkaline (pH 8.3 to 8.5 preferably) buffer at 19 to 25 C. for 30 to 120 minutes. The final reaction conditions consist of 0.15 M sodium borate at pH 8.3, 2 mg/ml recrystallized cyanuric chloride and 500 ug/ml respective oligonucleotide. The unreacted cyanuric chloride is removed by size exclusion chromatography on a G-50 Sephadex column.

The activated purified oligonucleotide is then reacted with a 100-fold molar excess of cystamine in 0.15 M sodium borate at pH 8.3 for 1 hour at room temperature. The unreacted cystamine is removed by size exclusion chromatography on a G-50 Sephadex column. The derived ODNs are then reacted with a variety of amides. The derived ODN preparation is divided into 12 portions and each portion is reacted (25 molar excess) with the pentafluorophenyl-esters of either: (1) 4-methoxybenzoic acid, (2) 4-fluorobenzoic acid, (3) toluic acid, (4) benzoic acid, (5) indole-3-acetic acid, (6) 2,6-difluorobenzoic acid, (7) nicotinic acid N-oxide, (8) 2-nitrobenzoic acid, (9) 5-acetylsalicylic acid, (10) 4-ethoxybenzoic acid, (11) cinnamic acid, (12) 3-aminonicotinic acid. The reaction is for 2 hours at 37° C. in 0.2 M NaBorate pH 8.3. The derived ODNs are purified by gel exclusion chromatography on G-50 Sephadex.

To cleave the tag from the oligonucleotide, the ODNs are adjusted to $1\times10^{-5}$ molar and then dilutions are made (12, 3-fold dilutions) in TE (TE is 0.01 M Tris, pH 7.0, 5 mM EDTA) with 50% EtOH (V/V). To 100 µl volumes of ODNs 25 µl of 0.01 M dithiothreitol (DTT) is added. To an identical set of controls no DDT is added. Incubation is for 30 minutes at room temperature. NaCl is then added to 0.1 M and 2 volumes of EtOH is added to precipitate the ODNs. The ODNs are removed from solution by centrifugation at 14,000×G at 4° C. for 15 minutes. The supernatants are reserved, dried to completeness. The pellet is then dissolved in 25 µl MeOH. The pellet is then tested by mass spectrometry for the presence of tags.

The mass spectrometer used in this work is an external ion source Fourier-transform mass spectrometer (FTMS). Samples prepared for MALDI analysis are deposited on the tip of a direct probe and inserted into the ion source. When the sample is irradiated with a laser pulse, ions are extracted from the source and passed into a long quadrupole ion guide that focuses and transports them to an FTMS analyzer cell located inside the bore of a superconducting magnet The spectra yield the following information. Peaks varying in intensity from 25 to 100 relative intensity units at the following molecular weights: (1) 212.1 amu indicating 4-methoxybenzoic acid derivative, (2) 200.1 indicating 4-fluorobenzoic acid derivative, (3) 196.1 amu indicating toluic acid derivative, (4) 182.1 amu indicating benzoic acid derivative, (5) 235.2 amu indicating indole-3-acetic acid derivative, (6) 218.1 amu indicating 2,6-difluorobenzoic derivative, (7) 199.1 amu indicating nicotinic acid N-oxide derivative, (8) 227.1 amu indicating 2-nitrobenzamide, (9) 179.18 amu indicating 5-acetylsalicylic acid derivative, (10) 226.1 amu indicating 4-ethoxybenzoic acid derivative, (11) 209.1 amu indicating cinnamic acid derivative, (12) 198.1 amu indicating 3-aminonicotinic acid derivative.

The results indicate that the MW-identifiers are cleaved from the primers and are detectable by mass spectrometry.

Example 5

Figure 3A:
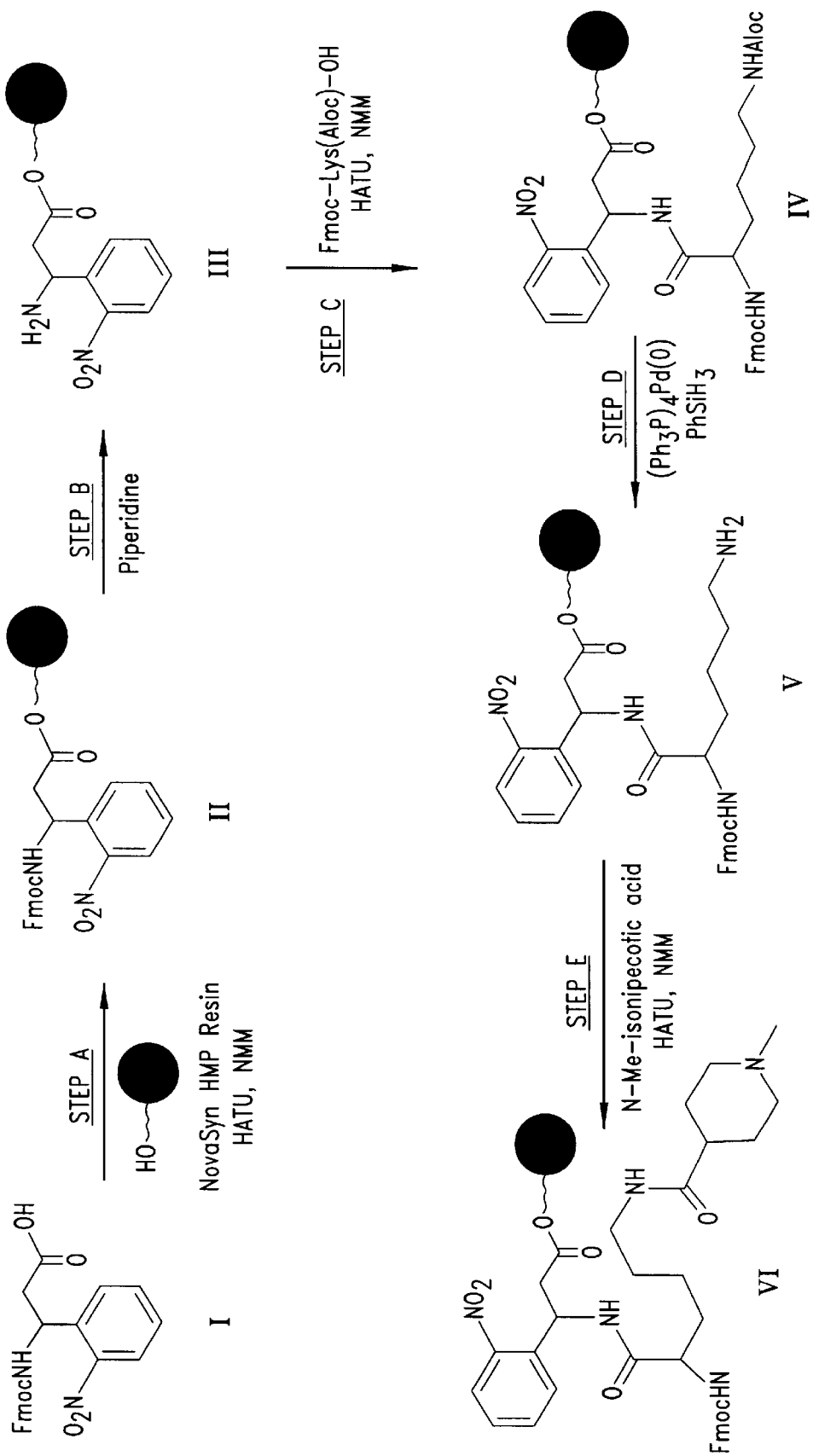
FIGS. 3A, 3B, and 3C; 4A, 4B, and 4C; 5A, 5B, and 5C;-6A, 6B, and 6C; and 8A, 8B, and 8C depict the flowchart for the synthesis of tetrafluorophenyl esters of a set of 36 photochemically cleavable mass spectroscopy tags.
Figure 3B:
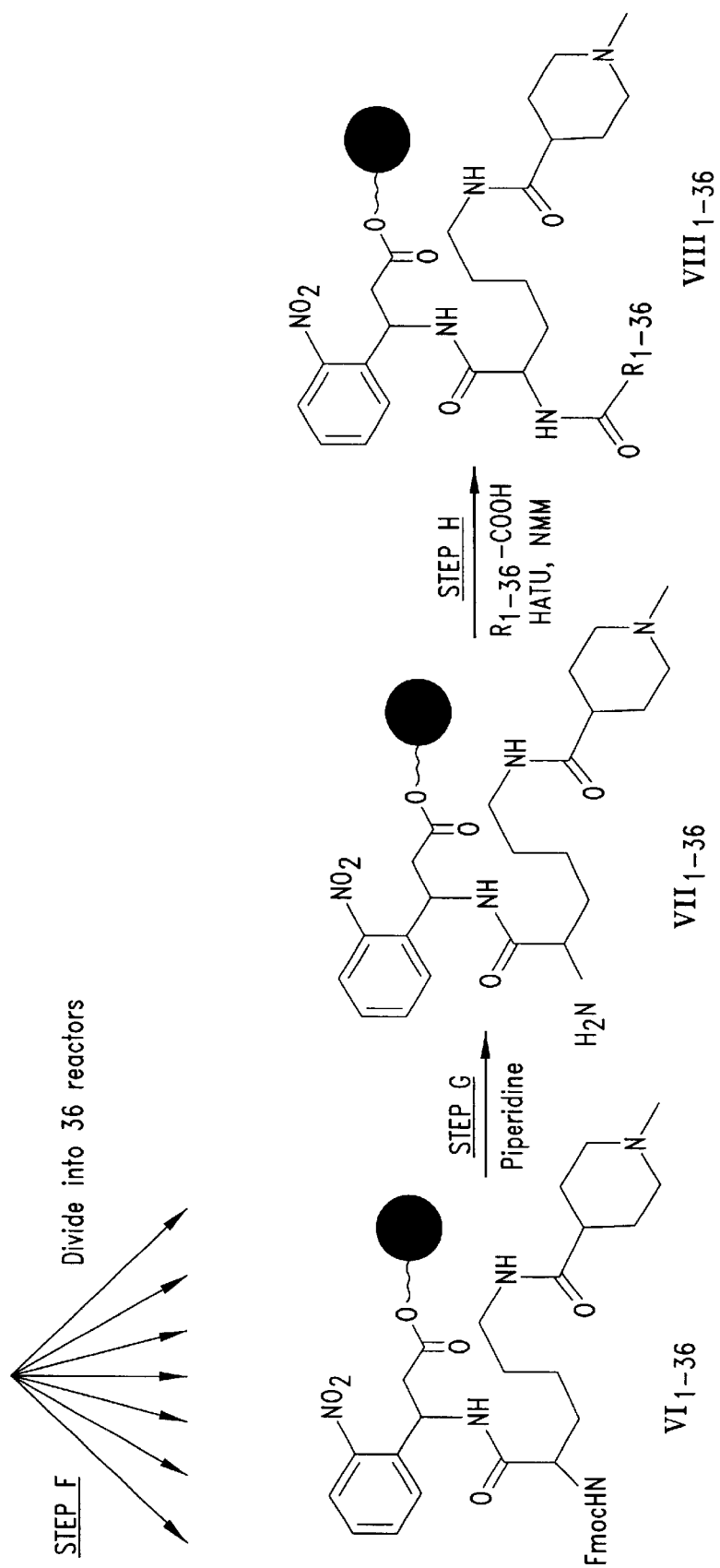
Figure 3C:
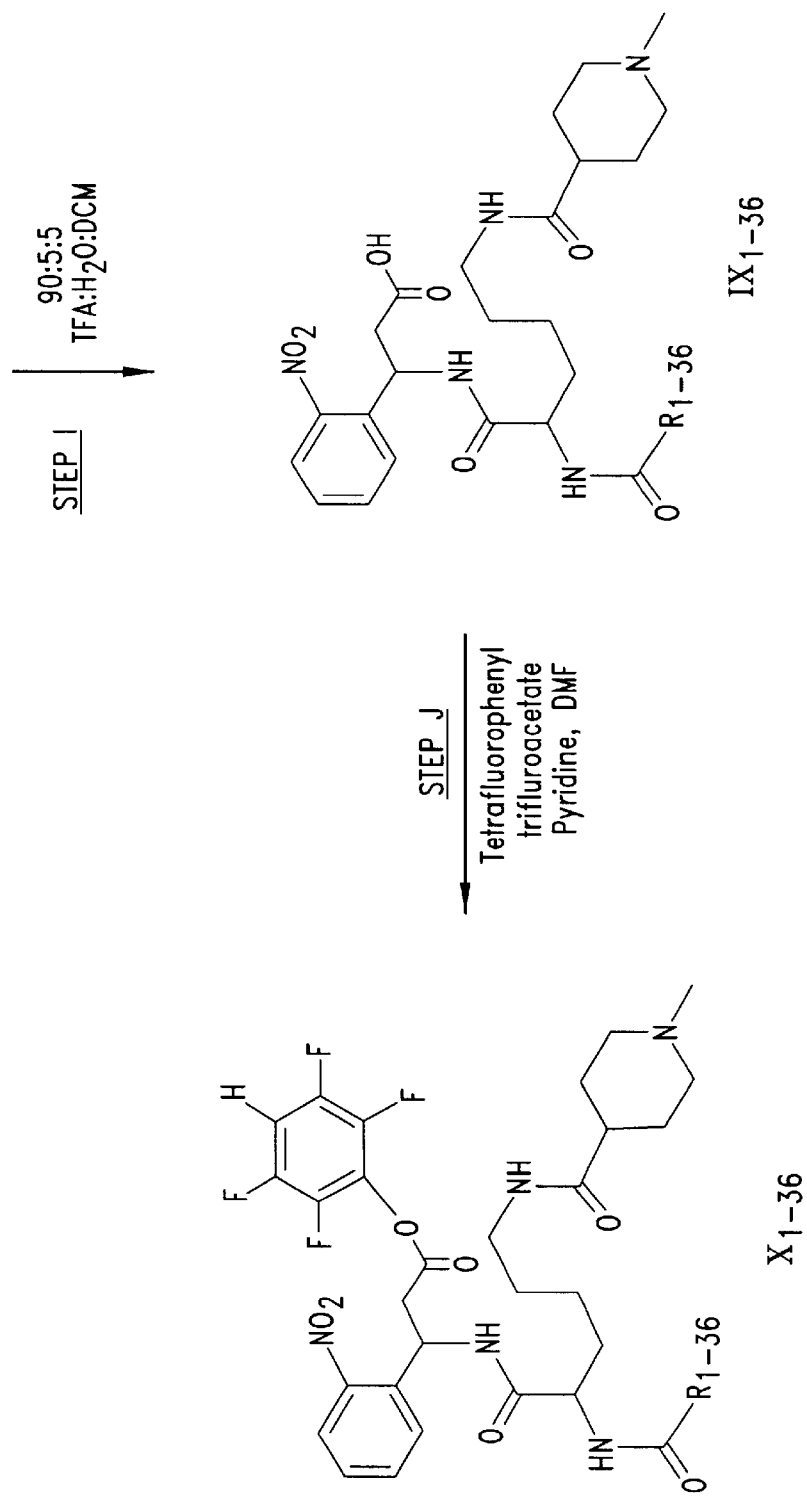

Preparation of a Set of Compounds of the Formula
$R_{1-36}$-Lys($\epsilon$-iNIP)-ANP-Tfp FIG. 3 illustrates the parallel synthesis of a set of 36 T—L—X compounds (X=$L_h$), where $L_h$ is an activated ester (specifically. tetrafluorophenyl ester), $L^2$ is an ortho-nitrobenzylamine group with $L^3$ being a methylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the $\epsilon$-amino group of the lysine.

Referring to FIG. 3:

Step A. NovaSyn HMP Resin (available from NovaBiochem; 1 eq.) is suspended with DMF in the collection vessel of the ACT357. Compound I (ANP available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound II.

Step B. The resin (compound II) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step C.

Step C. The deprotected resin from step B is suspended in DMF and to it is added an FMOC-protected amino acid, containing a protected amine functionality in its side chain (Fmoc-Lysine(Aloc)-OH, available from PerSeptive Biosystems; 3 eq.), HATU (3 eq.), and NMM (7.5 eq.) in DMF. The vessel is shaken for 1 hr. The solvent is removed and the resin washed with NMP (2×), MeOH (2×), and DMF (2×). The coupling of Fmoc-Lys(Aloc)-OH to the resin and the wash steps are repeated, to give compound IV.

Step D. The resin (compound IV) is washed with $CH_2Cl_2$ (2×), and then suspended in a solution of $(PPh_3)_4Pd$ (0) (0.3 eq.) and $PhSiH_3$ (10 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E. The deprotected resin from step D is coupled with N-methylisonipecotic acid as described in step C to give compound VI.

Step F. The Fmoc protected resin VI is divided equally by the ACT357 from the collection vessel into 36 reaction vessels to give compounds $VI_{1-36}$.

Step G. The resin (compounds $VI_{1-36}$) is treated with piperidine as described in step B to remove the FMOC group.

Step H. The 36 aliquots of deprotected resin from step G are suspended in DMF. To each reaction vessel is added the appropriate carboxylic acid ($R_{1-36}CO_2H$; 3 eq.), HATU (3 eq.), and NMM (7.5 eq.) in DMF. The vessels are shaken for 1 hr. The solvent is removed and the aliquots of resin washed with NMP (2×), MeOH (2×), and DMF (2×). The coupling of $R_{1-36}CO_2H$ to the aliquots of resin and the wash steps are repeated, to give compounds $VII_{1-36}$.

Step I. The aliquots of resin (compounds $VIII_{1-36}$) are washed with $CH_2Cl_2$ (3×). To each of the reaction vessels is added 90:5:5 TFA:H20:$CH_2Cl_2$ and the vessels shaken for 120 min. The solvent is filtered from the reaction vessels into individual tubes. The aliquots of resin are washed with $CH_2Cl_2$ (2×) and MeOH (2×) and the filtrates combined into the individual tubes. The individual tubes are evaporated in vacuo, providing compounds $IX_{1-36}$.

Step J. Each of the free carboxylic acids $IX_{1-36}$ is dissolved in DMF. To each solution is added pyridine (1.05 eq.), followed by tetrafluorophenyl trifluoroacetate (1.1 eq.). The mixtures are stirred for 45 min. at room temperature. The solutions are diluted with EtOAc, washed with 5% aq. $NaHCO_3$ (3×), dried over $Na_2SO_4$, filtered, and evaporated in vacuo, providing compounds $IX_{1-36}$.

Example 6

Figure 4A:
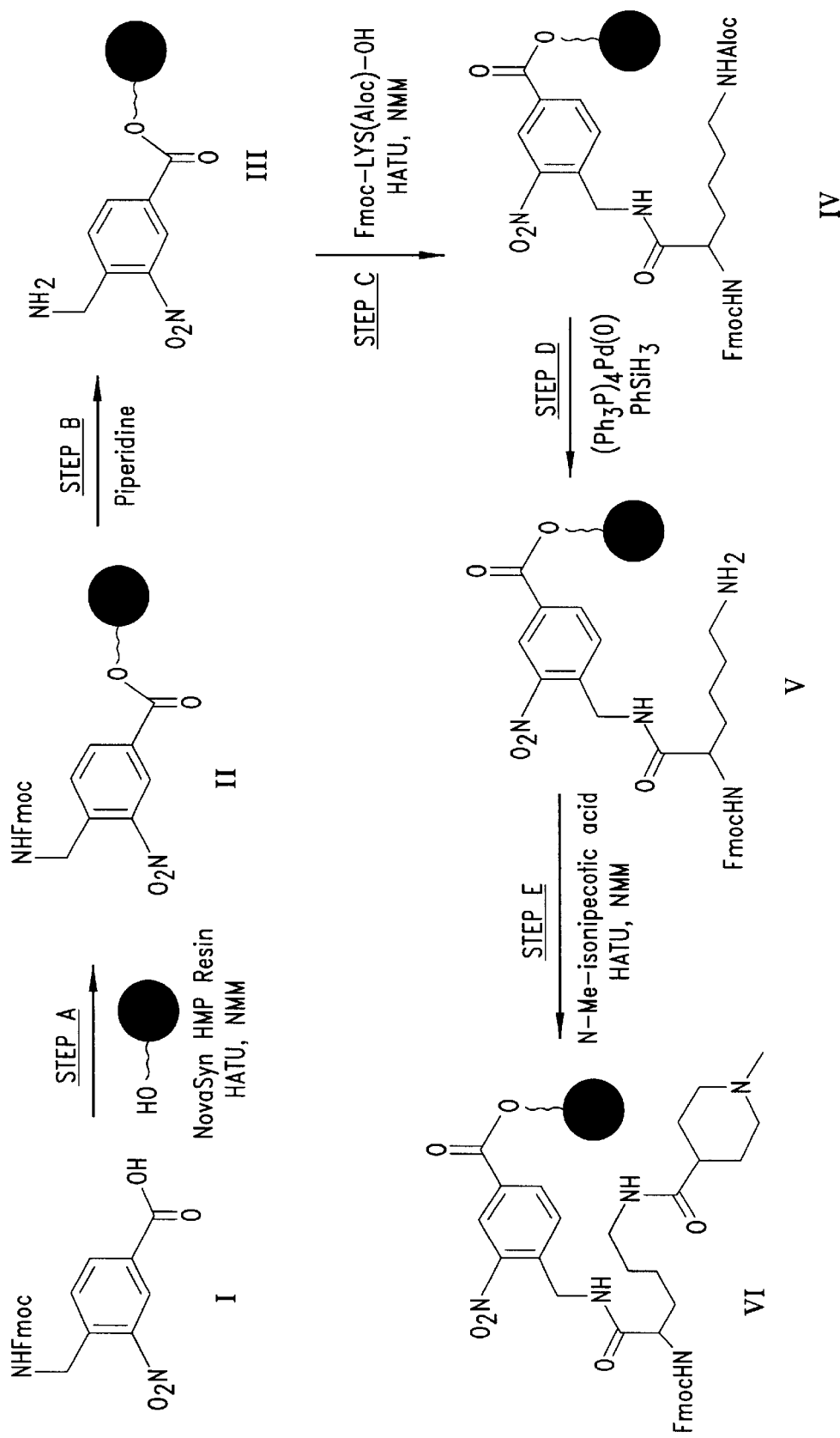
Figure 4B:
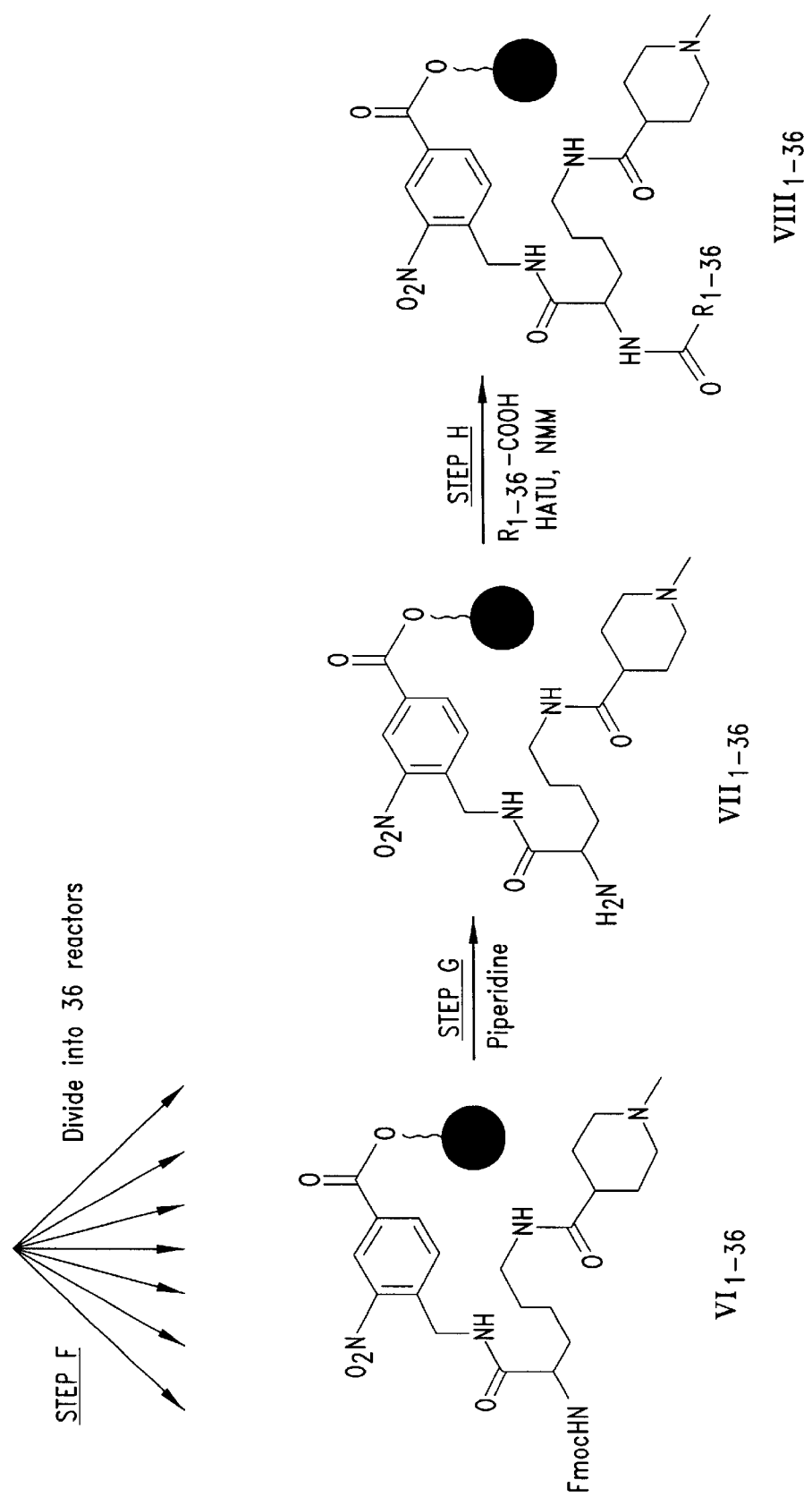
Figure 4C:
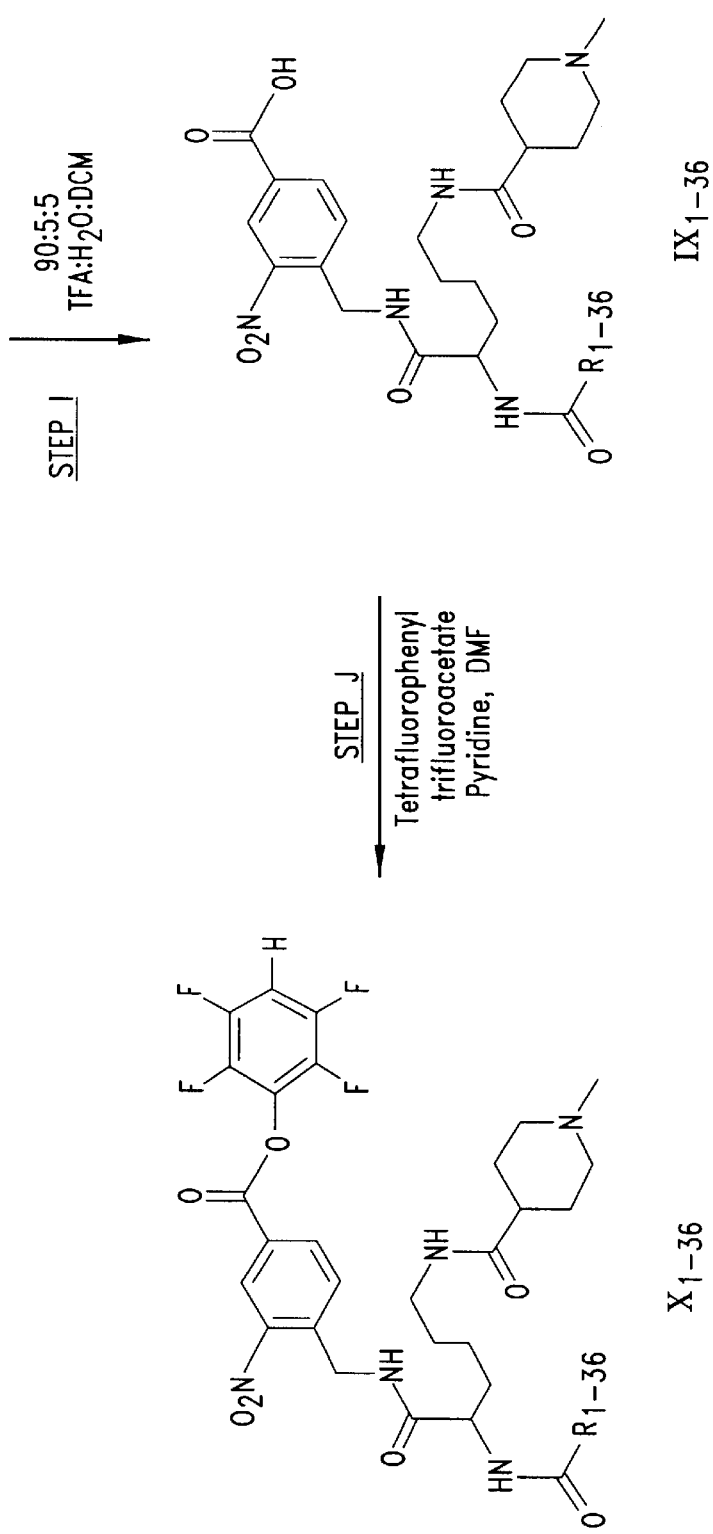

Preparation of a Set of Compounds of the formula
$R_{1-36}$-Lys($\epsilon$-iNIP)-NBA-Tfp FIG. 4 illustrates the parallel synthesis of a set of 36 T—L—X compounds (X=$L_h$), where $L_h$ is an activated ester (specifically, tetrafluorophenyl ester), $L^2$ is an ortho-nitrobenzylamine group with $L^3$ being a direct bond between $L_h$ and $L^2$, where $L_h$ is joined directly to the aromatic ring of the $L^2$ group, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec enhancer group (introduced via N-methylisonipecotic acid) is bonded through the ε-amino group of the. lysine.

Referring to FIG. 4

Step A. NovaSyn HMP Resin is coupled with compound I (NBA prepared according to the procedure of Brown et al., Molecular Diversity, 1, 4 (1995)) according to the procedure described in step A of Example 5, to give compound II.

Steps B–J. The resin (compound II) is treated as described in steps B–J of Example 5 to give compounds $X_{1-36}$.

Example 7

Figure 5A:
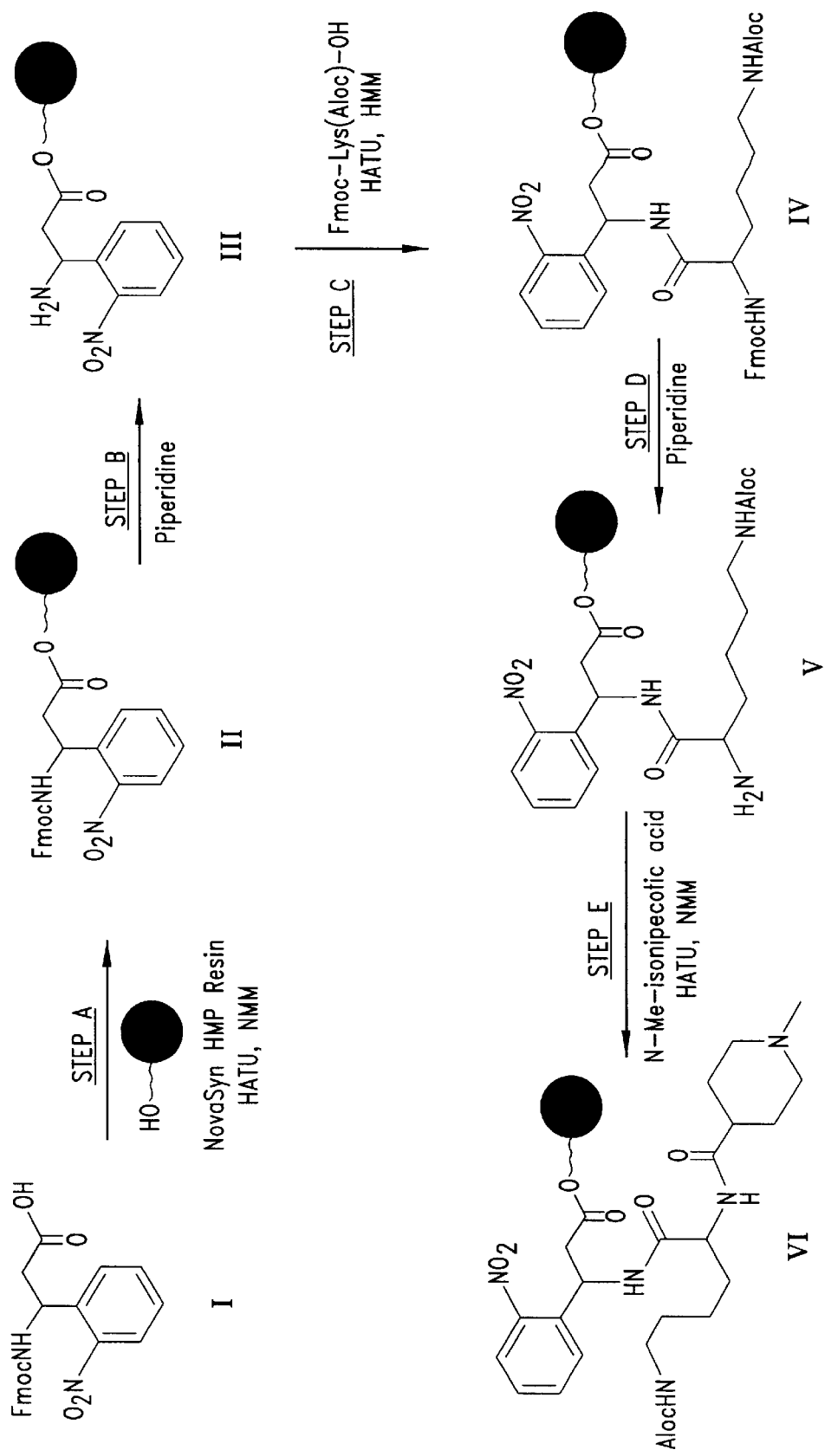
Figure 5B:
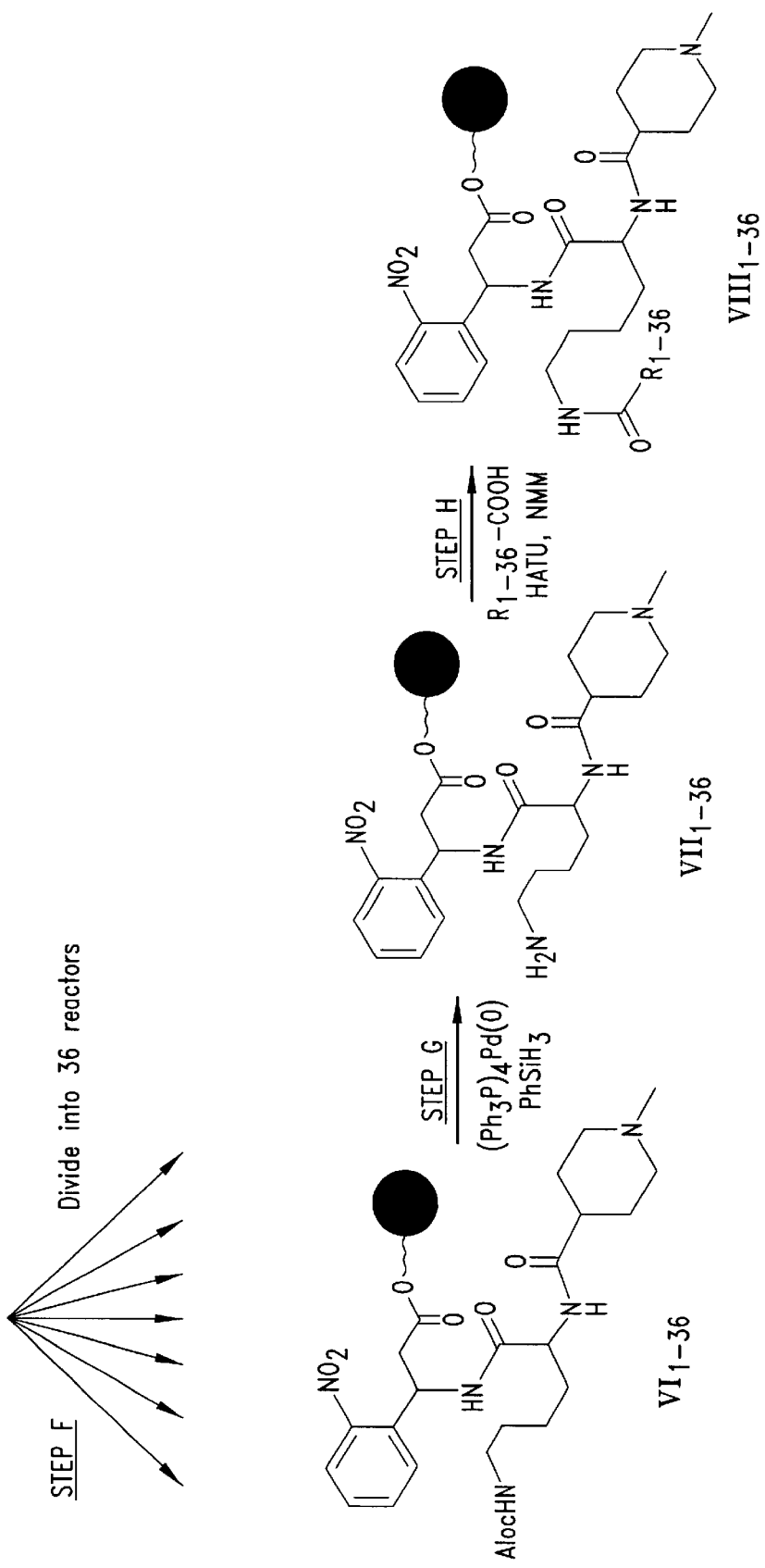
Figure 5C:
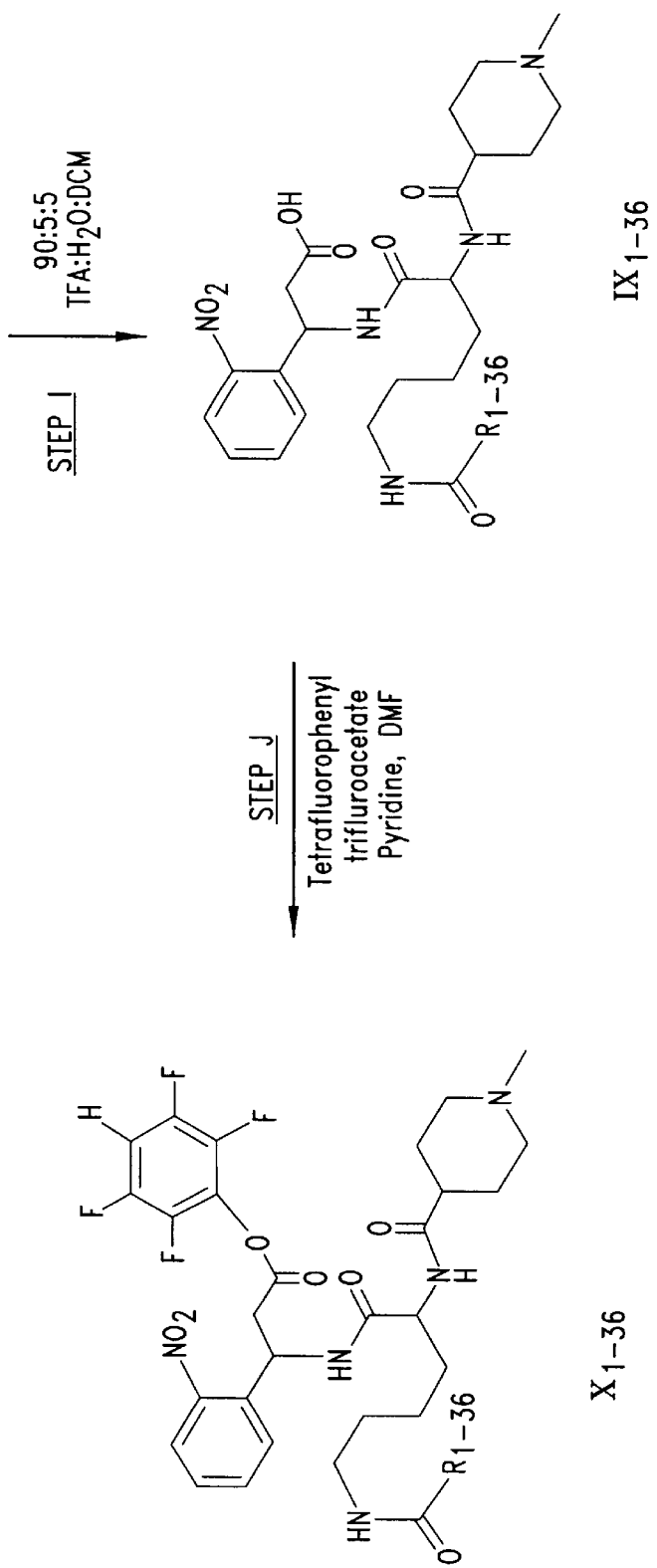

Preparation of a Set of Compounds of the Formula iNIP-Lys(ε-$R_{1-36}$)-ANP-Tfp FIG. 5 illustrates the parallel synthesis of a set of 36 T—L—X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the α-amino group of the lysine.

Referring to FIG. 5:

Steps A–C. Same as in Example 5.

Step D. The resin (compound IV) is treated with piperidine as described in step B of Example 5 to remove the FMOC group.

Step E. The deprotected α-amine on the resin in step D is coupled with N-methylisonipecotic acid as described in step C of Example 5 to give compound V.

Step F. Same as in Example 5.

Step G. The resin (compounds $VI_{1-36}$) are treated with palladium as described in step D of Example 5 to remove the Aloc group.

Steps H–J. The compounds $X_{1-36}$ are prepared in the same manner as in Example 5.

Example 8

Figure 6A:
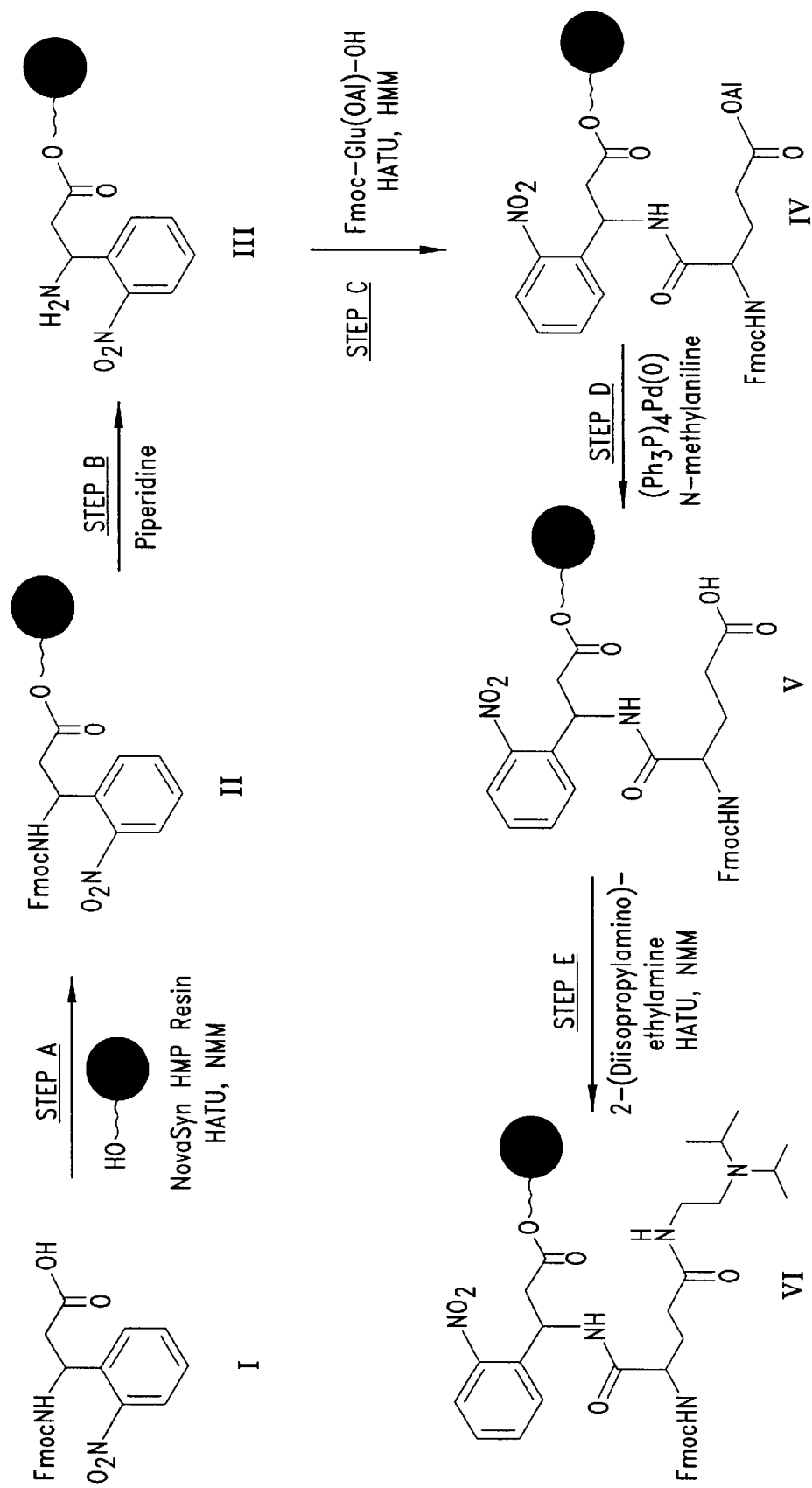
Figure 6B:
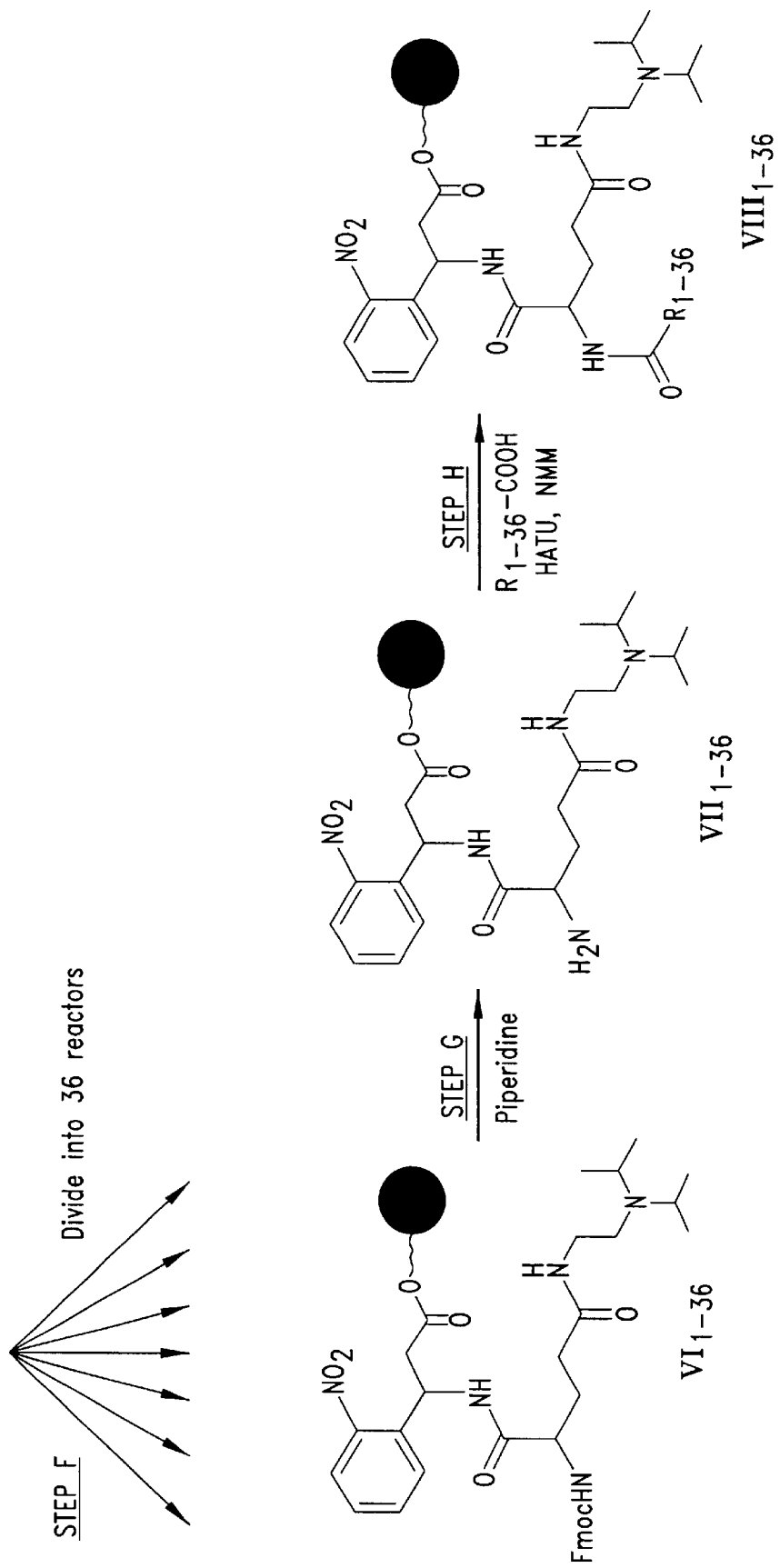
Figure 6C:
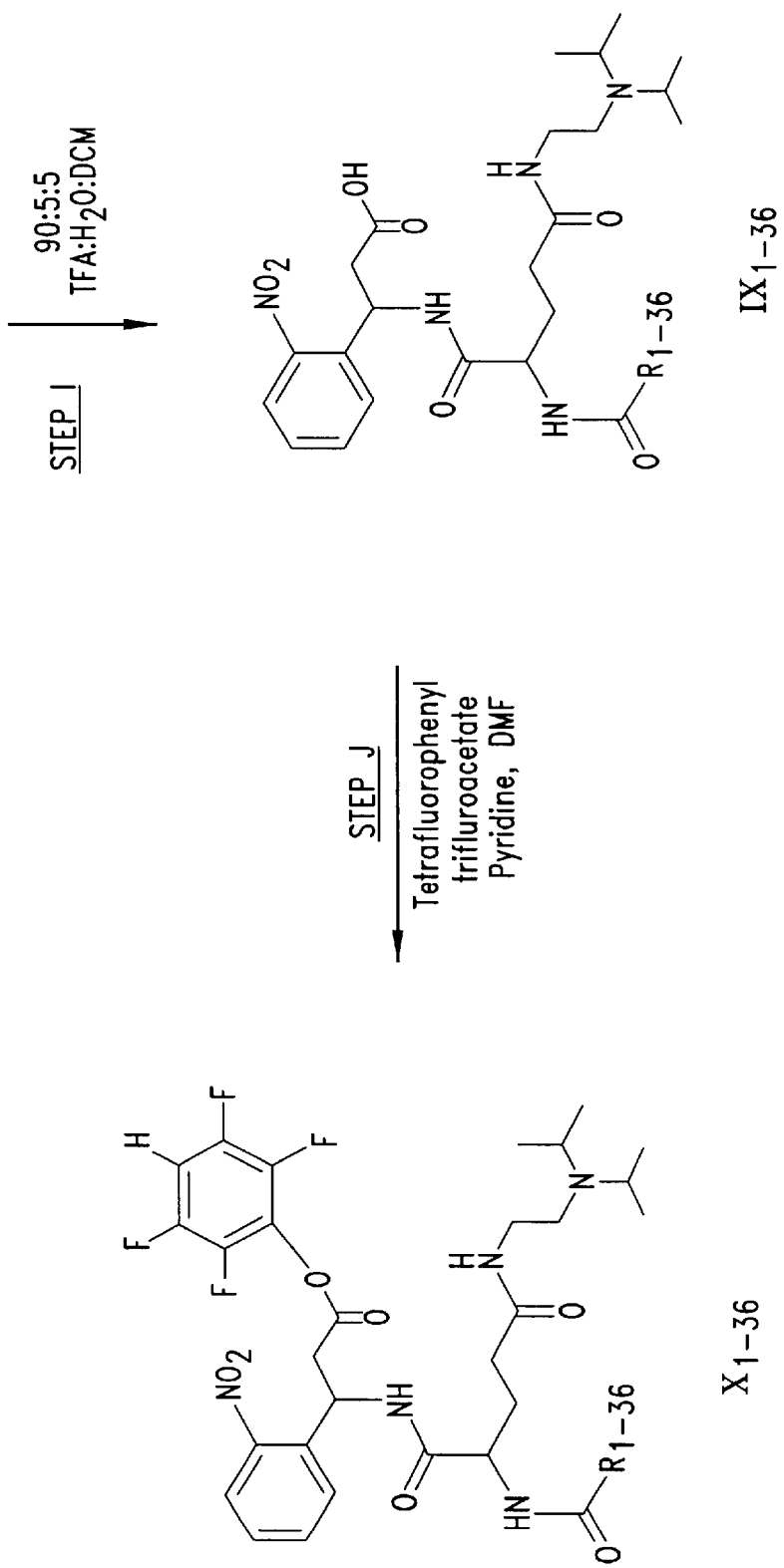

Preparation of a Set of Compounds of the Formula $R_{1-36}$-Glu(γ-DIAEA)-ANP-Tfp FIG. 6 illustrates the parallel synthesis of a set of 36 T—L—X compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the α-carboxylic acid group of glutamatic acid has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the aα-amino group of the glutamic acid, while a mass spec sensitivity enhancer group (introduced via 2-(diisopropylamino)ethylamine) is bonded through the γ-carboxylic acid of the glutamic acid.

Referring to FIG. 6:

Steps A–B. Same as in Example 5.

Step C. The deprotected resin (compound III) is coupled to Fmoc-Glu-(OAl)-OH using the coupling method described in step C of Example 5 to give compound IV.

Step D. The allyl ester on the resin (compound IV) is washed with $CH_2Cl_2$ (2×) and mixed with a solution of $(PPh_3)_4Pd(0)$ (0.3 eq.) and N-methylaniline (3 eq.) in $CH_2Cl_2$. The mixture is shaken for 1 hr. The solvent is removed and the resin is washed with $CH_2Cl_2$ (2×). The palladium step is repeated. The solvent is removed and the resin is washed with $CH_2Cl_2$ (2×), N,N-diisopropylethylammonium diethyldithiocarbamate in DMF (2×), DMF (2×) to give compound V.

Step E. The deprotected resin from step D is suspended in DMF and activated by mixing HATU (3 eq.), and NMM (7.5 eq.). The vessels are shaken for 15 minutes. The solvent is removed and the resin washed with NMP (IX). The resin is mixed with 2-(diisopropylamino)ethylamine (3 eq.) and NMM (7.5 eq.). The vessels are shaken for 1 hour. The coupling of 2-(diisopropylamino)ethylamine to the resin and the wash steps are repeated, to give compound VI.

Steps F–J. Same as in Example 5.

Example 9

Figure 7A:
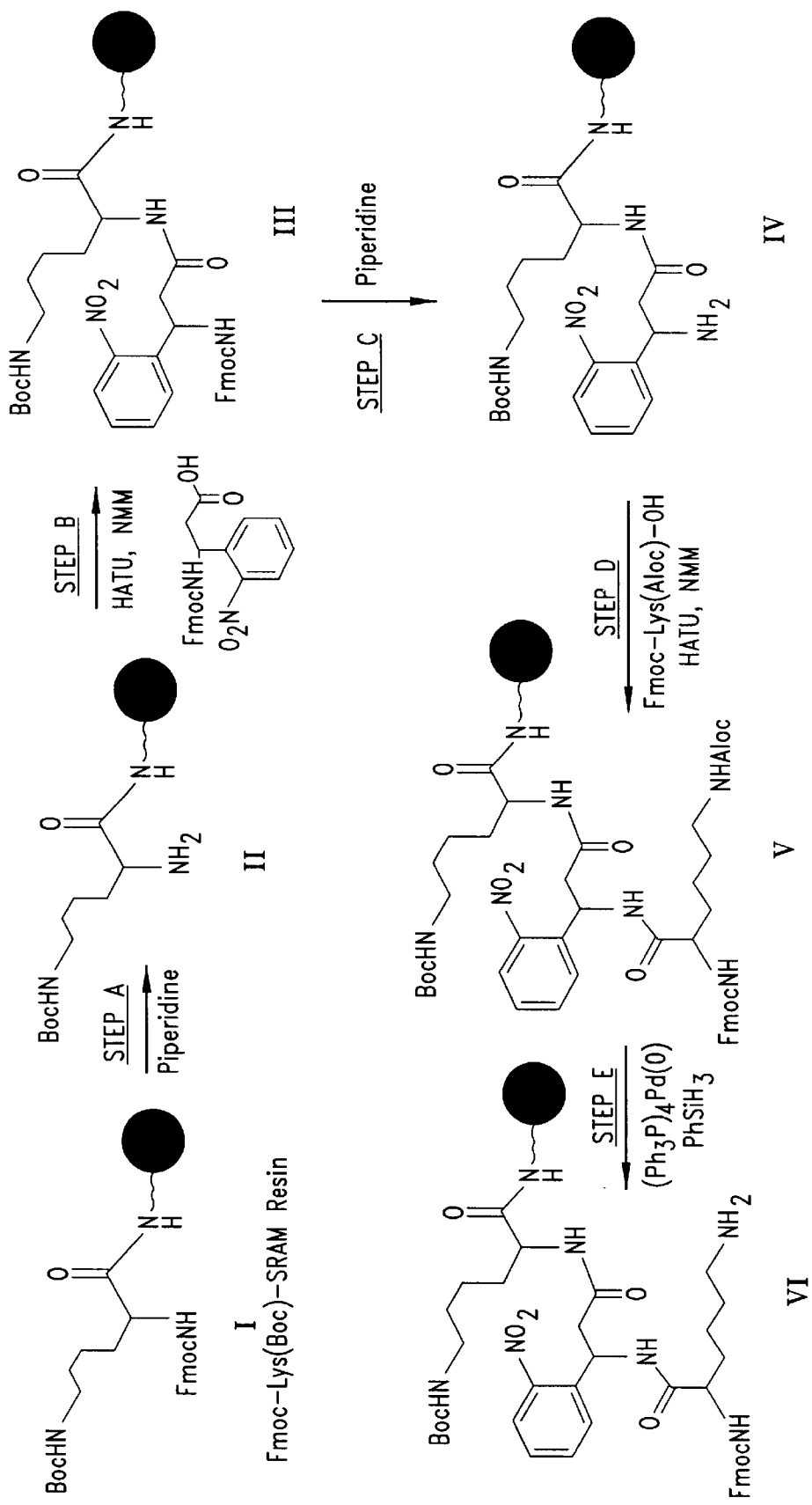
FIGS. 7A, 7B, and 7C depicts the flowchart for the synthesis of a set of 36 amine-terminated photochemically cleavable mass spectroscopy tags.
Figure 7B:
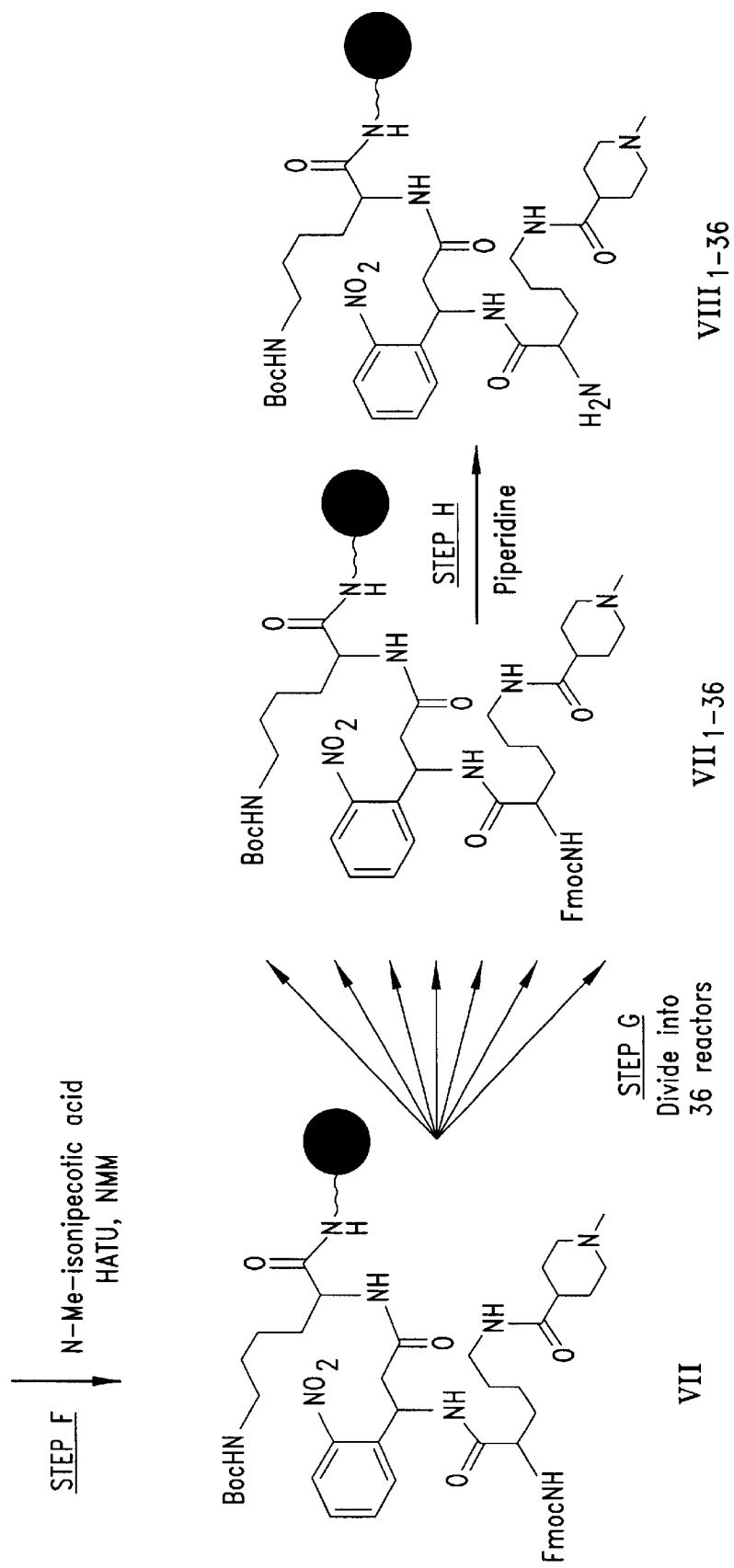
Figure 7C:
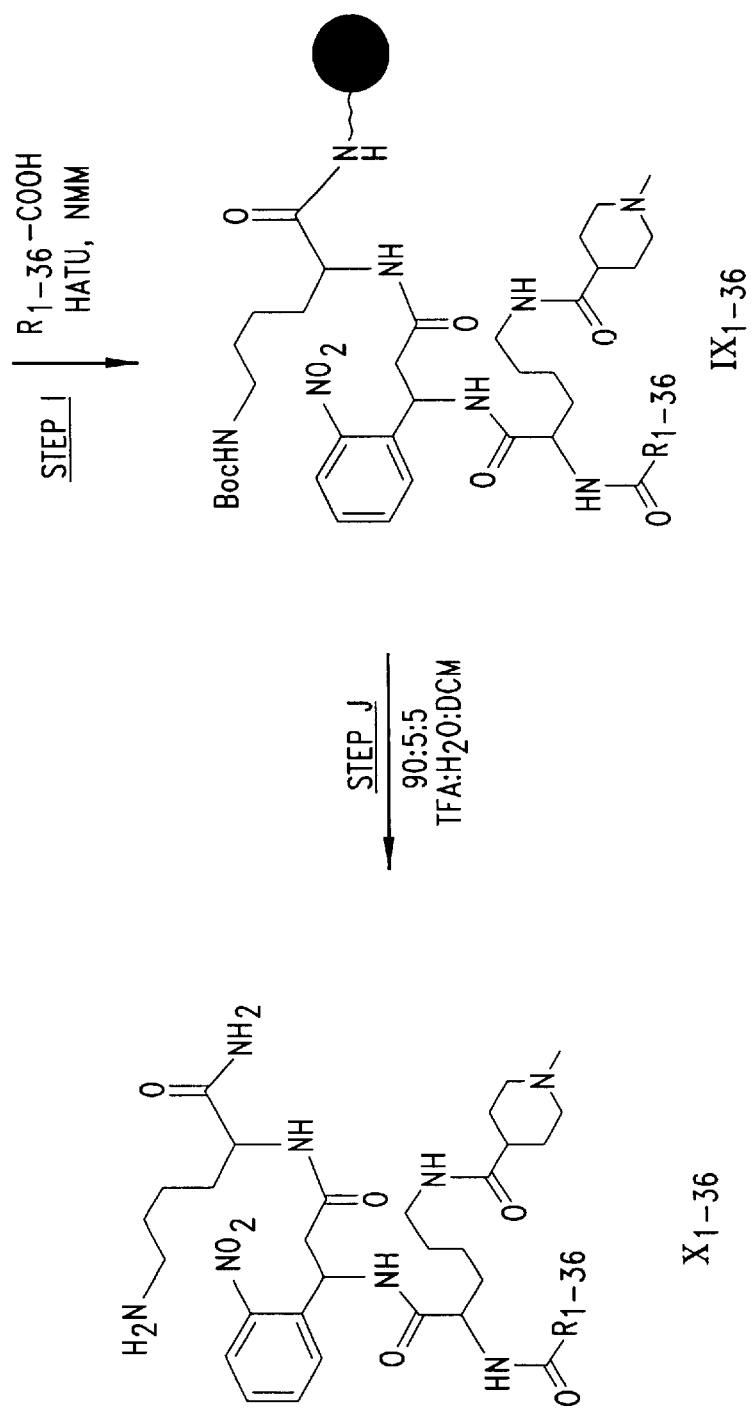

Preparation of a Set of Compounds of the Formula $R_{1-36}$-Lys(ε-iNIP)-ANP-Lys(ε-$NH_2$)-$NH_2$ FIG. 7 illustrates the parallel synthesis of a set of 36 T—L—X compounds (X=$L_h$), where $L_h$ is an amine (specifically, the ε-amino group of a lysine-derived moiety), $L^2$ is an ortho-nitrobenzylamine group with $L^3$ being a carboxamido-substituted alkyleneaminoacylalkylene group that links $L_h$ and $L^2$, T has a modular structure wherein the carboxylic acid group of lysine has been joined to the nitrogen atom of the $L^2$ benzylamine group to form an amide bond, and a variable weight component $R_{1-36}$, (where these R groups correspond to $T^2$ as defined herein, and may be introduced via any of the specific carboxylic acids listed herein) is bonded through the α-amino group of the lysine, while a mass spec sensitivity enhancer group (introduced via N-methylisonipecotic acid) is bonded through the ε-amino group of the lysine.

Referring to FIG. 7:

Step A. Fmoc-Lys(Boc)-SRAM Resin (available from ACT; compound I) is mixed with 25% piperidine in DMF and shaken for 5 min. The resin is filtered, then mixed with 25% piperidine in DMF and shaken for 10 min. The solvent is removed, the resin washed with NMP (2×), MeOH (2×), and DMF (2×), and used directly in step B.

Step B. The resin (compound II), ANP (available from ACT; 3 eq.), HATU (3 eq.) and NMM (7.5 eq.) in DMF are added and the collection vessel shaken for 1 hr. The solvent is removed and the resin washed with NMP (2×), MeOH (2×), and DMF (2×). The coupling of I to the resin and the wash steps are repeated, to give compound III.

Steps C–J. The resin (compound III) is treated as in steps B–I in Example 5 to give compounds $X_{1-36}$.

Example 10

Figure 8A:
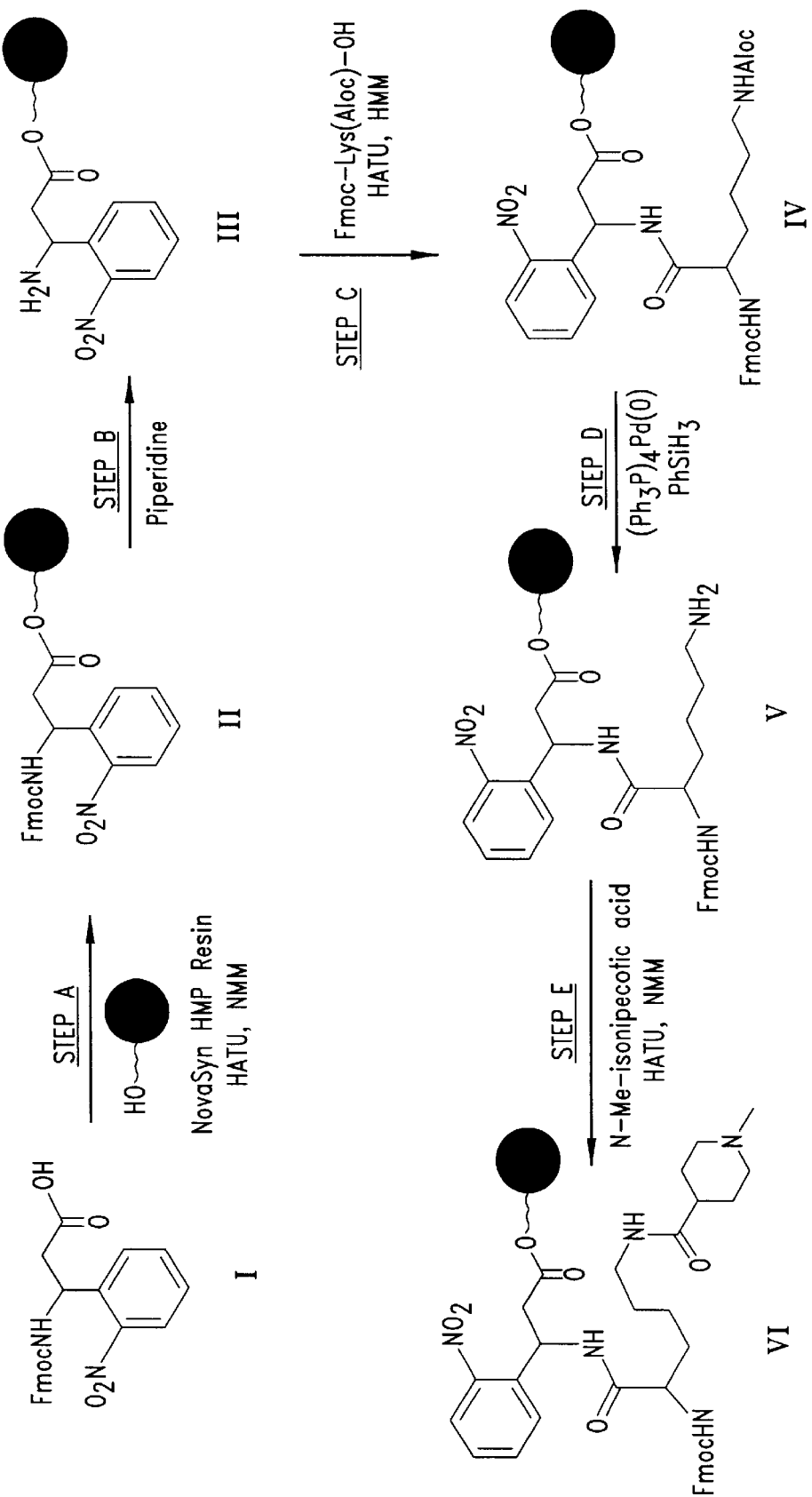
Figure 8B:
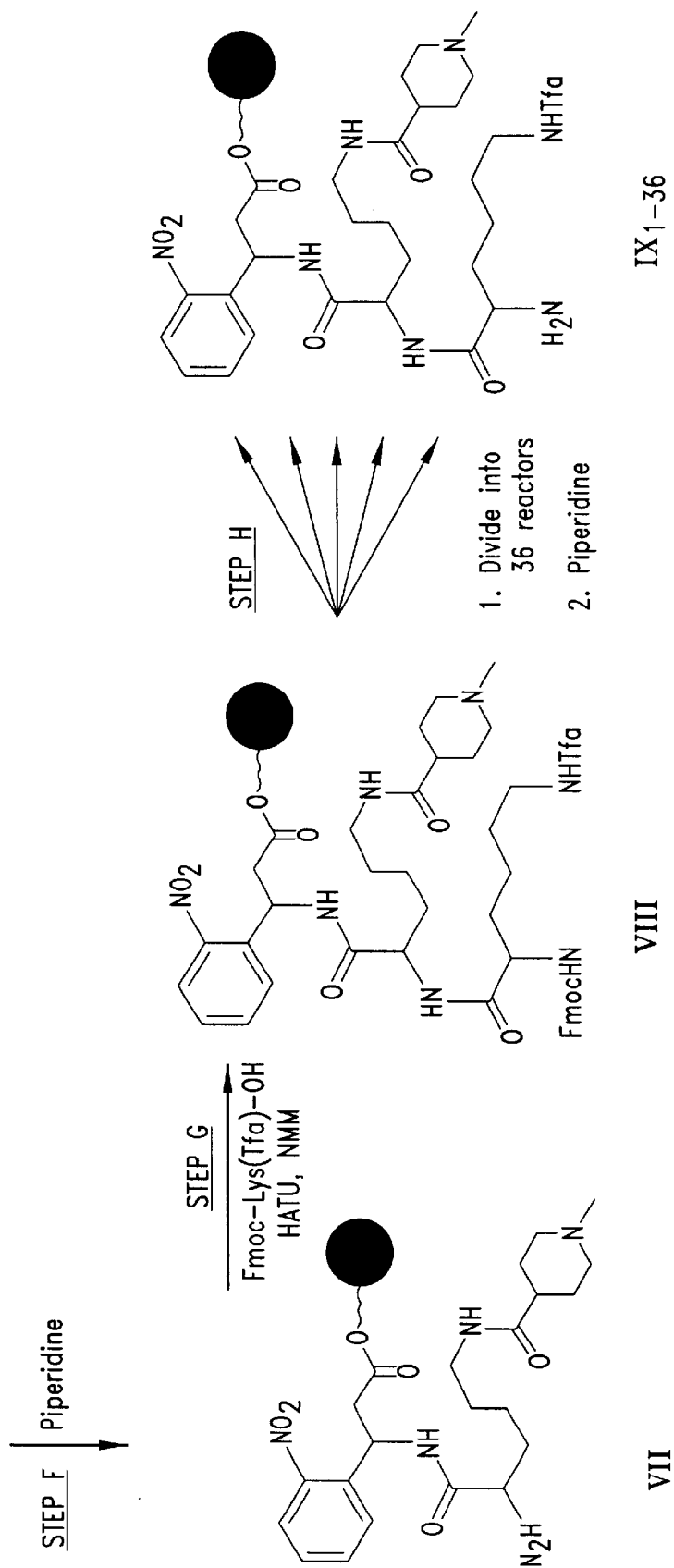
Figure 8C:
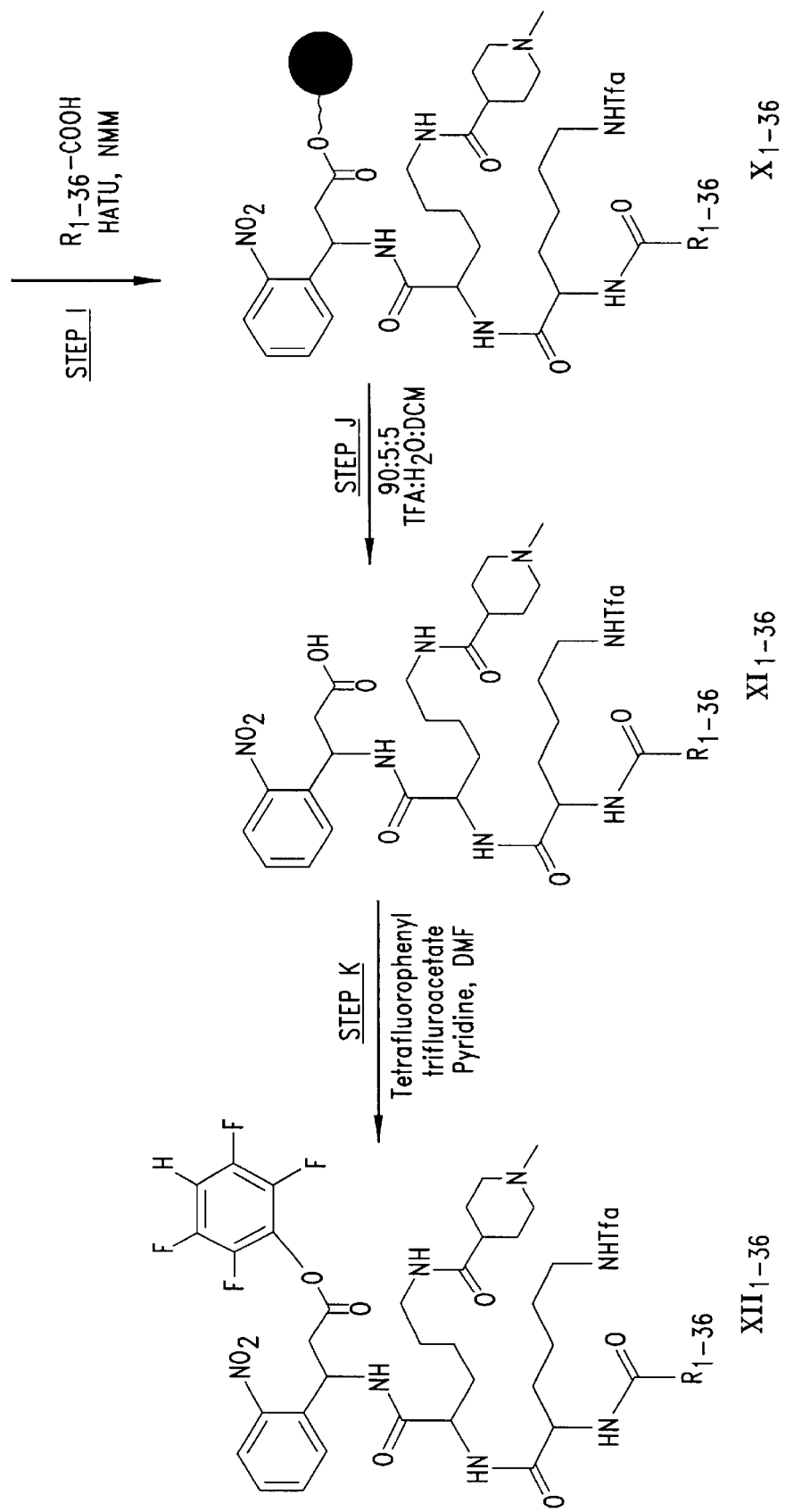

Preparation of a Set of Compounds of the Formula $R_{1-36}$-Lys(ε-Tfa)-Lys(ε-iINP)-ANP-Tfp FIG. 8 illustrates the parallel synthesis of a set of 36 T—L—X -compounds (X=$L_h$), where $L_h$ is an activated ester (specifically, tetrafluorophenyl ester), $L^2$ is an ortho-nitrobenzylamine group with $L^3$ being a methylene group that links $L_h$ and $L^2$, T has a modular structure wherein the carboxylic acid group of a first lysine has been joined to the nitrogen atom of the $L^2$ benzylamine group to form an amide bond, a mass spec sensitivity enhancer group (introduced via N-methylisonipecotic acid) is bonded through the ε-amino group of the first lysine, a second lysine molecle has been joined to the first lysine through the α-amino group of the first lysine, a molecular weight adjuster group (having a trifluoroacetyl structure) is bonded through the ε-amino group of the second lysine, and a variable weight component $R_{1-36}$, (where these R groups correspond to $T^2$ as defined herein, and may be introduced via any of the specific carboxylic acids listed herein) is bonded through the α-amino group of the second lysine. Referring to FIG. 8:

Steps A–E. These steps are identical to steps A–E in Example 5.

Step F. The resin (compound VI) is treated with piperidine as described in step B in Example 5 to remove the FMOC group.

Step G. The deprotected resin (compound VII) is coupled to Fmoc-Lys(Tfa)-OH using the coupling method described in step C of Example 5 to give compound VIII.

Steps H–K. The resin (compound VIII) is treated as in steps F–J in Example 5 to give compounds $X_{1-36}$.

Example 11

Figure 9:
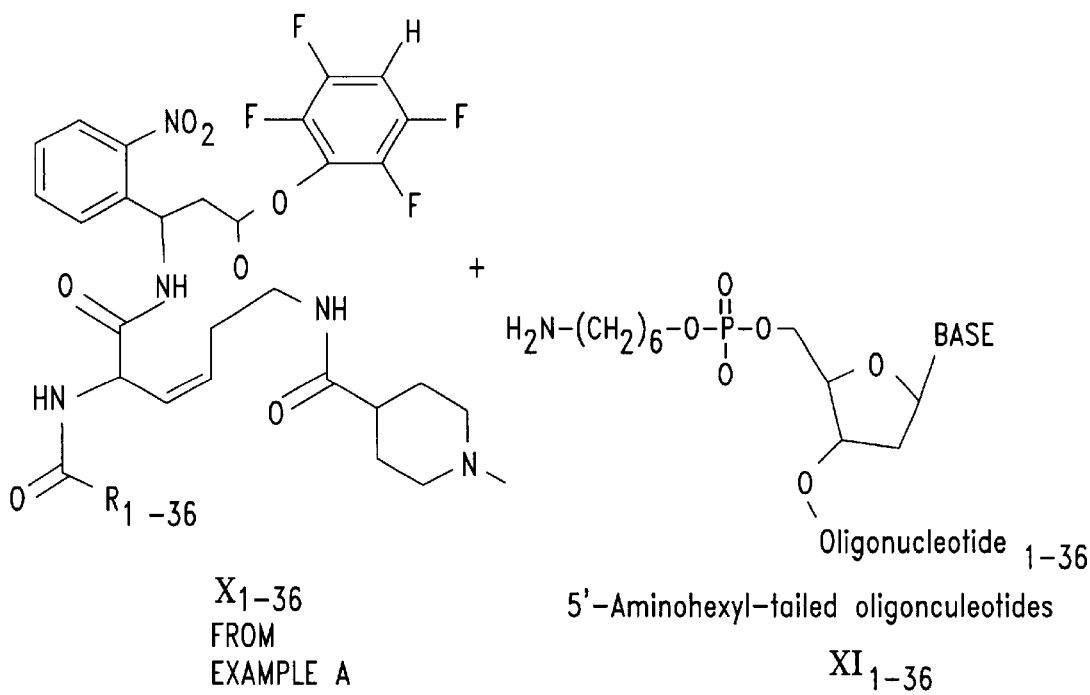
FIG. 9 depicts the synthesis of 36 photochemically cleavable mass spectroscopy tagged oligonucleotides made from the corresponding set of 36 tetrafluorophenyl esters of photochemically cleavable mass spectroscopy tag acids.
Figure 9:
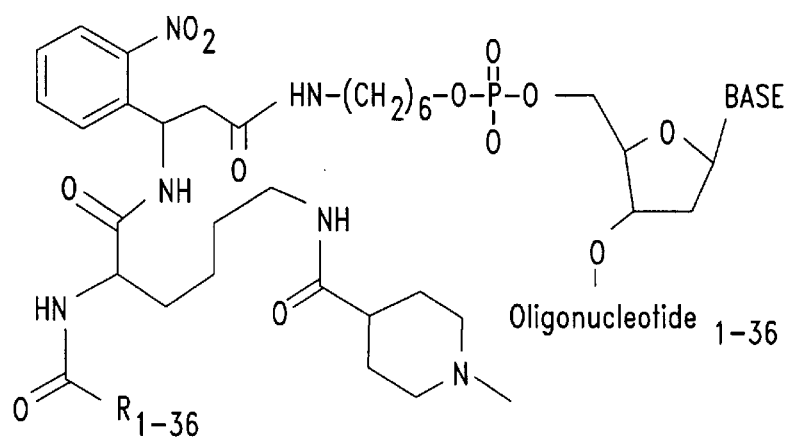

Preparation of a Set of Compounds of the Formula
$R_{1-36}$-Lys(ε-iNIP)-ANP-5'-AH-ODN FIG. 9 illustrates the parallel synthesis of a set of 36 T—L—X compounds (X=MOI, where MOI is a nucleic acid fragment, ODN) derived from the esters of Example 5 (the same procedure could be used with other T—L—X compounds wherein X is an activated ester). The MOI is conjugated to T—L through the 5' end of the MOI, via a phosphodiester-alkyleneamine group.

Referring to FIG. 9:

Step A. Compounds $XII_{1-36}$ are prepared according to a modified biotinylation procedure in Van Ness et al., Nucleic Acids Res., 19, 3345 (1991). To a solution of one of the 5'-aminohexyl oligonucleotides (compounds $XI_{1-36}$, 1 mg) in 200 mM sodium borate (pH 8.3, 250 mL) is added one of the Tetrafluorophenyl esters (compounds $X_{1-36}$ from Example A, 100-fold molar excess in 250 mL of NMP). The reaction is incubated overnight at ambient temperature. The unreacted and hydrolyzed tetrafluorophenyl esters are removed from the compounds $XII_{1-36}$ by Sephadex G-50 chromatography.

Example 12

Figure 10A:
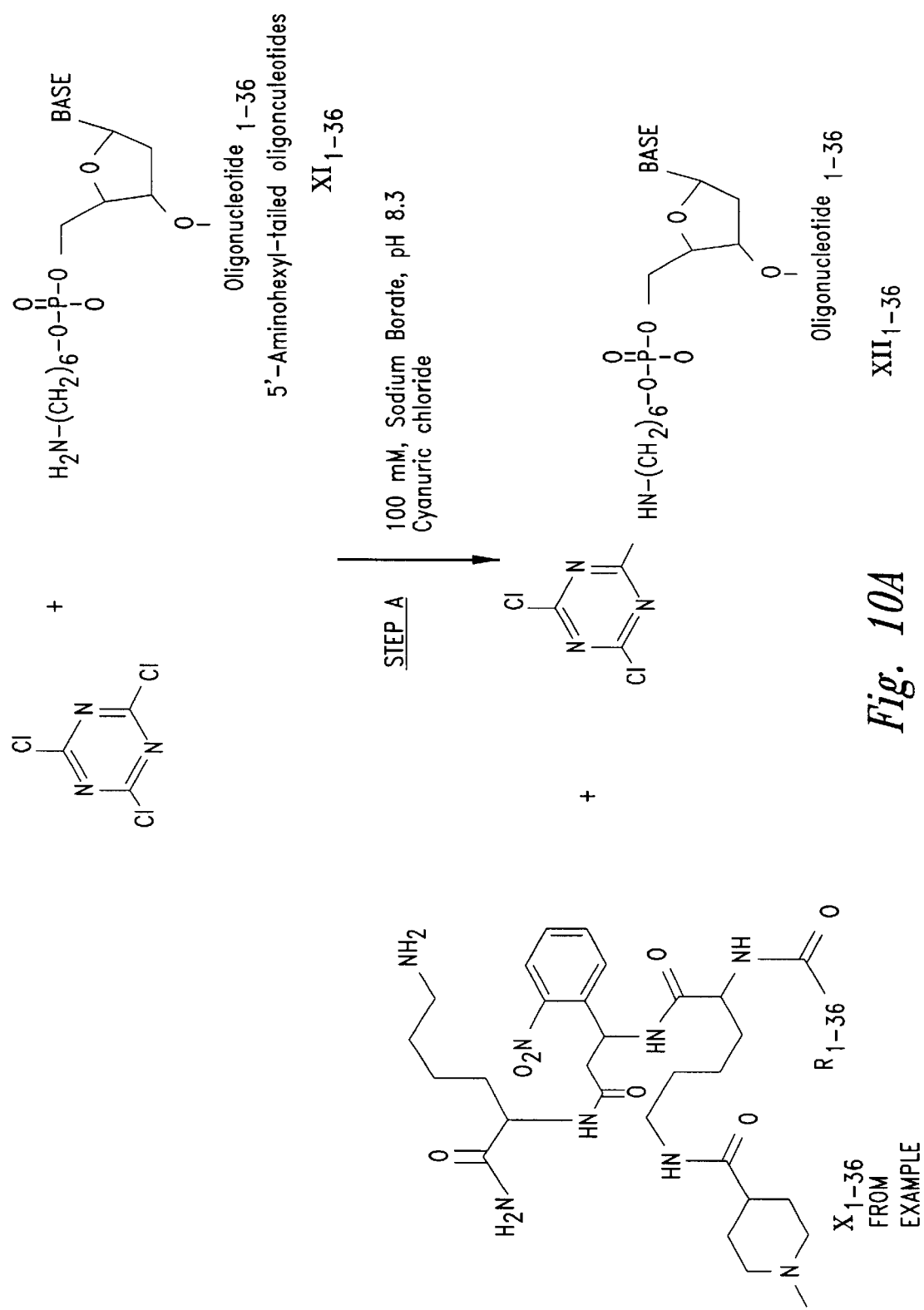
FIGS. 10A and 10B depicts the synthesis of 36 photochemically cleavable mass spectroscopy tagged oligonucleotides made from the corresponding set of 36 amine-terminated photochemically cleavable mass spectroscopy tags.
Figure 10B:
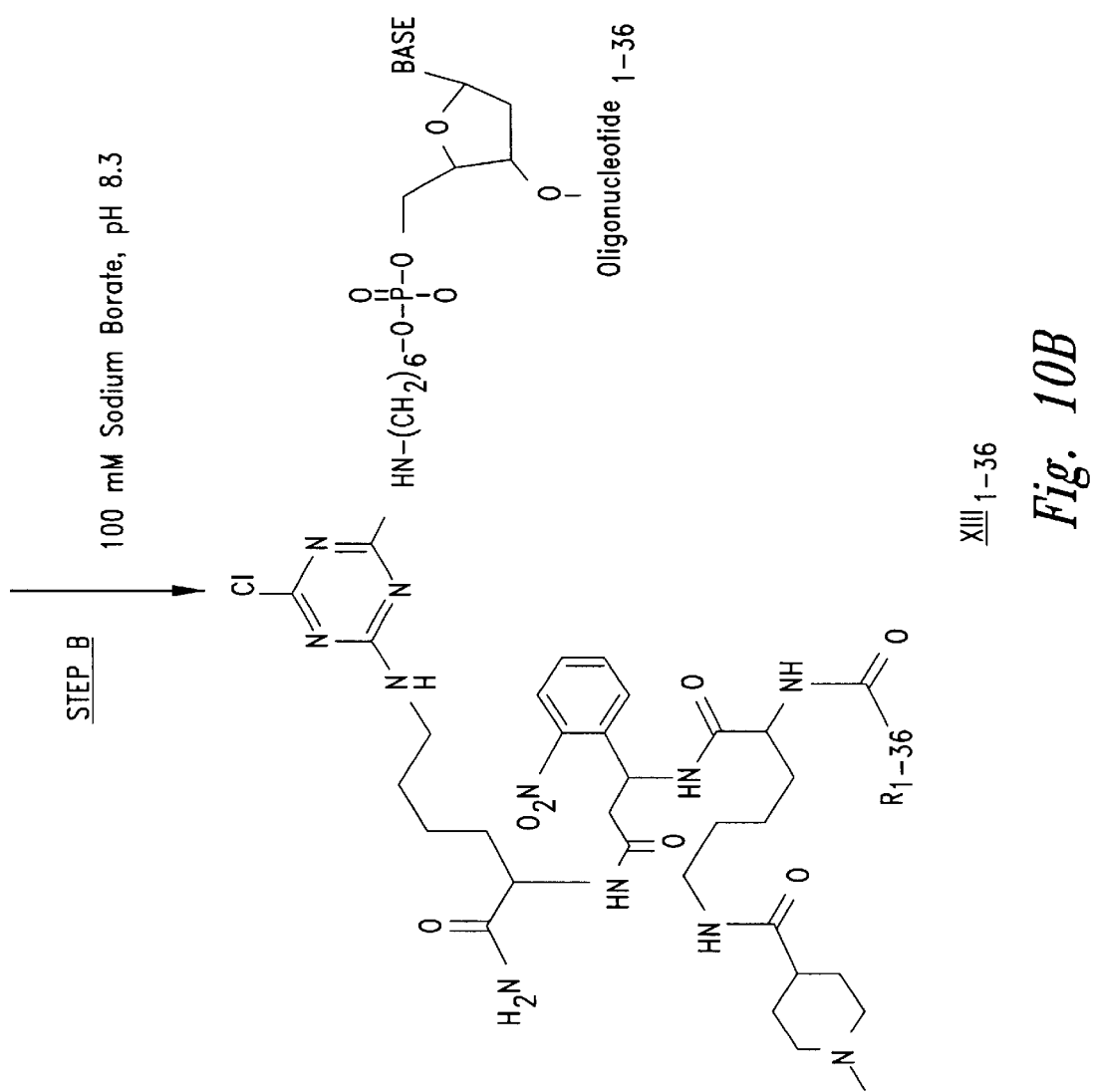

Preparation of a Set of Compounds of the Formula
$R_{1-36}$-Lys(ε-iNIP)-ANP-Lys(ε-(MCT-5'-AH-ODN))-$NH_2$ FIG. 10 illustrates the parallel synthesis of a set of 36 T—L—X compounds (X=MOI, where MOI is a nucleic acid fragment, ODN) derived from the amines of Example 11 (the same procedure could be used with other T—L—X compounds wherein X is an amine). The MOI is conjugated to T—L through the 5' end of the MOI, via a phosphodiester-alkyleneamine group.

Referring to FIG. 10:

Step A. The 5'-[6-(4,6-dichloro-1,3,5-triazin-2-ylamino) hexyl]oligonucleotides $XII_{1-36}$ are prepared as described in Van Ness et al., Nucleic Acids Res., 19, 3345 (1991).

Step B. To a solution of one of the 5'-[6-(4,6-dichloro-1,3, 5-triazin-2-ylamino)hexyl]oligonucleotides (compounds $XII_{1-36}$) at a concentration of 1 mg/ml in 100 mM sodium borate (pH 8.3) was added a 100-fold molar excess of a primary amine selected from $R_{1-36}$-Lys(ε-iNIP)-ANP-Lys (ε-$NH_2$)-$NH_2$ (compounds $X_{1-36}$ from Example 11). The solution is mixed overnight at ambient temperature. The unreacted amine is removed by ultrafiltration through a 3000 MW cutoff membrane (Amicon, Beverly, Mass.) using $H_2O$ as the wash solution (3×). The compounds $XIII_{36}$ are isolated by reduction of the volume to 100 mL.

Example 13

Demonstration of the simultaneous Detection of Multiple Tags by Mass Spectrometry This example provides a description of the ability to simultaneously detect multiple compounds (tags) by mass spectrometry. In this particular example, 31 compounds are mixed with a matrix, deposited and dried on to a solid support and then desorbed with a laser. The resultant ions are then introduced in a mass spectrometer.

The following compounds (purchased from Aldrich, Milwaukee, Wis.) are mixed together on an equal molar basis to a final concentration of 0.002 M (on a per compound) basis: benzamide (121.14), nicotinamide (122.13), pyrazinamide (123.12), 3-amino-4-pyrazolecarboxylic acid (127.10), 2-thiophenecarboxamide (127.17), 4-aminobenzamide (135.15), tolumide (135.1.7), 6-methylnicotinamide (136.15), 3-aminonicotinamide (137.14), nicotinamide N-oxide (138.12), 3-hydropicolinamide (138.13), 4-fluorobenzamide (139.13), cinnamamide (147.18), 4-methoxybenzamide (151.17), 2,6-difluorbenzamide (157.12), 4-amino-5-imidazole-carboxyamide (162.58), 3,4-pyridine-dicarboxyamide (165.16), 4-ethoxybenzamide (165.19), 2,3-pyrazinedicarboxamide (166.14), 2-nitrobenzamide (166.14), 3-fluoro-4-methoxybenzoic acid (170.4), indole-3-acetamide (174.2), 5-acetylsalicylamide (179.18), 3,5-dimethoxybenzamide (181.19), 1-naphthaleneacetamide (185.23), 8-chloro-3,5-diamino-2-pyrazinecarboxyamide (187.59), 4-trifluoromethyl-benzamide (189.00), 5-amino-5-phenyl-4-pyrazole-carboxamide (202.22), 1-methyl-2-benzyl-malonamate (207.33), 4-amino-2,3,5,6-tetrafluorobenzamide (208.11), 2,3-napthlenedicarboxylic acid (212.22). The compounds are placed in DMSO at the concentration described above. One μl of the material is then mixed with alpha-cyano-4-hydroxy cinnamic acid matrix (after a 1:10,000 dilution) and deposited on to a solid stainless steel support.

Figure 11:
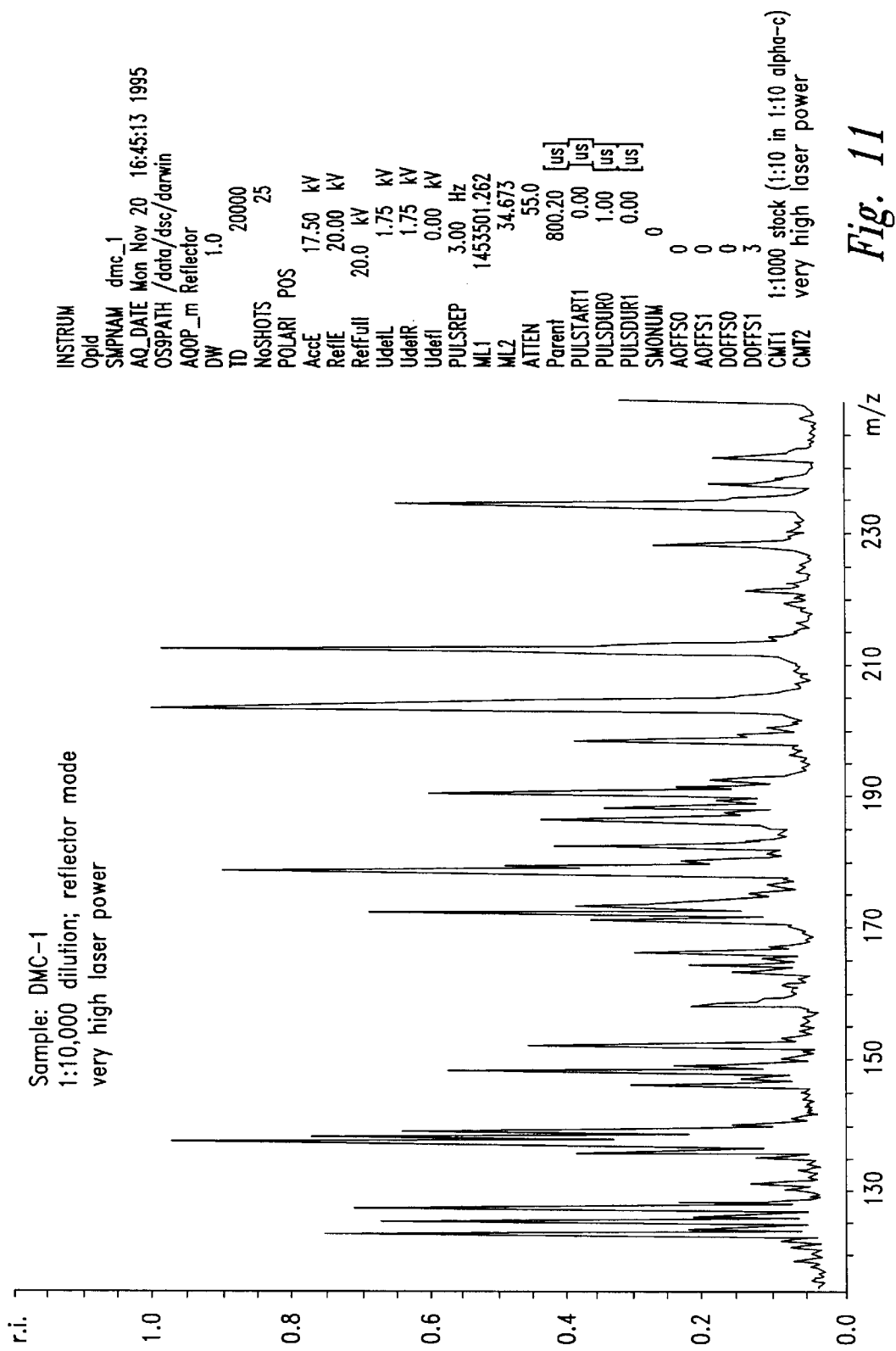
FIG. 11 illustrates the simultaneous detection of multiple tags by mass spectrometry.

The material is then desorbed by a laser using the Protein TOF Mass Spectrometer (Bruker, Manning Park, Mass.) and the resulting ions are measured in both the linear and reflectron modes of operation. The following m/z values are observed (FIG. 11):

121.1→benzamide (121.14)
122.1→nicotinamide (122.13)
123.1→pyrazinamide (123.12)
124.1
125.2
127.3→3-amino-4-pyrazolecarboxylic acid (127.10)
127.2→2-thiophenecarboxamide (127.17)
135.1→4-aminobenzamide (135.15)
135.1→tolumide (135.17)
136.2→6-methylnicotinamide (136.15)
137.1→3-aminonicotinamide (137.14)
138.2→nicotinamide N-oxide (138.12)
138.2→3-hydropicolinamide (138.13)
139.2→4-fluorobenzamide (139.13)
140.2
147.3→cinnamamide (147.18)

148.2
149.2
   4-methoxybenzamide (151.17)
152.2
   2,6-difluorbenzamide (157.12)
158.3
   4-amino-5-imidazole-carboxyamide (162.58)
163.3
165.2→3,4-pyridine-dicarboxyamide (165.16)
165.2→4-ethoxybenzamide (165.19)
166.2→2,3-pyrazinedicarboxamide (166.14)
166.2→2-nitrobenzamide (166.14)
   3-fluoro-4-methoxybenzoic acid (170.4)
171.1
172.2
173.4
   indole-3-acetamide (174.2)
178.3
179.3→5-acetylsalicylamide (179.18)
181.2→3,5-dimethoxybenzamide (181.19)
182.2→
   1-naphthaleneacetamide (185.23)
186.2
   8-chloro-3,5-diamino-2-pyrazinecarboxyamide (187.59)
188.2
189.2→4-trifluoromethyl-benzamide (189.00)
190.2
191.2
192.3
   5-amino-5-phenyl-4-pyrazole-carboxamide (202.22)
203.2
203.4
   1-methyl-2-benzyl-malonamate (207.33)
   4-amino-2,3,5,6-tetrafluorobenzamide (208.11)
212.2→2,3-napthlenedicarboxylic acid (212.22).
219.3
221.2
228.2
234.2
237.4
241.4

The data indicate that 22 of 31 compounds appeared in the spectrum with the anticipated mass, 9 of 31 compounds appeared in the spectrum with a n+H mass (1 atomic mass unit, amu) over the anticipated mass. The latter phenomenon is probably due to the protonation of an amine within the compounds. Therefore 31 of 31 compounds are detected by MALDI Mass Spectroscopy. More importantly, the example demonstrates that multiple tags can be detected simultaneously by a spectroscopic method.

The alpha-cyano matrix alone (FIG. 11) gave peaks at 146.2, 164.1, 172.1, 173.1, 189.1, 190.1, 191.1, 192.1, 212.1, 224.1, 228.0, 234.3. Other identified masses in the spectrum are due to contaminants in the purchased compounds as no effort was made to further purify the compounds.

Example 14

Microsatellite Markers: PCR Amplifications

The microsatellite markers are amplified utilizing the following standard PCR conditions. Briefly, PCR reactions are performed in a total volume of 50 µl, containing 40 ng of genomic DNA, 50 pmol of each primer, 0.125 mM dNTPs and 1 unit of Taq polymerase. 1×amplification buffer contains 10 mM Tris base, pH. 9, 50 mM KCl, 1.5 mM $MgCl_2$, 0.1% Triton X-100 and 0.01% gelatin. The reactions are performed using a "hot-start" procedure: Taq polymerase is added only after a first denaturation step of 5 minutes at 96° C. Amplification is carried out for 35 cycles: denaturation (94° C. for 40 sec) and annealing (55° C. for 30 sec). An elongation step (72° C. for 2 minutes) ends the process after the last annealing. Since the amplification products to be obtained are short (90 to 350 base pairs long) and the time interval to raise the temperature from 55° C. to 94° C. (obtained with a ramping rate of 1° C./second) is long enough, completion of DNA elongation can be achieved without a step at 72° C.

Example 15

Separation of DNA Fragments

Instrumentation

The separation of DNA fragments can be performed using an HPLC system assembled from several standard components. These components include a minimum of two high pressure pumps which pump solvent through a high pressure gradient mixer, an injector, HPLC column, and a detector. The injector is an automated, programmable autosampler capable of storing typically between eighty and one hundred samples at or below ambient temperatures to maintain the stability of the sample components. The autoinjector also is capable of making uL size injections in a reproducible manner completely unattended. The HPLC column is contained in a heated column compartment capable of holding a defined temperature to within 0.1° C. The column used in the examples below was purchased from SeraSep (San Jose, Calif.) under the name DNASep. This column is a 55×4.6 mm column with a 2.2 um non-porous polystyrenedivinylbenzene copolymer particle alkylated with C18. The packing material is stable within a pH range of 2–12 and tolerates temperatures as high as 70° C. Detection of analyte was performed using a single or multiple wavelength UV detector or diode array detector.

Methods

The methods applied in this example for separation of DNA fragments use ion-pair chromatography, a form of chromatography in which ions in solution can be paired or neutralized and separated as an ion pair on a reversed phase column. The lipophilic character and the concentration of the counterion determine the degree of retention of the analyte. In the case of a DNA molecule the lipophilic, cationic buffer component pairs with anionic phosphate groups of the DNA backbone. The buffer components also interact with the alkyl groups of the stationary phase. The paired DNA then elutes according to size as the mobile phase is made progressively more organic with increasing concentration of acetonitrile. Evaluation of the suitability of various amine salts was evaluated using enzymatic digests of plasmids or commercially available DNA ladders. The range of acetonitrile required to elute the DNA as well as the temperature of the column compartment varied with each buffer evaluated.

Buffers

The buffers evaluated for their ion-pairing capability were prepared from stock solutions. In order to keep the concentration of ion-pair reagent the same throughout the gradient, the ion-pair reagent was added to both the water and the acetonitrile mobile phases. The column was equilibrated with a new mobile phase for approximately 18 hours at a flow rate of 50 ul/minute before attempting any separation. Once a mobile phase had been evaluated, it was removed and the column cleaned with a flush of 800 mL 0.1% formic acid in 50% acetonitrile, followed by a flush with 800 mL 0.1% acetic acid in 50% acetonitrile before equilibration with a new mobile phase.

A. nn-Dimethyloctylammonium trifluoroacetate

A stock solution of 1 molar dimethyloctylammonium trifluoroacetate was prepared by mixing one half of an equivalent of trifluoroacetic acid in an appropriate volume of water and slowly adding one equivalent of nn-Dimethyloctylamine. The pH of this stock solution is 7. The stock solution was diluted with an appropriate volume of water or acetonitrile to working concentration.

B. nn-Dimethylheptylammonium acetate

A stock solution of 1 molar dimethylheptylammonium acetate was prepared by mixing one equivalent of glacial acetic acid in an appropriate volume of water and slowly adding one equivalent of nn-Dimethylheptylamine. The pH of this stock solution is 6.6. The stock solution was diluted with an appropriate amount of water or acetonitrile to working concentration.

C. nn-Dimethylhexylammonium acetate

A stock solution of 1 molar dimethylhexylammonium acetate was prepared by mixing one equivalent of glacial acetic acid in an appropriate volume of water and slowly adding one equivalent of nn-Dimethylhexylamine. The pH of this stock solution is 6.5. The stock solution was diluted with an appropriate volume of water or acetonitrile to working concentration.

D. nn-Dimethylbutylammonium acetate

A stock solution of 1 molar dimethylbutylammonium acetate was prepared by mixing one equivalent of glacial acetic acid in an appropriate volume of water and slowly adding one equivalent of nn-Dimethylbutylamine. The pH of the stock solution is 6.9. The stock solution was diluted with an appropriate volume of water or acetonitrile to working concentration.

E. nn-Dimethylisopropylammonium acetate

A stock solution of 1 molar dimethylisopropylammonium acetate was prepared by mixing one equivalent of glacial acetic acid in an appropriate volume of water and slowly adding one equivalent of nn-Dimethylisopropylamine. The pH of the stock solution is 6.9. The stock solution was diluted with an appropriate volume of water or acetonitrile to working concentration.

F. nn-Dimethylcyclohexylammonium acetate

A stock solution of 1 molar dimethylcyclohexylammonium acetate was prepared by mixing one equivalent of glacial acetic acid in appropriate volume of water and slowly adding one equivalent of nn-Dimethylcyclohexylamine. The pH of the stock solution is 6.5. The stock solution was diluted with an appropriate volume of water or acetonitrile to working concentration.

G. Methylpiperidine acetate

A stock solution of 1 molar methylpiperidine acetate was prepared by mixing one equivalent of glacial acetic acid in an appropriate volume of water and slowly adding one equivalent of 1-methylpiperidine. The pH of the solution is 7. The stock solution was diluted with an appropriate volume of water or acetonitrile to working concentration.

H. Methylpyrrolidine acetate

A stock solution of 1 molar piperidine acetate was prepared by mixing one equivalent of glacial acetic acid in an appropriate volume of water and slowly adding one equivalent 1-methylpyrrolidine. The pH of the stock solution is 7. The stock solution was diluted in an appropriate volume of water or acetonitrile to working concentration.

I. Triethylammonium acetate

A stock solution of 2 molar triethylammonium acetate pH 7.0 was purchased from Glenn Research Sterling, Va. The stock solution was diluted in an appropriate volume of water or acetontrile to working concentration.

Example 16

DNA Fingerprint

DNA fingerprinting adaptors are prepared comprising the following: a core sequence and an enzymes specific sequence. The structure of the EcoR1-adapter is 5'-CTCGTAGACTGCGTAC (Seq ID No. 6) the structure of the Mse 1-adapter is: 5"-GACGATGAGTCCTGAG (Seq ID No. 7).

Adapters for the rare cutter enzymes were identical to the EcoR1 with the exception that cohesive ends were used. ALPH primers consists of three parts: a core sequence, an enzyme specific sequence and a selective extension sequence. The EcoR1 and Mse1 primers are described as follows: EcoRI: 5'-gactgcgtaaa-aattc-NNN (Seq ID No. 8); Mse1: 5'-gatgagtcctgag-taa-NNN (Seq ID No. 9).

Genomic DNA was incubated for 1 hour at 37° C. with 5 units EcoRI and 5 units of MseI in 40 $\mu l$ volumes with 10 mM Tris-acetate pH 7.5, 10 mM MgAce, 50 mM KAcetate, 5 mM DTT, 50 ng/microliter BSA, 5 mM DTT. Next, 10 $\mu l$ of a solution containing 5 pMol EcoRI adapters, 50 pMol MseI adapters, 1 unit of T4 ligase, 1 mM ATP, in 10 mM Tris-acetate pH 7.5, 10 mM MgAce, 50 mM KAcetate, 5 mM DTT, 50 ng/microliter BSA was added and the incubation was continued for 3 hours at 37° C. Adapters were prepared by adding equimolar amounts of both strands: adapters were not phosphorylated. After ligation, the reaction mixture was diluted to 500 $\mu l$ with 10 mM Tris HCl, 0.1 mM EDTA pH8.0 and stored at −20° C.

Genetic fingerprinting reactions: Amplification reactions are described using DNA templates for the enzyme combination EcoRI/MseI. Genomic fingerprints with other enzyme combinations were performed with appropriate primers. The amplification reactions generally employed two oligonucleotides, one corresponding to the EcoRI pends and one corresponding to the MseI-ends. One of the two primers was labelled with the CMST tag, preferably the ECORI primer. The PCR s were performed using 5 ng labeled EcoRI primer, 30 ng MseI primer, 5 microliters of template DNA, 0.4 units Taq polymerase, 10 mM Tris-HCl, pH 8.3, 1.5 mM MgCL2, 50 mM KCl, 0.2 mM of dATP, dGTP, dCTP, dTTP. The PCR reactions differed depending on the nature of the selective amplification extensions of the DNA fingerprinting primers used for amplification. DNA fingerprinting reactions with primers having two two or three selective nucleotides were performed for 36 cycles with the following cycle profile: a 30 second DNA denaturation step, at 94° C., a 30 second annealing step at 55° C., and then a 1 minute extension step at 72° C. for 1 minute. The annealing temperature in the first step was 65° C. and was subsequently reduce for each cycle step by 0.7° C. in the next 12 cycles and was continued at 56° C. for the remaining 23 cycles. All amplifications were performed in a an MJ thermocycler (Watertown Mass.).

DNA fingerprinting of the complex genomes (such as humans) involve two amplification steps. The preamplification was performed with two DNA fingerprinting having a single selective nucleotide as described above with the exception that 30 ng of both DNA fingerprinting primers was used and that these primers were not labelled with CMST, after the preamplification step, the reaction mixtures were diluted 10-fold with with 10 mM Tris-HCl, 0.1 mM EDTA, pH 8.0, and used as templates for the second amplification reaction. The second amplification reaction was performed as described above for DNA fingerprinting reactions with primers having the longer selective extensions.

The products from the amplification reactions were analyzed by HPLC. HPLC was carried out using automated HPLC instrumentation (Rainin, Emeryville, Calif., or, Hewlett Packard, Palo Alto, Calif.). Unpurified DNA fingerprinting products which had been denatured for 3 minutes at 95 prior into injection into an HPLC were eluted with linear acetonitrile (ACN, J. T. Baker, N.J.) gradient of 1.8%/minute at a flow rate of 0.9 ml/minute, The start and end points were adjusted according to the size of the amplified products. The temperature required for the successful resolution of the molecules generated during the DNA fingerprinting technique was 50° C. The effluent from the HPLC was then directed into a mass spectrometer (Hewlett Packard, Palo Alto, Calif.) for the detection of tags.

The following fragments eluted in the order presented (The number sited are the positions within the lambda genome at which a cleavage site occurred): 47, 78, 91, 733, 1456, 2176, 3275, 3419, 4349, 444, 5268, 5709, 6076, 6184, 6551, 7024, 7949, 8062, 8200, 8461, 9079, 9253, 9692, 9952, 11083, 11116, 11518, 11584, 12619, 12967, 14108, 14892, 15628, 15968, 16034, 16295, 16859, 18869, 19137, 19482, 20800, 21226, 21441, 2635, 21702, 21903, 21948, 22724, 23048, 23084, 23111, 23206, 23279, 23285, 23479, 23498, 23555, 23693, 23887, 23979, 23987, 24073, 24102, 24751, 24987, 25170, 25255, 25353, 25437, 26104, 25578, 25746, 25968, 26133, 26426, 26451, 26483, 26523, 26585, 26651, 26666, 26679, 26693, 26763, 26810, 26984, 26993, 27038, 27092, 27203, 27317, 27683, 28456, 28569, 28922, 28972, 29374, 29981, 30822, 30620, 30639, 30722, 30735, 30756, 31169, 31747, 31808, 32194, 32218, 32641, 32704, 33222, 33351, 33688, 33736, 33748, 33801, 34202, 34366, 34406, 34590, 34618, 34684, 34735, 34753, 34831, 35062, 35269, 35534, 35541, 36275, 36282, 36303, 36430, 36492, 36531, 36543, 36604, 36736, 36757, 36879, 37032, 37442, 37766, 37783, 37882, 37916, 37994, 36164, 38287, 38412, 38834, 39168, 44972, 39607, 39835, 40127, 40506, 40560, 40881, 41017, 41423, 41652, 41715, 42317, 42631, 42651, 42673, 42814,. 43410, 43492, 43507, 43528, 43593, 44424, 44538, 44596, 44868, 45151, 45788, 46033, 46408, 46556, 46804, 46843, 46853, 46896, 46952, 47256, 47274, 47287, 47430, 47576, 47699, 47799, 48059, 48125, 48227, 48359, 48378. The average fragment length was about 160 nt. The observed sites of cleavage were largely (>95%) compatible with that predicted from an MSE1/RcoR1 digest map.

Example 17

Single Nucleotide Extension Assays

RNA preparation: Total RNA was isolated was prepared from Jurkat cells using (starting with 1×10$^9$ cells in exponential growth) using an RNA isolation kit from Promega (WI). RNA was stored in two aliquots: 1) stock aliquote in diethyl pyrocarbonate-treated ddH2O was stored at −20° C., and 2) long term storage as a suspension in 100% H$_2$O.

Reverse Transcription: Poly(dT) primed reverse transcription of total RNA was performed as described as described in Ausubel et al. (Ausubel et al., in Current Protocols in Molecular Biology, 1991, Greene Publishing Associates/Wiley-Interscience, NY, N.Y.) except that the reaction(s) were scaled to using 1 µg input total RNA. 20–50 units of reverse transcriptase (Promega) was diluted 10-fold in 10% glycerol, 10 mM KPO4 pH 7.4, 0.2% Triton X-100, and 2 mM DTT and placed on ice for 30 minutes prior to addition to the reactions. Gene-specific reverse transcription for GADPH and other control genes as described in the figures and tables were performed using 1 µg of total Jurkat RNA reversed transcribed in 10 mM Tris-HCl pH 8.3, 50 mM KCl, M MgCL2, 1 mM dNTPs, 2 U/µl RNAsin (Gibco-BRL), 0.1 µM oligomer and 0.125 U/µl of M-MLV reverse transcriptase (Gibco-BRL) in 20 µl reactions. Reactions were incubated in at 42° C. for 15 minutes, heat inactivated at 95° C. for 5 minutes , and diluted to 100 µl with a master mix of (10 mM Tris HCl pH 8.3, 1 mM NH4Cl, 1.5 M MgCl2, 100 mM KCl), 0.125 mM NTPs, 10 ng/ml of the respective oligonucleotide primers and 0.75 units of TAQ polymerase (Gibco-BRL) in preparation for PCR amplification.

PCR: PCR for each gene was performed with gene specific primers spanning a known intron/exon boundry (see tables below). All PCRs were done in 20 µl volumes containing 10 mM Tris HCl pH 8.3, 1 mM NH4Cl, 1.5 M MgCl2, 100 mM KCl), 0.125 mM NTPs, 10 ng/ml of the respective oligonucleotide primers and 0.75 units of TAQ polymerase (Gibco-BRL). Cycling parameters were 94° C. preheating step for 5 minutes followed by 94° C. denaturing step for 1 minute, 55° C. annealing step for 2 minutes, and a 72° C. extension step for 30 seconds to 1 minute and a final extension at 72° C. for 10 minutes. Amplifications were generally 30–45 in number.

Purification of templates: PCR products were gel purified as described by Zhen and Swank (Zhen and Swank, BioTechniques, 14(6):894–898, 1993). PCR products were resolved on 1% agarose gels run in 0.04 M Tris-acetate, 0.001 M EDTA (1×TEA) buffer and stained with ethidium bromide while visualizing with a UV light source. A trough was cut just in front of the band of interest and filled with 50–200 µl of 10% PEG in 1×TAE buffer. Electrophoresis was continued until the band had completely entered the trough. The contents was then removed and extracted with phenol, cholorform extracted, and then precipitated in 0.1 volume of 7.5 M ammonium acetate and 2.5 volumes of 100% EtOH. Samples were washed with 75% EtOH and briefly dried at ambient temperature. Quantitation of yield was done by electrophoresis of a small aliquot on 1% agarose gel in 1×TBE buffer with ethidium bromide staining and comparison to a known standard.

Each SNuPE reaction was carried out in a 50 µl volume containing about 100 ng of the amplified DNA fragment, 1 µM of the SNuPE primer, 2 units of Tag polymerase, and 1 ul of the appropriate dNTP. All dNTPs are unlabelled in this type of assay. The buffer used was 10 mM Tris-HCl (pH 8.3), with 50 mM KCl, 5mM MgCl2 and 0.001% (wt/vol) gelatin. The samples were subjected to one cycle consisting of a 2-minute denaturation period at 95° C., a 2 minute annealing period at 60° C. and a 2-minute primer extension period at 72° C. The sequence of the SNUPE primer for each family is described below.

Primer extensions: Single nucleotide primer extensions were performed as described in Singer-Sam et al., (Singer-Sam et al., PCR Methods and Applications 1:160–163, 1992) except that 1 mM Mg++, 0.1 µM primer, and 0.05 µM of each dNTP type was used in each reaction type. After each primer extension described above, one-fifth volume of a loading dye (80% formamide, 0.1% bromophenol blue, 0.1% xylene cyanol, 2 mM EDTA) was added, and the entire sample electrophoresed in 15% denaturing polyacrylamide gel. Gels were fixed in 10% glycerol, 10% methanol, 10% glacial acetic acid with constant shaking followed by washing steps with 10% glycerol. The gels were then dried at 55° C. for 3–5 hours.

The primers described in this experiment are described by Rychlik (Rychlik, *BioTechniques* 18:84–90, 1995) Primers may be synthesized or obtained as gel-flirtation grade primers from Midland Certified Reagent Company (Midland Tex.). The amplifications are either TAQ DNA polymerase-based (10 mM Tris-HCl pH 8.3, 1.5 mM MgCl2, 50 mM KCl) or Pfu DNA polymerase-based based (20 mM Tris-HCl pH 8.3, 2.0 mM MgCl2, 10 mM KCl, 10 mM (NH4)2SO4, 0.1% Triton X-100, 0.1 mg/ml bovine serum albumin). The total nucleoside triphosphate (NTPs) concentration in the reactions is 0.8 mM, the primer concentration is 200 nM (unless otherwise stated) and the template amount is 0.25 ng of bacteriophage lambda DNA per 20 μl reaction. Cycling parameters were 94° C. preheating step for 5 minutes followed by 94° C. denaturing step for 1 minute, 55° C. annealing step for 2 minutes, and a 72° C. extension step for 30 seconds to 1 minute and a final extension at 72° C. for 10 minutes. Amplifications were generally 30–45 in number.

Two regions in the bacteriophage lambda genome (GenBank Accession #J02459) were chosen as the priming sites for amplification. The 5'-primer has a stable GC-rich 3'-end: the 3' primer is chosen so that a 381 bp product will result. The 5' forward primer is H17: 5'-GAACGAAAACCCCCCGC (Seq ID No. 10). The 3'-reverse primer is RP 17: 5'-GATCGCCCCCAAAA (Seq ID No. 11).

The amplified product was then tested for the presence of a polymorphism at position 31245. The following primer was used in four, single nucleotide extension assays; SNE17: 5'-GAACGAAAACCCCCGC (Seq ID No. 12). The four single nucleotide extension assays were then carried as described above. All the reactions are then pooled and 5 μl of the pooled material was injected onto the HPLC column (SeraSep, San Jose, Calif.) without further purification.

HPLC was carried out using automated HPLC instrumentation (Rainin, Emeryville, Calif., or, Hewlett Packard, Palo Alto, Calif.). Unpurified SNEA products which had been denatured for 3 minutes at 95 prior into injection into an HPLC were eluted with linear acetonitrile (ACN, J. T. Baker, N.J.) gradient of 1.8%/minute at a flow rate of 0.9 ml/minute, The start and end points were adjusted according to the size of the SNEA product. The temperature required for the successful resolution of the SNEA molecules was 50° C. The effluent from the HPLC was then directed into a mass spectrometer (Hewlett Packard, Palo Alto, Calif.) for the detection of tags.

| Results: | | | |
|---|---|---|---|
| Tagged Primer | ddNTP type | retention time | extended? |
| SNE17-487 | ddATP | 2.5 minutes | no |
| SNE17-496 | ddGTP | 2.5 minutes | no |
| SNE17-503 | ddCTP | 4.6 minutes | yes |
| SNE17-555 | ddTTP | 2.5 minutes | no |

The results therefore indicate that the mass spectrometer tag (CMST) tag was detected at a retention time of 4.6 minutes indicating that the SNE17 primer was extended by one base (ddCTP) and therefore the polymorphism was position 31245 was in this case a "G". The SNE17-487, SNE17-496, and SNE17-555 tagged primers were not extended and their retention times on the HPLC was 2.5 minutes respectively.

Example 18

Figure 19A:
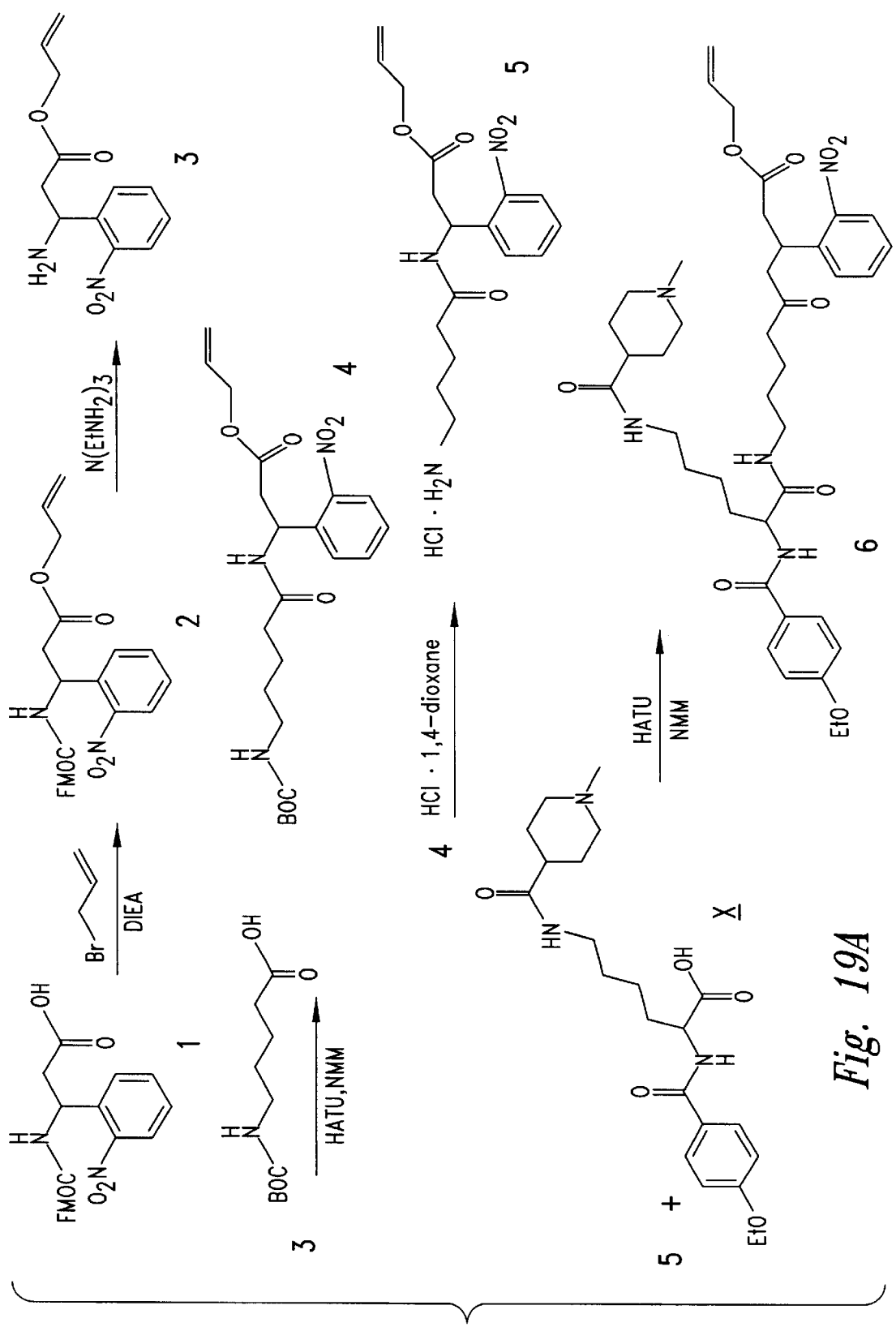
FIGS. 19A and 19B illustrate the preparation of a cleavable tag of the present invention.
Figure 19B:
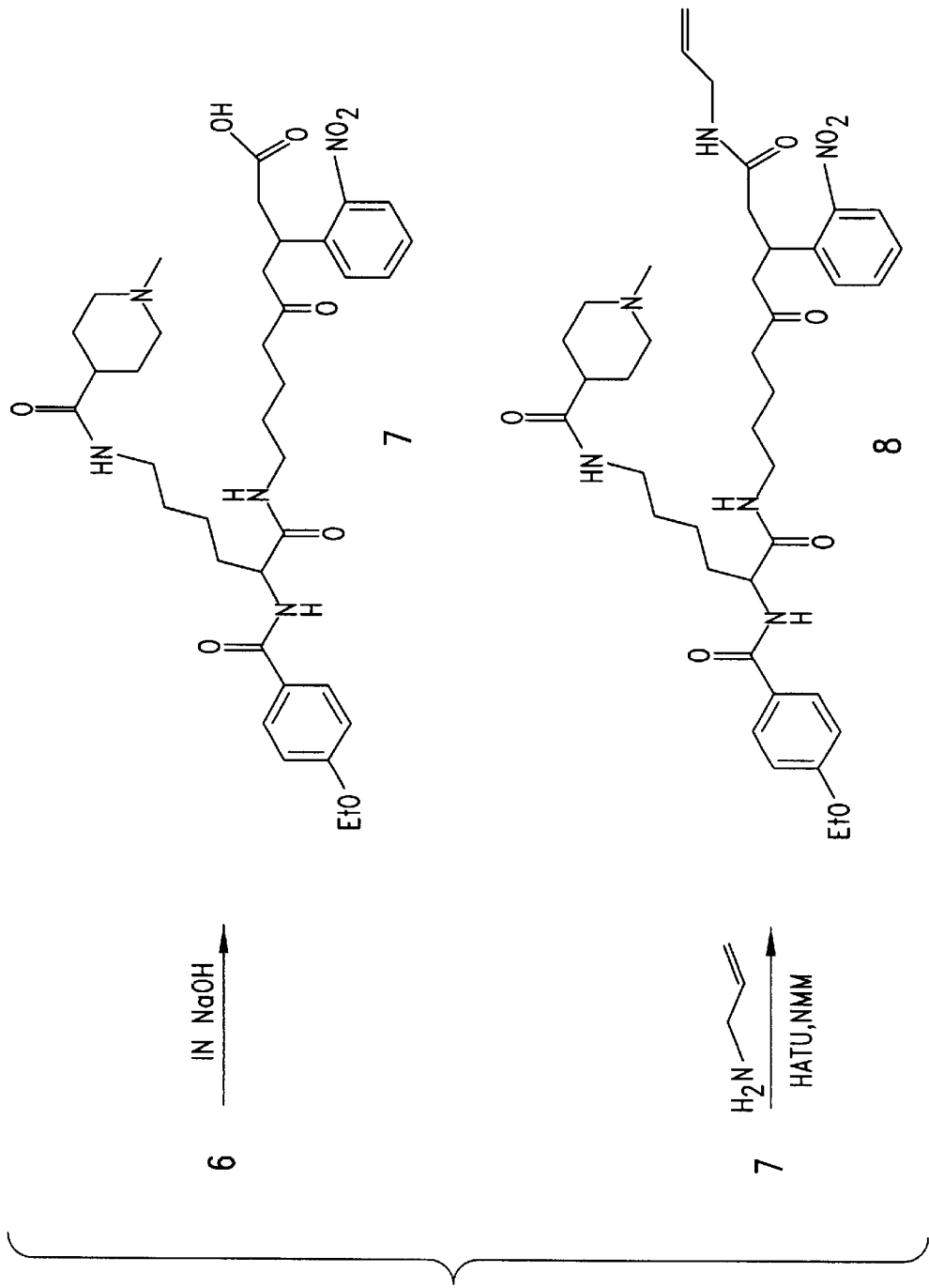

In this Example (18), all reactions were conducted in foil-covered flasks. The sequence of reactions A→F described in this Example is illustrated in FIGS. 19A and 19B. Compound numbers as set forth in this Example refer to the compounds of the same number in FIGS. 19A and 19B.

A. To a solution of ANP linker (compound 1, 11.2 mmol) and diisopropylethylamine (22.4 mmol) in CHCl$_3$ (60 mi) was added allyl bromide (22.4 mmol). The reaction mixture was refluxed for 3 hours, stirred at room temperature for 18 hours, diluted with CHCl$_3$ (200 ml), and washed with 1.0 M HCl (2×150 ml) and H$_2$O (2×150 ml). The organic extracts were dried (MgSO$_4$) and the solvent evaporated to give compound 2 as a yellow solid.

To a mixture of compound 2 in CH$_2$Cl$_2$ (70 ml), tris (2-aminoethyl) amine (50 ml) was added and the reaction mixture stirred at room temperature for 18 hours. The reaction was diluted with CH$_2$Cl$_2$ (150 ml) and washed with pH 6.0 phosphate buffer (2×150 ml). The organic extracts were dried (MgSO$_4$) and the solvent evaporated. The residue was subjected to column chromatography (hexane/EtOAc) to give 1.63 g (58%) of compound 3: $^1$H NMR (DMSO-d$_6$): δ 7.85 (dd, 2H), 7.70 (t, 1H), 7.43 (t, 1H), 5.85 (m, 1H), 5.20 (q, 2H), 4.58 (q, 1H), 4.50 (d, 2H), 2.70 (m, 2H), 2.20 (br s, 2H).

B. To a solution of Boc-5-aminopentanoic acid (1.09 mmol) and NMM (3.27 mmol) in dry DMF (6 ml), was added HATU (1.14 mmol) and the reaction mixture stirred at room temperature for 0.5 hours. A solution of compound 3 (1.20 mmol) in dry DMF (1 ml) was added and the reaction mixture stirred at room temperature for 18 hours. The reaction was diluted with EtOAc (50 ml) and washed with 1.0 M HCl (2×50 ml) and D.I. H$_2$O (2×50 ml). The organic extracts were dried (MgSO$_4$) and evaporated to dryness. The residue was subjected to column chromatography to give 420 mg (91%) of compound 4: $^1$H NMR (DMSO-d$_6$): δ 8.65 (d, 1H), 7.88 (d, 1H), 7.65 (m, 2H), 7.48 (t, 1H), 6.73 (br s, 1H), 5.85 (m, 1H), 5.55 (m, 1H), 5.23 (q, 2H), 4.55 (d, 2H), 2.80 (m, 2H), 2.05 (t, 2H), 1.33 (s, 9H), 1.20–1.30 (m, 4H).

C. A solution of compound 4 (0.9 mmol) in HCl.1,4-dioxane (20 mmol) was stirred at room temperature for 2 hours. The reaction mixture was concentrated, dissolved in MeOH and toluene, and concentrated again (5×5 ml) to give 398 mg (quantitative) of the compound 5: $^1$H NMR (DMSO-d$_6$): δ 8.75 (d, 1H), 7.88 (d, 1H), 7.65 (m, 2H),7.51 (t, 1H), 7.22 (m, 2H),5.85 (m, 1H), 5.57 (m, 1H), 5.23 (q, 2H), 4.55 (d, 2H), 2.80 (m, 2H), 2.71 (m, 2H), 2.07 (s, 2H), 1.40–1.48 (br s, 4H)

D. To a solution of compound 21 (0.48 mmol, prepared according to Example 20) and NMM (1.44 mmol) in dry DMF (3 ml), was added HATU (0.50 mmol) and the reaction mixture stirred at room temperature for 0.5 hours. A solution of compound 5 (0.51 mmol) in dry DMF (3 ml) was added and the reaction stirred at room temperature for 18 hours. The reaction mixture was diluted with EtOAc (75 ml) and washed with 5% Na$_2$CO$_3$ (3×50 ml). The organic extracts were dried (MgSO$_4$) and the solvent evaporated to give 281 mg (78%) of compound 6: $^1$H NMR (DMSO-d$_6$): δ 8.65 (d, 1H), 8.17 (d, 1H), 7.82–7.95 (m, 4H), 7.68 (m, 3H), 7.50 (t, 1H), 6.92 (d, 1H), 5.85 (m, 1H), 5.57 (m, 1H), 5.20 (q, 2H), 4.55 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.0 (m, 4H), 1.30 (q, 3H), 1.17–1.40 (m, 9H).

E. To a mixture of compound 6 (0.36 mmol) in THF (4 ml), was added 1 M NaOH (1 mmol) and the reaction stirred at room temperature for 2 hours. The reaction mixture was acidified to pH 7.0 with 1.0 M HCl (1 ml) and the solvent evaporated to give compound 7 (quantitative): $^1$H NMR (DMSO-d$_6$): δ 8.65 (d, 1H), 8.17 (d, 1H), 7.82–7.95 (m, 4H), 7.68 (m, 3H), 7.50 (t, 1H), 6.92 (d, 1H), 5.52 (m, 1H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

F. To a solution of compound 7 (0.04 mmol) and NMM (0.12 mmol) in dry DMF (0.4 ml), was added HATU (0.044 mmol) and the reaction stirred at room temperature for 0.5 hours. Allylamine (0.12 mmol) was added and the reaction mixture stirred at room temperature for 5 hours. The reaction mixture was diluted with EtOAc (15 ml) and washed with 5% Na$_2$CO$_3$ (3×10 ml). The organic extracts were dried (MgSO$_4$) and the solvent evaporated to yield 15 mg (49%) of compound 8: $^1$H NMR (DMSO-d$_6$) δ 8.49 (d, 1H), 8.17 (d, 1H), 7.82–7.95 (m, 4H), 7.68 (m, 3H), 7.50 (t, 1H), 6.92 (d, 1H), 5.72 (m, 1H), 5.50 (m, 1H), 5.03 (q, 2H), 4.37 (d, 2H), 4.30 (q, 1H), 4.05 (q, 2H), 2.95 (m, 4H), 2.80 (m, 2H), 2.72 (m, 2H), 2.05 (s, 3H), 2.01 (t, 2H), 1.58–1.77 (m, 3H), 1.50 (m, 4H), 1.30 (q, 3H), 1.17–1.40 (m, 9H).

Example 19

Figure 20A:
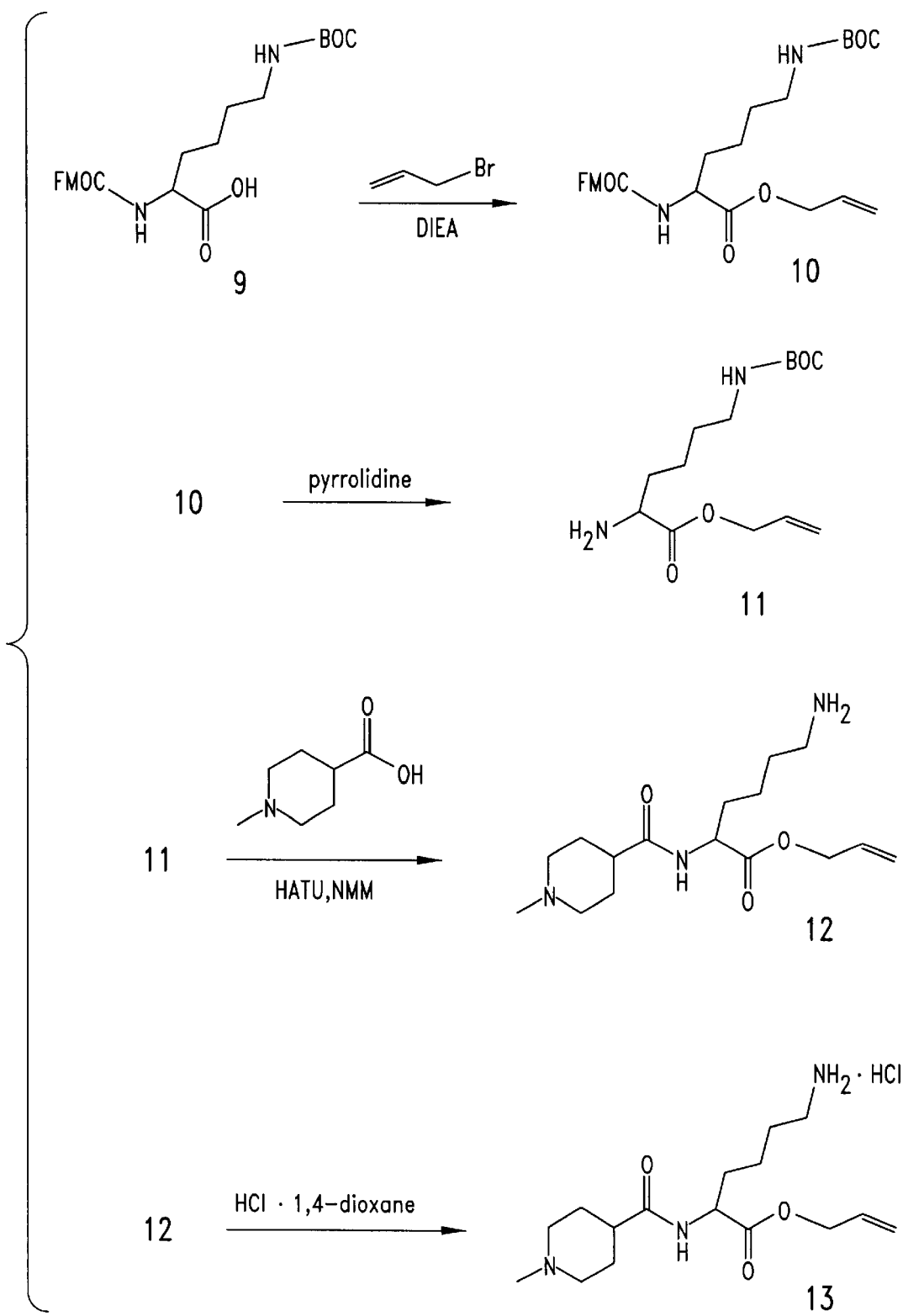
FIGS. 20A and 20B illustrate the preparation of a cleavable tag of the present invention.
Figure 20B:
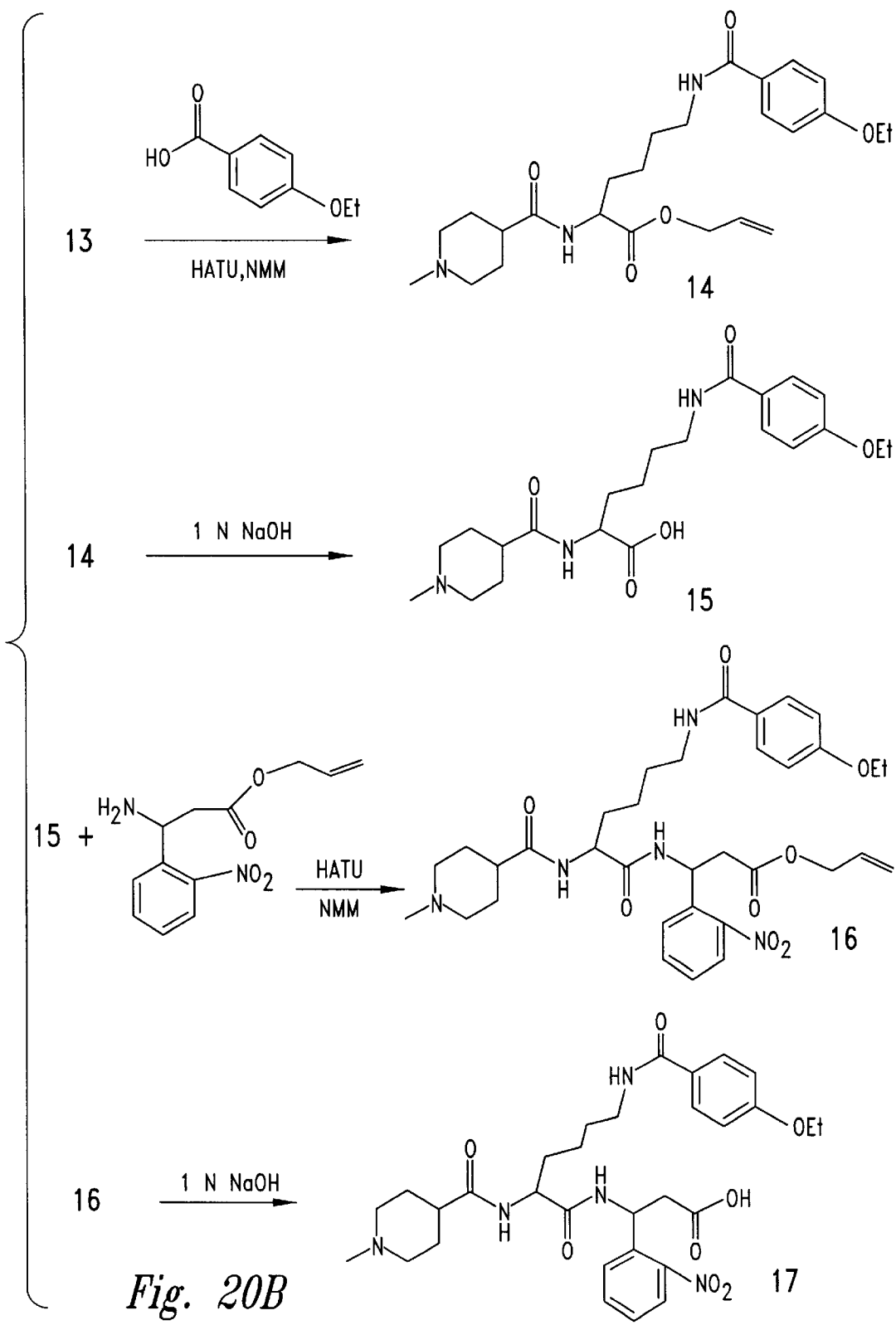

The sequence of reactions A→G as described in this Example 19 is illustrated in FIGS. 20A and 20B. Compound numbers as set forth in this Example refer to the compounds of the same number in FIGS. 20A and 20B.

A. To a solution of Fmoc-Lys(Boc)-OH (compound 9, 33.8 mmol) in CHCl$_3$ (200 ml), was added diisopropylethylamine (67.5 mmol) and allyl bromide (67.5 mmol). The reaction mixture was refluxed for 6 hours, stirred at room temperature for 16 hours, diluted with CHCl$_3$, washed with 1.0 M HCl (2×150 ml), saturated NaHCO$_3$ (1×150 ml) and D.I. H$_2$O (2×150 ml). The organic extracts were dried (MgSO$_4$) and the solvent evaporated to yield compound 10.

To a solution of compound 10 in CHCl$_3$ (90 ml), was added pyrrolidine (10 eq.) and the reaction was stirred at room temperature for 2.5 hours. The reaction mixture was diluted with CHCl$_3$ (150 ml) and washed with saturated NaHCO$_3$ (3×250 ml). The organic extracts were dried (MgSO$_4$) and the solvent evaporated. The residue was subjected to column chromatography (EtOAc/MeOH) to give 6.52 g (67%) of compound 11: $^1$H NMR (CDCl$_3$): δ 5.90 (m, 1H), 5.27 (m, 2H), 4.60 (d, 2H), 3.48 (t, 1H), 3.10 (d, 2H), 1.40–1.78 (m, 9H),1.40 (s, 9H).

B. To a solution of N-methylisonipecotic acid (1.60 mmol) and N-methyl morpholine (4.80 mmol) in dry DMF (5 ml), was added HATU (1.67 mmol). After 0.5 hours, a solution of compound 11 (1.75 mmol) in dry DMF (2 ml) was added and the reaction mixture stirred at room temperature for 18 hours. The reaction mixture was diluted with CH$_2$CL$_2$ (60 ml) and washed with saturated Na$_2$CO$_3$ (3×40 ml). The organic extracts were dried (MgSO$_4$) and the solvent evaporated. The residue was subjected to column chromatography (CH$_2$Cl$_2$/MeOH/triethylamine) to give 580 mg (88%) of compound 12: $^1$H NMR (DMSO): δ 8.12 (d, 1H), 6.77 (t, 1H), 5.90 (m, 1H), 5.27 (m, 2H), 4.53 (d, 2H), 4.18 (m, 1H),2.62–2.90 (m, 5H), 2.13 (s, 3H),1.85 (m, 2H),1.57 (m, 5H),1.35 (s, 9H), 1.00 (t, 2H).

C. A mixture of compound 12 (1.39 mmol) in HCl.1,4-dioxane (20 mmol) was stirred at room temperature for 4 hours. The reaction mixture was concentrated, dissolved in MeOH, coevaporated with toluene (5×5ml) to give 527 mg (quantitative) of compound 13: $^1$H NMR (DMSO-d$_6$): δ 8.12 (d, 1H), 6.77 (t, 1H), 5.90 (m, 1H), 5.27 (m, 2H), 4.53 (d, 2H), 4.18 (m, 1H),2.65–3.00 (m, 8H), 2.23 (s, 3H),1.85 (m, 2H),1.57 (m, 5H), 1.00 (t, 2H).

D. To a solution of 4-ethoxybenzoic acid (1 eq.) in dry DMF, is added NMM (3 eq.) and HATU (1.05 eq.). After 0.5 hours, a solution of compound 13 in dry DMF is added. After the completion of the reaction and basic workup, the compound 14 is isolated and purified.

E. To a solution of compound 14 in THF, is added 1N NaOH and the reaction mixture stirred at room temperature. After the completion of the reaction and acidification, the compound 15 is isolated.

F. To a solution of compound 15 (1 eq.) in dry DMF, is added NMM (3 eq.) and HATU (1.05 eq.). After 0.5 hours, a solution of compound 21 (ANP—allyl ester, prepared according to Example 20) in dry DMF is added. After the completion of the reaction and basic workup, the title compound 16 is isolated and purified.

G. To a solution of compound 16 in THF, is added 1N NaOH and the reaction mixture stirred at room temperature. After the completion of the reaction and acidification, the compound 17 is isolated.

Example 20

Figure 21:
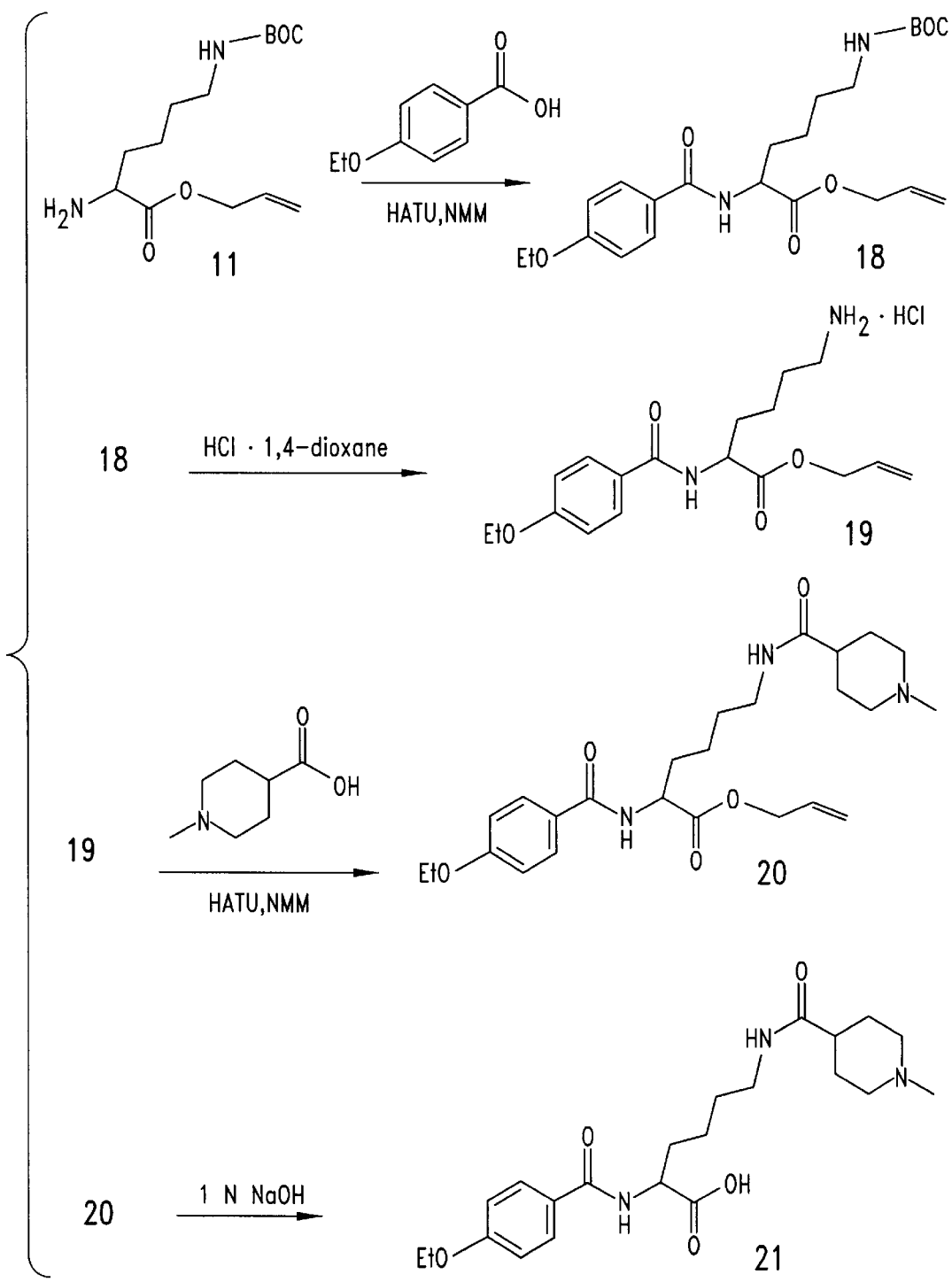
FIG. 21 illustrates the preparation of an intermediate compound useful in the preparation of a cleavable tag of the invention.

The sequence of reaction A through D as described in this Example 20 is illustrated in FIG. 21. Compound numbers as set forth in this Example, as well as Examples 18 and 19, refer to the compounds of the same number in FIG. 21.

A. To a solution of 4-ethoxybenzoic acid (7.82 mmol) and N-methyl morpholine (20.4 mmol) in CH$_2$Cl$_2$ (10 ml), was added HATU (7.14 mmol). After 0.25 hours, a solution of compound 11 (6.8 mmol) in CH$_2$Cl$_2$ (6 ml) was added and the reaction mixture stirred at room temperature for 18 hours. The reaction was diluted with CH$_2$Cl$_2$ (150 ml) and washed with 1.0 M HCl (3×50 ml) and saturated NaHCO$_3$ (3×50 ml). The organic extracts were dried (MgSO$_4$) and the solvent evaporated. The residue was subjected to column chromatography (CH$_2$Cl$_2$/MeOH) to give 2.42 g (82%) of compound 18: $^1$H NMR (CDCl$_3$): δ 7.78 (d, 2H), 6.91 (d, 2H), 6.88 (d, 1H), 5.83–5.98 (m, 1H), 5.21–5.38 (m, 2H), 4.80 (q, 1H), 4.66 (d, 2H), 4.06 (q, 2H), 3.11 (q, 2H), 1.90–2.04 (m, 1H), 1.68–1.87 (m, 1H), 1.39 (t, 3H), 1.34 (s, 9H), 1.32–1.58 (m, 4H).

B. A mixture of compound 18 (5.5 mmol) in HCl.1,4-dioxane (14.3 mmol) was stirred at room temperature for 1 hour. The reaction mixture was concentrated, dissolved in MeOH, azeotroped with toluene, and concentrated again (5×5 ml) to give a quantitative yield of compound 19.

C. To a solution of N-methylisonipecotic acid (6.21 mmol) in dry DMF (15 mL), was added NMM (21.6 mmol) and HATU (5.67 mmol). After 0.5 hours, a solution of compound 19 (5.4 mmol) in dry DMF (10 ml) was added and the reaction stirred at room temperature for 18 hours. The reaction mixture was brought to pH 12 with 1N NaOH (20 ml) and extracted with CHCl$_3$ (2×200 ml). The organic extracts were dried (MgSO$_4$) and the solvent evaporated to give 2.2 g (89%) of compound 20: $^1$H NMR (DMSO-d$_6$): δ 8.52 (d, 1H), 7.84 (d, 2H), 7.72 (t, 1H), 6.95 (d, 2H), 5.80–5.95 (m, 1H), 5.18–5.31 (dd, 2H), 4.58 (d, 2H), 4.37 (q, 1H), 4.08 (q, 2H), 3.01 (d, 2H), 2.08 (s, 3H), 1.95 (m, 1H), 1.63–1.82 (m, 4H), 1.51 (m, 4H), 1.32 (t, 3H), 1.22–1.41 (m, 6H).

D. To a solution of compound 20 (4.4 mmol) in THF (10 ml), is added 1N NaOH (4.4 mmol) and the reaction mixture stirred at room temperature for 1 hour. The reaction was concentrated, dissolved in THF/toluene (2×5 ml), concentrated, dissolved in CH$_2$Cl$_2$/toluene (1×5 ml) and concentrated again to give a quantitative yield of compound 21: $^1$H NMR (DMSO-d$_6$): δ 7.76 (d, 2H), 6.96 (d, 2H), 4.04 (q, 2H), 3.97 (d, 1H), 2.97 (d, 2H), 2.64 (d, 2H), 2.08 (s, 3H), 1.95 (m, 1H), 1.58–1.79 (m, 4H), 1.44 (m, 6H), 1.30 (t, 3H), 1.11–1.35 (m, 4H).

From the foregoing, it will be appreciated that, although specific embodiments of the invention have been described herein for purposes of illustration, various modifications may be made without deviating from the spirit and scope of the invention.

We claim:

1. A method for determining the identity of a nucleic acid molecule, comprising sequentially:
    (a) generating tagged nucleic acid molecules from one or more selected target nucleic acid molecules, wherein a tag is correlative with a particular nucleic acid fragment and detectable by non-fluorescent spectrometry or potentiometry;
    (b) separating said tagged molecules by size;
    (c) cleaving said tag from said tagged molecule; and
    (d) detecting said tag by non-fluorescent spectrometry or potentiometry, and therefrom determining the identity of said nucleic acid molecule.

2. A method for detecting a selected nucleic acid molecule, comprising sequentially:
    (a) combining a tagged nucleic acid probe with target nucleic acid molecules under conditions and for a time sufficient to permit hybridization of said tagged nucleic acid probe to a complementary selected target nucleic acid sequence, wherein said tagged nucleic acid probe is detectable by non-fluorescent spectrometry or potentiometry;
    (b) increasing or decreasing the size of said hybridized tagged probes, the size of unhybridized probes or target molecules, or the size of the probe:target hybrids;
    (c) separating the tagged probes by size;
    (d) cleaving said tag from said tagged probe; and
    (e) detecting said tag by non-fluorescent spectrometry or potentiometry, and therefrom detecting said selected nucleic acid molecule.

3. The method according to claims 1 or 2 wherein the detection of the tag is by mass spectrometry, infrared spectrometry, ultraviolet spectrometry, or, potentiostatic amperometry.

4. The method according to claim 1 wherein greater than 4 tagged nucleic acid fragments are generated and wherein each tag is unique for a selected nucleic acid fragment.

5. The method according to claim 2 wherein greater than 4 tagged nucleic acid probes are utilized and wherein each tag is unique for a selected nucleic acid probe.

6. The method according to claims 1 or 2 wherein said target nucleic acid molecule is generated by primer extension.

7. The method according to claim 2 wherein the size of said hybridized tagged probes, unhybridized probes or target molecules, or probe:target hybrids are altered by a method selected from the group consisting of polymerase extension, ligation, exonuclease digestion and endonuclease digestion.

8. The method according to claims 1 or 2 wherein said tagged molecules are separated by a method selected from the group consisting of gel electrophoresis, capillary electrophoresis, micro-channel electrophoresis, HPLC, size exclusion chromatography and filtration.

9. The method according to claims 1 or 2 wherein said tagged molecules are cleaved by a method selected from the group consisting of oxidation, reduction, acid-labile, base labile, enzymatic, electrochemical, thermal and photolabile methods.

10. The method according to claim 1 or 2 wherein said tag is detected by a method selected from a group consisting of time-of-flight mass spectrometry, quadrupole mass spectrometry, magnetic sector mass spectrometry and electric sector mass spectrometry.

11. The method according to claim 10 wherein said tag is detected by potentiostatic amperometry utilizing detectors selected from the group consisting of coulometric detectors and amperometric detectors.

12. The method according to claims 1 or 2 wherein the steps of separating, cleaving and detecting are performed in a continuous manner.

13. The method according to claims 1 or 2 wherein the steps separating, cleaving and detecting are performed in a continuous manner on a single device.

14. The method according to claim 13 wherein the steps of separating, cleaving and detecting are automated.

15. The method according to claims 1 or 2 wherein said tagged molecules or probes are generated from 5'-tagged oligonucleotide primers.

16. The method according to claims 1 or 2 wherein said tagged molecules or probes are generated from tagged dideoxynucleotide terminators.

17. A method for genotyping a selected organism, comprising sequentially:
    (a) generating tagged nucleic acid molecules from a selected target molecule, wherein a tag is correlative with a particular fragment and may be detected by non-fluorescent spectrometry or potentiometry;
    (b) separating said tagged molecules by sequential length;
    (c) cleaving said tag from said tagged molecule; and
    (d) detecting said tag by non-fluorescent spectrometry or potentiometry, and therefrom determining the genotype of said organism.

18. A method for genotyping a selected organism, comprising sequentially:
    (a) combining a tagged nucleic acid molecule with a selected target molecule under conditions and for a time sufficient to permit hybridization of said tagged molecule to said target molecule, wherein a tag is correlative with a particular fragment and may be detected by non-fluorescent spectrometry or potentiometry;
    (b) separating said tagged molecules by sequential length;
    (c) cleaving said tag from said tagged molecule; and
    (d) detecting said tag by non-fluorescent spectrometry or potentiometry, and therefrom determining the genotype of said organism.

19. The method according to claims 17 or 18 wherein said tagged molecules are generated from a pool of clones selected from the group consisting of genomic clones, cDNA clones and RNA clones.

20. The method according to claims 17 or 18 wherein said tagged molecules are generated by polymerase chain reaction.

21. The method according to claims 17 or 18 wherein the detection of the tag is by mass spectrometry, infrared spectrometry, ultraviolet spectrometry, or, potentiostatic amperometry.

22. The method according to claims 17 or 18 wherein greater than 4 tagged nucleic acid molecules are generated and wherein each tag is unique for a selected nucleic acid fragment.

23. The method according to claims 17 or 18 wherein said target nucleic acid molecule is generated by primer extension.

24. The method according to claims 17 or 18 wherein said tagged molecules are separated by a method selected from the group consisting of gel electrophoresis, capillary electrophoresis, micro-channel electrophoresis, HPLC, size exclusion chromatography and filtration.

25. The method according to claims 17 or 18 wherein said tagged molecules are cleaved by a method selected from the group consisting of oxidation, reduction, acid-labile, base labile, enzymatic electrochemical, thermal and photolabile methods.

26. The method according to claims 17 or 18 wherein said tag is detected by time-of-flight mass spectrometry, quadrupole mass spectrometry, magnetic sector mass spectrometry and electric sector mass spectrometry.

27. The method according to claims 17 or 18 wherein said tag is detected by potentiostatic amperometry utilizing detectors selected from the group consisting of coulometric detectors and amperometric detectors.

28. The method according to claims 17 or 18 wherein the steps of separating, cleaving and detecting are performed in a continuous manner.

29. The method according to claims 17 or 18 wherein the steps of separating, cleaving and detecting are performed in a continuous manner on a single device.

30. The method according to claims 17 or 18 wherein the steps of separating, cleaving and detecting are automated.

31. The method according to claims 17 or 18 wherein said tagged molecules are generated from non-3'-tagged oligonucleotide primers.

32. The method according to claims 17 or 18 wherein said tagged molecules are generated from tagged dideoxynucleotide terminators.

33. The method according to claims 1, 2, or 17 wherein said target molecule is obtained from a biological sample.

34. A method for detecting a single selected nucleotide within a nucleic acid molecule, comprising sequentially:

(a) hybridizing in at least two separate reactions a tagged primer and a target nucleic acid molecule under conditions and for a time sufficient to permit hybridization of said primer to said target nucleic acid molecule, wherein each reaction contains an enzyme which will add a nucleotide chain terminator, and, a nucleotide chain terminator complementary to adenosine, cytosine, guanosine, thymidine or uracil, and wherein each reaction contains a different nucleotide chain terminator;

(b) separating said tagged primers by size;

(c) cleaving said tag from said tagged primer; and (d) detecting said tag by non-fluorescent spectrometry or potentiometry, and therefrom determining the presence of said selected nucleotide within said nucleic acid molecule.

35. The method according to claim 34 wherein said tagged primers are separated by liquid chromatography.

36. The method according to claim 34 wherein said tagged primers are separated by HPLC.

37. The method according to claim 34 wherein said tag is detected by mass spectrometry, infrared spectrometry, ultraviolet spectrometry, or, potentiostatic amperometry.

38. The method according to claim 34 wherein said enzyme is a polymerase.

39. The method according to claim 34 wherein said target nucleic acid molecule is genomic DNA.

40. The method according to claim 34 wherein each reaction has a different tag on said primer.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:1:

TGTAAAACGA CGGCCAGT                          18

(2) INFORMATION FOR SEQ ID NO:2:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:2:

AAGCTTCGAC TGT                              13

(2) INFORMATION FOR SEQ ID NO:3:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:3:

AAGCTTTGGT CAG                              13

(2) INFORMATION FOR SEQ ID NO:4:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:4:

AAGCTTCTCA ACG                              13

(2) INFORMATION FOR SEQ ID NO:5:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:5:

AAGCTTAGTA GGC                                                           13

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

CTCGTAGACT GCGTACC                                                       17

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:7:

GACGATGAGT CCTGAG                                                        16

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:8:

GACTGCGTAA AAATTCNNN                                                     19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:9:

GATGAGTCCT GAGTAANNN                                                     19

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

GAACGAAAAC CCCCCGC                                                       17

(2) INFORMATION FOR SEQ ID NO:11:

(i) SEQUENCE CHARACTERISTICS:
        (A) LENGTH: 20 base pairs
        (B) TYPE: nucleic acid -continued

```
    (C) STRANDEDNESS: single
    (D) TOPOLOGY: linear (xi) SEQUENCE DESCRIPTION: SEQ ID NO:11:

GATCGCCCCC AAAACACATA                                            20
```